(12) United States Patent
Li et al.

(10) Patent No.: US 12,006,368 B2
(45) Date of Patent: *Jun. 11, 2024

(54) ANTI-FRIZZLED ANTIBODIES AND METHODS OF USE

(71) Applicant: Surrozen Operating, Inc., South San Francisco, CA (US)

(72) Inventors: Yang Li, Mountain View, CA (US); Tom Zhiye Yuan, Union City, CA (US); Aaron Ken Sato, Burlingame, CA (US); Wen-Chen Yeh, Belmont, CA (US); Chenggang Lu, South San Francisco, CA (US); Parthasarathy Sampathkumar, South San Francisco, CA (US); Claudia Yvonne Janda, South San Francisco, CA (US)

(73) Assignee: Surrozen Operating, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/954,482

(22) PCT Filed: Dec. 19, 2018

(86) PCT No.: PCT/US2018/066618
§ 371 (c)(1),
(2) Date: Jun. 16, 2020

(87) PCT Pub. No.: WO2019/126399
PCT Pub. Date: Jun. 27, 2019

(65) Prior Publication Data
US 2021/0087280 A1 Mar. 25, 2021

Related U.S. Application Data

(60) Provisional application No. 62/680,508, filed on Jun. 4, 2018, provisional application No. 62/607,877, filed on Dec. 19, 2017.

(51) Int. Cl.
*C07K 16/28* (2006.01)
(52) U.S. Cl.
CPC ...... *C07K 16/2863* (2013.01); *C07K 2317/24* (2013.01); *C07K 2317/55* (2013.01); *C07K 2317/565* (2013.01); *C07K 2317/569* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,132,405 A | 7/1992 | Huston et al. |
| 5,151,510 A | 9/1992 | Stec et al. |
| 6,005,079 A | 12/1999 | Casterman et al. |
| 6,528,624 B1 | 3/2003 | Idusogie et al. |
| 6,538,124 B1 | 3/2003 | Idusogie et al. |
| 6,765,087 B1 | 7/2004 | Casterman et al. |
| 6,838,254 B1 | 1/2005 | Hamers et al. |
| 7,297,775 B2 | 11/2007 | Idusogie et al. |
| 7,317,091 B2 | 1/2008 | Lazar et al. |
| 7,364,731 B2 | 4/2008 | Idusogie et al. |
| 7,657,380 B2 | 2/2010 | Lazar et al. |
| 7,662,925 B2 | 2/2010 | Lazar et al. |
| 7,982,013 B2 | 7/2011 | Gurney et al. |
| 8,202,966 B2 | 6/2012 | McCarthy |
| 8,221,751 B2 | 7/2012 | Nakamura et al. |
| 8,343,922 B2 | 1/2013 | Wu et al. |
| 8,461,155 B2 | 6/2013 | Wu et al. |
| 8,507,442 B2 | 8/2013 | Gurney et al. |
| 8,637,506 B2 | 1/2014 | Wu et al. |
| 8,715,941 B2 | 5/2014 | Abo et al. |
| 8,846,041 B2 | 9/2014 | Bourhis et al. |
| 8,859,736 B2 | 10/2014 | Ma et al. |
| 8,883,735 B2 | 11/2014 | Jenkins et al. |
| 8,975,044 B2 | 3/2015 | Gurney et al. |
| 9,359,444 B2 | 6/2016 | Dupont et al. |
| 9,573,998 B2 * | 2/2017 | Gurney ............. A61K 31/7068 |
| 2003/0099647 A1 | 5/2003 | Deshpande et al. |
| 2003/0157109 A1 | 8/2003 | Corvalan et al. |
| 2003/0165500 A1 | 9/2003 | Rhee et al. |
| 2005/0261181 A1 | 11/2005 | Wu et al. |
| 2006/0127393 A1 | 6/2006 | Li et al. |
| 2007/0196872 A1 | 8/2007 | Bex et al. |
| 2007/0207522 A1 | 9/2007 | Laurie et al. |
| 2008/0131435 A1 | 6/2008 | Stavenhagen et al. |
| 2008/0138344 A1 | 6/2008 | Stavenhagen et al. |
| 2008/0286261 A1 | 11/2008 | Morgan et al. |
| 2009/0028869 A1 | 1/2009 | Dodel et al. |
| 2009/0092599 A1 | 4/2009 | Lazar et al. |
| 2009/0291088 A1 | 11/2009 | Hariharan et al. |
| 2009/0311243 A1 | 12/2009 | Brockbank et al. |
| 2010/0104574 A1 | 4/2010 | Gurney et al. |
| 2010/0129375 A1 | 5/2010 | Junge et al. |

(Continued)

FOREIGN PATENT DOCUMENTS

| | | |
|---|---|---|
| CN | 101951954 A | 1/2011 |
| CN | 103002911 A | 3/2013 |

(Continued)

OTHER PUBLICATIONS

Ettenberg S.A. et al. (Aug. 3, 20101) "Inhibition of tumorigenesis driven by different Wnt proteins requires blockade of distinct ligand-binding regions by LRP6 antibodies" Proc Natl Acad Sci USA, 107(35):15473-15478.

(Continued)

*Primary Examiner* — Marianne P Allen
(74) *Attorney, Agent, or Firm* — Cooley LLP

(57) ABSTRACT

The present invention provides anti-Fzd monoclonal antibodies and related compositions, which may be used in any of a variety of therapeutic methods for the treatment of diseases.

8 Claims, 11 Drawing Sheets
Specification includes a Sequence Listing.

(56) References Cited

U.S. PATENT DOCUMENTS

| | | |
|---|---|---|
| 2010/0254979 A1 | 10/2010 | Staunton et al. |
| 2010/0254980 A1 | 10/2010 | Cong et al. |
| 2011/0105606 A1 | 5/2011 | Rabbani et al. |
| 2011/0223140 A1 | 9/2011 | Park et al. |
| 2011/0243963 A1 | 10/2011 | Abo et al. |
| 2012/0322717 A9 | 12/2012 | Liu et al. |
| 2013/0064823 A1 | 3/2013 | Cong et al. |
| 2013/0095097 A1 | 4/2013 | Blankenship et al. |
| 2013/0095104 A1 | 4/2013 | Cummings et al. |
| 2013/0183320 A1 | 7/2013 | Wu et al. |
| 2013/0253172 A1 | 9/2013 | Gurney et al. |
| 2013/0274215 A1 | 10/2013 | Thies et al. |
| 2013/0295105 A1 | 11/2013 | Gurney et al. |
| 2014/0044713 A1 | 2/2014 | De Lau et al. |
| 2014/0050725 A1 | 2/2014 | Jenkins et al. |
| 2014/0154252 A1 | 6/2014 | Thompson et al. |
| 2014/0200179 A1 | 7/2014 | Garcia et al. |
| 2014/0242078 A1 | 8/2014 | Dupont et al. |
| 2014/0363439 A1 | 12/2014 | Bourhis et al. |
| 2015/0119555 A1 | 4/2015 | Jung et al. |
| 2015/0209407 A1 | 7/2015 | Pignolo |
| 2015/0232554 A1 | 8/2015 | Gurney et al. |
| 2015/0376252 A1 | 12/2015 | Xu et al. |
| 2016/0002312 A1 | 1/2016 | Ilan |
| 2016/0024196 A1 | 1/2016 | Majeti et al. |
| 2016/0152947 A1 | 6/2016 | Pioszak |
| 2016/0194394 A1 | 7/2016 | Sidhu et al. |
| 2016/0264960 A1 | 9/2016 | Ishii |
| 2016/0312207 A1 | 10/2016 | Kuo et al. |
| 2017/0071937 A1 | 3/2017 | Karp et al. |
| 2017/0218077 A1 | 8/2017 | Raum et al. |
| 2017/0218078 A1 | 8/2017 | Raum et al. |
| 2017/0240631 A1 | 8/2017 | Monroe et al. |
| 2017/0253670 A1 | 9/2017 | Klein et al. |
| 2017/0306029 A1 | 10/2017 | Garcia et al. |
| 2017/0349659 A1 | 12/2017 | Garcia et al. |
| 2018/0066067 A1 | 3/2018 | Cong et al. |
| 2019/0093072 A1 | 3/2019 | Koehler et al. |
| 2019/0093079 A1 | 3/2019 | Loose et al. |
| 2020/0024338 A1 | 1/2020 | Luca et al. |
| 2020/0048324 A1 | 2/2020 | Zhang et al. |
| 2020/0199237 A1 | 6/2020 | Garcia et al. |
| 2020/0199238 A1 | 6/2020 | Garcia et al. |
| 2020/0308287 A1 | 10/2020 | Li et al. |
| 2021/0079089 A1 | 3/2021 | Li et al. |
| 2021/0292422 A1 | 9/2021 | Li |
| 2021/0380678 A1 | 12/2021 | Zhang et al. |
| 2021/0403578 A1 | 12/2021 | Garcia et al. |
| 2022/0064337 A1 | 3/2022 | Li et al. |
| 2022/0112278 A1 | 4/2022 | Li et al. |
| 2022/0175884 A1 | 6/2022 | Lee et al. |
| 2022/0195053 A1 | 6/2022 | Li et al. |
| 2022/0275095 A1 | 9/2022 | Li et al. |

FOREIGN PATENT DOCUMENTS

| | | |
|---|---|---|
| CN | 103998462 A | 8/2014 |
| EP | 1716181 B1 | 12/2009 |
| EP | 2910550 A2 | 8/2015 |
| EP | 3191526 A4 | 3/2018 |
| JP | 2011503025 A | 1/2011 |
| JP | 2012503990 A | 2/2012 |
| JP | 2012506568 A | 3/2012 |
| JP | 2012516685 A | 7/2012 |
| JP | 2013527761 A | 7/2013 |
| JP | 2017530099 A | 10/2017 |
| WO | WO-9627011 A1 | 9/1996 |
| WO | WO-9850431 A2 | 11/1998 |
| WO | WO-02092635 A2 | 11/2002 |
| WO | WO 2004/063351 A2 | 7/2004 |
| WO | WO-2005032574 A1 | 4/2005 |
| WO | WO-2006040163 A1 | 4/2006 |
| WO | WO 2006/079372 A1 | 8/2006 |
| WO | WO 2006/088494 A9 | 8/2006 |
| WO | WO 2006/105338 A2 | 10/2006 |
| WO | WO-2007012449 A1 | 2/2007 |
| WO | WO 2007/024249 A2 | 3/2007 |
| WO | WO-2007146968 A2 | 12/2007 |
| WO | WO-2007148417 A1 | 12/2007 |
| WO | WO 2008/084402 A2 | 7/2008 |
| WO | WO-2008134632 A1 | 11/2008 |
| WO | WO 2009/064944 A2 | 5/2009 |
| WO | WO-2009056634 A2 | 5/2009 |
| WO | WO-2009080251 A1 | 7/2009 |
| WO | WO-2010016766 A2 | 2/2010 |
| WO | WO 2010/037041 A2 | 4/2010 |
| WO | WO-2010054010 A1 | 5/2010 |
| WO | WO 2010/090513 A2 | 8/2010 |
| WO | WO-2011088226 A2 | 7/2011 |
| WO | WO-2011090762 A1 | 7/2011 |
| WO | WO 2011/119661 A1 | 9/2011 |
| WO | WO-2011123785 A2 | 10/2011 |
| WO | WO 2011/138392 A1 | 11/2011 |
| WO | WO 2012/014076 A2 | 2/2012 |
| WO | WO-2012058768 A1 | 5/2012 |
| WO | WO-2012103360 A2 | 8/2012 |
| WO | WO-2012140274 A2 | 10/2012 |
| WO | WO-2012140274 A9 | 3/2013 |
| WO | WO-2013092001 A1 | 6/2013 |
| WO | WO 2013/109819 A1 | 7/2013 |
| WO | WO-2014029752 A1 | 2/2014 |
| WO | WO-2014124326 A1 | 8/2014 |
| WO | WO-2014159580 A1 | 10/2014 |
| WO | WO-2015036582 A2 | 3/2015 |
| WO | WO-2015063187 A1 | 5/2015 |
| WO | WO 2015/109212 A1 | 7/2015 |
| WO | WO 2016/023019 A2 | 2/2016 |
| WO | WO 2016/040895 A1 | 3/2016 |
| WO | WO-2016168607 A1 | 10/2016 |
| WO | WO-2016205551 A2 | 12/2016 |
| WO | WO-2016205566 A1 | 12/2016 |
| WO | WO 2017/136820 A2 | 8/2017 |
| WO | WO-2017127933 A1 | 8/2017 |
| WO | WO-2017152102 A2 | 9/2017 |
| WO | WO2018132572 A1 | 7/2018 |
| WO | WO2018140821 A1 | 8/2018 |
| WO | WO-2018220080 A1 | 12/2018 |
| WO | WO 2019/126398 A1 | 6/2019 |
| WO | WO 2019/126401 A1 | 6/2019 |
| WO | WO2019126399 A1 | 6/2019 |
| WO | WO-2019159084 A1 | 8/2019 |
| WO | WO 2020/010308 A1 | 1/2020 |
| WO | WO2020014271 A1 | 1/2020 |
| WO | WO 2020/132356 A1 | 6/2020 |
| WO | WO 2020/167848 A1 | 8/2020 |
| WO | WO 2020/185960 A1 | 9/2020 |
| WO | WO 2020/206005 A1 | 10/2020 |
| WO | WO2021003416 A1 | 1/2021 |
| WO | WO 2021/173726 A1 | 9/2021 |
| WO | WO2022104280 A1 | 5/2022 |
| WO | WO2022192445 A1 | 9/2022 |
| WO | WO-2023044348 A1 | 3/2023 |

OTHER PUBLICATIONS

GenBank Accession No. AF177394.2 "*Homo sapiens* dickkopf-1 (DKK-1) mRNA, complete cds" Dec. 20, 2016, 2 pages.
GenBank Accession No. AF177395.1 "*Homo sapiens* dickkopf-2 (DKK-2) mRNA, complete cds" Dec. 20, 2016, 2 pages.
GenBank Accession No. NM_014419.4 "*Homo sapiens* dickkopf like acrosomal protein 1 (DKKL1), transcript variant 1, mRNA" Feb. 18, 2021, 4 pages.
GenBank Accession No. NM_014420.3 "*Homo sapiens* dickkopf WNT signaling pathway inhibitor 4 (DKK4), mRNA" Feb. 15, 2021, 4 pages.
GenBank Accession No. NM_014421.3 "*Homo sapiens* dickkopf WNT signaling pathway inhibitor 2 (DKK2), mRNA" Feb. 13, 2021, 4 pages.
GenBank Accession No. NM_015881.6 "*Homo sapiens* dickkopf WNT signaling pathway inhibitor 3 (DKK3), transcript variant 1, mRNA" Feb. 23, 2021, 5 pages.
GenBank Accession No. NP_036374.1 "dickkopf-related protein 1 precursor [*Homo sapiens*]" Mar. 3, 2021, 3 pages.

(56) References Cited

OTHER PUBLICATIONS

GenBank Accession No. NP_055236.1 "dickkopf-related protein 2 precursor [*Homo sapiens*]" Feb. 13, 2021, 3 pages.
Gong, S. et al. (2017) "Fabs-in-tandem immunoglobulin is a novel and versatile bispecific design for engaging multiple therapeutic targets" mAbs, 9(7):1118-1128, DOI: 10.1080/19420862.2017.1345401.
Gong, Y. et al. (2010) "Wnt Isoform-Specific Interactions with Coreceptor Specify Inhibition or Potentiation of Signaling by LRP6 Antibodies" PLoS One, 5(9):e12682, doi:10.1371/journal.pone.0012682; 17 pages.
Gurney, A. et al. (Jul. 2012) "Wnt pathway inhibition via the targeting of Frizzled receptors results in decreased growth and tumorigenicity of human tumors" Proc Natl Acad Sci USA, 109(29):11717-11722.
International Patent Application No. PCT/US2018/066618, by Surrozen, Inc.: International Search Report and Written Opinion, including Notification of Transmittal; dated May 8, 2019, 12 pages.
Janda, C.Y. et al. (2012) "Structural basis of Wnt recognition by Frizzled" Science, 337(6090):59-64. NIH Public Access Author Manuscript [online]; retrieved from: https://www.ncbi.nlm.nih.gov/pmc/articles/PMC3577348/pdf/nihms443661.pdf; 18 pages.
Joiner, D.M. et al. (Jan. 2013) "LRP5 and LRP6 in development and disease" Trends in Endocronology and Metabolism, 24(1):31-39.
Katoh, M. et al. (Sep. 2017) "Molecular genetics and targeted therapy of WNT-related human diseases (Review)" Intl J Mol Med, 40(3):587-606.
Krupnik, V.E. et al. (1999) "Functional and structural diversity of the human Dickkopf gene family" Gene, 238(2):301-313.
Sato, T. et al. (May 14, 2009) "Single Lgr5 stem cells build crypt-villus structures in vitro without a mesenchymal niche" Nature, 459:262-265, www.nature.com/doifinder/10.1038/nature07935; with "Methods", 1 page.
Sato, T. et al. (2011) "Long-term Expansion of Epithelial Organoids From Human Colon, Adenoma, Adenocarcinoma, and Barrett's Epithelium" Gastroenterology, 141:1762-1772.
Steinhart, Z. et al. (Jan. 2017) "Genome-wide CRISPR screens reveal a Wnt-FZD5 signaling circuit as a druggable vulnerability of RNF43-mutant pancreatic tumors" Nat Med, 23(1):60-68.
Brinkmann, U. et al (2017) The making of bispecific antibodies. MAbs, 9(2):182-212.
Adams, T.S. et al. (Jul. 2020) Single-cell RNA-seq reveals ectopic and aberrant lung-resident cell populations in idiopathic pulmonary fibrosis. Sci Adv, 6:eaba1983, 16 pages.
Ahn, V. E., et al. (2011) "Structural basis of Wnt signaling inhibition by Dickkopf binding to LRP5/6" Developmental cell, 21(5):862-873.
Aihara, E. et al. (2017) "Trefoil factor peptides and gastrointestinal function" Annual Review of Physiology, 79:357-380.
Akhmetshina, A. et al. (Mar. 2012) Activation of canonical Wnt signalling is required for TGF-β-mediated fibrosis. Nature Communications, 3:735; DOI:10.1038/ncomms1734, 12 pages.
Alsafadi, H. et al. (Mar. 2017) An ex vivo model to induce early fibrosis-like changes in human precision-cut lung slices. Am J Physiol Lung Cell Mol Physiol, 312:L896-L902.
Antoni, L. et al. (2014) "Intestinal barrier in inflammatory bowel disease" World Journal of Gastroenterology: WJG, 20(5):1165-1179.
Aran et al. (2019) "Reference-based analysis of lung single-cell sequencing reveals a transitional profibrotic macrophage". Nature Immunology, 20(2): 163-172.
Arike, L. et al. (2017) "Intestinal Muc2 mucin O-glycosylation is affected by microbiota and regulated by differential expression of glycosyltranferases" Glycobiology, 27(4):318-328.
Atkinson, P.J., et al. (2014) "Hair cell regeneration after ATOH1 gene therapy in the cochlea of profoundly deaf adult guinea pigs." PLoS ONE 9(7):e102077.
Baarsma, H. et al. (2017) Noncanonical WNT-5A signaling impairs endogenous lung repair in COPD. J Exp Med, 214:143-163.

Baarsma, H.A., and M. Königshoff (2017). 'WNT-er is coming' : WNT signalling in chronic lung diseases. Thorax, 72:746-759.
Bafico, A. et al. (Jul. 2001) "Novel mechanism of Wnt signalling inhibition mediated by Dickkopf-1 interaction with LRP6/Arrow" Nature Cell Biology, 3(7):683-686.
Barbas et al., (1995) "Human autoantibody recognition of DNA" Proceedings of the National Academy of Sciences, 92(7):2529-2533.
Barbas et al., (1994) "Recognition of DNA by synthetic antibodies" Journal of the American Chemical Society, 116(5):2161-2162.
Barkauskas, C.E. et al. (Jul. 2013) Type 2 alveolar cells are stem cells in adult lung. Journal of Clinical Investigation 123(7):3025-3036.
Barkauskas et al. (2017) "Lung organoids: current uses and future promise". Development, 144(6): 986-997.
Barker et al. (2007). "Identification of stem cells in small intestines and colon by marker gene Lgr5." Nature Publishing Group. vol. 449, No. 25 1003-7.
Barker et al. (2009) Crypt stem cells as the cells-of-origin of intestinal cancer. Nature, 457(7229):608-611, Methods, 1 page; doi:10.1038/nature07602.
Barker et al. (2010). "Lgr5-'-ve stem cells drive self-renewal in the stomach and build long-lived gastric units in vitro." Cell Stem Cell. vol. 6, 25-36.
Barnes et al. (2015) "Chronic obstructive pulmonary disease". Nature Reviews, Disease Primer, 1: 1-21.
Basil et al., (2022) "Human distal airways contain a multipotent secretory cell that can regenerate alveoli". Nature, 604(7904): 120-126.
Bergström, J.H. et al. (2014) "AGR2, an endoplasmic reticulum protein, is secreted into the gastrointestinal mucus" PLoS One, 9(8):e104186.
Bergström, J.H. et al. (Nov. 2016) "Gram-positive bacteria are held at a distance in the colon mucus by the lectin-like protein ZG16" Proceedings of the National Academy of Sciences, 113(48):13833-13838.
Beumer, J. et al. (2016) "Regulation and plasticity of intestinal stem cells during homeostasis and regeneration" Development, 143(20):3639-3649.
Bhalla, P. et al. (Apr. 2015) Disseminated, persistent, and fatal infection due to the vaccine strain of varicella-zoster virus in an adult following stem cell transplantation.Clin Infect Dis, 60(7):1068-1074. doi: 10.1093/cid/ciu970.
Bird, R.E. et al. (Oct. 1988) "Single-chain antigen-binding proteins." Science 242(4877):423-426.
Blagodatski et al. (2014) "Targeting the Wnt pathways for therapies". Molecular Cell Therapy 2(28): 15 pages.
Bohne, B.A. et al. (1976) Irreversible Inner Ear Damage From Rock Music. Trans Sect Otolaryngol Am Acad Ophthalmol Otolaryngol. 82(1):50-59.
Bourhis et al. (2010) "Reconstitution of a Frizzled8.Wnt3a.LRP6 signaling complex reveals multiple Wnt and Dkk1 binding sites on LRP6" The Journal of Biological Chemistry, 285:12 9172-9179.
Bradley, P. et al. (Sep. 2005) "Toward high-resolution de novo structure prediction for small proteins." Science 309(5742):1868-1871.
Bramhall et al. (2014). "Lgr5-Positive Supporting Cells Generate New Hair Cells in the Postnatal Cochlea." Stem Cell Reports. 2(3): 311-322.
Bramhall, N.F. et al. (2017) Auditory Brainstem Response Altered in Humans With Noise Exposure Despite Normal Outer Hair Cell Function. Ear Hear, 38(1):e1-e12. U.S. Department of Veterans Affairs Public Access Author Manuscript, 27 pages.
Cao et al. (2016) "Targeting of the pulmonary capillary vascular niche promotes lung alveolar repair and ameliorates fibrosis". Nature Medicine, 22(2): 154-162.
Cao, H. et al. (2018) Inhibition of Wnt/β-catenin signaling suppresses myofibroblast differentiation of lung resident mesenchymal stem cells and pulmonary fibrosis. Scientific Reports, 8:13644; DOI.10.1038/s41598-018-28968-9, 14 pages.

(56) References Cited

OTHER PUBLICATIONS

Carlier, F.M. et al. (2020). Canonical WNT pathway is activated in the airway epithelium in chronic obstructive pulmonary disease. EBioMedicine, 61:103034; https://doi.org/10.1016/j.ebiom.2020.103034, 17 pages.

Chai et al. (2011). "Dynamic Expression of Lgr5, a Wnt Target Gene, in the Developing and Mature Mouse Cochlea." J. Assoc. Res. Otolaryngology. 12(4): 455-469.

Chang et al (2015) "Structure and functional properties of Norrin mimic Wnt for signaling with Frizzled4, Lrp5/6, and proteoglycane" Life 4 1-27.

Chen et al. (2009). "Aminoglycoside-induced histone deacetylation and hair cell death in the mouse cochlea," J. Neurochem., 108(5): 1226-1236.

Chen, H. et al. (2020) "Development of Potent, Selective Surrogate WNT Molecules and Their Application in Defining Frizzled Requirements." Cell Chem Biol 27:598-609, e594.

Chen, M. et al. (Jul. 2017) Acute inflammation regulates neuroregeneration through the NF-κB pathway in olfactory epithelium. Proceedings of the National Academy of Sciences, 114(30):8089-8094. https://doi.org/10.1073/pnas.1620664114.

Chen, X. et al. (Aug. 2016). Inhibition of Wnt/β-catenin signaling suppresses bleomycin-induced pulmonary fibrosis by attenuating the expression of TGF-β1 and FGF-2. Experimental and Molecular Pathology, 101(1):22-30. HHS Public Access Author Manuscript, 17 pages.

Chen, X. et al. (2018). The hedgehog and Wnt/β-catenin system machinery mediate myofibroblast differentiation of LR-MSCs in pulmonary fibrogenesis. Cell Death & Disease, 9:639; DOI:10.1038/s11419-018-0692-9, 15 pages.

Cheng, H. et al. (1974) Origin, differentiation and renewal of the four main epithelial cell types in the mouse small intestine. V. Unitarian theory of the origin of the four epithelial cell types. American Journal of Anatomy, 141(4):537-561.

Cheng, Z. et al. (Oct. 2011) Crystal structures of the extracellular domain of LRP6 and its complex with DKK1. Nat Struct Mol Biol, 18(11):1204-1210. NIH Public Access Author Manuscript; 20 pages.

Chilosi et al. (2003) "Aberrant Wnt/β-catenin pathway activation in idiopathic pulmonary fibrosis". The American Journal of Pathology, 162(5): 1495-1502.

Clevers et al (2012) "Wnt/b-Catenin signaling and disease" Cell, 149:1192-1205.

Conlon, T.M. et al. (Dec. 2020). Inhibition of LTβR signalling activates WNT-induced regeneration in lung. Nature, 588(7836):151-156. HHS Public Access Author Manuscript, 50 pages.

Conte et al. (2014) "Effect of pirfenidone on proliferation, TGF-β-induced myofibroblast differentiation and fibrogenic activity of primary human lung fibroblasts". European Journal of Pharmaceutical Sciences, 58: 13-19.

Cooper, H.S. et al. (1993) "Clinicopathologic study of dextran sulfate sodium experimental murine colitis" Laboratory Investigation, 69(2):238-249.

Cox et al. (2014). "Spontaneous Hair Cell Regeneration in the Neonatal Mouse Cochlea in Vivo." Development. vol. 141, No. 4, pp. 816-829.

Davidson, G. (2010) "The Cell Cycle and Wnt." Cell Cycle, 9(9):1667-1668.

De Lau, W. et al. (Aug. 2011) "Lgr5 homologues associate with Wnt receptors and mediate R-spondin signalling" Nature, 476(7360):293-297.

De Visser, K., et al. (2012) Developmental stage-specific contribution of LGR5+ cells to basal and luminal epithelial lineages in the postnatal mammary gland. J Pathol, 228:300-309.

Degryse, A. et al. (2010) Repetitive intratracheal bleomycin models several features of idiopathic pulmonary fibrosis. Am J Physiol Lung Cell Mol Physiol, 299:L442-L452.

Deng, S. et al (2019) "Bitter peptides increase engulf of phagocytes in vitro and inhibit oxidation of myofibrillar protein in peeled shrimp (*Litopenaeus vannamei*) during chilled storage." Aquaculture Reports, 15:100234. 8 pages.

Desai et al. (2014) "Alveolar progenitor and stem cells in lung development, renewal and cancer". Nature, 507(7491): 190-194.

Deshaies, R. J. (Apr. 2020) "Multispecific drugs herald a new era of biopharmaceutical innovation." Nature, 580(7803):329-338.

Dijksterhuis et al. (2015) "Systematic mapping of Wnt-Fzd protein interactions reveals functional selectivity by distinct Wnt-Fzd pairs" The Journal of Biology Chemist 290:11 6789-6798.

Dorofeyev, A.E., et al. (2013) "Mucosal Barrier in Ulcerative Colitis and Crohn's Disease" Gastroenterology Research and Practice, 2013:431231, 9 pages.

Drucker, D. (1999) "Glucagon-like Peptide 2" TEM, 10(4):153-156.

Farin et al. (2012). "Redundant sources of Wnt regulate intestinal stem cells and promote formation ofPaneth cells," Gastroenterology, 143: 1518-1529.

Fedi, P. et al. (Jul. 1999) "Isolation and Biochemical Characterization of the Human Dkk-1 Homologue, a Novel Inhibitor of Mammalian Wnt Signaling." Journal of Biological Chemistry, 274(27):19465-19472.

Fong, Y.W. et al. (Nov. 2014) "The dyskerin ribonucleoprotein complex as an OCT4/SOX2 coactivator in embryonic stem cells" eLife, 3:e03573, 30 pages.

Fowler, T. W et al. (2021) "Development of selective bispecific Wnt mimetics for bone loss and repair." Nature Communications, 12(1):3247, pp. 1-13. https://doi.org/10.1038/s41467-021-23374-8.

Frank et al. (2016) "Emergence of a wave of Wnt signaling that regulates lung alveologenesis by controlling epithelial self-renewal and differentiation". Cell Reports, 17(9): 2312-2325.

Fuerer, C. and R. Nusse (2010) "Lentiviral Vectors to Probe and Manipulate the Wnt Signaling Pathway" PLoS One 5z92):e9370, 7 pages.

Fujii, M. et al. (Dec. 2018) "Human Intestinal Organoids Maintain Self-Renewal Capacity and Cellular Diversity in Niche-Inspired Culture Condition" Cell Stem Cell, 23:787-793.

Fujioka et al. (2015). "Manipulating cell fate in the cochlea: a feasible therapy for hearing loss." Trends Neurosci. 38, 139-44.

Gadkar, K. et al. (2015) "Design and pharmacokinetic characterization of novel antibody formats for ocular therapeutics." Investigative Ophthalmology & Visual Science, 56(9):5390-5400.

GenBank Accession No. NP_004054.3 "cadherin-17 precursor [*Homo sapiens*]" May 25, 2022, 4 pages.

GenBank Accession No. NP_005805.1 "cell surface A33 antigen precursor [*Homo sapiens*]" Jun. 3, 2022, 4 pages.

GenBank Accession No. NP_149038.3 "mucin-13 precursor [*Homo sapiens*]" Oct. 17, 2021, 4 pages.

"GenVec Provides Investor Update: Highlights ongoing Initiatives Involving the AdenoVerse Gene Delivery Platform" GenVec Press Release, Jan. 20, 2016, 1 page.

"GenVec Provides Update on Hearing Loss Clinical Program: Data Safety Monitoring Board Recommends Trial Continue" GenVec Press Release, May 2, 2016, 1 page.

Getz, J.A., et al., "Protease-resistant Peptide Ligands From a Knottin Scaffold Library," ACS Chemical Biology, Aug. 19, 2011, vol. 6(8), pp. 837-844.

Ghossaini, S. N., et al. (2013) "Round window membrane permeability to golimumab in guinea pigs: a pilot study." The Laryngoscope 123(11):2840-2844.

Gibbs, S. et al. (1993) Molecular Characterization and Evolution of the SPRR Family of Keratinocyte Differentiation Markers Encoding Small Proline-Rich Proteins. Genomics, 16:630-637.

Giotti et al. (2019) "Assembly of a parts list of the human mitotic cell cycle machinery" Journal of Molecular Cell Biology, 11(8):703-718.

Glinka et al. (1998) "Dickkopf-1 is a member of a new family of secreted proteins and functions in head induction." Nature, 391(6665):357-362.

Golde, et al. (2013) "γ-Secretase inhibitors and modulators." Biochimica et Biophysica Acta (BBA)—Biomembranes, 1828(12):2898-2907.

Gougelet, A., et al. (2014) "T-cell factor 4 and β-catenin chromatin occupancies pattern zonal liver metabolism in mice." Hepatology, 59(6):2344-2357. https://doi.org/10.1002/hep.26924.

Gubbels et al. (2008) "Functional auditory hair cells produced in the mammalian cochlea by in utero gene transfer." Nature, 455(7212):537-541.

(56) References Cited

OTHER PUBLICATIONS

Guo, L. et al. (2016) WNT/β-catenin signaling regulates cigarette smoke-induced airway inflammation via the PPARd/p38 pathway. Lab Invest, 96:218-229.

Haas, M. et al. (2019) DeltaN-Tp63 Mediates Wnt/β-Catenin-Induced Inhibition of Differentiation in Basal Stem Cells of Mucociliary Epithelia. Cell Reports, 28:3338-3352.

Habermann, A.C. et al. (Jul. 2020) Single-cell RNA sequencing reveals profibrotic roles of distinct epithelial and mesenchymal lineages in pulmonary fibrosis. Sci Adv, 6:eaba1972, 15 pages.

Haegebarth et al. (2009). "Wnt Signaling, Lgr5, and Stem Cells in the Intestine and Skin." The American Journal of Pathology. vol. 174, No. 3, pp. 715-721.

Hao, H-X. et al. (May 10, 2012) "ZNRF3 promotes Wnt receptor turnover in an R-spondin-sensitive manner" Nature, 485(7397):195-200.

Hawkins et al. (1976) "Hearing Loss and Cochlear Pathology in Monkeys After Noise Exposure" Acta Oto-Laryngologica 81(3-6):337-343.

Head et al. (2013) "Activation of canonical Wnt/β-catenin signaling stimulates proliferation in neuromasts in the zebrafish posterior lateral line." Developmental Dynamics 242(7):832-846.

Henderson et al. (2010) "Inhibition of Wnt/β-catenin/CREB binding protein (CBP) signaling reverses pulmonary fibrosis". Proceedings of the National Academy of Sciences, 107(32): 14309-14314.

Hirata et al. (2013) "Dose-dependent roles for canonical Wnt signalling in de novo crypt formation and cell cycle properties of the colonic epithelium" Development and Stem Cells, 140:66-75.

Ho et al. (2006) "Cysteine-Rich Domains of Muc3 Intestinal Mucin Promote Cell Migration, Inhibit Apoptosis, and Accelerate Wound Healing" Gastroenterology, 131:1501-1517.

Hollnagel, et al. (1999) "Id genes are direct targets of bone morphogenetic protein induction in embryonic stem cells." Journal of Biological Chemistry 274(28):19838-19845.

Holmen et al. (2005) "Wnt-independent activation of B-catenin mediated by a Dkk1-Fz5 fusion protein" Biochemical and Biophysical Research Communications, 328(2):533-539.

Hu et al., (2018) "Long-Term Expansion of Functional Mouse and Human Hepatocytes as 3D Organoids." Cell, 175:1591-1606, e19. doi:10.1016/j.cell.2018.11.013.

Huch et al., (2013) "In vitro expansion of single Lgr5+ liver stem cells induced by Wnt-driven regeneration." Nature 494(7436):247-250.

International Preliminary Report on Patentability for International Patent Application No. PCT/US2018/066618, dated Jun. 23, 2020, 7 pages.

Izumikawa et al. (2005). "Auditory Hair Cell Replacement and Hearing Improvement by Atohl Gene Therapy in Deaf Mammals." Nat Med., 11(3): 271-276.

Izumikawa et al. (2008) "Response of the flat cochlear epithelium to forced expression of Atoh1." Hearing Research, 240(1-2):52-56.

Jacques, B.E. et al. (2013) A dual function for canonical Wnt/β-catenin signaling in the developing mammalian cochlea. Development, 139:4395-4404. Erratum, Development 140:247.

Janda, C.Y. et al. (May 11, 2017) "Surrogate Wnt agonists that phenocopy canonical Wnt and β-catenin signaling" Nature, 545(7653):234-237. HHS Public Access Author Manuscript, 35 pages.

Jiang et al. (2016) "A chronic obstructive pulmonary disease susceptibility gene, FAM13A, regulates protein stability of β-catenin". American Journal of Respiratory and Critical Care Medicine, 194(2): 185-197.

Jiang, X. et al., (2015) "Dishevelled promotes Wnt receptor degradation through recruitment of ZNRF3/RNF43 E3 ubiquitin ligases." Molecular Cell, 58(3):522-533.

Jin, Y-R. and J.K. Yoon (Dec. 2012) "The R-spondin family of proteins: Emerging regulators of WNT signaling" Int J Biochem Cell Biol, 44(12):2278-2287, doi: 10.1016/j.biocel.2012.09.006.

Kahn, M. (Jul. 2014) "Can we safely target the WNT pathway?" Nature Reviews, 13(7):513-532.

Kawamoto et al. (2003). "Math1 gene transfer generates new cochlear hair cells in mature guinea pigs in vivo." Journal of Neuroscience. 23(11): 4395-400.

Ke et al. (2013) "Structure and function of Norrin in assembly and activation of a Frizzled 4-Lrp5/6 complex" Genes and Development 27(21):2305-2319; Supplement Material.

Kechai, et al. (2015) "Recent advances in local drug delivery to the inner ear." International journal of pharmaceutics, 494(1):83-101.

Kelley, M.W. (Oct. 2007) Has hair cell loss MET its match? Proc Natl Acad Sci USA, 104(42):16400-16401.

Kelly et al. (2012) "Contractility in type III cochlear fibrocytes is dependent on non-muscle myosin II and intercellular gap junctional coupling." Journal of the Association for Research in Otolaryngology, 13(4):473-484.

Kim, H.-T. et al. (Dec. 2019) WNT/RYK signaling restricts goblet cell differentiation during lung development and repair. Proc Natl Acad Sci USA, 116(51):25697-25706.

Kim, K. A. et al. (2005) "Mitogenic Influence of Human R-Spondin1 on the Intestinal Epithelium." Science, 309(5738):1256-1259. https://doi.org/10.1126/science.1112521.

Kim, T.H. et al. (2011). Blockade of the Wnt/β-Catenin Pathway Attenuates Bleomycin-Induced Pulmonary Fibrosis. Tohoku Journal of Experimental Medicine, 223:45-54.

Kim, Y. S. et al. (2010) "Intestinal Goblet Cells and Mucins in Health and Disease: Recent Insights and Progress" Current Gastroenterology Rep, 12:319-330.

Kinchen et al. (2018) "Structural remodeling of the human colonic mesenchyme in inflammatory bowel disease." Cell, 175(2):372-386.

King et al. (2011) Idiopathic pulmonary fibrosis:. The Lancet, 378(9807): 1949-1961.

Kipp, A., et al. (2007). "Activation of the glutathione peroxidase 2 (GPx2) promoter by β-catenin." Biological Chemistry, 388(10):1027-1033. https://doi.org/10.1515/BC.2007.137.

Kneidinger et al. (2011) "Activation of the WNT/β-catenin pathway attenuates experimental emphysema". American Journal of Respiratory and Critical Care Medicine, 183(6): 723-733.

Knight, M.N. and K. Hankenson (2014) "R-spondins: Novel matricellular regulators of the skeleton" Matrix Biology, 37:157-161.

Königshoff, M. et al. (May 2008) Functional Wnt Signaling Is Increased in Idiopathic Pulmonary Fibrosis. PLoS ONE, 3(5):e2142; doi:10.1371/journal.pone.0002142, 12 pages.

Kobayashi et al. (2020) "Persistence of a regeneration-associated, transitional alveolar epithelial cell state in pulmonary fibrosis". Nature Cell Biology, 22(8): 934-946.

Koo, B.K. et al. (2012) "Tumour suppressor RNF43 is a stem-cell E3 ligase that induces endocytosis of Wnt receptors." Nature, 488:665-669.

Kraft et al. (2013) "Atoh1 induces auditory hair cell recovery in mice after ototoxic injury." The Laryngoscope, 123(4):992-999.

Krausova et al. (2014) "Wnt signaling in adult intestinal stem cells and cancer." Cellular Signalling, 26(3):570-579. https://doi.org/10.1016/j.cellsig.2013.11.032.

Kruis, W. et al. (2019) Budesonide Suppositories Are Effective and Safe for Treating Acute Ulcerative Proctitis. Clin Gastroenterol Hepatol, 17:98-106.

Kumagai, K. et al. (Dec. 2010) Up-regulation of EGF receptor and its ligands, AREG, EREG, and HB-EGF in oral lichen planus. Oral Surg Oral Med Oral Pathol Oral Radiol Endod, 110(6):748-754.

Kuo et al. (2015). "In Vivo Cochlear Hair Cell Generation and Survival by Coactivation of beta-Catenin and Atoh1." Journal of Neuroscience, vol. 35, No. 30, p. 10786-10798.

Kyritsis, N. et al. (2012) "Acute Inflammation Initiates the Regenerative Response in the Adult Zebrafish Brain." Science, 338(6112):1353-1356. https://doi.org/10.1126/science.1228773.

Lam et al. (2014) "Wnt coreceptor Lrp5 is a driver of idiopathic pulmonary fibrosis". American Journal of Respiratory and Critical Care Medicine, 190(2): 185-195.

Lebensohn et al. (2018) "R-spondins can potentiate WNT signaling without LGRs." Elife 7:e33126, 1-18 pages.

Lehrnbecher et al., (1999)"Variant genotypes of the low-affinity Fcγ receptors in two control populations and a review of low-affinity Fcγ

(56) References Cited

OTHER PUBLICATIONS receptor polymorphisms in control and disease populations." Blood, The Journal of the American Society of Hematology, 94(12):4220-4232.
Lim, X, et al., (2013) "Interfollicular epidermal stem cells self-renew via autocrine Wnt signaling." Science, 342(6163):1226-1230.
Liu et al. (2012) "Age-dependent in vivo conversion of mouse cochlear pillar and Deiters' cells to immature hair cells by Atoh1 ectopic expression." Journal of Neuroscience. 32(19):6600-6610.
Liu et al. (2014) "In vivo generation of immature inner hair cells in neonatal mouse cochleae by ectopic Atoh1 expression." PloS one, 9(2):e89377, 12 pages.
Liu, J. et al. (2005) "A small-molecule agonist of the Wnt signaling pathway" Angew. Chem. Int. Ed., 44(13):1987-1990.
Mah, A.T. et al. (2016). Wnt pathway regulation of intestinal stem cells. Journal of Physiology, 594(17):4837-4847. https://doi.org/10.1113/JP271754.
Mahtouk, K. et al. (2005). Expression of EGF-family receptors and amphiregulin in multiple myeloma. Amphiregulin is a growth factor for myeloma cells. Oncogene, 24:3512-3524.
Mao, B. et al. (May 2001) LDL-receptor-related protein 6 is a receptor for Dickkopf proteins. Nature 411:321-325.
Mao, B. et al. (Jun. 2002) Kremen proteins are Dickkopf receptors that regulate Wnt/beta-catenin signalling. Nature, 417:664-667.
Markovic, M.A. and P.L. Brubaker (2019). The roles of glucagon-like peptide-2 and the intestinal epithelial insulin-like growth factor-1 receptor in regulating microvillus length. Scientific Reports, 9:13010, 13 pages.
Mccann, K.L. et al. (2020). H/ACA snoRNA levels are regulated during stem cell differentiation. Nucleic Acids Research, 48(15):8686-8703. https://doi.org/10.1093/nar/gkaa612.
Mclean et al. (2017). "Clonal Expansion of Lgr5-Positive Cells from Mammalian Cochlea and High-Purity Generation of Sensory Hair Cells." Cell Reports, vol. 18, No. 8, p. 1917-1929.
Meteoglu, I. et al. (2008) Id-I: Regulator of EGFR and VEGF and potential target for colorectal cancer therapy. J Exp Clin Cancer Res, 27:69, doi: 10.1186/1756-9966-27-69; 7 pages.
Mikels et al. (2006) "Wnts as ligands: processing, secretion and reception" Oncogene, 25:7461-7468.
Milstein, C. et al. (Oct. 6, 1983). "Hybrid Hybridomas and Their Use in Immunohistochemistry," Nature, vol. 305, pp. 537-539.
Minear Steven et al, "Wnt proteins promote bone regeneration.", Science Translational Medicine Apr. 28, 2010, (Apr. 28, 2010), vol. 2, No. 29, ISSN 1946-6242, p. 29ra30, XP055449646.
Mitchell et al (1989) "Alpha-smooth muscle actin in parenchymal cells of bleomycin-injured rat lung". Laboratory Investigation; A Journal of Technical Methods and Pathology, 60(5): 643-650.
Mizutari et al. (2014). "Spontaneous Recovery of Cochlear Fibrocytes After Severe Degeneration Caused by Acute Energy Failure." Frontiers in Phamcacology, vol. 5, No. 198, pp. 1-3.
Molenaar, M. et al. (Aug. 1996) XTcf-3 Transcription Factor Mediates beta-Catenin-Induced Axis Formation in Xenopus Embryos. Cell, 86:391-399.
Murthy et al. (2022) "Human distal lung maps and lineage hierarchies reveal a bipotent progenitor". Nature, 604(7904): 111-119.
Muyldermans, S. (2013) Nanobodies: Natural Single-Domain Antibodies. Annu Rev Biochem, 82:775-797.
Nabhan, A.N. et al. (Mar. 2018). A single cell Wnt signaling niches maintain stemness of alveolar type 2 cells. Science, 359(6380):1118-1123. HHS Public Access Author Manuscript, 28 pages.
Nishino, J. et al. (Oct. 2008) Hmga2 Promotes Neural Stem Cell Self-Renewal in Young but Not Old Mice by Reducing p16Ink4a and p19Arf Expression. Cell, 135(2):227-239. https://doi.org/10.1016/j.cell.2008.09.017.
Nusse, R. (2005) "Wnt signaling in disease and in development" Cell Research, 15(1):28-32.
Oesterle, E.C. et al. (2008) Sox2 and Jagged1 Expression in Normal and Drug-Damaged Adult Mouse Inner Ear. J Assoc Res Otolaryngol (JARO), 9(1):65-89.
Pan, S. et al. (Jun. 2013) Lentivirus carrying the Atoh1 gene infects normal rat cochlea. 8(17):1551-1559.
Parisi, S. et al. (2020). HMGA Proteins in Stemness and Differentiation of Embryonic and Adult Stem Cells. International Journal of Molecular Sciences, 21(1):362, 17 pages. https://doi.org/10.3390/ijms21010362.
Park, J-S. et al. (2014) Human AP Endonuclease 1: A Potential Marker for the Prediction of Environmental Carcinogenesis Risk. Oxidative Medicine and Cellular Longevity, 2014:730301, http://dx.doi.org/10.1155/2014/730301, 15 pages.
Park, S-W. et al. (Apr. 2009) The protein disulfide isomerase AGR2 is essential for production of intestinal mucus. PNAS USA, 106(17):6950-6955.
Pavlovic, Z. et al. (2018) A synthetic anti-Frizzled antibody engineered for broadened specificity exhibits enhanced anti-tumor properties. mAbs, 10(8):1157-1167, DOI: 10.1080/19420862.2018.1515565.
Pinto, D. et al. (2003) Canonical Wnt signals are essential for homeostasis of the intestinal epithelium. Genes & Dev, 17:1709-1713.
Powell, A.E. et al. (Mar. 2012). The Pan-ErbB Negative Regulator Lrig1 Is an Intestinal Stem Cell Marker that Functions as a Tumor Suppressor. Cell, 149(1):146-158. https://doi.org/10.1016/j.cell.2012.02.042.
Rey, J-P. et al. (2010) "Wnt modulators in biotech pipeline" Developmental Dynamics, 239(1):102-114.
Reyfman, P.A. et al. (Jun. 2019) Single-Cell Transcriptomic Analysis of Human Lung Provides Insights into the Pathobiology of Pulmonary Fibrosis. American Journal of Respiratory and Critical Care Medicine, 199(12):1517-1536.
Rock et al. (2011) "Multiple stromal populations contribute to pulmonary fibrosis without evidence for epithelial to mesenchymal transition". Proceedings of the National Academy of Sciences, 108(52): E1475-E1483.
Ruzinova, M.B. and R. Benezra (Aug. 2003) Id proteins in development, cell cycle and cancer. TRENDS Cell Biol, 13(8):410-418.
Safdari Y., et al., "Antibody Humanization Methods—A Review and Update," Biotechnology and Genetic Engineering Reviews, Aug. 2013, vol. 29, No. 2, pp. 175-186.
Santos, A.J.M. et. al (Dec. 2018) The Intestinal Stem Cell Niche: Homeostasis and Adaptations. Trends in Cell Biol, 28(12):1062-1078, https://doi.org/10.1016/j.tcb.2018.08.001.
Schaefer, W. et al. (Jul. 2011) Immunoglobulin domain crossover as a generic approach for the produciton of bispecific IgG antibodies. Proc Natl Acad Sci USA, 108(27):11187-11192.
Schmid, A. et al. (2017) Modulation of Wnt signaling is essential for the differentiation of ciliated epithelial cells in human airways. FEBS Lett, 591:3493-3506.
Schuijers et al. (2012) Adult mammalian stem cells: the role of Wnt, Lgr5 and R-spondins. EMBO J, 31:2685-2696.
Schutgens, F. et al. (Mar. 2019) Tubuloids derived from human adult kidney and urine for personalized disease modeling. Nat Biotechnol, 37(3):303-313; doi: 10.1038/s41587-019-0048-8. Epub Mar. 4, 2019. PMID: 30833775.
Schwitalla, S. et al. (Jan. 2013) Intestinal Tumorigenesis Initiated by Dedifferentiation and Acquisition of Stem-Cell-like Properties. Cell, 152(1-2):25-38; https://doi.org/10.1016/j.cell.2012.12.012.
ScienceDaily (Aug. 27, 2019) "Researchers engineer antibodies that unlock body's regenerative potential" University of Toronto—Leslie Dan Faculty of Pharmacy [online]. Retrieved Mar. 28, 2021 from: www.sciencedaily.com/releases/2019/08/190827084747.htm, 3 pages.
Sebastian et al. (2017) "Wnt co-receptors Lrp5 and Lrp6 differentially mediate Wnt3a signaling in osteoblasts" PLoS One 12:11 1-19.
Semenov, M.V. et al. (2001) Head inducer Dickkopf-1 is a ligand for Wnt coreceptor LRP6. Curr Biol, 11:951-961.
Shi, F. et al. (Jul. 2012) Wnt-Responsive Lgr5-Expresesing Stem Cells Are Hair Cell Progenitors in the Cochlea. J Neurosci, 32(28):9639-9648.
Shi, J. et al. (2017). Distinct Roles of Wnt/ β-Catenin Signaling in the Pathogenesis of Chronic Obstructive Pulmonary Disease and

(56) References Cited

OTHER PUBLICATIONS

Idiopathic Pulmonary Fibrosis. Mediators of Inflammation, vol. 2017, Article ID 3520581, 16 pages.
Shi, S.Y., et al., "A biparatopic agonistic antibody that mimics fibroblast growth factor 21 ligand activity" Journal of Biological Chemistry (2018) 293(16):5909-5919.
Simillie, B. et al. (Jul. 2019). Intra- and Inter-cellular Rewiring of the Human Colon during Ulcerative Colitis. Cell, 178(3):714-730; https://doi.org/10.1016/j.cell.2019.06.029.
Skronska-Wasek, W. et al. (Jul. 2017). Reduced Frizzled Receptor 4 Expression Prevents WNT/β-Catenin-driven Alveolar Lung Repair in Chronic Obstructive Pulmonary Disease. American Journal of Respiratory and Critical Care Medicine, 196(2):172-185.
Spanjer et al. (2016) "TGF-β-induced profibrotic signaling is regulated in part by the WNT receptor Frizzled-8". The FASEB Journal, 30(5): 1823-1835.
Spiess, C. et al., "Alternative molecular formats and therapeutic applications for bispecific antibodies," Molecular Immunology, Oct. 2015, 67:95-106.
Staerz, U.D. et al. Apr. 1985) Hybrid antibodies can target sites for attack by T cells. Nature, 314(6012):628-631.
Strunz, M. et al. (2020). Alveolar regeneration through a Krt8+ transitional stem cell state that persists in human lung fibrosis. Nat Commun, 11:3559; https://doi.org/10.1038/s41467-020-17358-3, 20 pages.
Svensson, F. et al. (2018). The central exons of the human MUC2 and MUC6 mucins are highly repetitive and variable inn sequence between individuals. Scientific Reports, 8:17503, DOI: 10.1038/s41598-015-35499-w; 10 pages.
Takahashi et al. (2020). Stem Cell Signaling Pathways in the Small Intestine. Int J Mol Sci, 21:2032, doi:10.3390/ijms21062032; 18 pages.
Tao, Y. et al. (2019) "Tailored tetravalent antibodies potently and specifically activate Wnt/Frizzled pathways in cells, organoids and mice" eLife, 8:e46134, DOI: https://doi.org/10.7554/eLife.46134, 16 pages.
Tian, H. et al. (Oct. 2011) A reserve stem cell population in small intestine renders Lgr5-positive cells dispensable. Nature, 478:255-259, with Methods, 1 page; Corrigendum, 482:120 (Feb. 2012).
Tomita, H. et al. (2016) Aldehyde dehydrogenase 1A1 in stem cells and cancer. Oncotarget, 7(10):11018-11032.
Tu, S. et al. (2018) The role of Foxq1 in proliferation of human dental pulp stem cell. Biochem Biophys Res Commun, 497:543-549.
Ulsamer, A. et al. (Feb. 2012) Axin Pathway Activity Regulates in Vivo pY654-β-catenin Accumulation and Pulmonary Fibrosis. J Biol Chem, 287(7):5164-5172.
U.S. Appl. No. 62/641,217, filed Mar. 9, 2018.
U.S. Appl. No. 62/680,508, filed Jun. 4, 2018.
U.S. Appl. No. 62/680,515, filed Jun. 4, 2018.
U.S. Appl. No. 62/680,522, filed Jun. 4, 2018.
Van Der Post, S. et al. (2019) Structural weakening of the colonic mucus barrier is an early event in ulcerative colitis pathogenesis. 68:2142-2151.
Vincke, C. and S. Muyldermans (2012) "Introduction to heavy chain antibodies and derived Nanobodies" Methods Mol Biol, 911:15-26, doi: 10.1007/978-1-61779-968-6_2.
Vincke, C. et al., "General strategy to humanize a camelid single-domain antibody and identification of a universal humanized nanobody scaffold", J Biol Chem. (2009); 284(5):3273-3284.
Wang, R. et al. (2011) Down-Regulation of the Canonical Wnt β-Catenin Pathway in the Airway Epithelium of Healthy Smokers and Smokers with COPD. PLoS ONE, 6(4):e14793; doi:10.1371/journal.pone.0014793.
Wang, T. et al. (Apr. 2015) Lgr5+ cells regenerate hair cells via proliferation and direct transdifferentiation in damaged neonatal mouse utricle. Nat Commun, 6:6613; DOI: 10.1038/ncomms7613, 15 pages.

Wang, X. et al. (2015) Blocking the Wnt/β-Catenin Pathway by Lentivirus-Mediated Short Hairpin RNA Targeting β-Catenin Gene Suppresses Silica-Induced Lung Fibrosis in Mice. Int J Environ Res Public Health, 12:10739-10754.
Wang, X. et al. (2018) IgG Fc engineering to modulate antibody effector functions. Protein Cell, 9:63-73.
Wang, Z. et al. (2019) Wnt Signaling in vascular eye diseases. Prog Retin Eye Res, 70:110-133.
Wehkamp, J. et al. (2007) "The Paneth cell alpha-defensin deficiency of ileal Crohn's disease is linked to Wnt/Tcf-4" J Immunol, 179:3109-3118.
Wirtz, S. et al. (2017). Chemically induced mouse models of acute and chronic intestinal inflammation. Nature Protocols, 12(7), 1295-1309. https://doi.org/10.1038/nprot.2017.044.
Wong et al. (2015). "Mechanisms of sensorineural cell damage, death and survival in the cochlea." Frontiers in Aging Neuroscience. vol. 7, Article 58, pp. 1-15.
Wu, C. et al. "Simultaneous targeting of multiple disease mediators by a dual-variable-domain immunoglobulin", Nat Biotechnol. Nov. 2007;25(11):1290-7.
Wu et al. (2013). "In vivo delivery of Atoh1 gene to rat cochlea using a dendrimer-based nanocarrier." Journal of biomedical nanotechnology. 9(10): 1736-45.
Xie, Y. et al. (Oct. 2013) "Interaction with both ZNRF3 and LGR4 is required for the signalling activity of R-spondin" EMBO Reports, 14(12):1120-1126.
Xu et al. (2016) "Single-cell RNA sequencing identifies diverse roles of epithelial cells in idiopathic pulmonary fibrosis". JCI Insight, 1(20): 1-19.
Yan, K.S. et al. (May 2017). Non-equivalence of Wnt and R-spondin ligands during Lgr5+ intestinal stem-cell self-renewal. Nature, 545(7653):238-242. doi:10.1038/nature22313; HHS Public Access Author Manuscript, 36 pages.
Zacharias et al. (2018) "Regeneration of the lung alveolus by an evolutionarily conserved epithelial progenitor". Nature, 555(7695): 251-255.
Zapata, G. et al. (1995) Engineering linear F(ab')2 fragments for efficient production in *Escherichia coli* and enhanced antiproferative activity. Protein Eng. 8( 10): 1057-1062.
Zatorski, H. et al. (2019) Role of glucagon-like peptides in inflammatory bowel diseases-current knowledge and future perspectives. Nauryn-Schmiedeberg's Archives of Pharmacology, 392:1321-1330.
Zepp et al. (2017) "Distinct mesenchymal lineages and niches promote epithelial self-renewal and myofibrogenesis in the lung". Cell, 170(6): 1134-1148.
Zhang et al. (2014) "3D structural fluctuation of IgG1 antibody revealed by individual particle electron tomography" Scientific Reports 5:09803 1-13.
Zhang, M. et al. (Mar. 2020) Targeting the Wnt signaling pathway through R-spondin 3 identifies an anti-fibrosis treatment strategy for multiple organs. PLoS ONE, 15(3):e0229445.
Zhang, S. et al. (Jul. 2019) Frizzled-9+ Supporting Cells Are Progenitors for the Generation of Hair Cells in the Postnatal Mouse Cochlea. Front Mol Neurosci, 12:184, doi:10.3389/fnmol.2019.00184, 11 pages.
Zhang, T. et al. (2018) Overexpression of FOXQ1 enhances anti-senescence and migration effects of human umbilical cord mesenchymal stem cells in vitro and in vivo. Cell and Tissue Research, 373:379-393.
Zhao, J. et al. (2007). R-spondin1, A Novel Intestinotrophic Mitogen, Ameliorates Experimental Colitis in Mice. Gastroenterology, 132(4):1331-1343. https://doi.org/10.1053/j.gastro.2007.02.001.
Zheng, W. et al. (2006) Evaluation of AGR2 and AGR3 as cadidate genes for inflammatory bowel disease. Genes and Immunity, 7:11-18.
Zhou, B. et al. (Nov. 2020) The angiocrine Rspondin3 instructs interstitial macrophage transition via metabolic-epigenetic reprogramming and resolves inflammatory injury. Nat Immunol, 21:1430-1443, with Methods, 14 pages.
Hendrickx et al. "Non-conventional Frizzled ligands and Wnt receptors", Development, Growth & Differentiation, (2008); 50(4):229-243.

(56) References Cited

OTHER PUBLICATIONS

Lei et al. "MicroRNAs target the Wnt/β-catenin signaling pathway to regulate epithelial-mesenchymal transition in cancer (Review)", Oneal Rep, (2020); 44(4):1299-1313.

Moparthi et al. "Wnt signaling in intestinal inflammation", Differentiation, (2019); 108:24-32.

Park et al. "Unlike LGRA, LGR5 potentiates Wnt-beta-catenin signaling without sequestering E3 ligases", Sci Signal, (2020); 13(660):eaaz4051, 1 page.

Zoukhri "Mechanisms Involved in Injury and Repair of the Murine Lacrimal Gland: Role of Programmed Cell Death and Mesenchymal Stem Cells", Ocul Surf., (2010); 8(2):60-69.

Co-pending U.S. Appl. No. 17/429,584, inventor Yang; Li, filed Feb. 11, 2020.

Rong, Chen (2016) "Research progress of Wnt/ β-Catenin signaling pathway-specific molecular targeted drugs". J. Mod. Med. Health, 32(5):700-702, with Google Translation. doi: 10.3969/j.issn.1009-5519.2016.05.022.

Xiao, SA, et al., "Establishment of long-term serum-free culture for lacrimal gland stem cells aiming at lacrimal gland repair," Stem Cell Research & Therapy, (Jan. 8, 2020), 11:20, 13 pages.

\* cited by examiner

ANTI-FRIZZLED ANTIBODIES AND METHODS OF USE

CROSS REFERENCE TO RELATED APPLICATIONS

This application is a 35 U.S.C. 371 national stage filing of International Application No. PCT/US2018/066618, filed on Dec. 19, 2018, which claims priority to U.S. Provisional Application No. 62/607,877, filed Dec. 19, 2017, and U.S. Provisional Application No. 62/680,508, filed Jun. 4, 2018, all of which are incorporated by reference herein in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SRZN_004_02WO_ST25.txt. The text file is 539,347 bytes, was created on Dec. 19, 2018, and is being submitted electronically via EFS-Web.

BACKGROUND

Technical Field

The present invention relates generally to anti-Frizzled antibodies and antigen-binding fragments thereof, compositions, and methods of using the same. Such antibodies are useful, for example, in modulating Wnt signaling pathways.

Description of the Related Art

Wnt ("Wingless-related integration site" or "Wingless and Int-1" or "Wingless-Int") ligands and their signals play key roles in the control of development, homeostasis and regeneration of many essential organs and tissues, including bone, liver, skin, stomach, intestine, kidney, central nervous system, mammary gland, taste bud, ovary, cochlea and many other tissues (reviewed, e.g., by Clevers, Loh, and Nusse, 2014; 346:1248012). Modulation of Wnt signaling pathways has potential for treatment of degenerative diseases and tissue injuries.

One of the challenges for modulating Wnt signaling as a therapeutic is the existence of multiple Wnt ligands and Wnt receptors, Frizzled 1-10 (Fzd1-10), with many tissues expressing multiple and overlapping Fzds. Canonical Wnt signals also involve Low-density lipoprotein (LDL) receptor-related protein 5 (LRP5) or Low-density lipoprotein (LDL) receptor-related protein 6 (LRP6) as co-receptors, which are broadly expressed in various tissues, in addition to Fzds. Accordingly, there is clearly a need in the art for binding moieties, such as antibodies, that specifically bind to one or more Fzd, LRP5, or LRP6. The present invention addresses this need.

BRIEF SUMMARY

In various embodiments, the present invention provides anti-Fzd antibodies and antigen-binding fragments thereof and related methods of use. In one embodiment, the disclosure provides an isolated antibody, or an antigen-binding fragment thereof, that binds to one or more Frizzled receptor, comprising a sequence comprising: (i) CDRH1, CDRH2 and CDRH3 sequences set forth for any of the antibodies of Table 1A; and/or (ii) CDRL1, CDRL2 and CDRL3 sequences set forth for any of the antibodies of Table 1A, or a variant of said antibody, or antigen-binding fragment thereof, comprising one or more amino acid modifications, wherein said variant comprises less than 8 amino acid substitutions in said CDR sequences. In particular embodiments, the antibody or antigen-binding fragment thereof comprises a heavy chain variable region comprising an amino acid sequence having at least 90% identity to the amino acid sequence set forth in any of SEQ ID NOs:1-37, 66 or 68 or a heavy chain variable region comprising the amino acid sequence set forth in any of SEQ ID NOs:1-37, 66 or 68. In particular embodiments, the antibody, or antigen-binding fragment thereof, comprises a light chain variable region comprising an amino acid sequence having at least 90% identity to the amino acid sequence set forth in any of SEQ ID NOs:38-65, 67 or 69 or a light chain variable region comprising the amino acid sequence set forth in any of SEQ ID NOs:38-65, 67 or 69.

In particular embodiments, any of the antibodies, or antigen-binding fragments thereof, are humanized. In certain embodiments, any of the antibodies, or antigen-binding fragments thereof, are a single chain antibody, a scFv, a univalent antibody lacking a hinge region, a VHH or single domain antibody (sdAb), or a minibody. In particular embodiments, any of the antibodies, or antigen-binding fragments thereof, are a Fab or a Fab' fragment.

In certain embodiments, any of the antibodies, or antigen-binding fragments thereof, are a fusion protein. In certain embodiments, the antibody, or antigen-binding fragment thereof, is fused to a polypeptide sequence that binds LRP5 or LRP6. In certain embodiments, the polypeptide sequence that binds LRP5 or LRP6 is an antibody, or an antigen-binding fragment thereof, that binds to LRP5 or LRP6.

In particular embodiments of any of the antibodies, or antigen-binding fragments thereof, the antibody, or antigen-binding fragment thereof, binds to one or more of Frizzled 1 (Fzd1), Frizzled 2 (Fzd2), Frizzled 3 (Fzd3), Frizzled 4 (Fzd4), Frizzled 5 (Fzd5), Frizzled 6 (Fzd6), Frizzled 7 (Fzd7), Frizzled 8 (Fzd8), Frizzled 9 (Fzd9), and Frizzled 10 (Fzd10). In certain embodiments, any of the antibodies, or antigen-binding fragments thereof, bind to two or more of Frizzled 1 (Fzd1), Frizzled 2 (Fzd2), Frizzled 3 (Fzd3), Frizzled 4 (Fzd4), Frizzled 5 (Fzd5), Frizzled 6 (Fzd6), Frizzled 7 (Fzd7), Frizzled 8 (Fzd8), Frizzled 9 (Fzd9), and Frizzled 10 (Fzd10). In certain embodiments, any of the antibodies, or antigen-binding fragments thereof, bind to: (i) Fzd1, Fzd2, Fzd7 and Fzd9; (ii) Fzd1, Fzd2 and Fzd7; (iii) Fzd5 and Fzd8; (iv) Fzd5, Fzd7 and Fzd8; (v) Fzd1, Fzd4, Fzd5 and Fzd8; (vi) Fzd1, Fzd2, Fzd5, Fzd7 and Fzd8; (vii) Fzd4 and Fzd9; (viii) Fzd9 and Fzd10; (ix) Fzd5, Fzd8 and Fzd10; (x) Fzd4, Fzd5 and Fzd8; (xi) Fzd1, Fzd5, Fzd7 and Fzd8 or (xii) Fzd1, Fzd2, Fzd 4, Fzd5, Fzd7 and Fzd 8.

In a related embodiment, the disclosure provides an isolated antibody, or an antigen-binding fragment thereof, that competes with any of the antibodies disclosed herein for binding to a human Fzd receptor.

In particular embodiments, any of the antibodies, or antigen-binding fragments thereof, bind to the Fzd with a KD of 50 µM or lower.

In particular embodiments, any of the antibodies, or antigen-binding fragments thereof, modulate a Wnt signaling pathway in a cell, optionally a mammalian cell. In particular embodiments, any of the antibodies, or antigen-binding fragments thereof increase signaling via a Wnt signaling pathway in the cell. In particular embodiments, any of the antibodies, or antigen-binding fragments thereof decrease signaling via a Wnt signaling pathway in the cell. In certain embodiments, the Wnt signaling pathway is a canonical Wnt signaling pathway or a non-canonical Wnt signaling pathway.

In a further related embodiment, the present disclosure provides an isolated polynucleotide encoding an antibody, or antigen-binding fragment thereof, disclosed herein. In certain embodiments, the present disclosure provides an expression vector comprising the isolated polynucleotide and an isolated host cell comprising the expression vector.

In another embodiment, the present disclosure provides a pharmaceutical composition comprising a physiologically acceptable excipient, diluent, or carrier, and a therapeutically effective amount of the isolated antibody, or antigen-binding fragment thereof, disclosed herein.

In a further embodiment, the present disclosure provides a method for agonizing a Wnt signaling pathway in a cell, comprising contacting the cell with an isolated antibody, or antigen-binding fragment thereof, disclosed herein that increases Wnt signaling. In particular embodiments, the antibody, or antigen-binding fragment thereof, is a fusion protein comprising a polypeptide sequence that binds LRP5 or LRP6.

In another embodiment, the present disclosure provides a method for inhibiting a Wnt signaling pathway in a cell, comprising contacting the cell with the isolated antibody, or antigen-binding fragment thereof, disclosed herein the inhibits Wnt signaling.

In another embodiment, the present disclosure includes a method for treating a subject having a disease or disorder associated with reduced Wnt signaling, comprising administering to the subject an effective amount of a pharmaceutical composition comprising an isolated antibody, or antigen-binding fragment thereof, disclosed herein that is an agonist of a Wnt signaling pathway. In particular embodiments, the disease or disorder is selected from the group consisting of: bone fractures, stress fractures, vertebral compression fractures, osteoporosis, osteoporotic fractures, nonunion fractures, delayed union fractures, spinal fusion, preoperative optimization for spine surgeries, osteonecrosis, osseointegration of implants or orthopedic devices, osteogenesis imperfecta, bone grafts, tendon repair, tendon-bone integration, tooth growth and regeneration, maxillofacial surgery, dental implantation, periodontal diseases, maxillofacial reconstruction, osteonecrosis of the jaw, hip or femoral head, avascular necrosis, alopecia, hearing loss, vestibular hypofunction, macular degeneration, age-related macular degeneration (AMD), vitreoretinopathy, retinopathy, diabetic retinopathy, diseases of retinal degeneration, Fuchs' dystrophy, cornea diseases, stroke, traumatic brain injury, Alzheimer's disease, multiple sclerosis, diseases affecting blood brain barrier (BBB), spinal cord injuries, spinal cord diseases, oral mucositis, short bowel syndrome, inflammatory bowel diseases (IBD), Crohn's disease (CD), ulcerative colitis (UC), in particular CD with fistula formation, metabolic syndrome, dyslipidemia, diabetes, pancreatitis, exocrine pancreatic insufficiency, wound healing, diabetic foot ulcers, pressure sores, venous leg ulcers, epidermolysis bullosa, dermal hypoplasia, myocardial infarction, coronary artery disease, heart failure, hematopoietic cell disorders, immunodeficiencies, graft versus host diseases, acute kidney injuries, chronic kidney diseases, chronic obstructive pulmonary diseases (COPD), idiopathic pulmonary fibrosis, acute liver failure of all causes, acute liver failure drug-induced, alcoholic liver diseases, chronic liver failure of all causes, cirrhosis, liver fibrosis of all causes, portal hypertension, chronic liver insufficiency of all causes, nonalcoholic steatohepatitis (NASH), nonalcoholic fatty liver disease (NAFLD) (fatty liver), alcoholic hepatitis, hepatitis C virus-induced liver diseases (HCV), hepatitis B virus-induced liver diseases (HBV), other viral hepatitis (e.g., hepatitis A virus-induced liver diseases (HAV) and hepatitis D virus-induced liver diseases (HDV)), primary biliary cirrhosis, autoimmune hepatitis, livery surgery, liver injury, liver transplantation, "small for size" syndrome in liver surgery and transplantation, congenital liver disease and disorders, any other liver disorder or detect resulting from genetic diseases, degeneration, aging, drugs, or injuries.

In another related embodiment, the present disclosure provides a method for treating or preventing a bone disease or disorder in a subject in need thereof, comprising providing to the subject an effective amount of a pharmaceutical composition comprising an isolated antibody, or antigen-binding fragment thereof, disclosed herein that is an agonist of a Wnt signaling pathway. In certain embodiments, the isolated antibody, or antigen binding fragment thereof, binds Fzd1, Fzd2, and FZD7. In certain embodiments, the isolated antibody, or antigen binding fragment thereof, binds Fzd1, Fzd2, FZD7, Fzd5 and Fzd8. Other Fzd molecules that bind to additional Fzd receptors can also be used with LRP5 and/or LRP6 binders.

In another related embodiment, the present disclosure provides a method for increasing bone mineral density, increasing bone volume, increasing bone cortical thickness, increasing bone mineral apposition rate, increasing bone stiffness, increasing bone biomechanical strength, increasing resistance to bone fracture, or decreasing bone loss associated with osteoporosis, in a subject in need thereof, comprising providing to the subject an effective amount of a pharmaceutical composition comprising an isolated antibody, or antigen-binding fragment thereof, disclosed herein that is an agonist of a Wnt signaling pathway. In certain embodiments, the isolated antibody, or antigen binding fragment thereof, binds Fzd1, Fzd2, and FZD7. In certain embodiments, the isolated antibody, or antigen binding fragment thereof, binds Fzd1, Fzd2, FZD7, Fzd5 and Fzd8.

In a related embodiment, the present disclosure provides a method for treating a subject having a disease or disorder associated with increased or enhanced Wnt signaling, comprising administering to the subject an effective amount of the pharmaceutical composition comprising an isolated antibody, or antigen-binding fragment thereof, disclosed herein that is an inhibitor of a Wnt signaling pathway. In certain embodiments, the disease or disorder is selected from the group consisting of: tumors and cancers, degenerative disorders, fibrosis, heart failure, coronary artery disease, heterotopic ossification, osteopetrosis, and congenital high bone mass disorders.

In a further related embodiment, the present disclosure provides an isolated antibody, or an antigen-binding fragment thereof, that binds one or more Frizzled receptor, where the antibody or antigen-binding fragment thereof binds: an epitope within a region of Frizzled 1 comprising or consisting of amino acid residues 115-230; an epitope within a region of Frizzled 3 comprising or consisting of amino acid residues 29-78; an epitope within a region of Frizzled 4 comprising or consisting of amino acid residues 50-147; an epitope within a region of Frizzled 5 comprising or consisting of amino acid residues 37-149; an epitope within a region of Frizzled 8 comprising or consisting of amino acid residue 55-137; an epitope within a region of Frizzled 9 comprising or consisting of amino acid residues 59-152; or an epitope within a region of Frizzled 10 comprising or consisting of amino acid residues 35-124.

In certain embodiments, the present disclosure provides an isolated antibody, or an antigen-binding fragment thereof, that binds one or more Frizzled receptor, wherein the antibody or antigen-binding fragment thereof contacts the Frizzled receptor with a distance of less than 5 angstroms at any of the sets of amino acid residues indicated in Table 3.

DETAILED DESCRIPTION

Figure 1:
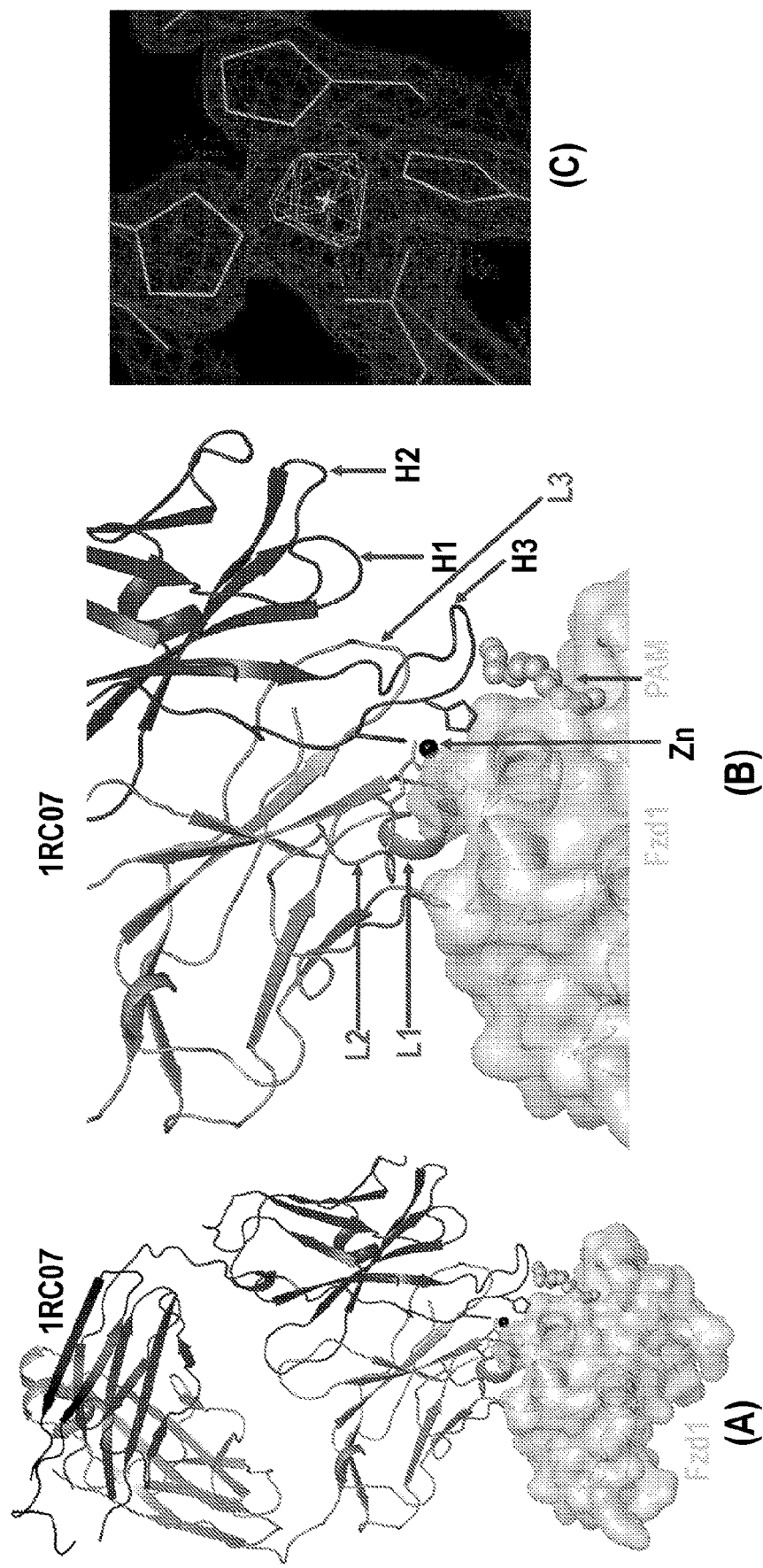
FIG. 1. (A) shows a graphic depiction of the Fzd1:1RC07 complex. Fzd1 is shown in light grey and the heavy and light chains of 1RC07 are medium and dark grey respectively (B) is a closer view of the Fzd1:1RC07 interface with the position of the CRD loops marked (C) is a closer view of the $Zn^{+2}$ binding with $2mF_o-DF_c$ (at $2.0\sigma$) and the anomalous-difference maps (at $15.0\sigma$), shown in blue and yellow mesh, respectively.

The present disclosure relates to antibodies and antigen-binding fragments thereof that specifically bind to one or more Fzd receptor, including antibodies having particular Fzd receptor specificity and/or functional properties. One embodiment of the invention encompasses specific humanized antibodies and fragments thereof capable of binding to one or more Fzd receptor and modulate downstream Wnt pathway signaling and related biological effects.

Embodiments of the invention pertain to the use of anti-Fzd antibodies or antigen-binding fragments thereof for the diagnosis, assessment and treatment of diseases and disorders associated with Wnt signaling pathways. In certain embodiments, the subject antibodies and antigen-binding fragments thereof are used to modulate a Wnt signaling pathway in a cell or tissue. In certain embodiments, the subject antibodies and antigen-binding fragments thereof are used in the treatment or prevention of diseases and disorders associated with aberrant or deregulated (e.g., either increased or reduced) Wnt signaling, or for which either decreasing or increasing Wnt signaling would provide a therapeutic benefit.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of subjects.

Embodiments of the present invention relate to antibodies and antigen-binding fragments thereof that bind to one or more Fzd receptor. Sequences of illustrative antibodies, or antigen-binding fragments, or complementarity determining regions (CDRs) thereof, are set forth in Table 1A and SEQ ID NOs:1-65.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')2, Fv), single chain (scFv), VHH or sdAb (also known as a nanobody), synthetic variants thereof, naturally occurring variants, fusion proteins comprising an antibody or an antigen-binding fragment thereof, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965, WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chain that binds to the antigen of interest, in particular to one or more Fzd receptor. In this regard, an antigen-binding fragment of the herein described antibodies may comprise 1, 2, 3, 4, 5, or all 6 CDRs of a VH and VL sequence set forth herein from antibodies that bind one or more Fzd receptor. An antigen-binding fragment of the Fzd-specific antibodies described herein is capable of binding to a Fzd receptor. As used herein, the term encompasses not only isolated fragments but also polypeptides comprising an antigen-binding fragment of an antibody disclosed herein, such as, for example, fusion proteins comprising an antigen-binding fragment of an antibody disclosed herein.

In certain embodiments, an antibody or antigen-binding fragment thereof, modulates Wnt signaling events in a cell contacted with the antibody or antigen-binding fragment thereof. In certain embodiments, the antibody or antigen-binding fragment thereof increases Wnt signaling, while in other embodiments, it decreases Wnt signaling. In certain embodiments, the antibody or antigen-binding fragment thereof binds specifically to and/or modulates the biological activity of the human Wnt signaling pathway.

The term "antigen" refers to a molecule or a portion of a molecule capable of being bound by a selective binding agent, such as an antibody, and additionally capable of being used in an animal to produce antibodies capable of binding to an epitope of that antigen. In certain embodiments, an antibody is said to specifically bind an antigen when it preferentially recognizes its target antigen in a complex mixture of proteins and/or macromolecules. In certain embodiments, an antibody is said to specifically bind an antigen when the equilibrium dissociation constant is ≤$10^{-7}$ or $10^{-8}$ M. In some embodiments, the equilibrium dissociation constant may be ≤$10^{-9}$ M or ≤$10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin CDRs and variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu). Alternatively, CDRs may be determined by using "IMGT®, the international ImMunoGeneTics Information System® available at http://www.imgt.org (see, e.g., Lefranc, M.-P. et al. (1999) *Nucleic Acids Res.*, 27:209-212; Ruiz, M. et al. (2000) *Nucleic Acids Res.*, 28:219-221; Lefranc, M.-P. (2001) *Nucleic Acids Res.*, 29:207-209; Lefranc, M.-P. (2003) *Nucleic Acids Res.*, 31:307-310; Lefranc, M.-P. et al. (2004) In Silico Biol., 5, 0006 [Epub], 5:45-60 (2005)]; Lefranc, M.-P. et al. (2005) *Nucleic Acids Res.*, 33:D593-597; Lefranc, M.-P. et al. (2009) *Nucleic Acids Res.*, 37:D1006-1012; Lefranc, M.-P. et al. (2015) *Nucleic Acids Res.*, 43:D413-422).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (scFv), VHH or sdAb, variants thereof, fusion proteins comprising an antigen-binding fragment of a monoclonal antibody, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (Ill et al., *Prot. Eng.* 10: 949-57 (1997); minibodies (Martin et al., *EMBO J* 13: 5305-9 (1994); diabodies (Holliger et al., PNAS 90: 6444-8 (1993); or Janusins (Traunecker et al., *EMBO J* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to one or more Fzd receptor through one binding domain and to a second molecule through a second binding domain. These antibodies may be produced through recombinant molecular biological techniques or may be physically conjugated together.

A single chain Fv (scFv) polypeptide is a covalently linked $V_H::V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, a Fzd binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells.

In certain embodiments, the antibodies of the present disclosure may take the form of a VHH or sdAb. VHH or sdAb technology was originally developed following the discovery and identification that camelidae (e.g., camels and llamas) possess fully functional antibodies that consist of heavy chains only and therefore lack light chains. These heavy-chain only antibodies contain a single variable domain(VHH) and two constant domains (CH2, CH3). The cloned and isolated single variable domains have full antigen binding capacity and are very stable. These single variable domains, with their unique structural and functional properties, form the basis of "VHH or sdAb". VHH or sdAb are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of VHH or sdAb have been produced. VHH or sdAb may be formulated as a ready-to-use solution having a long shelf life. The Nanoclone® method (see, e.g., WO 06/079372) is a proprietary method for generating VHH or sdAb against a desired target, based on automated high-throughput selection of B-cells. VHH or sdAb are single-domain antigen-binding fragments of camelid-specific heavy-chain only antibodies. VHH or sdAb, typically have a small size of around 15 kDa.

In certain embodiments, the anti-Fzd antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., Nature (1988) 332:323-327). Illustrative methods for humanization of the anti-Fzd antibodies disclosed herein include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-Fzd antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-Fzd antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, antibodies or antigen-binding fragments thereof disclosed herein include fusion proteins, e.g., Wnt signaling pathway agonist fusion proteins, also referred to herein as "Wnt surrogates." Wnt surrogates of the present invention are usually biologically active in binding to a cognate Frizzled receptor, and in activation of Wnt signaling, i.e., the surrogate is a Wnt agonist. The term "Wnt agonist activity" refers to the ability of an agonist to mimic the effect or activity of a Wnt protein binding to a frizzled protein. The ability of the agonists of the invention to mimic the activity of Wnt can be confirmed by a number of assays. The agonists of the invention typically initiate a reaction or activity that is similar to or the same as that initiated by the receptor's natural ligand. In particular, the agonists of the invention enhance the canonical Wnt/β-catenin signaling pathway. As used herein, the term "enhances" refers to a measurable increase in the level of Wnt/β-catenin signaling compared with the level in the absence of an agonist of the invention.

In particular embodiments, a Wnt signaling pathway agonist fusion protein (or Wnt surrogate) comprises an anti-Fzd antibody, or antigen-binding fragment thereof, disclosed herein fused to a polypeptide that specifically binds to LRP5 and/or LRP6. In particular embodiments, the polypeptide that specifically binds to LRP5 and/or LRP6 is an antibody or antigen-binding fragment thereof. If certain embodiments, it is an antibody or antigen-binding fragment thereof disclosed in the U.S. provisional patent application No. 62/607,879, titled, "Anti-LRP5/6 antibodies and Methods of Use," filed on Dec. 19, 2017, which is incorporated herein by reference in its entirety.

Suitable LRP5/6 binding domains include, without limitation, de novo designed LRP5/6 binding proteins, antibody derived binding proteins, e.g. scFv, Fab, etc. and other portions of antibodies that specifically bind to one or more Fzd proteins; VHH or sdAb derived binding domains; knottin-based engineered scaffolds; naturally occurring LRP5/6, including without limitation, DKK1, DKK2, DKK3, DKK4, sclerostin; Wise; fusion proteins comprising any of the above; derivatives of any of the above; variants of any of the above; and biologically active fragments of any of the above, and the like. A LRP5/6 binding domain may be affinity selected to enhance binding.

Members of the Dickkopf (DKK) gene family (see Krupnik et al. (1999) Gene 238(2):301-13) include DKK-1, DKK-2, DKK-3, and DKK-4, and the DKK-3 related protein Soggy (Sgy). hDKKs 1-4 contain two distinct cysteine-rich domains in which the positions of 10 cysteine residues are highly conserved between family members. Exemplary sequences of human DKK genes and proteins are publicly available, e.g. Genbank accession number NM_014419 (soggy-1), NM_014420 (DKK4); AF177394 (DKK-1), AF177395 (DKK-2); NM_015881 (DKK3); and NM_014421 (DKK2). In some embodiments of the invention, the Lrp6 binding moiety is a DKK1 peptide, including without limitation the C-terminal domain of human DKK1. The C-terminal domain may comprise the sequence: KMYHTKGQEGSVCLRSSDCASGLCCARHFWSKICK-PVLKEGQVCTKHRRKG SHGLEIFQR-CYCGEGLSCRIQKDHHQASNSSRLHTCQRH (SEQ ID NO:70; see Genbank accession number NP_036374) or a biologically active fragment thereof.

Binding of DKK proteins to LRP5/6 are discussed, for example in Brott and Sokol Mol. Cell. Biol. 22 (17), 6100-6110 (2002); and Li et al. J. Biol. Chem. 277 (8), 5977-5981 (2002), each herein specifically incorporated by reference. The corresponding region of human DKK2 (Genbank reference NP_055236) may comprise the sequence: KMSHIKGHEGDPCLRSSDCIEGFCCARHFVVTKICK-PVLHQGEVCTKQRKKGS HGLEIFQRCD-CAKGLSCKVWKDATYSSKARLHVCQK (SEQ ID NO:71) or a biologically active fragment thereof.

Antibodies that specifically bind to LRP5 or LRP6 are known in the art and are commercially available, or can be generated de novo. LRP5, LRP6 or fragments thereof can be used as an immunogen or in screening assays to develop an antibody. Examples of known antibodies include, without limitation, those described in Gong et al. (2010) PLoS One. 5(9):e12682; Ettenberg et al. (2010) Proc Natl Acad Sci USA. 107(35):15473-8; and those commercially available from, for example Santa Cruz biotechnology antibody clone 1A12, which was raised against synthetic LRP5/6 of human origin and binds to both the full length and proteolytic fragment of LRP 6 and LRP 5 of mouse and human origin; the monoclonal antibody 2611; Cell Signaling Technology antibody specific for LRP5 (D80F2), catalog number 5731; etc.

In some embodiments, the LRP5/6 binding domain or element may be selected from any domain that binds LRP5/6 at high affinity, e.g. a $K_D$ of at least about $1\times10^{-7}$ M, at least about $1\times10^{-8}$ M, at least about $1\times10^{-9}$ M, at least about $1\times10^{-19}$ M. Suitable LRP5/6 binding domains include, without limitation, de novo designed LRP5/6 binding proteins, antibody derived binding proteins, e.g. scFv, Fab, etc. and other portions of antibodies that specifically bind to one or more Fzd proteins; VHH or sdAb derived binding domains; knottin-based engineered scaffolds; naturally occurring LRP5/6 binding proteins or polypeptides, including without limitation, Norrin, DKK1, DKK2, DKK3, DKK4, sclerostin; and the like. In certain embodiments the LRP5/6 binding domain is a c-terminal portion of DKK1. A LRP5/6 binding domain may be affinity selected to enhance binding.

The anti-Fzd antibody, or antigen binding fragment thereof, and the LRP516 binding domain may be directly joined, or may be separated by a linker, e.g. a polypeptide linker, or a non-peptidic linker, etc. The region of the Wnt surrogate that binds one or more Fzd receptor and the polypeptide that binds LRP5 and/or LRP6 may be contiguous or separated by a linker, e.g. a polypeptide linker, or a non-peptidic linker, etc. The length of the linker, and therefore the spacing between the binding domains can be used to modulate the signal strength, and can be selected depending on the desired use of the Wnt surrogate. The enforced distance between binding domains can vary, but in certain embodiments may be less than about 100 angstroms, less than about 90 angstroms, less than about 80 angstroms, less than about 70 angstroms, less than about 60 angstroms, or less than about 50 angstroms. In some embodiments the linker is a rigid linker, in other embodiments the linker is a flexible linker. Where the linker is a peptide linker, it may be from about 1, 2, 3, 4, 5, 6, 7, 8, 9, 10, 11, 12, 13, 14, 15, 16, 17, 18, 19, 20 21, 22, 23, 24, 25, 26, 27, 28, 29, 30 or more amino acids in length, and is of sufficient length and amino acid composition to enforce the distance between binding domains. In some embodiments, the linker comprises or consists of one or more glycine and/or serine residues.

A Wnt surrogate can be multimerized, e.g. through an Fc domain, by concatenation, coiled coils, polypeptide zippers, biotin/avidin or streptavidin multimerization, and the like. The Wnt surrogate can also be joined to a moiety such as PEG, Fc, etc. as known in the art to enhance stability in vivo.

In certain embodiments, a Wnt surrogate direct activates canonical Wnt signaling through binding to one or more Fzd proteins and to LRP5/6, particularly by binding to these proteins on a cell surface, e.g. the surface of a human cell. The direct activation of Wnt signaling by a Wnt surrogate is in contrast to potentiation of Wnt signaling, which enhances activity only when native Wnt proteins are present.

Wnt surrogates of the present activate Wnt signaling, e.g., by mimicking the effect or activity of a Wnt protein binding to a frizzled protein. The ability of the Wnt surrogates of the invention to mimic is the activity of Wnt can be confirmed by a number of assays. The Wnt surrogates typically initiate a reaction or activity that is similar to or the same as that initiated by the receptors natural ligand. In particular, the Wnt surrogates of the invention enhance the canonical Wnt/β-catenin signaling pathway. As used herein, the term "enhances" refers to a measurable increase in the level of Wnt/β-catenin signaling compared with the level in the absence of a Wnt surrogate of the Invention.

In certain embodiments, an antibody or antigen-binding fragment thereof disclosed herein inhibits Wnt pathway signaling. In particular embodiments, binding of an anti-Fzd antibody or antigen-binding fragment thereof blocks or inhibits the binding of endogenous Wnt to one or more Fzd receptor on a cell surface, thus reducing or inhibiting Wnt signaling.

Various methods are known in the art for measuring the level of canonical Wnt/β-catenin signaling. These include, but are not limited to assays that measure; Wnt/β-catenin target gene expression; TCF reporter gene expression; β-catenin stabilization; LRP phosphorylation; Fuxin translocation from cytoplasm to cell membrane and binding to LRP. The canonical Wnt/β-catenin signaling pathway ultimately leads to changes in gene expression through the transcription factors TCF7, TCF7L1, TCF7 L2 (a.k.a. TCF4), and LEF. The transcriptional response to Wnt activation has been characterized in a number of cells and tissues. As such, global transcriptional profiling by methods well known in the art can be used to assess Wnt/β-catenin signaling activation or inhibition.

Changes in Wnt responsive gene expression are generally mediated by TCF and LEF transcription factors. A TCF reporter assay assesses changes in the transcription of TCF/LEF controlled genes to determine the level of Wnt/β-catenin signaling. A TCF reporter assay was first described by Korinek, V. et al., 1997. Also known as TOP/FOP this method involves the use of three copies of the optimal TCF motif CCTTTGATC, or three copies of the mutant motif CCTTTGGCC, upstream of a minimal c-Fos promoter driving luciferase expression (pTOPFl_ASH and pFOPFl_ASH, respectively) to determine the transactivational activity of endogenous p-cateniniTCF4. A higher ratio of these two reporter activities (TOPIFOP) indicates higher β-cateniniTCF4 activity, whereas a lower ratio of these two reporter activities indicates lower β-cateniniTCF4 activity.

Various other reporter transgenes that respond to Wnt signals exist intact in animals and therefore, effectively reflect endogenous Wnt signaling. These reporters are based on a multimerized TCF binding site, which drives expression of Lacy. or GFP, which are readily detectable by methods known in the art. These reporter genes include: TOP-GAL, BAT-GAL, ins-TOPEGFP, ins-TOPGAL, LEF-EGFP, Axin2-LacZ, Axin2-d2EGFP, Lgr5tm1 (cre/ERT2), TOPdGFP.

The recruitment of dephosphorylated β-catenin to the membrane, stabilization and phosphorylation status of β-catenin, and translocation of β-catenin to the nucleus (Klapholz-Brown Z et al., PLoS One. 2(9) e945, 2007), in some cases mediated by complex formation with TCF transcription factors and TNIK are key steps in the Wnt signaling pathway. Stabilization is mediated by Disheveled family proteins that inhibit the "destruction" complex so that degradation of intracellular β-catenin is reduced, and translocation of p-catenin to the nucleus follows thereafter. Therefore, measuring the level and location of p-catenin in a cell is a good reflection of the level of Wnt/p-catenin signaling. A non-limiting example of such an assay is the "Biolmage β-Catenin Redistribution Assay" (Thermo Scientific) which provides recombinant U20S cells that stably express human β-catenin fused to the C-terminus of enhanced green fluorescent protein (EGFR). Imaging and analysis is performed with a fluorescence microscope or HCS platform allowing the levels and distribution of EGFP-β-catenin to be visualized.

Another way, in which the destruction complex is inhibited, is by removal of Axin by recruitment of Axin to the cytoplasmic tail of the Wnt co-receptor LRP. Axin has been shown to bind preferentially to a phosphorylated form of the LRP tail. Visualization of Axin translocation, for example with a GFP-Axin fusion protein, is therefore another method for assessing levels of Wnt/β-catenin signaling.

In certain embodiments, a Wnt signaling pathway agonist enhances or increases canonical Wnt pathway signaling, e.g., β-catenin signaling, by at least 30%, 35%, 40%, 45%, 50%, 60%, 70%, 75%, 80%, 85%, 90%, 95%, 100%, 110%, 150%. 200%, 250%, 300%, 400% or 500%, as compared to the 8-catenin signaling induced by a neutral substance or negative control as measured in an assay described above, for example as measured in the TOPFlash assay. A negative control may be included in these assays. In particular embodiments, Wnt agonists may enhance β-catenin signaling by a factor of 2×, 5×, 10×, 100×, 1000×, 10000× or more as compared to the activity in the absence of the agonist when measured in an assay described above, for example when measured in the TOPFlash assay, or any of the other assays mentioned herein.

In certain embodiments, a Wnt signaling pathway antagonist or inhibitor inhibits or decreases canonical Wnt pathway signaling, e.g., p-catenin signaling, by at least 10%, 20%, 30%, 40%, 50%, 60%, 70%, 75%, 80%, 90%, 95%, or 100%, as compared to the β-catenin signaling observed in the presence of a neutral substance or negative control as measured in an assay described above, for example as measured in the TOPFlash assay. A positive control may be included in these assays.

"Wnt gene product" or "Wnt polypeptide" when used herein encompass native sequence Wnt polypeptides, Wnt polypeptide variants, Wnt polypeptide fragments and chimeric Wnt polypeptides. In particular embodiments, a Wnt polypeptide is a native human full length mature Wnt protein.

For example, human native sequence Wnt proteins of interest in the present application include the following: Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (Ref Seq.: NM_030753), Wnt3a (GenBank Accession No. NM_033131), Wnt-4 (GenBank Accession No, NM_030761), Wnt-5A (GenBank Accession No. M1_003392), Wnt-5B (GenBank Accession No. NM_032642), Wnt-6 (GenBank Accession No. M1_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No, NM_003396), Wnt-1 OA (GenBank Accession No. NM_025216), Wnt-10B (GenBank Accession No.

NM_003394), Wnt-11 (GenBank Accession No. NM_004826), Wnt 16 (GenBank Accession No. NM_016087)). Although each member has varying degrees of sequence identity with the family, all encode small (i.e., 39-46 kD), acylated, palmitoylated, secreted glycoproteins that contain 2324 conserved cysteine residues whose spacing is highly conserved (McMahon, A P et al., Trends Genet. 1992; 8: 236-242; Miller, J R. Genome Biol. 2002; 3(1): 3001.1-3001.15). Other native sequence Wnt polypeptides of interest include orthologs of the above from any mammal, including domestic and farm animals, and zoo, laboratory or pet animals, such as dogs, cats, cattle, horses, sheep, pigs, goats, rabbits, rats, mice, frogs, zebra fish, fruit fly, worm, etc.

"Wnt pathway signaling" or "Wnt signaling" is used herein to refer to the mechanism by which a biologically active Wnt exerts its effects upon a cell to modulate a cell's activity. Wnt proteins modulate cell activity by binding to Wnt receptors, including proteins from the Frizzled (Fzd) family of proteins, proteins from the ROR family of proteins, the proteins LRP5, LRP6 from the LRP family of proteins, the protein FRL1/crypto, and the protein Derailed/Ryk. Once activated by Wnt binding, the Wnt receptor(s) will activate one or more intracellular signaling cascades. These include the canonical Wnt signaling pathway; the Wnt/planar cell polarity (Wnt/PCP) pathway; the Wnt-calcium (Wnt/$Ca^{2+}$) pathway (Giles, R H et al. (2003) Biochim Biophys Acta 1653, 1-24; Peifer, M. et al. (1994) Development 120: 369-380; Fapkoff, J. et al (1996) Mol. Cell Bol. 16: 2126-2134; Veeman, M. T. et al. (2003) Dev. Cell 5: 367-377); and other Wnt signaling pathways as is well known in the art.

For example, activation of the canonical Wnt signaling pathway results in the inhibition of phosphorylation of the intracellular protein 8-catenin, leading to an accumulation of 3-catenin in the cytosol and its subsequent translocation to the nucleus where it interacts with transcription factors, e.g. TCF/LEF, to activate target genes. Activation of the Writ/PCP pathway activates RhoA, c-Jun N-terminal kinase (JNK), and nemo-like kinase (NLK) signaling cascades to control such biological processes as tissue polarity and cell movement. Activation of the Wnt/$Ca^{2+}$ by, for example, binding of Wnt-4, Wnt-5A or Wnt-11, elicits an intracellular release of calcium ions, which activates calcium sensitive enzymes like protein kinase C (PKC), calcium-calmodulin dependent kinase II (CernKII) or calcineurin (CaCN). By assaying for activity of the above signaling pathways, the biological activity of an antibody or antigen-binding fragment thereof, e.g., a Wnt surrogate, can be readily determined.

In certain embodiments, functional properties of anti-Fzd antibodies and antigen-binding fragments thereof may be assessed using a variety of methods known to the skilled person, including e.g., affinity/binding assays (for example, surface plasmon resonance, competitive inhibition assays), cytotoxicity assays, cell viability assays, cell proliferation or differentiation assays in response to a Wnt, cancer cell and/or tumor growth inhibition using in vitro or in vivo models, including but not limited to any described herein. Other assays may test the ability of antibodies described herein to block normal Wnt/Fzd-mediated responses. The antibodies and antigen-binding fragments thereof described herein may also be tested for effects on Fzd receptor internalization, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

In certain embodiments, a Fzd-binding antibody or antigen-binding fragment thereof, e.g., a Wnt surrogate, comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds one or more Fzd receptors. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for one or more Fzd receptor. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to one or more Fzd receptor. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody or antigen binding domain specific for a Fzd receptor, the method comprising providing by way of addition, deletion, substitution or insertion of one or more amino acids in the amino acid sequence of a VH domain set out herein or a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for one or more Fzd receptor and optionally with one or more desired properties. The VL domains may have an amino acid sequence which is substantially as set out herein. An analogous method may be employed in which one or more sequence variants of a VL domain disclosed herein are combined with one or more VH domains.

In particular embodiments, anti-Fzd antibodies, and antigen-binding fragments thereof, are water soluble. By "water soluble" it is meant a composition that is soluble in aqueous buffers in the absence of detergent, usually soluble at a concentration that provides a biologically effective dose of the polypeptide. Compositions that are water soluble form a substantially homogenous composition that has a specific activity that is at least about 5% that of the starting material from which it was purified, usually at least about 10%, 20%, or 30% that of the starting material, more usually about 40%. 50%, or 60% that of the starting material, and may be about 50%, about 90% or greater. Anti-Fzd antibodies and antigen-binding fragments thereof, including Wnt surrogates, of the present invention typically form a substantially homogeneous aqueous solution at concentrations of at least 25 µM and higher, e.g. at least 25 µM, 40 µM, or 50 µM, usually at least 60 70 µM, 80 µM, or 90 µM, sometimes as much as 100 µM, 120 µM, or 150 µM. In other words, compositions of the present invention typically form a substantially homogeneous aqueous solution at concentrations of about 0.1 mg/ml, about 0.5 mg/ml, of about 1 mg/ml or more.

An antigen or epitope that "specifically binds" or "preferentially binds" (used interchangeably herein) to an antibody or antigen-binding fragment thereof is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target antigen, e.g., a Fzd receptor, if it binds with greater affinity, avidity, more readily, and/or with greater duration than it binds to other substances. For example, an antibody that specifically or preferentially binds to the Fzd1 receptor is an antibody that binds to the Fzd1 receptor with greater affinity, avidity, more readily, and/or with greater duration than it binds to other Fzd receptors or non-Fzd proteins. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

In some embodiments the anti-Fzd antibody, or antigen-binding fragment thereof, binds to one, two, three, four, five or more different frizzled proteins, e.g., one or more of human frizzled proteins Fzd1, Fzd2, Fzd3. Fzd4, Fzd5, Fzd6, Fzd7, Fzd8, Fzd9, Fzd10. In some embodiments, the antibody based signaling agonist binds to Fzd1, Fzd2, Fzd5, Fzd7 and Fzd8. In various embodiments, the anti-Fzd antibody, or antigen-binding fragment thereof, binds to: (i) Fzd1, Fzd2, Fzd7 and Fzd9; (ii) Fzd1, Fzd2 and Fzd7; (iii) Fzd5 and Fzd8; (iv) Fzd5, Fzd7 and Fzd8; (v) Fzd1, Fzd4, Fzd5 and Fzd8; (vi) Fzd1, Fzd2, Fzd5, Fzd7 and Fzd8; (vii) Fzd4 and Fzd9; (viii) Fzd9 and Fzd10; (ix) Fzd5, Fzd8 and Fzd10; (x) Fzd4, Fzd5 and Fzd8; (xi) Fzd1, Fzd5, Fzd7 and Fzd8; or (xii) Fzd1, Fzd4, Fzd5, Fzd7 and Fzd8. In some embodiments the frizzled binding moiety is selective for one or more frizzled protein of interest, e.g. having a specificity for the one or more desired frizzled protein of at least 10-fold, 25-fold, 50-fold, 100-fold, 200-fold or more relative to other frizzled proteins.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_D$. See, generally, Davies et al. (1990) Annual Rev. Biochem. 59:439-473. In certain embodiment, the anti-Fzd antibodies bind one or more Fzd receptors with a $K_D$ of less than or equal to about $1\times10^{-4}$ M, less than or equal to about $1\times10^{-5}$ M, less than or equal to about $1\times10^{-6}$ M, less than or equal to about $1\times10^{-7}$ M, less than or equal to about $1\times10^{-8}$ M, less than or equal to about $1\times10^{-9}$ M, or at least about $1\times10^{-19}$ M. In certain embodiments, the anti-Fzd antibodies described herein bind one or more Fzd receptor with a $K_D$ of less than about 10,000 nM, less than about 1000 nM, less than about 100 nM, less than about 10 nM, less than about 1 nM or less than about 0.1 nM, and in some embodiments, the antibodies may have even higher affinity for one or more Fzd receptor. In certain embodiments, the anti-Fzd antibodies described herein have an affinity $K_D$ of about 100, 150, 155, 160, 170, 175, 180, 185, 190, 191, 192, 193, 194, 195, 196, 197, 198 or 199 picomolar, and in some embodiments, the antibodies may have even higher affinity for one or more Fzd receptor.

An antibody or antigen-binding fragment thereof according to certain embodiments includes antibodies and antigen binding fragments thereof that compete for binding to one or more Fzd receptor with any antibody described herein which both (i) specifically binds to the one or more Fzd receptor and/or (ii) comprises a VH and/or VL domain (or a VH and/or VL CDR set) disclosed herein, or (iii) comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to one or more Fzd receptor.

In this regard, as used herein, the terms "competes with", "inhibits binding" and "blocks binding" (e.g., referring to inhibition/blocking of binding of a Wnt to one or more Fzd receptor or referring to inhibition/blocking of binding of an anti-Fzd antibody to a Fzd receptor) are used interchangeably and encompass both partial and complete inhibition/blocking. The inhibition/blocking of a Wnt to one or more Fzd receptor preferably reduces or alters the normal level or type of cell signaling that occurs when the Wnt binds to the Fzd receptor without inhibition or blocking. Inhibition and blocking are also intended to include any measurable decrease in the binding of a Wnt to a Fzd receptor when in contact with an anti-Fzd antibody as disclosed herein as compared to the ligand not in contact with an anti-Fzd antibody, e.g., the blocking of binding of the Wnt to the Fzd receptor by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans, there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG, the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cγ2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 1IIS and 1IIX) (Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a $K_d$ for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical; however, FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Subjects with the V158 allotype respond favorably to rituximab treatment; however, subjects with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehmbecher et al., 1999, Blood 94:4220-4232; Cartron et al., 2002, Blood 99:754-758). Thus 80-90% of humans are poor responders, that is, they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of a Fzd-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-Fzd antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599, US20080131435, US20080138344, and published International Applications WO2006/105338; WO2004/063351; WO2006/088494; WO2007/024249.

In certain embodiments, the Fc region may be derived from any of a variety of different Fcs, including but not limited to, a wild-type or modified IgG1, IgG2, IgG3, IgG4 or other isotype, e.g., wild-type or modified human IgG1, human IgG2, human IgG3, human IgG4, human IgG4Pro (comprising a mutation in core hinge region that prevents the formation of IgG4 half molecules), human IgA, human IgE, human IgM, or the modified IgG1 referred to as IgG1 LALAPG. The L235A, P329G (LALA-PG) variant has been shown to eliminate complement binding and fixation as well as Fc-y dependent antibody-dependent cell-mediated cytotoxity (ADCC) in both murine IgG2a and human IgG1. In particular embodiments of any of the IgG disclosed herein, the IgG comprises one or more of the following amino acid substitutions: N297G, N297A, N297E, L234A, L235A, or P236G.

Thus, in certain embodiments, antibody variable domains with the desired binding specificities are fused to immunoglobulin constant domain sequences. In certain embodiments, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

In another contemplated embodiment, a Fzd-specific antibody or antigen-binding fragment thereof as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bisazido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737) [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

In certain embodiments, anti-LRP5/6 antibodies and antigen-binding fragments thereof are monoclonal antibodies. In certain embodiments, they are humanized.

The present invention further provides in certain embodiments an isolated nucleic acid encoding an antibody or antigen-binding fragment thereof as described herein, for instance, a nucleic acid that codes for one or more CDR or VH or VL domain as described herein. Nucleic acids include DNA and RNA. These and related embodiments may include polynucleotides encoding antibodies that bind one or more Fzd receptors as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked.

The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-Fzd antibodies and antigen-binding fragments thereof described herein. In certain embodiments, polynucleotides are provided that comprise some or all of a polynucleotide sequence encoding an antibody or antigen-binding fragment thereof as described herein and complements of such polynucleotides.

It will be appreciated by those of ordinary skill in the art that, as a result of the degeneracy of the genetic code, there are many nucleotide sequences that encodes an antibody as described herein. Some of these polynucleotides bear minimal sequence identity to the nucleotide sequence of the native or original polynucleotide sequence that encode antibodies that bind to a Fzd receptor. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phages are readily commercially-available and their use is generally well-known to those skilled in the art. Double-stranded plasmids are also routinely employed in site directed mutagenesis that eliminates the step of transferring the gene of interest from a plasmid to a phage.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments thereof in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as a Fzd-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to a Fzd receptor of the present disclosure, or sequences that have deletions from, additions to, and/or substitutions of one or more amino acid of an anti-Fzd antibody. Thus, a "polypeptide" or a "protein" can comprise one (termed "a monomer") or a plurality (termed "a multimer") of amino acid chains.

The term "isolated protein" or "isolated antibody" referred to herein means that a subject protein or antibody is (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to one or more Fzd receptor). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies and antigen-binding fragments thereof disclosed herein. In certain embodiments, such variant antibodies or antigen-binding fragments, or CDRs thereof, bind to one or more Fzd receptor at least about 50%, at least about 70%, and in certain embodiments, at least about 90% as well as an antibody sequence specifically set forth herein. In further embodiments, such variant antibodies or antigen-binding fragments, or CDRs thereof, bind to one or more Fzd receptor with greater affinity than the antibodies set forth herein, for example, that bind quantitatively at least about 105%, 106%, 107%, 108%, 109%, or 110% as well as an antibody sequence specifically set forth herein.

In particular embodiments, the antibody or antigen-binding fragment thereof, e.g., a Fab, scFv, VHH or sdAb, or Wnt surrogate, may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and/or b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., one or more Fzd receptors). In a further embodiment, the antibody, or antigen-binding fragment thereof, is a variant antibody or antigen-binding fragment thereof wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

In particular embodiments, a subject antibody or antigen-binding fragments thereof, e.g., a Fab, scFv, VHH or sdAb, or Wnt surrogate, may have: a) a heavy chain variable region having an amino acid sequence that is at least 80% identical, at least 95% identical, at least 90%, at least 95% or at least 98% or 99% identical, to the heavy chain variable region of an anti-Fzd antibody or antigen-binding fragments thereof described herein; and/or b) a light chain variable region having an amino acid sequence that is at least 80% identical, at least 85%, at least 90%, at least 95% or at least 98% or 99% identical, to the light chain variable region of an anti-Fzd antibody or antigen-binding fragments thereof described herein. The amino acid sequences of illustrative antigen-binding fragments thereof are set forth in SEQ ID NOs:1-65.

In particular embodiments, the antibody or antigen-binding fragment thereof, e.g., a Fab, scFv, VHH or sdAb, or Wnt surrogate, may comprise one or more, two or more, three or more, four or more, five or more, or six of the CDRs identified in Table 1A for any particular antibody. In certain embodiments, the antibody or antigen-binding fragment thereof comprises a CDRH1 comprising or consisting of any of SEQ ID NOs:72-312 or 1327-1347; a CDRH2 comprising or consisting of any of SEQ ID NOs:313-574 or 1348-1360; a CDRH3 comprising or consisting of any of SEQ ID NOs: 575-930, 1361-1387 or 1436-1443; a CDRL1 comprising or consisting of any of SEQ ID NOs: 931-1060 or 1388-1406; a CDRL2 comprising or consisting of any of SEQ ID NOs: 1061-1158 or 1407-1419; and/or a CDRL3 comprising or consisting of any of SEQ ID NOs: 1159-1326, 1420-1435 or 1444-1453.

A polypeptide has a certain percent "sequence identity" to another polypeptide, meaning that, when aligned, that percentage of amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0.

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., Fzd receptor, such as Fzd1). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

Determination of the three-dimensional structures of representative polypeptides (e.g., variant Fzd-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 Prot. Sci. 3:2378; Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007); Raman et al. Science 327:1014-1018 (2010). Some additional non-limiting examples of computer algorithms that may be used for these and related embodiments, such as for rational design of Fzd-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

In particular embodiments, the disclosure provides antibodies or antigen-binding fragments thereof that bind to a region of one or more Fzd receptor at a region described in Table 3. In certain embodiments, they bind to a region of LRP6 that comprises or consists of amino acid residues 637-878, where the amino acid sequence and numbering is consist with that described in the Examples. In certain embodiments, they bind to an epitope within the region of LRP6 comprising amino acids 637-878. In certain embodiments, the antibody or antigen-binding fragment thereof contacts the LRP6 at any or all of the contact points disclosed in Table 3. In one embodiment, the core interaction-site or epitope on LRP6 (inter-atomic distances between Lrp6E3E4 and VHH26 less than or equal to 5.0 Å) includes: Arg639, Ala640, Lys622, Glu663, Ile681, Ser682, Lys684, Asp705, Tyr706, Glu708, Thr724, Gly725, Arg751, Try767, Gly768, Gly769, Arg792, Leu810, Asp811, His834, Phe836, Trp850, Ser851, Arg853, Asp874, Tyr875, and Met877 of LRP6. In another embodiment, the core interaction-site (inter-atomic distances between Lrp6E3E4 and VHH36 less than or equal to 5.0 Å) includes: Glu663, Ser665, Ile681, Tyr706, Glu708, Thr724, Ser749, Arg751, Trp767, Gly768, Arg792, Leu810, Asn813, Pro833, His834, Phe836, Trp850, Ser851, Arg853, Asp874, Try875, and Met877 of LRP6.

The disclosure also provides antibodies and antigen-binding fragments thereof that bind to one or more Frizzled receptors at specific contact points, including any of those disclosed in Table 3, which indicates specific sets of contact points for binding of various anti-Fzd antibodies or fragments thereof.

In another embodiment of invention, the anti-Fzd antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see e.g., U.S. Pat. No. 7,462,697). Thus, illustrative methods for making the anti-Fzd antibodies of the present disclosure include the RabMab® rabbit monoclonal antibody technology described, for example, in U.S. Pat. Nos. 5,675,063 and 7,429,487. In this regard, in certain embodiments, the anti-Fzd antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions

Pharmaceutical compositions comprising an anti-Fzd antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises one or more Wnt polypeptides or Norrin polypeptides.

In further embodiments, pharmaceutical compositions comprising a polynucleotide comprising a nucleic acid sequence encoding an anti-Fzd antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises one or more polynucleotides comprising a nucleic acid sequence encoding a Wnt polypeptide or Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same polynucleotide.

In further embodiments, pharmaceutical compositions comprising an expression vector, e.g., a viral vector, comprising a polynucleotide comprising a nucleic acid sequence encoding an anti-Fzd antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises an expression vector, e.g., a viral vector, comprising a polynucleotide comprising a nucleic acid sequence encoding a Wnt polypeptide or Norrin polypeptide. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same polynucleotide, e.g., expression cassette.

The present invention further contemplates a pharmaceutical composition comprising a cell comprising an expression vector comprising a polynucleotide comprising a promoter operatively linked to a nucleic acid encoding an anti-Fzd antibody or antigen-binding fragment thereof described herein and one or more pharmaceutically acceptable diluent, carrier, or excipient. In particular embodiments, the pharmaceutical composition further comprises a cell comprising an expression vector comprising a polynucleotide comprising a promoter operatively linked to a nucleic acid sequence encoding a Wnt polypeptide or a Norrin polypeptide. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same polynucleotide, e.g., expression cassette and/or in the same cell. In particular embodiments, the cell is a heterologous cell or an autologous cell obtained from the subject to be treated. In particular embodiments, the cell is a stem cell, e.g., an adipose-derived stem cell or a hematopoietic stem cell.

The present disclosure contemplates pharmaceutical compositions comprising a first molecule for delivery of anti-Fzd antibody or antigen-binding fragment thereof, e.g., a Wnt surrogate, as a first active agent and a second molecule for delivery of a Wnt polypeptide or Norrin polypeptide. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

The subject molecules, alone or in combination, can be combined with pharmaceutically-acceptable carriers, diluents, excipients and reagents useful in preparing a formulation that is generally safe, non-toxic, and desirable, and includes excipients that are acceptable for mammalian, e.g., human or primate, use. Such excipients can be solid, liquid, semisolid, or, in the case of an aerosol composition, gaseous. Examples of such carriers, diluents and excipients include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

Pharmaceutical compositions may further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to allow it to be drawn into a syringe and provided to a subject using a syringe. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the anti-Fzd antibody or antigen-binding fragment thereof (or encoding polynucleotide or cell comprising the same) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the pharmaceutical compositions are prepared with carriers that will protect the antibody or antigen-binding fragment thereof against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

It may be advantageous to formulate the pharmaceutical compositions in dosage unit form for ease of administration and uniformity of dosage. Dosage unit form as used herein refers to physically discrete units suited as unitary dosages for the subject to be treated; each unit containing a predetermined quantity of active antibody or antigen-binding fragment thereof calculated to produce the desired therapeutic effect in association with the required pharmaceutical carrier. The specification for the dosage unit forms are dictated by and directly dependent on the unique characteristics of the antibody or antigen-binding fragment thereof and the particular therapeutic effect to be achieved, and the limitations inherent in the art of compounding such an active antibody or antigen-binding fragment thereof for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active antibody or antigen-binding fragment thereof.

The present invention includes pharmaceutically acceptable salts of the anti-Fzd antibodies or antigen-binding fragments thereof, e.g., Wnt surrogates, described herein. The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see "Handbook of Pharmaceutical Salts: Properties, Selection, and Use" by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N-N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In some embodiments, the pharmaceutical composition provided herein comprise a therapeutically effective amount of an anti-Fzd antibody or antigen-binding fragment thereof, e.g., a Wnt surrogate, described herein in admixture with a pharmaceutically acceptable carrier, diluent and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer may be in the range of 6.5 to 7.75, preferably 7 to 7.5, and most preferably 7.2 to 7.4.

Methods of Use

The present disclosure also provides methods for using the Fzd-specific antibodies, antigen-binding fragments thereof, e.g., Wnt surrogates, disclosed herein, e.g., to modulate a Wnt signaling pathway, e.g., to increase or decrease Wnt signaling, and the administration of Fzd-specific antibodies, antigen-binding fragments thereof, and Wnt surrogates disclosed herein in a variety of therapeutic settings. Provided herein are methods of treatment using the antibodies that bind one or more Fzd receptors or antigen-binding fragments thereof. In one embodiment, an antibody, or antigen-binding fragment thereof, of the present invention is provided to a subject having a disease involving inappropriate or deregulated Wnt signaling, e.g., increased or reduced Wnt signaling.

Increasing Wnt Pathway Signaling and Related Therapeutic Methods

In certain embodiments, an anti-Fzd antibody or antigen-binding fragment thereof, e.g., a Wnt surrogate, may be used to increase Wnt signaling in a tissue or cell. Thus, in some aspects, the present invention provides a method for increasing Wnt signaling or enhancing Wnt signaling in a tissue or cell, comprising contacting the tissue or cell with an effective amount of an anti-Fzd antibody or antigen-binding fragment thereof, e.g., a Wnt surrogate, disclosed herein, wherein the anti-Fzd antibody or antigen-binding fragment thereof is a Wnt signaling pathway agonist. In some embodiments, contacting occurs in vitro, ex vivo, or in vivo. In particular embodiments, the cell is a cultured cell, and the contacting occurs in vitro. In certain embodiments, the method comprises further contacting the tissue or cell with one or more Wnt polypeptides or Norrin polypeptides.

In related aspects, the present invention provides a method for increasing Wnt signaling in a tissue or cell, comprising contacting the tissue or cell with an effective amount of a polynucleotide comprising an anti-Fzd antibody or antigen-binding fragment thereof, e.g., a Wnt surrogate, of the present invention. In certain embodiments, the target tissue or cell is also contacted with a polynucleotide comprising a nucleic acid sequence that encodes a Wnt polypeptide or a Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same polynucleotide.

In related aspects, the present invention provides a method for increasing Wnt signaling in a tissue or cell, comprising contacting the tissue or cell with an effective amount of a vector comprising a nucleic acid sequence encoding an anti-Fzd antibody or antigen-binding fragment thereof, e.g., a Wnt surrogate. In certain embodiments, the tissue or cell is also contacted with a vector comprising a nucleic acid sequence that encodes a Wnt polypeptide or a Norrin polypeptide. In certain embodiments, the vector is an expression vector, and may comprise a promoter operatively linked to the nucleic acid sequence. In particular embodiments, the vector is a viral vector. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same vector, e.g., in the same expression cassette.

In related aspects, the present invention provides a method for increasing Wnt signaling in a tissue, comprising contacting the tissue with an effective amount of a cell comprising a nucleic acid sequence encoding an anti-Fzd antibody or antigen-binding fragment thereof, e.g., a Wnt surrogate, of the present invention. In certain embodiments, the tissue is also contacted with a cell comprising a nucleic acid sequence that encodes a Wnt polypeptide or Norrin polypeptide. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same cell. In particular embodiments, the cell is a heterologous cell or an autologous cell obtained from the subject to be treated. In certain embodiments, the cell was transduced with a vector comprising an expression cassette encoding the anti-Fzd antibody or antigen-binding fragment thereof, e.g., a Wnt surrogate, or the Wnt polypeptide or Norrin polypeptide. In particular embodiments, the cell is a stem cell, e.g., an adipose-derived stem cell or a hematopoietic stem cell.

Anti-Fzd antibodies and antigen-binding fragments thereof, e.g., Wnt surrogates, may be used in to treat a disease, disorder or condition, for example, by increasing Wnt signaling in a targeted cell, tissue or organ. Thus, in some aspects, the present invention provides a method for treating a disease or condition in a subject in need thereof, e.g., a disease or disorder associated with reduced Wnt signaling, or for which increased Wnt signaling would provide a therapeutic benefit, comprising contacting the subject with an effective amount of a composition of the present disclosure. In particular embodiments, the composition is a pharmaceutical composition comprising any of: an anti-Fzd antibody or antigen-binding fragment thereof, e.g., a Wnt surrogate; a polynucleotide comprising a nucleic acid sequence encoding an anti-Fzd antibody or antigen-binding fragment thereof, e.g., a Wnt surrogate, e.g., a DNA or mRNA, optionally a modified mRNA; a vector comprising a nucleic acid sequence encoding an anti-Fzd antibody or antigen-binding fragment thereof, e.g., a Wnt surrogate, e.g., an expression vector or viral vector; or a cell comprising a nucleic acid sequence encoding an anti-Fzd antibody or antigen-binding fragment thereof, e.g., a Wnt surrogate, e.g., a cell transduced with an expression vector or viral vector encoding an anti-Fzd antibody or antigen-binding fragment thereof, e.g., a Wnt surrogate. In particular embodiments, the disease or condition is a pathological disease or disorder, or an injury, e.g., an injury resulting from a wound. In certain embodiments, the wound may be the result of another therapeutic treatment. In certain embodiments, the disease or condition comprises impaired tissue repair, healing or regeneration, or would benefit from increased tissue repair, healing or regeneration. In some embodiments, contacting occurs in vivo, i.e., the subject composition is administered to a subject.

In certain embodiments, the method comprises further contacting the subject with a pharmaceutical composition comprising one or more Wnt polypeptides or Norrin polypeptides. The present disclosure contemplates contacting a subject with a first molecule for delivery of an anti-Fzd antibody or antigen-binding fragment thereof, e.g., a Wnt surrogate, as a first active agent and a second molecule for delivery of a Wnt polypeptide or Norrin polypeptide. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a polynucleotide comprising a nucleic acid sequence encoding an anti-Fzd antibody or antigen-binding fragment thereof, e.g., a Wnt surrogate, disclosed herein. In certain embodiments, the subject is also contacted with a pharmaceutical composition comprising an effective amount of a polynucleotide comprising a nucleic acid sequence that encodes a Wnt polypeptide or a Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same polynucleotide.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a vector comprising a nucleic acid sequence encoding an anti-Fzd antibody or antigen-binding fragment thereof, e.g., a Wnt surrogate. In certain embodiments, the subject is also contacted with a pharmaceutical composition comprising an effective amount of a vector comprising a nucleic acid sequence that encodes a Wnt polypeptide or a Norrin polypeptide. In certain embodiments, the vector is an expression vector, and may comprise a promoter operatively linked to the nucleic acid sequence. In particular embodiments, the vector is a viral vector. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same vector, e.g., in the same expression cassette.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a cell comprising a nucleic acid sequence encoding an anti-Fzd antibody or antigen-binding fragment thereof, e.g., a Wnt surrogate. In certain embodiments, the subject is also contacted with a cell comprising a nucleic acid sequence that encodes a Wnt polypeptide or a Norrin polypeptide. In certain embodiments, the nucleic acid sequence encoding the anti-Fzd antibody or antigen-binding fragment thereof, e.g., a Wnt surrogate, and the nucleic acid sequence encoding the Wnt polypeptide or Norrin polypeptide are present in the same cell. In particular embodiments, the cell is a heterologous cell or an autologous cell obtained from the subject to be treated. In certain embodiments, the cell was transduced with a vector comprising an expression cassette encoding the anti-Fzd antibody or antigen-binding fragment thereof, e.g., a Wnt surrogate, or the Wnt polypeptide or Norrin polypeptide. In particular embodiments, the cell is a stem cell, e.g., an adipose-derived stem cell or a hematopoietic stem cell.

Wnt signaling plays key roles in the developmental process and maintenance of stem cells. Reactivation of Wnt signals is associated with regeneration and repair of most tissues after injuries and diseases. Anti-Fzd antibody or antigen-binding fragment thereof, e.g., a Wnt surrogate, molecules are expected to provide benefit of healing and tissue repair in response to injuries and diseases. Causes of tissue damage and loss include but are not limited to aging, degeneration, hereditary conditions, infection and inflammation, traumatic injuries, toxins/metabolic-induced toxicities, or other pathological conditions. Wnt signals and enhancers of Wnt signals have been shown to activate adult, tissue-resident stem cells. In some embodiments, the compounds of the invention are administered for use in treating diseased or damaged tissue, for use in tissue regeneration and for use in cell growth and proliferation, and/or for use in tissue engineering.

Human diseases associated with mutations of the Wnt pathway provide strong evidence for enhancement of Wnt signals in the treatment and prevention of diseases. Preclinical in vivo and in vitro studies provide additional evidence of involvement of Wnt signals in many disease conditions and further support utilization of an anti-Fzd antibody or antigen-binding fragment thereof, e.g., a Wnt surrogate, in various human diseases.

Human diseases associated with mutations of the Wnt pathway provide strong evidence for enhancement of Wnt signals in the treatment and prevention of diseases. Preclinical in vivo and in vitro studies provide additional evidence of involvement of Wnt signals in many disease conditions and further support utilization of a Wnt surrogate molecule in various human diseases. For example, compositions of the present invention may be used to promote or increase bone growth or regeneration, bone grafting, healing of bone fractures, treatment of osteoporosis and osteoporotic fractures, spinal fusion, spinal cord injuries, including vertebral compression fractures, pre-operative spinal surgery optimization, osseointegration of orthopedic devices, tendon-bone integration, tooth growth and regeneration, dental implantation, periodontal diseases, maxillofacial reconstruction, and osteonecrosis of the jaw. They may also be used in the treatment of alopecia; enhancing regeneration of sensory organs, e.g. treatment of hearing loss, including regeneration of inner and outer auditory hair cells treatment of vestibular hypofunction, treatment of macular degeneration, treatment of retinopathies, including vitreoretinopathy, diabetic retinopathy, other diseases of retinal degeneration, Fuchs' dystrophy, other cornea disease, etc.; treatment of stroke, traumatic brain injury, Alzheimer's disease, multiple sclerosis, muscular dystrophy, muscle atrophy as a result of sarcopenia or cachexia, and other conditions affecting the degeneration or integrity of the blood brain barrier. The compositions of this invention may also be used in treatment of oral mucositis, treatment of short bowel syndrome, inflammatory bowel diseases (IBD), including Crohn's disease (CD) and ulcerative colitis (UC), in particular CD with fistula formation, other gastrointestinal disorders; treatment of metabolic syndrome, dyslipidemia, treatment of diabetes, treatment of pancreatitis, conditions where exocrine or endocrine pancreas tissues are damaged; conditions where enhanced epidermal regeneration is desired, e.g., epidermal wound healing, treatment of diabetic foot ulcers, syndromes involving tooth, nail, or dermal hypoplasia, etc., conditions where angiogenesis is beneficial; treatment of myocardial infarction, coronary artery disease, heart failure; enhanced growth of hematopoietic cells, e.g. enhancement of hematopoietic stem cell transplants from bone marrow, mobilized peripheral blood, treatment of immunodeficiencies, graft versus host diseases, etc.; treatment of acute kidney injuries, chronic kidney diseases; treatment of lung diseases, chronic obstructive pulmonary diseases (COPD), pulmonary fibrosis, including idiopathic pulmonary fibrosis, enhanced regeneration of lung tissues. The compositions of the present invention may also be used in enhanced regeneration of liver cells, e.g. liver regeneration, treatment of cirrhosis, enhancement of liver transplantations, treatment of acute liver failure, treatment of chronic liver diseases with hepatitis C or B virus infection or post-antiviral drug therapies, alcoholic liver diseases, alcoholic hepatitis, non-alcoholic liver diseases with steatosis or steatohepatitis, and the like. The compositions of this invention may treat diseases and disorders including, without limitation, conditions in which regenerative cell growth is desired.

Human genetics involving loss-of-function or gain-of-function mutations in Wnt signaling components show strong evidence supporting enhancing Wnt signals for bone growth. Conditions in which enhanced bone growth is desired may include, without limitation, fractures, grafts, ingrowth around prosthetic devices, osteoporosis, osteoporotic fractures, spinal fusion, vertebral compression fractures, pre-operative optimization for spinal surgeries, osteonecrosis of the jaw, dental implantation, periodontal diseases, maxillofacial reconstruction, and the like. An anti-Fzd antibody or antigen-binding fragment thereof, e.g., a Wnt surrogate, enhances and promotes Wnt signals which are critical in promoting bone regeneration. Methods for regeneration of bone tissues benefit from administration of the compounds of the invention, which can be systemic or localized. In some embodiments, bone marrow cells are exposed to molecules of the invention, such that stem cells within that marrow become activated.

In some embodiments, bone regeneration is enhanced by contacting a responsive cell population, e.g. bone marrow, bone progenitor cells, bone stem cells, etc. with an effective dose of an anti-Fzd antibody or antigen-binding fragment thereof, e.g., a Wnt surrogate, disclosed herein. Methods for regeneration of bone tissues benefit from administration of the anti-Fzd antibody or antigen-binding fragment thereof, e.g., a Wnt surrogate disclosed herein, which can be systemic or localized. In some such embodiments, the contacting is performed in vivo. In other such embodiments, the contacting is performed ex vivo. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, polymeric microspheres, nanoparticles, bone cements, and the like.

Compositions comprising one or more anti-Fzd antibody or antigen-binding fragment thereof, e.g., a Wnt surrogate, disclosed herein can be used for the in vivo treatment of skeletal tissue deficiencies. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions. The compositions of the present invention can be used as part of a regimen for restoring cartilage function to a connective tissue, for the repair of defects or lesions in cartilage tissue such as degenerative wear and arthritis, trauma to the tissue, displacement of torn meniscus, meniscectomy, a luxation of a joint by a torn ligament, malalignment of joints, bone fracture, or by hereditary disease.

An anti-Fzd antibody or antigen-binding fragment thereof, e.g., a Wnt surrogate, may also be used for treatment of periodontal diseases.

Periodontal diseases are a leading cause of tooth loss and are linked to multiple systemic conditions. In some embodiments, tooth or underlying bone regeneration is enhanced by contacting a responsive cell population. In some such embodiments, the contacting is performed in vivo. In other such embodiments, the contacting is performed ex vivo, with subsequent implantation of the activated stem or progenitor cells. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, polymeric microspheres, nanoparticles, and the like.

Studies have shown that biology of Wnt signaling and R-spondins are capable of promoting sensory hair cell regeneration in the inner ear following injuries, aging, or degeneration. Loss of sensory hair cells in the inner ear involved in hearing loss or vestibular hypofunction may also benefit from the compositions of the invention. In the inner ear, the auditory organ houses mechanosensitive hair cells required for translating sound vibration to electric impulses. The vestibular organs, comprised of the semicircular canals (SSCs), the utricle, and the saccule, also contain sensory hair cells in order to detect head position and motion. Compositions of the present invention can be used, for example, in an infusion; in a matrix or other depot system; or other topical application to the ear for enhancement of auditory regeneration.

An anti-Fzd antibody or antigen-binding fragment thereof, e.g., a Wnt surrogate, may also be used in regeneration of retinal tissue. In the adult mammalian retina, Muller glia cells are capable of regenerating retinal cells, including photoreceptors, for example after neurotoxic injury in vivo. Wnt signaling and enhancers of Wnt signals can promote proliferation of Muller glia-derived retinal progenitors after damage or during degeneration. The compositions of the invention may also be used in the regeneration of tissues and other cell types in the eye. For examples age-related macular degeneration (AMD), other retina degenerative diseases, cornea diseases, Fuchs' dystrophy, vitreoretinopathy, hereditary diseases, etc. can benefit from the compositions of the present inventions. AMD is characterized by progressively decreased central vision and visual acuity. Fuchs' dystrophy is characterized by progressive loss of cornea endothelial cells. Wnt signal and enhancing of Wnt signal can promote regeneration of cornea endothelium, retina epithelium, etc. in the eye tissue. In other embodiments, compositions of the present invention can be used, for example, in an infusion; in a matrix or other depot system; or other topical application to the eye for retinal regeneration and treatment of macular degeneration.

Specific populations of proliferating cells for homeostatic renewal of hepatocytes have been identified through lineage tracing studies, for example Axin2-positive cells in pericentral region. Lineage tracing studies also identified additional potential liver progenitor cells, including but not limited to Lgr-positive cells. The self-renewing liver cells and other populations of potential progenitor cells, including Lgr5-positive and Axin2-positive cells, are identified to be capable of regeneration responding to Wnt signals and/or R-spondins following injuries. Numerous preclinical models of acute liver injury and failure and chronic liver diseases showed recovery and regeneration of hepatocytes benefit from enhancing Wnt signals. The compositions of this invention may be used in treatment of acute liver failure, acute alcoholic liver injuries, treatment of chronic liver diseases with hepatitis C or B virus infection or post-antiviral drug therapies, chronic alcoholic liver diseases, alcoholic hepatitis, non-alcoholic fatty liver diseases and non-alcoholic steatohepatitis (NASH), treatment of cirrhosis and severe chronic liver diseases of all causes, and enhanced regeneration of liver cells. Methods for regeneration of liver tissue benefit from administration of the compounds of the invention, which can be systemic or localized. These include, but are not limited to, methods of systemic administration and methods of localized administration e.g. by injection into the liver tissue, by injection into veins or blood vessels leading into the liver, by implantation of a sustained release formulation, and the like.

Wnt signals play an important role in regeneration of various epithelial tissues. Various epidermal conditions benefit from treatment with the compounds of the present invention. Mucositis occurs when there is a breakdown of the rapidly divided epithelial cells lining the gastro-intestinal tract, leaving the mucosal tissue open to ulceration and infection. The part of the epithelial lining that covers the mouth, called the oral mucosa, is one of the most sensitive parts of the body and is particularly vulnerable to chemotherapy and radiation. Oral mucositis is probably the most common, debilitating complication of cancer treatments, particularly chemotherapy and radiation. In addition, the compositions of the invention may also benefit treatment of short bowel syndrome, inflammatory bowel diseases (IBD), or other gastrointestinal disorders. Other epidermal conditions include epidermal wound healing, diabetic foot ulcers, syndromes involving tooth, nail, or dermal hypoplasia, and the like. Molecules of the present invention may be used in all these conditions, where regenerative cells are contacted with compounds of the invention. Methods for regeneration of epithelial tissues benefit from administration of the compounds of the invention, which can be systemic or localized. Contacting can be, for example, topical, including intradermal, subdermal, in a gel, lotion, cream etc. applied at targeted site, etc.

In addition to skin and gastrointestinal tract, Wnt signals and enhancement and promotion of Wnt signals also play an important role in repair and regeneration of tissues including pancreas, kidney, and lung in preclinical models. An anti-Fzd antibody or antigen-binding fragment thereof, e.g., a Wnt surrogate, may benefit various disease conditions involving exocrine and endocrine pancreas, kidney, or lung. The anti-Fzd antibody or antigen-binding fragment thereof, e.g., a Wnt surrogate, may be used in treatment of metabolic syndrome; treatment of diabetes, treatment of acute or chronic pancreatitis, exocrine pancreatic insufficiency, treatment of acute kidney injuries, chronic kidney diseases, treatment of lung diseases, including but not limited to chronic obstructive pulmonary diseases (COPD), other conditions that cause loss of lung epithelial tissues. Methods for regeneration of these tissues benefit from administration of the compounds of the invention, which can be systemic or localized.

Epidermal Wnt signaling, in coordination with signaling via other development factors, is critical for adult hair follicle regeneration. Hair loss is a common problem, and androgenetic alopecia, often called male pattern baldness, is the most common form of hair loss in men. In some embodiments, hair follicle regeneration is enhanced by contacting a responsive cell population with a molecule of the present invention. In some such embodiments, the contacting is performed in vivo. In other such embodiments, the contacting is performed ex vivo. The molecule may be localized to the site of action, e.g. topical lotions, gels, creams and the like.

Stroke, traumatic brain injury, Alzheimer's disease, multiple sclerosis and other conditions affecting the blood brain barrier (BBB) may be treated with an anti-Fzd antibody or antigen-binding fragment thereof, e.g., a Wnt surrogate. Angiogenesis is critical to ensure the supply of oxygen and nutrients to many tissues throughout the body, and is especially important for the CNS as the neural tissue is extremely sensitive to hypoxia and ischemia. CNS endothelial cells which form the BBB differ from endothelial cells in non-neural tissue, in that they are highly polarized cells held together by tight junctions and express specific transporters. Wnt signaling regulates CNS vessel formation and/or function. Conditions in which the BBB is compromised can benefit from administration of the compounds of the invention, which can be systemic or localized e.g. by direct injection, intrathecal administration, implantation of sustained release formulations, and the like. In addition, Wnt signal is actively involved in neurogenesis and plays a role of neuroprotection following injury. The compositions of the present invention may also be used in treatment of spinal cord injuries, other spinal cord diseases, stroke, traumatic brain injuries, etc.

Wnt signals also play a role in angiogenesis. An anti-Fzd antibody or antigen-binding fragment thereof, e.g., a Wnt surrogate, may benefit conditions where angiogenesis is beneficial, treatment of myocardial infarction, coronary artery disease, heart failure, diabetic retinopathy, etc., and conditions from hereditary diseases. Methods for regeneration of these tissues benefit from administration of the compounds of the invention, which can be systemic or localized.

In certain embodiments, methods of the present invention promote tissue regeneration, e.g., in a tissue subjected to damage or tissue or cell reduction or loss. The loss or damage can be anything which causes the cell number to diminish, including diseases or injuries. For example, an accident, an autoimmune disorder, a therapeutic side-effect or a disease state could constitute trauma. Tissue regeneration increases the cell number within the tissue and preferably enables connections between cells of the tissue to be re-established, and more preferably the functionality of the tissue to be regained.

Reducing Wnt Pathway Signaling and Related Therapeutic Methods

In certain embodiments, an anti-Fzd antibody or antigen-binding fragment thereof, may be used to decrease or inhibit Wnt signaling in a tissue or cell. Thus, in some aspects, the present invention provides a method for decreasing Wnt signaling or inhibiting Wnt signaling in a tissue or cell, comprising contacting the tissue or cell with an effective amount of an anti-Fzd antibody, or antigen-binding fragment thereof, disclosed herein, wherein the anti-Fzd antibody or antigen-binding fragment thereof is a Wnt signaling pathway antagonist or inhibitor. In some embodiments, contacting occurs in vitro, ex vivo, or in vivo. In particular embodiments, the cell is a cultured cell, and the contacting occurs in vitro.

In related aspects, the present invention provides a method for decreasing or inhibiting Wnt signaling in a tissue or cell, comprising contacting the tissue or cell with an effective amount of a polynucleotide comprising an anti-Fzd antibody or antigen-binding fragment thereof, of the present invention, wherein the anti-Fzd antibody or antigen-binding fragment thereof is a Wnt signaling pathway antagonist or inhibitor. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences In related aspects, the present invention provides a method for decreasing or inhibiting Wnt signaling in a tissue or cell, comprising contacting the tissue or cell with an effective amount of a vector comprising a nucleic acid sequence encoding an anti-Fzd antibody or antigen-binding fragment thereof, wherein the anti-Fzd antibody or antigen-binding fragment thereof is a Wnt signaling pathway antagonist or inhibitor. In certain embodiments, the vector is an expression vector, and may comprise a promoter operatively linked to the nucleic acid sequence. In particular embodiments, the vector is a viral vector.

In related aspects, the present invention provides a method for decreasing or inhibiting Wnt signaling in a tissue, comprising contacting the tissue with an effective amount of a cell comprising a nucleic acid sequence encoding an anti-Fzd antibody or antigen-binding fragment thereof, wherein the anti-Fzd antibody or antigen-binding fragment thereof is a Wnt signaling pathway antagonist or inhibitor. In particular embodiments, the cell is a heterologous cell or an autologous cell obtained from the subject to be treated. In certain embodiments, the cell was transduced with a vector comprising an expression cassette encoding the anti-Fzd antibody or antigen-binding fragment thereof, wherein the anti-Fzd antibody or antigen-binding fragment thereof is a Wnt signaling pathway antagonist or inhibitor. In particular embodiments, the cell is a stem cell, e.g., an adipose-derived stem cell or a hematopoietic stem cell.

Anti-Fzd antibodies and antigen-binding fragments thereof, wherein the anti-Fzd antibody or antigen-binding fragment thereof is a Wnt signaling pathway antagonist or inhibitor, may be used in to treat a disease, disorder or condition, for example, by decreasing or inhibiting Wnt signaling in a cell, tissue or organ. Thus, in some aspects, the present invention provides a method for treating a disease or condition in a subject in need thereof, e.g., a disease or disorder associated with increased or deregulated Wnt signaling, or for which decreased Wnt signaling would provide a therapeutic benefit, comprising contacting the subject with an effective amount of a composition comprising an anti-Fzd antibody or antigen-binding fragment thereof, wherein the anti-Fzd antibody or antigen-binding fragment thereof is a Wnt signaling pathway antagonist or inhibitor. In particular embodiments, the composition is a pharmaceutical composition comprising any of: an anti-Fzd antibody or antigen-binding fragment thereof; a polynucleotide comprising a nucleic acid sequence encoding an anti-Fzd antibody or antigen-binding fragment thereof, e.g., a DNA or mRNA, optionally a modified mRNA; a vector comprising a nucleic acid sequence encoding an anti-Fzd antibody or antigen-binding fragment thereof, e.g., an expression vector or viral vector; or a cell comprising a nucleic acid sequence encoding an anti-Fzd antibody or antigen-binding fragment thereof, e.g., a cell transduced with an expression vector or viral vector encoding an anti-Fzd antibody or antigen-binding fragment thereof. In particular embodiments, the disease or condition is a pathological disease or disorder, or an injury. In some embodiments, contacting occurs in vivo, i.e., the subject composition is administered to a subject.

In related aspects, the present invention provides a method for treating a disease or condition, e.g., a disease or disorder associated with increased Wnt signaling, or for which reduced Wnt signaling would provide a therapeutic benefit, comprising contacting a subject in need thereof with a pharmaceutical composition comprising an effective amount of a polynucleotide comprising a nucleic acid sequence encoding an anti-Fzd antibody or antigen-binding fragment thereof, wherein the antibody or antigen-binding fragment thereof is a Wnt signaling pathway antagonist or inhibitor, disclosed herein. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences In related aspects, the present invention provides a method for treating a disease or condition, e.g., a disease or disorder associated with increased Wnt signaling, or for which decreased Wnt signaling would provide a therapeutic benefit, comprising contacting a subject in need thereof with a pharmaceutical composition comprising an effective amount of a vector comprising a nucleic acid sequence encoding an anti-Fzd antibody or antigen-binding fragment thereof, wherein the antibody or antigen-binding fragment thereof is a Wnt signaling pathway antagonist or inhibitor. In certain embodiments, the vector is an expression vector, and may comprise a promoter operatively linked to the nucleic acid sequence. In particular embodiments, the vector is a viral vector.

In related aspects, the present invention provides a method for treating a disease or condition, e.g., a disease or disorder associated with increased Wnt signaling, or for which decreased Wnt signaling would provide a therapeutic benefit, comprising contacting a subject in need thereof with a pharmaceutical composition comprising an effective amount of a cell comprising a nucleic acid sequence encoding an anti-Fzd antibody or antigen-binding fragment thereof, wherein the antibody or antigen-binding fragment thereof is a Wnt signaling pathway antagonist or inhibitor. In particular embodiments, the cell is a heterologous cell or an autologous cell obtained from the subject to be treated. In certain embodiments, the cell was transduced with a vector comprising an expression cassette encoding the anti-Fzd antibody or antigen-binding fragment thereof. In particular embodiments, the cell is a stem cell, e.g., an adipose-derived stem cell or a hematopoietic stem cell.

In certain embodiments, methods of treating or preventing diseases or disorders in a subject in need thereof, by providing to the subject an effective amount of an anti-Fzd antibody, or an antigen-binding fragment thereof, wherein the antibody or the antigen-binding fragment thereof is an inhibitor of a Wnt signaling pathway, may be used to treat a cancer or tumor, e.g., a solid or liquid tumor. Examples of cancers and tumors that may be treated include, but are not limited to: colon tumors (e.g. colon cancer or adenoma), stomach tumors (e.g., stomach cancer), small intestine tumors (e.g., small intestinal cancer), liver tumors (e.g., liver cancer), pancreas tumors (e.g., pancreatic cancer), lung tumors (e.g., lung cancer), ovary tumors (e.g., ovarian cancer), kidney (e.g., kidney cancer), brain tumors (e.g., brain cancer), spinal cord tumors (e.g., spinal cord cancer), skin tumors (e.g., skin cancer or melanoma), head and neck tumors (e.g., head and neck cancer), gastointestinal tract tumors (e.g., gastrointestinal cancer, esophageal cancer, oral mucosa cancer, tongue cancer, stomach cancer, intestinal cancer, colon cancer), breast tumors (e.g., breast cancer), prostate tumors (e.g., prostate cancer), bone tumors (e.g., bone cancer), vascular tumors, Wilms tumor, leukemina/lymphoma, soft tissue tumors (e.g., soft tissue sarcoma or synovial sarcoma) and metastatic cancers, etc.

In certain embodiments, methods of treating or preventing diseases or disorders in a subject in need thereof, by providing to the subject an effective amount of an anti-Fzd antibody, or an antigen-binding fragment thereof, wherein the antibody or the antigen-binding fragment thereof is an inhibitor of a Wnt signaling pathway, may be used to treat degenerative diseases. Examples of degenerative diseases that may be treated include, but are not limited to osteoarthritis, cartilage degeneration, sports injuries (e.g., cartilage injury), retinopathy, atherosclerosis, neurodegenerative disorders, and vascular disorders e.g. vasculitis, conditions with abnormal angiogenesis.

In certain embodiments, methods of treating or preventing diseases or disorders in a subject in need thereof, by providing to the subject an effective amount of an anti-Fzd antibody, or an antigen-binding fragment thereof, wherein the antibody or the antigen-binding fragment thereof is an inhibitor of a Wnt signaling pathway, may be used to treat fibrosis. Examples of fibrosis that may be treated include, but are not limited to, lung fibrosis (including but not limited to COPD and idiopathic pulmonary fibrosis), kidney fibrosis (e.g. end stage renal failure), liver fibrosis, congenital liver storage diseases, and cardiac fibrosis.

In certain embodiments, methods of treating or preventing diseases or disorders in a subject in need thereof, by providing to the subject an effective amount of an anti-Fzd antibody, or an antigen-binding fragment thereof, wherein the antibody or the antigen-binding fragment thereof is an inhibitor of a Wnt signaling pathway, may be used to treat heart failure, e.g., congestive heart failure, systolic heart failure, heart failure with preserved ejection fraction, or coronary artery disease.

In certain embodiments, methods of treating or preventing diseases or disorders in a subject in need thereof, by providing to the subject an effective amount of an anti-Fzd antibody, or an antigen-binding fragment thereof, wherein the antibody or the antigen-binding fragment thereof is an inhibitor of a Wnt signaling pathway, may be used to treat heterotopic ossification, osteopetrosis, or congenital high bone mass disorders.

The terms "administering" or "introducing" or "providing", as used herein, refer to delivery of a composition to a cell, to cells, tissues and/or organs of a subject, or to a subject. Such administering or introducing may take place in vivo, in vitro or ex vivo.

In particular embodiments, a pharmaceutical composition is administered parenterally, e.g., intravenously, orally, rectally, or by injection. In some embodiments, it is administered locally, e.g., topically or intramuscularly.

In some embodiments, a composition is administered to target tissues, e.g., to bone, joints, ear tissue, eye tissue, gastrointestinal tract, skin, a wound site or spinal cord. Methods of the invention may be practiced in vivo or ex vivo. In some embodiments, the contacting of a target cell or tissue with a tissue-specific Wnt signal enhancing molecule is performed ex vivo, with subsequent implantation of the cells or tissues, e.g., activated stem or progenitor cells, into the subject. The skilled artisan can determine an appropriate site of and route of administration based on the disease or disorder being treated.

The dose and dosage regimen may depend upon a variety of factors readily determined by a physician, such as the nature of the disease or disorder, the characteristics of the subject, and the subject's history. In particular embodiments, the amount of anti-Fzd antibody or antigen-binding fragment thereof, e.g., a Wnt surrogate, administered or provided to the subject is in the range of about 0.01 mg/kg to about 50 mg/kg, 0.1 mg/kg to about 500 mg/kg, or about 0.1 mg/kg to about 50 mg/kg of the subject's body weight.

The terms "treatment", "treating" and the like are used herein to generally mean obtaining a desired pharmacologic and/or physiological effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent (e.g., anti-Fzd antibody or antigen-binding fragment thereof) may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. In some embodiments, the subject method results in a therapeutic benefit, e.g., preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Promoting Cell, Tissue and Organoid Growth and Related Methods

Other embodiments relate, in part, to the use of the Wnt surrogate molecules disclosed herein to promote or enhance the growth or proliferation of cells, tissues and organoids, for example, by contacting cells or tissue with one or more Wnt surrogate, optionally in combination with a Norrin or Rspondin polypeptide. In certain embodiments, the cells or tissue are contacted ex vivo, in vitro, or in vivo. Such methods may be used to generate cells, tissue or organoids for therapeutic use, e.g., to be transplanted or grafted into a subject. They may also be used to generate cells, tissue or organoids for research use. The Wnt surrogate molecules have widespread applications in non-therapeutic methods, for example in vitro research methods.

The invention provides a method for tissue regeneration of damaged tissue, such as the tissues discussed above; comprising administering a Wnt surrogate molecule to cells. The Wnt surrogate molecule may be administered directly to the cells in vivo, administered to a subject orally, intravenously, or by other methods known in the art, or administered to ex vivo cells. In some embodiments where the Wnt surrogate molecule is administered to ex vivo cells, these cells may be transplanted into a subject before, after or during administration of the Wnt surrogate molecule.

Wnt signaling is a key component of stem cell culture. For example, the stem cell culture media as described in WO2010/090513; WO2012/014076, Sato et al., 2011 (GASTROENTEROLOGY 2011; 141: 1762-1772) and Sato et al., 2009 (Nature 459, 262-5). The Wnt surrogate molecules disclosed herein are suitable alternatives to Rspondin for use in these stem cell culture media, or may be combined with Rspondin.

Accordingly, in one embodiment, the disclosure provides a method for enhancing the proliferation of stem cells comprising contacting stem cells with one or more Wnt surrogate molecules disclosed herein. In one embodiment, the disclosure provides a cell culture medium comprising one or more Wnt surrogate molecules disclosed herein. In some embodiments, the cell culture medium may be any cell culture medium already known in the art that normally comprises Wnt or Rspondin, but wherein the Wnt or Rspondin is replaced (wholly or partially) or supplemented by Wnt surrogate molecule(s) disclosed herein. For example, the culture medium may be as described in as described in WO2010/090513, WO2012/014076, Sato et al., 2011 (GASTROENTEROLOGY 2011; 141: 1762-1772) and Sato et al., 2009 (Nature 459, 262-5), which are hereby incorporated by reference in their entirety.

Stem cell culture media often comprise additional growth factors. This method may thus additionally comprise supplying the stem cells with a growth factor. Growth factors commonly used in cell culture medium include epidermal growth factor (EGF, (Peprotech), Transforming Growth Factor-alpha (TGF-alpha, Peprotech), basic Fibroblast Growth Factor (bFGF, Peprotech), brain-derived neurotrophic factor (BDNF, R&D Systems), Hepatocyte Growth Factor (HGF) and Keratinocyte Growth Factor (KGF, Peprotech, also known as FGF7). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound/molecule which is proteolytically cleaved to generate the 53-amino acid peptide hormone that stimulates cells. EGF or other mitogenic growth factors may thus be supplied to the stem cells. During culturing of stem cells, the mitogenic growth factor may be added to the culture medium every second day, while the culture medium is refreshed preferably every fourth day. In general, a mitogenic factor is selected from the groups consisting of: i) EGF, TGF-alpha, and KGF, ii) EGF, TGF-alpha, and FGF7; iii) EGF, TGF-alpha, and FGF; iv) EGF and KGF; v) EGF and FGF7; vi) EGF and a FGF; vii) TGF-alpha and KGF; viii) TGF-alpha, and FGF7; ix) or from TGF-alpha and a FGF. In certain embodiments, the disclosure includes a stem cell culture media comprising a Wnt surrogate molecule disclosed herein, e.g., optionally in combination with one or more of the growth factors or combinations thereof described herein.

These methods of enhancing proliferation of stem cells can be used to grow new organoids and tissues from stem cells, as for example described in WO2010/090513 WO2012/014076, Sato et al., 2011 (GASTROENTEROLOGY 2011: 141: 1762-1772) and Sato et al., 2009 (Nature 459, 262-5).

In some embodiments; the Wnt surrogate molecules are used to enhance stem cell regeneration. Illustrative stem cells of interest include but are not limited to: muscle satellite cells; hematopoietic stem cells and progenitor cells derived therefrom (U.S. Pat. No. 5,061,620): neural stem cells (see Morrison et al. (1999) Cell 96: 737-749); embryonic stem cells; mesenchymal stem cells; mesodermal stem cells; liver stem cells; adipose-tissue derived stem cells, etc.

Diagnostic and Related Methods

Other embodiments of the present invention relate, in part, to diagnostic applications for detecting the presence of cells or tissues expressing one or more Fzd receptors. Thus, the present disclosure provides methods of detecting one or more Fzd receptor in a sample, such as detection of cells or tissues expressing Fzd1. Such methods can be applied in a variety of known detection formats, including, but not limited to immunohistochemistry (INC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA). In particular embodiments, a method comprises contacting a tissue or cell, e.g., obtained from a subject, with an antibody or antigen-binding fragment thereof disclosed herein, and then determining an amount of binding of the antibody or antigen-binding fragment thereof to the tissue or cell, thus determining the presence of or an amount of the Fzd receptor(s) in the tissue or cell.

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies and antigen-binding fragments thereof described herein are conjugated to a detectable label that may be detected directly or indirectly. In this regard, an antibody "conjugate" refers to an anti-Fzd antibody or antigen-binding fragment thereof that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to an antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), ß-galactosidase (GAL), glucose-6-phosphate dehydrogenase, ß-N-acetylglucosamimidase, ß-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BLIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BLIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting one or more Fzd receptor or cells or tissues expressing one or more Fzd receptors in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

Example 1

Characterization of Anti-Fzd Antibodies

Antibody Fab, scFv and VHH or sdAb fragments disclosed herein were sequenced and sub-cloned into mammalian expression vectors for expression, purification, and characterization of binding affinities to various Fzd receptors.

Soluble recombinant proteins were prepared by transfection of respective expression vectors into Expi293F cells (Thermo Fisher Scientific, Waltham, MA) according to the manufacturer's instructions. Briefly, four days after the transfection, cell culture medium was collected after spin down the cell pellet. The media were incubated with either Protein A resin (REPLIGEN, Waltham, MA) for collecting proteins containing human IgG-Fc portion, or Nickel affinity resin (Roche, Basel, Switzerland) for collecting proteins conjugated with His-tag. Proteins were eluted with 10 mM glycine, pH 3.5 from Protein A resin, or with 150 mM imidazole, pH 7.4 from Nickel affinity resin, respectively.

Subsequently, the protein elutes were fractionated and further purified by size-exclusion chromatography (SEC). SEC was performed by a fast protein liquid chromatography using a Superdex 200 Increase 10/300 GL (GE Healthcare, Pittsburgh, PA) in HBS buffer (10 mM HEPES, 150 mM NaCl, pH7.4). Each protein was injected onto the column at a volume of 475 µl or 500 µl. The absorbance at 280 nm was monitored, and the 500 µl fractions of all elutes were collected. Each collected faction near main peak was further analyzed by SDS-Polyacrylamide Gel Electrophoresis (SDS-PAGE) to confirm the content. SDS-PAGE was performed using Tris-HCl 4-15% gel (Bio-Rad, Hercules, CA) under both non-reducing and reducing conditions. The samples were prepared in Laemmli sample buffer and heated at 100° C. for 5 min.

Protein concentrations were determined using a Nano-Drop Spectrophotometer (Thermo Scientific) by the direct UV A280 method. The relationship of absorbance to protein concentration is linear based on Beer-Lamber equation, $A=\varepsilon lc$; A is the absorbance value, $\varepsilon$ is the wavelength-dependent extinction coefficient, l is the path length in centimeters, and c is the protein concentration. The experimental extinction coefficients of all produced proteins were estimated by their amino acid sequences.

Binding kinetics of antibody fragments to a variety of Fzd cysteine rich domain (CRD) protein targets (Fzd1, Fzd2, Fzd3, Fzd4, Fzd5, Fzd6, Fzd7, Fzd8, Fzd9 and/or Fzd10 CRDs) was determined by bio-layer interferometry (BLI) using Octet Red 96 (PALL ForteBio, Fremont, CA) instruments at 30° C., 1000 rpm with streptavidin (SA) biosensors. C-terminal biotinylated Fzd CRD recombinant protein was diluted to 20 nM in the running buffer (PBS, 0.05% Tween-20, 0.5% BSA, pH 7.2) and captured to the SA biosensor until coupling length reached 0.2 nm. Following capture of the Fzd CRD, the SA biosensor with captured biotinylated-Fzd CRD was dipped into wells containing the relevant antibody fragment at 7 different concentrations (0, 1.37, 4.12, 12.4, 37, 111.1, 333.3, 1000 nM) in running buffer, plus a well with only running buffer as a reference channel. Kip was determined by global fitting, 1:1 binding model according to manufacturer recommended settings.

Table 1A provides the heavy chain CDRs (CDRH1, CDRH2, and CDRH3) and light chain CDRs (CDRL1, CDRL2, and CDRL3) for the indicated antibody clones. The Abgenesis software from Distributed Bio was used to map the specificity determining regions (SDRs) shown below, which include the Kabat definition of CDRs (Padlan et al. FASEB J. 9, 133-139 (1995).

Where light chain CDRs are not provided, the antibody fragment did not comprise a light chain, e.g., the antibody was an Fab or VHH or sdAb. Table 1A also indicates the initial Fzd receptor the antibody fragment was shown to bind. The Fzd receptor to which each clone was initially identified as binding was determined by detection of phage-displayed antibody fragments bound to target antigen immobilized on Nunc Maxisorb microtiter plates (Thermo Fisher Scientific, Waltham, MA) by single-dose or dose-dependent ELISA. Detection of bound phage was determined calorimetrically by turnover of TMB substrate (Thermo Fisher Scientific, Waltham, MA) at 415 nm by anti-M13-HRP antibody (GE Healthcare, Pittsburgh, PA). Clones were identified as binding to a Fzd receptor when the fold OD 450 nm over background was greater than a threshold level.

TABLE 1A

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 001S-A01 | Fzd1 | YTFTSYGIS | 300 | GWISAYNGN TNYA | 477 | CARASAWTPYGAFD IW | 649 | SGGSSNIGSHT VS | 1052 | SNYQRPS | 1150 | CAAWDGSLF GHWVF | 1159 |
| 001S-B01 | Fzd1 | GSISSGGY SWS | 195 | GSIYHSGSTYY N | 454 | CARFYDILTGYSYFD YW | 715 | RSSRSLLDTDD GNTYLD | 1040 | TLSHRAS | 1153 | CMQSIQLPW TF | 1188 |
| 001S-E01 | Fzd1 | GSISNYY WS | 194 | GEIDRSGDTN YN | 397 | CARVRARRFLVSDRS AFDIW | 842 | SGNTLGSHYVS | 1051 | QD5KRPS | 1140 | CQVWDSSTV VF | 1323 |
| 001S-F01 | Fzd1 | GSIGNNY YZG | 193 | GSIYFTGGTYY N | 454 | CARVMLITDAFDIW | 839 | RSSQSLLHSNG YNYLD | 1036 | LGSNRAS | 1131 | CMQGTHWP YTF | 1182 |
| 001S-G01 | Fzd1 | GSISSSSYY WG | 197 | GYIYYSGSTYY N | 496 | CARATYGGDAFDIW | 657 | TRSSSNIGAGY DVH | 1057 | GNSIRPS | 1114 | CGTWDSSLSA WVF | 1161 |
| 001S-H01 | Fzd1 | GSISSGGY YWS | 196 | GYIYYSGSTYY N | 496 | CARHAGFVGLADYF DYW | 772 | RSSQSLLHSNG YNYLD | 1036 | LGSKRAS | 1130 | CMQALQIPPT F | 1174 |
| 001S-A02 | Fzd1 | GSISSGGY YWS | 196 | GYIYYSGSTYY N | 496 | CARGKGYSYGYGKD WFDPW | 742 | QASQDIGKYLN | 938 | DASNLET | 1081 | CQQNDYLPLT F | 1223 |
| 001S-E02 | Fzd1 | GSIGNNY YWG | 192 | GSIYFTGGTYY N | 454 | CARVMLITDAFDIW | 839 | RSSQSLLHSNG YNYLD | 1036 | LGSNRAS | 1131 | CMQGTHWP YTF | 1182 |
| 001S-G02 | Fzd1 | GAIGTSY FWG | 179 | GSIYYTGNTY YN | 455 | CARIGIAVAAPVDH W | 779 | RASQSVGTYLT | 1008 | DASNRAT | 1084 | CMQATQFPL TF | 1178 |
| 001S-H02 | Fzd1 | GSISSSSYY WG | 197 | GYIYYSGSTYY N | 496 | CARATYGGDAFDIW | 657 | TRSSSNIGAGY DVH | 1057 | GNSIRPS | 1114 | CGTWDSSLSA WVF | 1161 |
| 001S-A03 | Fzd1 | GSISSGGY YWS | 196 | GYIYYSGSTYY N | 496 | CARVRDYYDSSGYYY DYFDYW | 843 | RASRSISSYFN | 1026 | AASSLQS | 1071 | CQQADTFPPT F | 1206 |
| 001S-B03 | Fzd1 | ASFSGHY WT | 72 | GEIDHTGSTN YE | 396 | CARGGQGYDWGH YHGLDVW | 732 | SGDKVGHKYA S | 1050 | EDSQRPS | 1095 | CQAWDSSTD VVF | 1194 |
| 001S-H08 | Fzd5 | RAFTDNV MA | 239 | ATISGGGGST FDD | 375 | CAAASSLTSTPYDLW | 575 | | | | | | |
| 001S-A09 | Fzd5 | RSFRTNAL G | 243 | AAISWTGGST YYA | 331 | CNTVTYTGGSYKNY W | 902 | | | | | | |
| 001S-B09 | Fzd5 | SIDSINAM A | 266 | AALTSGGITY HA | 337 | CNVITIVRGMGPRAY W | 903 | | | | | | |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 001S-C09 | Fzd5 | SIFSINAMG | 267 | ATIQSGGRTNYA | 374 | CNVITIVRGMGPRAYW | 903 | | | | | | |
| 001S-C07 | Fzd8 | YTFTSYGIS | 300 | GWISAYNGNTNYA | 477 | CARDGTPFYSGSYYGSW | 669 | QGDSLRTYYAS | 949 | GKNNRPS | 1113 | CNSRDNSGKHKVF | 1193 |
| 001S-D07 | Fzd8 | GTFSSYAIS | 207 | GRIIPILGIANYA | 438 | CARVPTSPYDILTGPFDYW | 841 | RSSQSLLHSNGFNYVD | 1034 | FGSYRAS | 1100 | CMQNLQTPWTF | 1184 |
| 001S-E07 | Fzd8 | ASVSNSAAWN | 73 | GRTYRSKWYNDYA | 451 | CARWKNYFDPW | 850 | RASQGIRSDLA | 967 | AASTLES | 1073 | CLQDYSYPRTF | 1167 |
| 001S-H07 | Fzd8 | FTFSSYAMS | 141 | STISGGGGSTYYA | 553 | CAKDLVPWGSSAPNIW | 601 | RASQSVSVSYLA | 1019 | GASRAT | 1107 | CQQYGSSPPTF | 1302 |
| 004S-E05 | Fzd5 | FTFSTYEMN | 156 | SGVSWNGSRTHYV | 525 | CARGQSEKWWSGLYGMDVW | 753 | RASQGISSALA | 973 | AASALQS | 1061 | CQQTYSTPRTF | 1286 |
| 004S-E03 | Fzd5 | GTFSTYAIS | 210 | GWINSGNGNTKYS | 472 | CWTGLLWFGESTDAFDIW | 928 | RASQSISSYLN | 996 | AASSLQS | 1071 | CQQSYSTPLTF | 1264 |
| 004S-G06 | Fzd5 | GTFTYRYLH | 218 | GGIPIFGTGNYA | 410 | CASSMVRVPYYGMDVW | 861 | RASQSISSYLN | 996 | AASSLQS | 1071 | CQQSYSTPLTF | 1264 |
| 001S-D09 | Fzd8 | GPFNLFAMG | 184 | AGISRTGGNTGYA | 354 | CASKTTINSGWSREYHYW | 855 | | | | | | |
| 001S-E09 | Fzd8 | GPFNLFAMG | 184 | AGISRTGGNTGYA | 354 | CASKTTINSGWSREYHYW | 855 | | | | | | |
| 001S-F09 | Fzd8 | GFFSSFTMG | 181 | AAISRNGVYTRFA | 318 | CNALAPGVRGSW | 884 | | | | | | |
| 001S-G09 | Fzd8 | SLFRLNGMG | 270 | ATISTRGTTHYA | 376 | CTDEESW | 908 | | | | | | |
| 001S-H09 | Fzd8 | GPFNLLAMG | 185 | AGISRTGGNTGYA | 354 | CASKTTINSGWSREYHYW | 855 | | | | | | |
| 001S-A10 | Fzd8 | SVVNFVVMG | 274 | AAITSGGSTNYA | 334 | CNRVGSREYSYW | 898 | | | | | | |
| 001S-B10 | Fzd8 | RTSDLYTMG | 262 | AAIGYKVKWNGERTYYL | 313 | CNAVTYNGYTIW | 891 | | | | | | |
| 001S-G12 | Fzd1 | SIFSSNTIY | 269 | ALITTSGNTNYA | 364 | CNAGAPAWTYRMGTYYPQFGSW | 883 | | | | | | |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 SEQ ID CDRL1 | CDRL2 SEQ ID CDRL2 | CDRL3 SEQ ID CDRL3 |
|---|---|---|---|---|---|---|---|---|---|---|
| 002S-A01 | Fzd1 | STFSTYA MG | 272 | AAISGSGENT YYA | 317 | CVKFGMNLGYSGYD YW | 925 | | | |
| 002S-B01 | Fzd1 | STFSNYA MG | 271 | AAISWGGGS TFYS | 320 | CAAGPIARWYRGD MDYW | 578 | | | |
| 002S-C01 | Fzd1 | RMFSNYA MG | 241 | AAISGGSGT YYS | 319 | CAAGPIARWYRGD MDYW | 578 | | | |
| 002S-D01 | Fzd1 | RTDGGYV MG | 247 | ATVTWRTGT TYYA | 378 | CAAGPIARWYRGD MDYW | 578 | | | |
| 002S-E01 | Fzd1 | RTFSSAA MG | 255 | AAISWSGGSTA YYA | 330 | CATLTPYGTVASY | 871 | | | |
| 002S-F01 | Fzd1 | RTFSSYA MG | 257 | AAVNWSGGS TYYA | 339 | CAAVFLSRNYEIQEY YRYQ | 586 | | | |
| 002S-G01 | Fzd1 | RTFSSYA MG | 257 | AAISWSGGST YYA | 327 | CAAGPIARWYRGD MDYW | 578 | | | |
| 002S-H01 | Fzd1 | RSFSTYP MG | 246 | TVISGSGGST YYS | 574 | CAAGPIARWYRGD MDYW | 578 | | | |
| 002S-A02 | Fzd1 | RRFTTYG MG | 242 | AAVTWRSGS TYYA | 345 | CYLEGPLDVYW | 929 | | | |
| 002S-B02 | Fzd1 | RTFNRHV MG | 251 | AAISWSGDST YYA | 324 | CAKLGGSSWLREYD YW | 621 | | | |
| 002S-C02 | Fzd1 | RTFRAYA MG | 252 | SAISWSGGST YYA | 510 | CAAGPIARWYRGD MDYW | 578 | | | |
| 002S-D02 | Fzd1 | RTFSEYA MG | 253 | AAISWSGGST HYA | 326 | CNADSLRGIDYW | 881 | | | |
| 002S-E02 | Fzd1 | FTFREYA MT | 113 | SGISRDGGRT SYS | 520 | CAPRVLVTAPSGGM DYW | 631 | | | |
| 002S-F02 | Fzd1 | GDFTNYA MA | 180 | AAVNWRGD GTYYS | 338 | CAAVFLSRNYEIQEY YRYQ | 586 | | | |
| 002S-G02 | Fzd1 | RTFGTWA MG | 250 | AAISYNGFST YYS | 333 | CAAGPIARWYRGD MDYW | 578 | | | |
| 002S-H02 | Fzd1 | RTFSSYA MG | 257 | AAISWSGGST YYA | 327 | CAAGPIARWYRGD MDYW | 578 | | | |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 002S-D03 | Fzd1 | RTFGSYAMG | 249 | AAISWSGGSTYYA | 327 | CAAGPIARWYRGDMDYW | 578 | | | | | | |
| 002S-E03 | Fzd1 | SIFSIYAMG | 268 | AVVATGATNYA | 390 | CNMRGNWYREGRPAEFLSW | 897 | | | | | | |
| 002S-F03 | Fzd1 | RTSSSYAMG | 263 | AAISWSGGSTYYA | 327 | CAAGPIARWYRGDMDYW | 578 | | | | | | |
| 002S-G03 | Fzd1 | RTFGSYAMG | 249 | AAISWSGGSTYYA | 327 | CAAGPIARWYRGDMDYW | 578 | | | | | | |
| 002S-H03 | Fzd1 | QTFTAYAMG | 237 | AAISWSGSATHYA | 329 | CNAWLVAGSRGTSADYW | 893 | | | | | | |
| 002S-A04 | Fzd1 | RTFSSYAMG | 257 | AAISWSGRSTYYA | 328 | CAAGPIARWYRGDMDYW | 578 | | | | | | |
| 002S-B04 | Fzd1 | RTFSSYAMG | 257 | AAISWSGGSTYYA | 327 | CAAGPNYSMFMPSSSRLIW | 579 | | | | | | |
| 002S-C04 | Fzd1 | RRFTTYGMG | 242 | AAVTWRAGSTYYA | 344 | CSADKLDYLDDQPFKTWDYW | 907 | | | | | | |
| 002S-D04 | Fzd1 | GTSSTYAMG | 220 | AAINRSGGSTYYA | 314 | CAVFLSRNYEIQEYYRYQ | 586 | | | | | | |
| 002S-E04 | Fzd1 | GTFSTYAMG | 211 | AAISWSGDSTYYL | 325 | CAAGPIARWYRGDMDYW | 578 | | | | | | |
| 004S-H04 | Fzd5 | GTFSSYAIS | 207 | GWISTNGATNYA | 484 | CARGGAGRFGEGMDVW | 723 | RASQSISSYLN | 996 | AASSLQS | 1071 | CQQSYSTPLTF | 1264 |
| 001S-A04 | Fzd5 | YTFTSYGIS | 300 | GWISAYNGNTNYA | 477 | CASSKEKATYYYGMDVW | 860 | GLSSGSVSTNYYPS | 931 | YINTRSS | 1157 | CLLYLGRGIWVF | 1165 |
| 001S-D03 | Fzd5 | GTFSSYAIS | 207 | GRIIPILGIANYA | 438 | CARLDPGYYYGMDVW | 783 | TGTSSDVGGYNSVS | 1055 | DVTKRPS | 1092 | CFSYAGSRF | 1160 |
| 001S-F03 | Fzd5 | GTFSSYAIS | 207 | GGIIPIFGTANYA | 408 | CARVIFSTVTTNDIW | 836 | TRSSGSIASNYVQ | 1056 | ENDKRPS | 1096 | CQSYDYDHRWVF | 1322 |
| 004S-E04 | Fzd5 | YTFSGYYLH | 284 | GTVTPILGTANYA | 456 | CARVDGSYYGIDYW | 830 | RASQSISSYLN | 996 | AASSLQS | 1071 | CQQSYSTPLTF | 1264 |
| 004S-A06 | Fzd5 | GSFSNYAIS | 190 | GRIIPILGSANYA | 439 | CARTYLKAFDIW | 827 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 004S-F04 | Fzd5 | YTFTNNF MH | 292 | GRINPNSGGT NYA | 446 | CARDRFDNWFDPW | 685 | RASQGISSALA | 973 | AASTLQS | 1075 | CQQSYNTPW TF | 1243 |
| 001S-C03 | Fzd5 | GTFSSYAI S | 207 | GRIIPILGIANY A | 438 | CAREGRSRVYGGNS FDYW | 705 | RSSQSLLRRNG HNYVD | 1037 | MGSNRAP | 1132 | CMHGLHPPF TF | 1173 |
| 003S-A01 | Fzd1 | YIFTDYYM H | 278 | GGIIPIFGTAN YA | 408 | CARMSSDYYDSSGY YRRGMDVW | 792 | RASQGISNNLN | 969 | GASTLQS | 1109 | CQQADSFPPT F | 1205 |
| 003S-E01 | Fzd1 | YIFTDYYM H | 278 | GGIIPIFGTAN YA | 408 | CARAWKGLWFGEG TFDYW | 658 | RASQSISSYLN | 996 | AASSLQS | 1071 | CQQSYSTPLT F | 1264 |
| 003S-F01 | Fzd1 | GTFSSYAI S | 207 | GWINAGNGN TTYA | 465 | CARLAFDIW | 782 | RASQGISNYLA | 996 | AASSLQS | 1071 | CQQSYSTPLT F | 1264 |
| 003S-A02 | Fzd1 | YTFTGYY MH | 288 | GWINAGNGN TTYA | 465 | CAKDRGNYGDYLDY W | 604 | RASQSIGRWLA | 971 | EVSSVQG | 1098 | CQQSYSTPLA F | 1262 |
| 003S-C02 | Fzd1 | FTFSNSD MN | 128 | ALISYDGSHT YYA | 363 | CTRGSRIGMFDPW | 912 | RASQGISNNLN | 982 | AASRLQS | 1067 | CQQGFNFPLT F | 1217 |
| 003S-E02 | Fzd1 | GTFSYTIS | 208 | GGIIPISGKTD YA | 414 | CARARGGDSPLSL | 646 | RASQVSVSDLA | 969 | TASSLQS | 1152 | CLQDYSYPYT F | 1168 |
| 003S-F02 | Fzd1 | GTFSSYAI N | 204 | GGIIPIFGTAN YA | 408 | CARGGWRPDYYGS GSYYSFDYW | 737 | RASESVSSSS FA | 1013 | GASTRAT | 1111 | CQQYETWPV LTF | 1297 |
| 003S-G02 | Fzd1 | FTFGTYW VT | 110 | SGITGSSGRT FYA | 523 | CARMKDWFGAFDI W | 791 | RASESVSSSS | 953 | GASTRAT | 1111 | CQQYNNWP PNYTF | 1312 |
| 003S-C03 | Fzd1 | FTFSRYA MS | 134 | SYISGDSGYT NYA | 566 | CARGLVIATNWFDP W | 746 | QANQDISNYL N | 935 | AASSLQS | 1071 | CQQTYNPPR TF | 1281 |
| 003S-D03 | Fzd1 | YTFTSYYM H | 301 | GWINTYNGN TNYP | 474 | CAESLTTADW | 588 | RASQGISNNLN | 969 | AASSLQR | 1070 | CQQSYSTPFT F | 1260 |
| 003S-E03 | Fzd1 | GWVNPTTGM | 278 | GWVNPTTGN TGYA | 493 | CARNVEGATSFPEFD YW | 795 | RASQSISSYLN | 969 | SASNLQS | 1146 | CQQSYSPPPY TF | 1256 |
| 003S-H03 | Fzd1 | YIFTDYYM H | 278 | GGIIPIFGTAN YA | 408 | CAKDIGSSWYYYMD VW | 598 | RASQSISSYLN | 996 | AASSLQS | 1071 | CQQSYSTPLT F | 1264 |
| 003S-A04 | Fzd1 | FTFGTYW VT | 110 | SGITGSSGRT FYA | 523 | CARMKDWFGAFDI W | 791 | RTSERSSISS FA | 1046 | GASTRAT | 1111 | CQQYNNWP RNYTF | 1312 |
| 003S-C04 | Fzd1 | FAVSSSY MS | 82 | ASIWFDGSN QDYA | 372 | CAPNESGNVDYW | 630 | RASQGISNNLN | 969 | KASSLEN | 1119 | CQQSYSTPHT F | 1261 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 003S-D04 | Fzd1 | FTFSSYAMH | 141 | SAISGSGGSTYYA | 507 | CARDHGSWYQNTDAFDIW | 671 | QASQDIGNYLN | 939 | DVSNLER | 1091 | CQHLNSYPPGDTF | 1197 |
| 003S-G04 | Fzd1 | FRFISHPIH | 91 | GRVIPILGVTNYA | 453 | CASSSDYGDYLKEPNYGMDVW | 863 | RASQSISYLN | 996 | AASSLQS | 1071 | CQQSYSTPLTF | 1264 |
| 003S-D05 | Fzd2 | FTFSNYAMT | 130 | SAIGTGGGTYYA | 502 | CATAYRPGGLDVW | 866 | RSSQSLLHSDGKTYLY | 1032 | LGSNRAS | 1131 | CMQNTHWPLTR | 1186 |
| 003S-E05 | Fzd2 | FTFSSYTMS | 149 | GRIKSKANGGTTDYA | 444 | CARGSSSWYDW | 760 | KSSQSLLHSDGKTYLY | 932 | LGSNRAS | 1131 | CMQNTHWPLTR | 1186 |
| 003S-A06 | Fzd2 | FTFADYGMH | 102 | SYISSGSYTIYYS | 567 | CARGTFDWLLSPSYDYW | 762 | RASQGISNNLN | 969 | AASRLES | 1066 | CQQSYSTPLTF | 1264 |
| 003S-C06 | Fzd2 | FTFSNYGMH | 131 | SAISNSGGSTYYA | 508 | CTSSFLTGSQP5GYW | 915 | RASQDISSYLA | 962 | AASSLQS | 1071 | CQQSYRTPLTF | 1245 |
| 003S-G06 | Fzd2 | FTFSDYGMH | 121 | SSTSGSGGNSKYS | 549 | CARHNPGYMGYYYGMDVW | 774 | RASQSVSSNLA | 1014 | DASNRAT | 1084 | CQHRTSWPLTF | 1200 |
| 003S-H06 | Fzd2 | GTFSSYTIS | 208 | GLVDPEDGETIYA | 429 | CTILPAAAAGTYYYYGMDVW | 909 | RASQRVGNNLA | 981 | DASIRAT | 1080 | CQQYKDWPT | 1307 |
| 003S-B07 | Fzd2 | FTFSDHYMS | 119 | SSITRTPSGGTTEYA | 546 | CARDGGYW | 665 | RASQSVGSYLA | 1007 | GSSNRAA | 1115 | CQQYGTSLLT | 1306 |
| 003S-D07 | Fzd2 | YTFTNNFMH | 292 | GIINPSGGSTSYA | 422 | CARATSLGRRYCSSTSCYPRDAFDIW | 656 | QASQGISNNLN | 946 | LGSDRAS | 1127 | CQQSYSTPFTF | 1260 |
| 003S-E07 | Fzd2 | YTFTNNFMH | 292 | GWINPNSGGTKYA | 470 | CARSVGEVGATMLGIGVVYWFDPW | 823 | RASQSISSYLN | 996 | AASSLQS | 1071 | CQQSYSTPFTF | 1260 |
| 003S-A08 | Fzd2 | FTFSNYAMT | 130 | SAIGTGGGTYYA | 502 | CATAYRPGGLDVW | 866 | RSSQSLLHSDGKTYLY | 1032 | LGFNRAS | 1126 | CMQNTHWPLTR | 1186 |
| 003S-C08 | Fzd2 | LTVSTNFMS | 234 | AGIGWDSTNIGYA | 349 | CARDLVAARPSNWDYW | 679 | RASQGIRNDLG | 966 | GASTLQR | 1108 | CQQSYSTPRVTF | 1266 |
| 003S-E08 | Fzd2 | FTFRNSAMH | 115 | STISGSGGSTYYS | 554 | CARGGGYSSSW | 726 | RSSRSLLHSDGKTYLY | 1041 | LGSNRAS | 1131 | CMQSSHWPKTF | 1191 |
| 003S-G09 | Fzd4 | FTFDHNPMN | 108 | SAIGAGGGTYYA | 500 | CASPTVTRR | 857 | RASQSISYLN | 996 | AASSLQS | 1071 | CQQSYSTPLTF | 1264 |
| 003S-C10 | Fzd4 | GTFSSYAIS | 207 | GWINAGNGNTTYA | 465 | CARHYYGSGSYPDW | 777 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 003S-D10 | Fzd4 | FNFGIYSMT | 86 | SYISGDSGYTNYA | 566 | CARVGPGGWFDPW | 833 | RASQGISSYLA | 974 | AASNLLG | 1063 | CQQTYSTPWTF | 1288 |
| 003S-E10 | Fzd4 | FTFSSYAMH | 141 | AGISASGGSTYYA | 351 | CARPSTTGTKAPDIW | 798 | RASQSIGSNLD | 983 | AASTLET | 1074 | CQQSYSVPDTF | 1272 |
| 003S-A11 | Fzd4 | GTFSSYAIS | 207 | GWINAGNGNTTYA | 465 | CARHYYGSGSYPDW | 777 | RASQSISZYZN | 1001 | ZASSLQS | 1158 | CQQSYSTPLTF | 1264 |
| 003S-G11 | Fzd4 | GTFSSYAIS | 207 | GRIIPIFGTVNYA | 437 | CARGARLDYW | 717 | RASQSISSYLN | 996 | AASSLQS | 1071 | CQQSYSTPLTF | 1264 |
| 003S-H11 | Fzd4 | YTFTGYYMH | 288 | GGIIPIPGTPHVA | 411 | CASTDPSGLDYW | 864 | RASQSIGSNLD | 983 | DASSLES | 1085 | CQQSFIMPLTF | 1232 |
| 003S-C12 | Fzd4 | GTFSSYAIS | 207 | GWINPNSGGTNYA | 471 | CARGGSSDVR | 735 | RASQSISSYLN | 996 | AASSLQS | 1071 | CQQSYSTPLTF | 1264 |
| 003S-F12 | Fzd4 | FTFSSYAMH | 141 | SVISTSGDTVLYT | 559 | CARGGSSDVR | 735 | RASQSISSYLN | 996 | AASSLQS | 1071 | CQQSYSTPLTF | 1264 |
| 004S-B01 | Fzd4 | GTFSSYAIS | 207 | GIINPSGGSTSYA | 422 | CAKDGVVR | 595 | RAIQSISSYLN | 951 | AASSLQS | 1071 | CQQSYSTPLTF | 1264 |
| 004S-C01 | Fzd4 | FTFSNHYTS | 127 | STISSSGGRTFYA | 557 | CARASRIDGGWPIIDHL | 651 | RASQDIRDELA | 959 | AASTLQS | 1075 | CQQADSFPLTF | 1204 |
| 004S-D01 | Fzd4 | FTFTNYAMS | 161 | SAISGSGGSTYYA | 507 | CARATGFGTVVFDYW | 654 | RASQSISSYLN | 996 | AASSLQS | 1071 | CQQSYSTPLTF | 1264 |
| 004S-E01 | Fzd4 | GTFSSYAIS | 207 | GWINAGNGNTTYA | 465 | CARHYYGSGSYPDW | 777 | ZACLRIISYLN | 1059 | FASSLQS | 1099 | CQQSYSTPLTF | 1264 |
| 004S-F01 | Fzd4 | GTFSSYAIS | 207 | GWINAGNGNTTYA | 465 | CARDGVE | 670 | RASQGISNWLA | 970 | DASSLES | 1086 | CQQSHITPYT | 1235 |
| 004S-H01 | Fzd4 | FTFSNYAMH | 129 | ALMSPDGTIIYYA | 365 | CAKGIVGDYGAPDIW | 614 | RASQSISSYLN | 996 | AASSLQS | 1071 | CQQSYSTPLTF | 1264 |
| 004S-B02 | Fzd4 | FTFSSYGMH | 143 | SSINNSRTVFYA | 537 | CAKDHLAVADAHGR | 597 | RASQSISSYLN | 996 | AASSLQS | 1071 | CQQSYSTPLTF | 1264 |
| 004S-E02 | Fzd4 | FTFSSYAMH | 141 | AVISYDGSNEYYA | 383 | CAGGEVYEL | 589 | RASQSISSYLN | 996 | AASSLQS | 1071 | CQQSYSTPLTF | 1264 |
| 004S-F02 | Fzd4 | FTFSTYAMH | 155 | AVISSDGNNKYYT | 382 | CAAPDVVVTADGYYW | 582 | RASQGISSALA | 973 | AASTLQS | 1075 | CQQANTVPFTF | 1214 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 004S-G02 | Fzd4 | FTFANYAMN | 104 | ALISYDGGTKYYA | 362 | CAKTLVITSHALHIW | 625 | RASQSISSYLN | 996 | AASSLQS | 1071 | CQQSYSTPLTF | 1264 |
| 004S-H02 | Fzd4 | FTFANYAMH | 103 | ALISYDGGNKYYA | 361 | CAKTLVITSHALHIW | 625 | RASQSISSYLN | 996 | AASSLQS | 1071 | CQQSYSTPLTF | 1264 |
| 001S-E03 | Fzd5 | GSFSGYYWH | 188 | GEINHSGSTNYN | 398 | CARGRRLVRFTVTSAFDIW | 755 | TGSSNIGAGFGVH | 1054 | SDRNRPS | 1149 | CQSYDSSLRASVF | 1321 |
| 001S-B05 | Fzd5 | GTFSSYAIS | 207 | GGIIPILGIANYA | 413 | CARIPKPRGYSYGDNGSW | 780 | RSSQSLLHSNGNTYLD | 1035 | LGSDRTS | 1128 | CMQSLQTPYTF | 1190 |
| 004S-A07 | Fzd6 | GNFKNYGIT | 183 | GRIIPALGTANYA | 434 | CARQYCSGGSCYPDAPDIR | 805 | RASQDIRSALA | 960 | QASSLIS | 1139 | CQQSYSMPQTF | 1253 |
| 004S-B07 | Fzd6 | FTFSSYSMN | 146 | GVISKDGDNKYYA | 460 | CASSRDGYNRLAPDIW | 862 | QASQDIRNYLN | 940 | AASSLQS | 1071 | CQQSRFWT | 1238 |
| 004S-A08 | Fzd6 | GTFSSYAIS | 207 | GRIIPILGIANYA | 438 | CARDGGDYGMDVW | 664 | RASQSISSYLN | 996 | AASSLQS | 1071 | CQQSYSTPLTF | 1264 |
| 004S-B08 | Fzd6 | YTFTNNFMH | 292 | GRINPNSGGTNYA | 446 | CASQNYYGSGSYPGFDYW | 858 | RASQSISSYLN | 996 | AASSLQS | 1071 | CQQSYSTPLTF | 1264 |
| 004S-D08 | Fzd6 | YTFTFYRYLH | 303 | GGIIPIFGTANYA | 408 | CATHDSSGYYSFDYW | 870 | RASQSISSYLN | 996 | AASSLQS | 1071 | CQQSYSTPLTF | 1264 |
| 004S-E08 | Fzd6 | FSVSSNYMN | 101 | SAIGTGGGTYYA | 502 | CTTRTYDSSGYYETQNYMDVW | 921 | RSSRSLLHSNGNTYLQ | 1042 | LGSNRAS | 1131 | CVQTTQSPLTF | 1326 |
| 004S-G08 | Fzd6 | FTFSDYYMS | 122 | AAISYDESNKFYA | 332 | CARSAVAGAFDIW | 813 | RASQSISSYLN | 996 | AASSLQS | 1071 | CQQSYSTPLTF | 1264 |
| 004S-A09 | Fzd6 | FTFRDYAMN | 112 | SGISWNSGSIGYA | 522 | CARRSGYSGSVYYYYGMDVW | 810 | RASQSISSYLN | 996 | AASSLQS | 1071 | CQQSYSTPLTF | 1264 |
| 004S-B09 | Fzd6 | FTFSSFGMH | 135 | AGINWNGGSVVYA | 350 | CARGPSHQHTFDIW | 751 | RASQGISSALA | 973 | AASSLQS | 1071 | CQQSYSHTAFTF | 1249 |
| 004S-C09 | Fzd6 | YTFTNNFMH | 292 | GGFDPEDGETIYA | 401 | CARVGRGYSFDYW | 834 | RASQSISSYLN | 996 | AASSLQS | 1071 | CQQSYSTPLTF | 1264 |
| 004S-E09 | Fzd6 | DTFSNYVIS | 77 | GRISAYNGYKSYA | 447 | CARSSGYVGWFDP | 821 | RASQSISSYLN | 996 | AASSLQS | 1071 | CQQSYSTPLTF | 1264 |
| 004S-F09 | Fzd6 | FTFSNYYTS | 132 | SYISGAGGSTEYA | 565 | CARLPRRSGKGSAFDIW | 785 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 004S-H09 | Fzd6 | GTFSSYTIS | 208 | GWMNPNSGNTGYA | 490 | CARVGATSAGGMDVW | 832 | RASQSISSYLN | 996 | AASSLQS | 1071 | CQQSYSTPLTF | 1264 |
| 004S-C10 | Fzd6 | YIFTDYYMH | 278 | GLVDPEDGETIYA | 429 | CAHSDFFSGLSFGDW | 590 | RASQSISSYLN | 996 | AASSLQS | 1071 | CQQSYSTPLTF | 1264 |
| 004S-D10 | Fzd6 | FTFSNSDMN | 128 | SSISTSGGSTYYA | 544 | CARGSYW | 761 | RASQNINNYLA | 979 | RASTLQS | 1143 | CQQSYSYPYTI | 1317 |
| 004S-E10 | Fzd6 | TTLNKYAIS | 275 | GRITPVVGVTNYA | 448 | CALSSSWYGGFDYW | 628 | RASQSISSYLN | 996 | AASSLQS | 1071 | CQQSYSTPLTF | 1264 |
| 004S-F10 | Fzd6 | GFTFSDHY | 182 | ALVGYDGSQQFYG | 367 | CNTGIPMLYW | 900 | RASQSISSYLN | 996 | AASSLQS | 1071 | CQQSYSTPLTF | 1264 |
| 004S-G10 | Fzd6 | FTFSDYYMS | 122 | SAISGSGFTYYA | 506 | CARVSRGFAPDYW | 845 | RASQSISSYLN | 996 | AASSLQS | 1071 | CQQSYSTPLTF | 1264 |
| 004S-A11 | Fzd6 | GTFSSYAIS | 207 | GRIIPILGIANYA | 438 | CARESVNNYYYMDVW | 710 | RASQSISSYLN | 996 | AASSLQS | 1071 | CQQSYSTPLTF | 1264 |
| 004S-C11 | Fzd6 | FTFSSYAMH | 141 | ALTSYDGSKKFYA | 366 | CAKTGRGYAFDIW | 623 | RASQSISSYLN | 996 | AASSLQS | 1071 | CQQSYSTPLTF | 1264 |
| 004S-E11 | Fzd6 | FTFSSYNMN | 145 | GRIKSKANGGTTDYA | 444 | CAKAGQQLDW | 593 | RASQSISSYLN | 996 | AASSLQS | 1071 | CQQSYSTPLTF | 1264 |
| 004S-H11 | Fzd6 | FTFTSSAMQ | 162 | GGIIPIFGTANYA | 408 | CATVQTNYDSSGRFSYRAHYFDYW | 874 | RASQSIRWLA | 992 | AASSLQS | 1071 | CQQVVSYPLTF | 1318 |
| 004S-A12 | Fzd6 | YTFTNNFMH | 292 | GRINPNSGGTNYA | 446 | CARGQGYSSGWYRGDAFDIW | 752 | RASQSISSYLN | 996 | AASSLQS | 1071 | CQQSYSTPLTF | 1264 |
| 004S-D12 | Fzd6 | FAPDDYAMH | 79 | GFIRSKAYGGTTEYA | 399 | CAKDRGYSSGWYLDYW | 605 | RASQSISSYLN | 996 | AASSLQS | 1071 | CQQSYSTPLTF | 1264 |
| 005S-H01 | Fzd7 | FNFSSYTMR | 87 | SVIYGGGNTNYA | 561 | CARGGSGGNLSYW | 733 | RASQSISSYLN | 996 | AASSLQS | 1071 | CQQSYSTPLTF | 1264 |
| 005S-A02 | Fzd7 | GTFSSYAIS | 207 | GMIIPFLGITNYA | 430 | CTRPYDAFDIW | 913 | RASQSISSYLN | 996 | AASSLQS | 1071 | CQQSYSTPLTF | 1264 |
| 005S-C02 | Fzd8 | YTFASYGMH | 283 | GWINAGNGNTTYA | 465 | CARLSVWKWEQVTNWFDPW | 787 | RASQSISSYLN | 996 | AASSLQS | 1071 | CQQSYSTPLTF | 1264 |
| 005S-E02 | Fzd8 | GTFTSYAIS | 216 | GWINAGNGNTKYS | 464 | CTTGLFPYYRYNWNNDAFDIW | 919 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 005S-A03 | Fzd8 | GTFSSYAIS | 207 | GWMNPNSGNTGYA | 490 | CAKWHIGATGNWFDPW | 626 | RASQSISSYLN | 996 | AASSLQS | 1071 | CQQSYSTPLTF | 1264 |
| 005S-H03 | Fzd8 | YTFTNNFMH | 292 | GGIFPIYGISTYA | 403 | CARDRPTSSWYAFDYW | 689 | RASQGISNNLN | 969 | DASTLQT | 1089 | CQQSFSSAPITF | 1233 |
| 005S-F04 | Fzd8 | FSFSSTAMS | 95 | SYISSSGSITHYA | 568 | CARYGDYGDYW | 851 | RASQSISSYLN | 996 | AASSLQS | 1071 | CQQSYSTPLTF | 1264 |
| 005S-H04 | Fzd8 | YTFTNNFMH | 292 | GWINAGNGNTTYA | 465 | CARVATGNAFDIW | 829 | RASQSISSYLN | 996 | AASSLQS | 1071 | CQQSYSTPLTF | 1264 |
| 005S-B05 | Fzd8 | FTFSSYWMH | 152 | AGISGSGKTTFYA | 353 | CARGGLLFDYW | 728 | QASQDISNYLN | 943 | KASSLES | 1120 | CQQSYSTPRTF | 1265 |
| 005S-F05 | Fzd8 | FTFTSSAVQ | 164 | GWMNPNSGNTGYA | 490 | CARRTAVAGTIDYW | 811 | RASQSISSYLN | 996 | AASSLQS | 1071 | CQQSYSTPLTF | 1264 |
| 005S-G05 | Fzd8 | GTFSSYAIS | 207 | GWISPYNGNTNYA | 480 | CARGGWTNYGGNLDYW | 738 | RASQSISSYLN | 996 | AASSLQS | 1071 | CQQSYSTPLTF | 1264 |
| 005S-H05 | Fzd8 | YTFTSYMH | 301 | GRINPNSGGTNYA | 446 | CARVPDFWSGYLDYW | 840 | RASQGISRTLZ | 972 | AASSLQS | 1071 | CQQTYSMPITF | 1284 |
| 005S-D06 | Fzd8 | YTFTYRYLH | 303 | GGIIPIFGTANYA | 408 | CARDSYPYGMDVW | 697 | RASQSISSYLN | 996 | AASSLQS | 1071 | CQQSYSTPLTF | 1264 |
| 005S-F06 | Fzd8 | GTFSSYAIS | 207 | GRVIPILGVTNYA | 453 | CAREYLGSFDIW | 712 | RASQSVGSNLA | 1006 | GASSRAT | 1107 | CQQYGSSPPFTF | 1301 |
| 005S-A07 | Fzd8 | FTFTGSAVQ | 160 | GGILPIYGTTKYA | 418 | CARGARLYGFDYW | 719 | RASQSVSRNLA | 1012 | GASTRAT | 1111 | CQQRSNWPITF | 1226 |
| 005S-B07 | Fzd9 | FTFTSSAVQ | 164 | GWMNPNSGNTGYA | 490 | CARGRGQQWLTGYYGMDVW | 754 | RASQGISSALA | 973 | GASTIQS | 1109 | CLQDYNYPFTF | 1166 |
| 005S-C07 | Fzd9 | FTFSSYSMN | 146 | SYIENDGSITTYA | 562 | CARAPYYYGSGSLFRLDYW | 645 | RASQSISSYLN | 996 | AASSLQS | 1071 | CQQSYSTPLTF | 1264 |
| 005S-D07 | Fzd9 | GTFNSYAIA | 203 | GGIIPIFGTANYA | 408 | CARAGSGYYNFDYW | 637 | RASQSINRWLA | 988 | AASSLQS | 1071 | CQQTYNIPITF | 1280 |
| 005S-F07 | Fzd9 | FSFSSYGMH | 96 | AYINSRGSLMYYA | 392 | CAKTKLPIW | 624 | RASQSINRNYLG | 987 | AASRVT | 1072 | CQQDSWPPTF | 1294 |
| 005S-G07 | Fzd9 | GSFSGYAIN | 186 | GGIIPIFGTANYA | 408 | CATGYYYDYYFDYW | 869 | RASQGISNNLN | 969 | AASSLQS | 1071 | CQHYNLPLTF | 1202 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 005S-H07 | Fzd9 | GTFTNNFMH | 214 | GLVDPEDGETIYA | 429 | CARTYRIVGATPRYYYYGMDVW | 828 | RASQTINNQLA | 1023 | KASNLET | 1118 | CQQANSFPVTF | 1210 |
| 005S-B08 | Fzd9 | YIFTDYYMH | 278 | GWINPNSGGTIYA | 469 | CARGPRDSGYYPGGAFDIW | 750 | RASQSISSYLN | 996 | AASSLQS | 1071 | CQQSYSTPLTF | 1264 |
| 005S-D08 | Fzd9 | FAFSSHWMH | 80 | SAIDGSGGSTYYA | 499 | CARDRQLGWAHWYFDLW | 691 | RASQSISSYLN | 996 | AASSLQS | 1071 | CQQSYSTPLTF | 1264 |
| 005S-G08 | Fzd9 | YTFTGYYMH | 288 | GWINAGNGNTTYA | 465 | CARDRDYW | 684 | QTSQDINNNLN | 950 | KASLES | 1120 | CQQSYSSPPTF | 1258 |
| 005S-C09 | Fzd9 | FTFSSYGMH | 143 | SAIGTGGGTYVA | 502 | CALLVGAARGISYYYYYGMDVW | 627 | QASQDISNYLN | 943 | AASTLQS | 1075 | CLQHKSFPTF | 1170 |
| 005S-D09 | Fzd9 | YTFTSYAMH | 298 | GWINAGNGNTTYA | 465 | CARDRPYSSGWYYPAFDIW | 690 | RASQSVSSNQLA | 1015 | GASTRAT | 1111 | CQQRYNWPPSITF | 1230 |
| 005S-E09 | Fzd9 | FNLRRVNMN | 89 | SRISNSGSLVYYA | 534 | CARDADSGYYRYDAFDIW | 659 | RASQSVSSNLA | 1014 | DASNRAT | 1084 | CQQRNNWLYTF | 1225 |
| 005S-A10 | Fzd9 | YTFTDYYMH | 285 | GIINPSGGSTSYA | 422 | CARHVYGSGTYNNWFDPW | 775 | RASQSISSYLN | 996 | AASSLQS | 1071 | CQQSYSTPLTF | 1264 |
| 005S-O10 | Fzd9 | YTFTSYYMH | 301 | GWMSPNSANTGYA | 490 | CARGGPIHYYYYYMDVW | 731 | RASQGISNNLN | 969 | AASLQS | 1075 | CQQTNLFPYT | 1277 |
| 005S-B11 | Fzd9 | GAFSTSSIS | 178 | GRIIPVLGTANYA | 443 | CAKGGWRSSFDPW | 612 | RASQSVSSNLA | 1014 | GASTRAT | 1111 | CQQYNSWPL | 1313 |
| 005S-C11 | Fzd9 | YTFTSYDIN | 299 | GGFDPEDGETIYA | 401 | CAKAGDWGLYGMDVW | 592 | RASQSISRWLA | 992 | AASSLQS | 1071 | CQQTNTFPFTF | 1278 |
| 005S-D11 | Fzd9 | FTFTGSAVQ | 160 | GGILPIYGTTKYA | 418 | CARGARLYGFDYW | 719 | RASQSVSRKLA | 1011 | GASTRAT | 1111 | CQQRSNWPITF | 1226 |
| 005S-E11 | Fzd9 | YTFTNNFMH | 292 | GWINPNSGDTKFA | 468 | CAREANYDILTGYIRPDAPDIW | 703 | RASQSLRSKLA | 1004 | GASTLQS | 1111 | CQQYANSPWTF | 1293 |
| 005S-G11 | Fzd9 | GTFSSYAIS | 207 | GWINAGNGNTKYS | 464 | CTTTEYSSSPDYYYGMDVW | 922 | QASQDISNYLN | 943 | GASTRAT | 1109 | CQQLSRYPSLF | 1222 |
| 005S-H11 | Fzd9 | GTFTRNSIS | 215 | GGIIPIFGTANYA | 408 | CARSSDLRIFDYW | 819 | RASQSVSSNLA | 1014 | GASNRPT | 1103 | CQQYGSSPYT | 1305 |
| 005S-H11 | Fzd10 | YTFASYDIH | 282 | GWINAGNGNTTYA | 465 | CARDGIWDIFDYW | 666 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 005S-E12 | Fzd10 | YIFTDYYMH | 278 | GVIFPVYPTPDYA | 458 | CARGGSTGYYGMDVW | 736 | RASQSVGRWMA | 1005 | AASSLQS | 1071 | CQQANTFPFTF | 1213 |
| 005S-F12 | Fzd10 | GTFSSYAIS | 207 | GRIVPIVDVVKYA | 450 | CARDTCSSTSCSPDYKYA | 698 | RASQSISSYLN | 996 | AASSLQS | 1071 | CQQSYSTPLTF | 1264 |
| 006S-A01 | Fzd10 | FTFSSYSMN | 146 | SAIGTGGGTYYA | 502 | CAREGWFGESPFGMDVW | 707 | RASQSISSYLN | 996 | AASSLQS | 1071 | CQQSYSTPLTF | 1264 |
| 006S-F01 | Fzd10 | YTFTRYAVH | 294 | GWISTFNDNTNYA | 483 | CASPTGMTTNFDYW | 856 | RASQSISSYLN | 996 | AASSLQS | 1071 | CQQSYSTPLTF | 1264 |
| 006S-H01 | Fzd10 | YIFTDYYMH | 278 | GGIIPIPGTANYA | 278 | CAKGSYYYDSSGYYWDAFDIW | 620 | RASQGISNNLN | 969 | AASNLET | 1062 | CQQTSSTPLTF | 1279 |
| 006S-A02 | Fzd10 | YIFTDYYMH | 278 | GGIIPLFGTTDYA | 416 | CARDITGADGMDVW | 672 | RASQSISSYLN | 996 | AASSLQS | 1071 | CQQSYSTPLTF | 1264 |
| 006S-D02 | Fzd10 | GTFSSYAIS | 207 | GRIIPTVGTANYA | 442 | CARDVCSGGSCSPDVW | 699 | RASQGISNNLN | 969 | DASSLES | 1085 | CQQTYNTPRTF | 1282 |
| 006S-E02 | Fzd10 | FTFTSSATQ | 163 | GGIIPIFGTANYA | 408 | CARDGSSGWYSPNAFDIW | 667 | RASQGISNNLN | 969 | AASSLQS | 1071 | CLQHNGYPITF | 1171 |
| 006S-H02 | Fzd10 | FTFRMYGMH | 114 | SRISPDGRTTTYA | 535 | CARSPRWDAFDIW | 817 | RSSQSLLHSNGYNYLD | 1036 | RVSRFS | 1145 | CMQGTHWPPTF | 1182 |
| 006S-A03 | Fzd10 | YIFTDYYMH | 278 | GWINAGNGNTTYA | 465 | CARDPIMFGDQPGWFDPW | 681 | RASESVSSNLA | 952 | GASSRAT | 1107 | CQQYNKSPSF | 1311 |
| 006S-B03 | Fzd10 | GTFSSYAIS | 207 | GWINAGNGNTKYA | 463 | CAREGYDFWSGPYAFDIW | 708 | RASQTISRYLN | 1024 | EVSSLQG | 1097 | CQQSYSTPWTF | 1270 |
| 006S-C03 | Fzd10 | GTFSSNVIS | 205 | GGIIPIPGTANYA | 408 | CARGGYYYGMDVW | 740 | RASQSISSYLN | 996 | AASSLQS | 1071 | CQQSYSTPLTF | 1264 |
| 014S-B01 | Fzd1 | YIFTDYYMH | 278 | GGIIPIPGTANYA | 408 | CARMSSDYYDSSGYYRRGMDVW | 792 | RASQGISNNLN | 969 | GASTLQS | 1109 | CQQADSFPPTF | 1205 |
| 014S-D01 | Fzd4 | GTFSSYAIS | 207 | GWINAGNGNTTYA | 465 | CARHYYGSGSYPDW | 777 | RASQSISSHZN | 994 | AASSLQS | 1071 | CQQSYSTPLTF | 1264 |
| 014S-E01 | Fzd4 | GTFSSYAIS | 207 | GWINAGNGNTTYA | 465 | CARHYYGSGSYPDW | 777 | RASQSIZZYZN | 1003 | AASSLQS | 1071 | CQQSYSTPLTF | 1264 |
| 014S-G01 | Fzd4 | GTFSSYAIS | 207 | GWMNPNNGNTTYA | 488 | CARHYYGSGNYRDW | 776 | RASQSISSYLN | 996 | AASSLQS | 1071 | CQQSYSTPFTF | 1260 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 014S-A02 | Fzd4 | FTFSSNAMH | 137 | SGISGSGGSTYYA | 515 | CAKPGIAAAGTNWFDPW | 622 | RASQGISSALA | 973 | GASTVES | 1112 | CQQSYSTPRTF | 1265 |
| 014S-B02 | Fzd4 | FTFSSYAMH | 141 | SGISGSGSSTYYA | 518 | CARPSTISFGMDVW | 799 | RASQSVSSNLA | 1014 | GASTRAT | 1111 | CQQYDTPLRTF | 1295 |
| 014S-C02 | Fzd5 | YTFTSYYMH | 301 | GRINPNSGGTNYA | 446 | CARVPDFWSGYLDYW | 840 | RASQGISSALA | 973 | AASSLQS | 1071 | CQQTYSMPITF | 1284 |
| 014S-D02 | Fzd5 | GTFSTYAIS | 210 | GIINPSGGSTSYA | 422 | CARAKGSGWYVGSAFDIW | 641 | RASQSISSYLN | 996 | AASSLQS | 1071 | CQQSYSTPLTF | 1264 |
| 014S-E02 | Fzd5 | FTFSDSYMS | 120 | GFIRSKAYGGTTEYA | 399 | CARATQELLLPYGMDVW | 655 | RASQGVSTZLS | 977 | AASSLQS | 1071 | CQQSYSTPLTF | 1264 |
| 014S-F02 | Fzd5 | YTFTSYYMH | 301 | GRINPNSGGTNYA | 446 | CARVPDFWSGYLDYW | 840 | RASQGISSALA | 973 | ATSTLQS | 1079 | CQQTYSMPITF | 1284 |
| 014S-G02 | Fzd6 | YTFTSYYMN | 301 | GIISPSGGSTSYA | 425 | CARWGDYGDLYYFDYW | 848 | RASQVSVSWLA | 1018 | AASTLQT | 1076 | CQQVNSYPPTF | 1291 |
| 014S-H02 | Fzd6 | YIFTDYYMH | 278 | GRINPNSGGTNYA | 446 | CARARSSGWTDAFDIW | 648 | RASQSISSYLN | 996 | AASSLQS | 1071 | CQQSYSTPTF | 1268 |
| 014S-A03 | Fzd6 | GTFSSYAIS | 207 | GWINAGNGNTTYA | 465 | CARHYYGSGSYPDW | 777 | RASQSISSYLN | 996 | AASSLQS | 1071 | CQQSYSTPLTF | 1264 |
| 014S-B03 | Fzd8 | FTFSSYNMN | 145 | GRIKSKANGGTTDYA | 444 | CARAGDSPDYW | 636 | RASQSISSYLN | 996 | AASSLQS | 1071 | CQQSYSTPLTF | 1264 |
| 014S-E03 | Fzd8 | GTFSSYAIS | 207 | KYAGWISPYNGYT | 481 | CARAMWSYGQQNAFDIW | 642 | RASQSISSYLN | 996 | AASSLQS | 1071 | CQQSYSTPLTF | 1264 |
| 014S-G03 | Fzd8 | FTFTSSAVQ | 164 | GWMNPNSGNTGYA | 490 | CARRTAVAGTIDYW | 811 | RASQSISSYLN | 996 | AASSLQS | 1071 | CQQSYSTPLTF | 1264 |
| 014S-H03 | Fzd8 | YTFTSSAIH | 296 | GRINPNSGGTNYA | 446 | CARVKWELAIDYW | 837 | RASQSISSYLN | 996 | AASSLQS | 1071 | CQQSYSTPLTF | 1264 |
| 014S-B04 | Fzd8 | YIFTDYYMH | 278 | GWMNPNSGNTGYA | 490 | CARGGSRYDFWSGHWYFDLW | 734 | RASQGISNYLA | 971 | AASSLQS | 1071 | CQQSYSTPFTF | 1260 |
| 014S-E04 | Fzd8 | YTFTGYYMH | 288 | GRINPNSGGTNYA | 446 | CARDVPKLVTRGVAYGMDVW | 701 | RASQSISSYLN | 996 | AASSLQS | 1071 | CQQSYSTPLTF | 1264 |
| 014S-F04 | Fzd8 | YSFFTYGMN | 281 | GWINAGNGNTTYA | 465 | CARAAAGSYGGGYW | 633 | RASQGISNNLN | 969 | EASSVAS | 1093 | CQQSYSTPLNSF | 1273 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 014S-G04 | Fzd8 | FTFSSYGMS | 144 | SAISGSGGSTYYA | 507 | CARDLTPFTQQQLVLGLL | 677 | RASQSVSGYLA | 1010 | GASTRAA | 1110 | CQQYNWPPAF | 1315 |
| 014S-H04 | Fzd8 | FTFTSSAVQ | 164 | GRIVPAIGFTQYA | 449 | CARSGYNRRGYFDYW | 816 | RASQSISSYLN | 996 | AASSLQS | 1071 | CQQSYSTPLTF | 1264 |
| 014S-A05 | Fzd8 | GTFSSYAIS | 207 | GGIIPIFGTANYA | 408 | CARVTLGASVDAFDIW | 846 | RASQGISNNLN | 969 | DASSLES | 1085 | CLQHNSLPFTF | 1172 |
| 014S-B05 | Fzd8 | GTFSSYAIS | 207 | GWVSPNTGNTVYA | 494 | CTTDRRYSTYFDLW | 918 | RASQSVSSNLA | 1014 | GVSNRAT | 1117 | CQQYNIWPRTF | 1310 |
| 014S-C05 | Fzd8 | YTFASYGMH | 283 | GWINAGNGNTTYA | 465 | CARLSVWKWEQVTNWFDPW | 787 | RASQSISSYLN | 996 | AASSLQS | 1071 | CQQSYSTPLTF | 1264 |
| 014S-D05 | Fzd8 | GTFTSYAIS | 216 | GWINAGNGNTKYS | 464 | CTTGLFPYYRYNWNNDAFDIW | 919 | RASQZVSRZZA | 996 | AASSLQS | 1071 | CQQSYSTPLTF | 1264 |
| 014S-F05 | Fzd9 | FTFSSSWQ | 160 | GGILPIYGTTKYA | 418 | CARGARLYGCDYW | 718 | RVSQGISSALA | 1025 | GASTRAT | 1111 | CQQTFSVPWTF | 1276 |
| 014S-G05 | Fzd9 | FTFSSSWMH | 140 | SAIGTGGGTYYA | 502 | CARKVKGYCSGGSCYGYW | 781 | RASQSISSYLN | 1049 | AASSLQS | 1071 | CQQSYSTPLTF | 1264 |
| 014S-H05 | Fzd9 | FTFNYAMT | 130 | STISGSGVSTFYA | 555 | CARHGRIAADIW | 773 | RASQSVSRNLA | 996 | AASSLQS | 1071 | CQQSYSTPLTF | 1264 |
| 014S-A06 | Fzd9 | FTFZZSZVQ | 167 | GGILPIYGTTKYA | 418 | CARGARLYGFDYW | 719 | RASQSVSRNLA | 1012 | GASTRAT | 1111 | CQQRSNWPITF | 1226 |
| 014S-B06 | Fzd9 | FTFSSYSMN | 146 | SYIENDGSITTYA | 562 | CARAPYYYGSGSLFRLDYW | 645 | RASQSISSYLN | 996 | AASSLQS | 1071 | CQQSYSTPLTF | 1264 |
| 014S-C06 | Fzd10 | FTFTGSAVQ | 160 | GGILPIYGTTKYA | 418 | CARGARLYGFDYW | 719 | RASQSVSRNLA | 1012 | GASTRAT | 1111 | CQQRSNWPITF | 1226 |
| 014S-D06 | Fzd10 | FTFSRYAMH | 133 | SGIGVGGGTYYA | 512 | CARDAYNWFDPR | 660 | RASQSISSYLN | 993 | AASSLQS | 1071 | CQQRYSTPLTF | 1264 |
| 014S-F06 | Fzd10 | YIFTDYYMH | 278 | GVIFPVVPTPDYA | 458 | CARGGSTGYYGMDVW | 736 | RASQSVGRWMA | 1005 | AASSLQS | 1071 | CQQANTFPFTF | 1213 |
| 014S-G06 | Fzd10 | FTFSSYAMH | 141 | SAIGAGGGTYYA | 500 | CARDAYNWFDPW | 661 | RASQSISSYLN | 996 | AASSLQS | 1071 | CQQSYSTPLTF | 1264 |
| 014S-H06 | Fzd10 | FTFSSYDMN | 142 | SAIGTGGGTYYA | 502 | CARDAYNWFDPW | 661 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 014S-A07 | Fzd10 | FTFSNAQMS | 124 | SAIGTGGGTYA | 502 | CAREGSYDYDWYFDLW | 706 | RASQNIGSRLA | 978 | GASNRAS | 1102 | CQQYNHWPPLFTF | 1309 |
| 017S-E08 | Fzd8 | IIFSPNDMG | 223 | ALISSGGSTSYA | 359 | CHFGVASVGLNYW | 877 | | | | | | |
| 017S-H08 | Fzd8 | RTFSSFVMG | 256 | AAVSASGGYTWYA | 341 | CNLAQRGETYW | 895 | | | | | | |
| 017S-A09 | Fzd8 | LAFNGYTMG | 227 | AAISWSDNTYYA | 323 | CAAGFPTVFVVDGEYDYW | 577 | | | | | | |
| 017S-B09 | Fzd8 | FTLDYYAIS | 168 | ADITSGGSTNYA | 346 | CNAVTYNGYTIW | 891 | | | | | | |
| 017S-C09 | Fzd8 | LTFSDYTVG | 229 | ASSTGGVFENYA | 373 | CNAVTYNGYTIW | 891 | | | | | | |
| 018S-D06 | Fzd4 | RIFSSYAQA | 240 | PRIPSDSTTFYA | 497 | CEVHNFGATYW | 876 | | | | | | |
| 018S-E06 | Fzd4 | RTFSNYVMG | 254 | AVISRSGGNTYYT | 381 | CNAVSTDWTTDYW | 889 | | | | | | |
| 018S-F06 | Fzd4 | RTFSTYGMG | 259 | AAISWSDNTYYA | 323 | CNSFPLRLHDW | 899 | | | | | | |
| 018S-G06 | Fzd5 | LAIDDYYMV | 228 | SYISTSDGSTYYA | 571 | CNAVTYNGYSIW | 890 | | | | | | |
| 018S-H06 | Fzd5 | LAFNGYTMG | 227 | AQISWTGGSTDYA | 369 | CNADYGTWYGIGW | 882 | | | | | | |
| 018S-A07 | Fzd5 | LAFNGYTMG | 227 | AAISWMSNTYYA | 321 | CNMGLGYSEYRPLGYW | 896 | | | | | | |
| 018S-B07 | Fzd5 | SAFSNYAMG | 265 | AAITWSGARTYYA | 335 | CNAVWKFGTTHW | 892 | | | | | | |
| 018S-C07 | Fzd7 | LTIDDYYV | 233 | SYISAGDGFTYYA | 564 | CNAVTYNGYTIW | 891 | | | | | | |
| 017S-F09 | Fzd4 | GSFSGYYWS | 189 | GEINHSGSTNYN | 398 | CARDLRFYSSSWRRVGMDVW | 675 | RSSRSLLHTSGYNYLD | 1045 | LGSNRAS | 1131 | CMQGTRWPTF | 1183 |
| 017S-G09 | Fzd4 | YTITTYAIH | 305 | GWINADTGDTAYS | 462 | CARGWTTISSLGVWYNYLD | 769 | RSSRSLLHTNG | 1044 | LGSNRAS | 1131 | CMQALQTPLTF | 1175 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 017S-H09 | Fzd5 | NIFRIYAIA | 236 | AALTGQRTTNYA | 336 | CNTVTYNAGCYKKYW | 901 | | | | | | |
| 017S-A10 | Fzd5 | LAFNGYTMG | 227 | ASITWNGRYTYYA | 371 | CNARLDAVYGHSRYDSW | 885 | | | | | | |
| 017S-B10 | Fzd5 | NFFSNYPLG | 235 | GAISRTGSGTFYA | 393 | CAAGVTGSWRYW | 581 | | | | | | |
| 017S-C10 | Fzd8 | RSFSNYRVA | 245 | AVSWSVGMTYYA | 388 | CNAVTYNGYTIW | 891 | | | | | | |
| 017S-D10 | Fzd8 | GTFGSYAVG | 200 | GLISRNAGNTLYA | 427 | CNAVNGRLNYW | 888 | | | | | | |
| 017S-E10 | Fzd8 | RTFSSYSLA | 258 | AAVSASGANTYYA | 340 | CAAPQSPNMYIRTDQLWYKYW | 584 | | | | | | |
| 018S-D07 | Fzd1 | RSFSTYPMG | 246 | TVISGSGSTYYA | 573 | CAAGPTLPFRYW | 580 | | | | | | |
| 018S-E07 | Fzd1 | RAFSNYAMG | 238 | AAINWSGDSAYYA | 315 | CNARLSFAGGMGYW | 886 | | | | | | |
| 018S-F07 | Fzd1 | IKSMFDMNFMG | 224 | AFITRGRTTRYG | 347 | CNAVSTDWTRDYW | 889 | | | | | | |
| 018S-G07 | Fzd1 | LTIDDYYMV | 232 | SYIGTSDGTTYYA | 348 | CNAVTYNGYTIW | 891 | | | | | | |
| 018S-H07 | Fzd4 | RVFSSYAQA | 264 | AGIASDSTTFYA | 370 | CKVHNFGATYW | 880 | | | | | | |
| 018S-A08 | Fzd4 | RIFSSYAQA | 240 | ASIPSDCTTFYA | 370 | CKVHNFEATYW | 879 | | | | | | |
| 018S-B08 | Fzd4 | LTFSTYGMG | 231 | AAINWSGRSTVYA | 316 | CNSFPLRLHDW | 899 | | | | | | |
| 018S-C08 | Fzd4 | RTLSSYVVG | 261 | ALISLSGASTYYA | 358 | CNAVSTDWTTDYW | 889 | | | | | | |
| 018S-D08 | Fzd5 | IKSMFDMNFMG | 224 | AFITRGGTTRYG | 347 | CNAVSTDWTRDYW | 889 | | | | | | |
| 018S-E08 | Fzd5 | RTDGMQAMG | 248 | GAITWSLGSAFYA | 395 | CNVLAQNDGDYRTYG | 904 | | | | | | |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 018S-F08 | Fzd5 | RTFSSFVMG | 256 | AAVSASGGYTWYA | 341 | CNAVWKFGTTHW | 892 | | | | | | |
| 018S-G08 | Fzd5 | RTFSSFVMG | 256 | AAVSASGGYTWYA | 341 | CNAVCKFGTTHW | 887 | | | | | | |
| 018S-H08 | Fzd5 | RTFSSFVMG | 256 | AAVTASGGYAWYA | 343 | CNAVWKFGTTHW | 892 | | | | | | |
| 018S-A09 | Fzd8 | ITFSFNSVG | 226 | AVFIAGYGAYYA | 379 | CNGVTYNGYTIW | 894 | | | | | | |
| 018S-B09 | Fzd8 | HDFSSTYGVG | 221 | ATISWGGTNIA | 377 | CAAQKPYYNGHFYADDKHYDHW | 585 | | | | | | |
| 018S-C09 | Fzd8 | ITFGFDSVG | 225 | AVFNAGYRAYYA | 380 | CNAVTYNGYTIW | 891 | | | | | | |
| 018S-D09 | Fzd8 | RTFSWYSMG | 260 | AAVSWSGVSTYYP | 342 | CNAVTYNGYTIW | 891 | | | | | | |
| 018S-E09 | Fzd8 | ITFSFNSVG | 226 | AVFIAGYGAYYA | 379 | CIGVTYNGYTIG | 878 | | | | | | |
| 018S-F09 | Fzd8 | RTDGMQAMG | 248 | GAITWSLGIAFYA | 394 | CNVLAQNDGDYRTYW | 905 | | | | | | |
| 018S-G09 | Fzd8 | HDFSSTYGVG | 221 | AAISWRGTNIA | 322 | CAAQKPYYNGHFYADDKHYDHW | 585 | | | | | | |
| 021S-A01 | Fzd8 | DSVSNSAAWN | 74 | GRAYYKSRWYYDYA | 433 | CVRDLRPSGDLNFDYW | 926 | RASQSIGSSLH | 985 | YASQSVS | 1154 | CHQSGRVPVTF | 1162 |
| 021S-C01 | Fzd1 | GSISSGGYSWS | 195 | GSIYHSGSTYYN | 454 | CARFYYDILNGYSYFDYW | 714 | RSSRSLLDTDDGNTYLD | 1040 | TLSHRAS | 1153 | CMQSIQLPWTF | 1188 |
| 021S-D01 | Fzd1 | FTFSSYGMH | 143 | AVISYDGSNKYYA | 384 | CAKGSVFGLKAGGYADYW | 384 | RSSQSLVHSDGNTYLS | 1038 | KISNRFS | 1124 | CMQATQFPHTF | 1177 |
| 021S-E02 | Fzd8 | YTFTSYGIS | 300 | GWISAYNGNTNYA | 477 | CARDGTPFYSGSYYGSW | 669 | QGDSLRTYYAS | 949 | GKNNRPS | 1113 | CNSRDNSGKHKVF | 1193 |
| 021S-G02 | Fzd8 | DSVSNSGAWN | 76 | GRTYYRSKYYNGYA | 452 | PRLDYW | 930 | RSSQSLLDSDDGNTYLD | 1031 | MLSSRAP | 1134 | CMQRLEFPYTF | 1187 |
| 021S-A03 | Fzd8 | DSVSSNSAAWN | 74 | GRTYYRSKWYNDYA | 451 | CARSQATGERFDYW | 818 | RSSQNIFQSLN | 1029 | SASSLQS | 1148 | CQQSYNSPITF | 1240 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 022S-H06 | Fzd4 | FTFSSYAMS | 141 | SVISTSGGTVLYT | 560 | CADGSGTSHR | 587 | RASQSISSYLN | 996 | AASSLQS | 1071 | CQQSYSTPLTF | 1264 |
| 022S-A11 | Fzd10 | YIFTDYYMH | 278 | GGIFPIFGTANYA | 402 | CAKGSYYYDNSGYYWDAFDIW | 619 | RASQGISNNIN | 968 | AASNLET | 1062 | CQQTYSIPFTF | 1283 |
| 027S-H02 | Fzd5 | FTFSSYAMS | 141 | SAISGSGGSTYYA | 507 | CAKGLWGPLLNW | 615 | RASQSVSSNYLS | 1016 | GASSRAP | 1106 | CQQRTNWPPRVTF | 1228 |
| 027S-B03 | Fzd8 | DSVSNSATWN | 75 | GRTYYRSKWYSDYA | 451 | CTRGNWNVGLANW | 911 | SGTSSNIGAGYDVH | 1053 | GNNNRPS | 1113 | CSAWDDNLNGVVF | 1324 |
| 027S-E01 | Fzd5 | RSFSIYNTA | 244 | AAISWSGGSTYYA | 327 | CNVITIVRGMGPPAYW | 903 | | | | | | |
| 004S-D05 | Fzd5 | LTFSIYAMH | 230 | SAISGDGALTYYA | 504 | CARGVVPYSSKHKPSYYYYGMDVW | 767 | QASQDISNYLN | 943 | AASSLQS | 1071 | CQQSYSTPLTF | 1263 |
| 004S-D04 | Fzd5 | YDFTTYGIH | 277 | GGVIPAFGATDYS | 420 | CARGYYYGMDVW | 771 | RASQSISSYLN | 996 | AASSLQS | 1071 | CQQSYSTPLTF | 1264 |
| 004S-B05 | Fzd5 | GTFSSYAIS | 207 | GWINAGNGNTTYA | 465 | CASGLGYPDYW | 854 | RASQSISSYLN | 996 | AASSLQS | 1071 | CQQSYSTPLTF | 1264 |
| 004S-G03 | Fzd5 | YTFTNNFMH | 292 | GGIIPIPGTPHYA | 411 | CARTLTPPYYYGMDVW | 826 | RASQSISSYLN | 996 | AASSLQS | 1071 | CQQSYSTPLTF | 1264 |
| 004S-F03 | Fzd5 | FTFSNSDMN | 128 | SAIGTGGDTYYA | 501 | CTRDLYGGYRDYW | 910 | KSSCLSLLHSDGYTYLY | 933 | LGSNRAS | 1131 | CMQGLQTPWTF | 1180 |
| 004S-C04 | Fzd5 | YIFTGYYMH | 279 | GRINPNSGGTNYA | 446 | CARGGEYSSGWTYYYYYGMDVW | 724 | RATQTISTYLN | 1027 | AASRLQS | 1067 | CQQYSYPWTS | 1319 |
| 004S-B06 | Fzd5 | YTFTYRYLH | 303 | GMINPIGGSIYA | 431 | CARDVMDVW | 700 | RASQGISNNLN | 969 | AASALQS | 1061 | CQHLNNFPLTF | 1196 |
| 004S-F06 | Fzd5 | FSVGSNYMT | 100 | SSISSGNSYIYYA | 541 | CARGPKTWWEDRPDYW | 748 | RASQSISSYLN | 996 | AASSLQS | 1071 | CQQSYSTPLTF | 1264 |
| 004S-A04 | Fzd5 | FTFSTYSMI | 158 | GFIRSKDYGGTTEYA | 400 | CARLTGGAVAGTHRDYW | 789 | RASQGISNNLN | 969 | GASSLQS | 1105 | CQQSHSSPRTF | 1237 |
| 004S-A05 | Fzd5 | FTFSSYVMS | 150 | SAIGTGGGTYYA | 502 | CARGSSGYYVAW | 759 | RASQSISSYLN | 996 | AASSLQS | 1071 | CQQSYSTPLTF | 1264 |
| 004S-F05 | Fzd5 | FTFSNHYMS | 126 | AGVSIDANKKYYA | 356 | CARDQNDSWYRSDYW | 682 | RSSQSLLHSDGYTYLY | 1033 | LGSHRAS | 1129 | CMQGLQTPHTF | 1179 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 003S-C01 | Fzd1 | GTFSSYAIS | 207 | GRINPNSGGTNYA | 446 | CARGSGYDFFDYGMDVW | 758 | RASQSISNNLN | 990 | AASSLQS | 1071 | CQQSYNTPFTF | 1241 |
| 003S-H01 | Fzd1 | DTFSNYVLS | 78 | GLVDPEDGETIYA | 429 | CAKASTPMVQGAPDYW | 594 | RASQSIGSNLD | 983 | AASTLQS | 1075 | CQQNYATPRTF | 1224 |
| 003S-H02 | Fzd1 | GTFNRYAIT | 201 | GGIIPIFGTANYA | 408 | CATTQGVYSSSWYGGGRAFDIW | 873 | RASQSISSYLN | 996 | AASSLQS | 1071 | CQQSYSTPLTF | 1264 |
| 003S-H04 | Fzd1 | YTFTYRYLH | 303 | GRINPNSGGTNYA | 446 | CWGGSYYGDYW | 927 | RASQGISNNLN | 969 | AASSLQS | 1071 | CQQANSFPITF | 1208 |
| 003S-A05 | Fzd2 | FTFSSYAMH | 141 | SSISWNSGRVDYA | 545 | CARGSGIAASGSYW | 757 | TSSQSLLHSDGKTYLY | 1058 | LGSNRAS | 1131 | CMQGTHWPYTF | 1182 |
| 003S-B05 | Fzd2 | FTFSNAWMS | 125 | STIAGSGGRTYYS | 550 | CAKDSIGRRGRGAPQPYYYGMDVW | 606 | KSSQSLLHSDGKTYLY | 932 | LGSNRAS | 1131 | CMQSLQSPLTF | 1189 |
| 003S-F05 | Fzd2 | FSFSTYTMS | 98 | SRINGDGSSTRYA | 531 | CARAIVGATGLNRFKAFDIW | 640 | KSSQSLLHSDGKTYLY | 932 | LGSNRAS | 1131 | CMQNTHWPLTR | 1186 |
| 003S-G05 | Fzd2 | STFTNAWMS | 273 | SAIGTGGGTYA | 92 | CARDRVTLRGGYSYGTDAFDIW | 693 | RSSRSLLHSNGNTYLR | 1043 | LASRRAS | 1125 | CIQNTHWPLTR | 1164 |
| 003S-H05 | Fzd2 | FTLSTYNMN | 170 | SRINYDGSATTYA | 502 | CARDRDIVVVPAQRGEGGFDPW | 683 | KSSQSLLHSDGKTYLY | 932 | MGSYRAS | 1133 | CMQGTHWPLTF | 1181 |
| 003S-A07 | Fzd2 | FTFSSYAMS | 141 | SAISGSGGSTYYA | 507 | CAKGGRDGYKGYFDYW | 611 | KSSQSLLHSDGKTYLY | 932 | LGSNRAS | 1131 | CMQNTHWPLTL | 1185 |
| 003S-C07 | Fzd2 | FSFRSYSMS | 92 | SAIGTGGGTYA | 502 | CTTTTVTTSW | 923 | RTSQSVSSNLA | 1048 | DASNRAS | 1083 | CQQYGSSPYNF | 1304 |
| 003S-F07 | Fzd2 | FSFSSYGMS | 97 | SHISSGGATIDYA | 526 | CARDGGYW | 665 | RASQSISSYLN | 996 | AASSLQS | 1071 | CQQSYSTPLTF | 1264 |
| 003S-G07 | Fzd2 | FTFSSYWMH | 152 | SYISGDSGYTNYA | 566 | CARDNGYCSGGSCYATYYGMDVR | 680 | RASQAISSYLA | 957 | KASTLDT | 1122 | CQQADTFPFTF | 1206 |
| 003S-B08 | Fzd2 | FTFSSZZMH | 153 | AVISYDGSNRZYA | 385 | CARSYYDSSGYPRKDAFDIW | 824 | KSSQSLLHSDGKTYLY | 932 | LGSNRAS | 1131 | CMQTLKAPLTF | 1192 |
| 003S-F08 | Fzd2 | ZSVSSNYMS | 310 | SRINSDGSTISYA | 532 | CARARLLGGYYTPDRMDVW | 647 | RSSQYLSSAYLA | 1039 | GASRRAT | 1107 | CQQYGSSPTF | 1303 |
| 003S-H08 | Fzd2 | FTFNRHALS | 111 | ALISSNGDHKYYT | 360 | CARDLMVGRNKLDYW | 674 | QASQGISNNLN | 946 | AASSLQS | 1071 | CQQSYSTPAFTF | 1259 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 003S-A09 | Fzd2 | FTFSSSNMN | 139 | SGISGSGSSTYYA | 518 | CARGRVVGSSRDYW | 756 | RSSQSLLHSDGYTYLY | 1033 | LGSNRAS | 1131 | CMQGTHWPLTF | 1181 |
| 003S-B09 | Fzd2 | FNIRRZNMZ | 88 | SAIGTGGGTYYA | 502 | CARGDSGSYRDYW | 720 | RSSESLLHSDGKTYLY | 1028 | LGSNRAS | 1131 | CTQTVQFPITF | 1325 |
| 003S-C09 | Fzd2 | FTFSSSAMH | 138 | SGISGSGTTTYYR | 519 | CARRLIAVAGAEFDPW | 809 | RASQGISNNLN | 969 | SASNLQS | 1146 | CQQGYSAPWTF | 1270 |
| 003S-F09 | Fzd4 | FTFSNSDMN | 128 | GRIKSKAYGGTTEYA | 445 | CARQYYFDYW | 806 | RASQSISSYLN | 996 | AASSLQS | 1071 | CQQSYSTPLTF | 1264 |
| 003S-H09 | Fzd4 | FTFSFGMH | 135 | SVISSGGSPYYA | 558 | CATASGDFDYW | 865 | RASQGISNNLN | 984 | RASTLES | 1142 | CQQTYTTPRF | 1290 |
| 003S-A10 | Fzd4 | FTFDDYAMH | 105 | AIVSYDGTYKYYS | 357 | CARQTRGTTDGW | 804 | RASQSISSYLN | 969 | YASSLQS | 1156 | CQQSHSPPGTF | 1236 |
| 003S-B10 | Fzd4 | FTFSHSTH | 136 | SAISASGDSTFYA | 503 | CARPIVGATAFDIW | 797 | RASQSISSYLN | 996 | AASSLQS | 1071 | CQQSYSTPLTF | 1264 |
| 003S-G10 | Fzd4 | FTZSSYSMN | 177 | SYSSGNSGYTNYA | 572 | CARGVVGSGAFDIW | 765 | RASQSIVSYLN | 1002 | DASNLQS | 1082 | CQQGYSAPWTF | 1220 |
| 003S-B11 | Fzd4 | FTFSDYYMS | 122 | SAIDGAGRTYYT | 498 | CARAIPGDYDYW | 639 | RASQSISSYLN | 996 | AASSLQS | 1071 | CQQSYSTPLTF | 1264 |
| 003S-C11 | Fzd4 | FTFTSYAMH | 165 | GGIIPIFGIANYA | 405 | CARTGRGYYGMDVW | 825 | RASQSIGSNLD | 983 | AASTLQS | 1075 | CQQSYSTPRTF | 1265 |
| 003S-D11 | Fzd4 | FTFSSYSMS | 147 | SYISGDSGYTNYA | 566 | CARAGVATIAFDYW | 638 | RASQSISSYLN | 996 | AASSLQS | 1071 | CQQSYSTPLTF | 1264 |
| 003S-F11 | Fzd4 | FTFDDYGMH | 106 | SAISGSGGSTYYA | 507 | CTTPNYYDSR | 920 | RASQSISSYLN | 996 | AASSLQS | 1071 | CQQSYSTPLTF | 1264 |
| 003S-E12 | Fzd4 | GTFSSYAIS | 207 | GWINAGNGNTTYA | 465 | CARHYYGSGSYPDW | 777 | 2PZQT2ZSHLN | 1060 | PASSLQS | 1136 | CQQSYSTPLTF | 1264 |
| 004S-A01 | Fzd4 | FTFSTYGMH | 157 | SYISSSSSAIYYA | 569 | CARGGLDGPIDYR | 727 | RASQGISNNLN | 969 | AASTLQS | 1075 | CQQGNNFPFTF | 1218 |
| 004S-G01 | Fzd4 | FTVSHSMG | 173 | SLVSFDGSKEHYA | 528 | CARLGSTPDYW | 784 | RASQGISNNLN | 969 | AASSLQS | 1071 | CQQYTYPYTF | 1320 |
| 004S-C02 | Fzd4 | FTFSSYGMH | 143 | AVISYDGSNKYYA | 384 | CASDPVTAATR | 853 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 004S-D02 | Fzd4 | FSFSSYGMS | 97 | SGISGSGRSTYYA | 517 | CAKDGYW | 596 | RASQSISSYLN | 996 | AASSLQS | 1071 | CQQSYSTPLTF | 1264 |
| 004S-A03 | Fzd4 | FTFSSYAMH | 141 | SGINWNGGSTGYA | 513 | CARPAGSAQNWFDPW | 796 | RASQGISNNLN | 969 | DASNLET | 1081 | CHQSYSIPRTF | 1163 |
| 004S-B03 | Fzd4 | FSFSRYGMS | 94 | SGVGGSGGSTZYA | 524 | CARDGSW | 668 | RASQDVDTWLA | 963 | DASTLET | 1087 | CQQGYNIPWTF | 1219 |
| 004S-C03 | Fzd4 | YTFTSYAIS | 297 | GIINPSGGSTSYA | 422 | CARQIGWELMPDIW | 803 | QASQDISYLN | 944 | AASTLQS | 1075 | CQQAISFPLTF | 1207 |
| 004S-C05 | Fzd5 | ZZZTDYYZQ | 312 | GGMNZNRGNTGYA | 419 | CANGSYAQHLW | 629 | RASQSISSYLN | 996 | AASSLQS | 1071 | CQQSYSTPLTF | 1264 |
| 004S-G05 | Fzd5 | FTFSSYWMH | 152 | STISPSGLYIYQA | 556 | CAKDKVPYSYGPNFDYW | 600 | RASQSISSYLN | 996 | AASSLQS | 1071 | CQQSYSTPLTF | 1264 |
| 004S-E06 | Fzd5 | FFFSGYWMS | 83 | ANIKQDGSEKYYV | 368 | CARVFPLHDYW | 831 | QASQDISNYLN | 943 | KASSLES | 1120 | CQQANSFPYTF | 1211 |
| 004S-C06 | Fzd5 | FPFSTFSMN | 90 | AGISWNSGTIDYA | 355 | CARSGPAAMVYYYYGMDVW | 815 | RSSQNVSSYLA | 1030 | GASTRAT | 1111 | CQHRANWPQTF | 1198 |
| 004S-E07 | Fzd6 | FTLSSHHMN | 169 | SAIGTGGGTYYA | 502 | CAAPDYW | 583 | RASQSISSYLN | 996 | AASSLQS | 1071 | CQQSYSTPLTF | 1264 |
| 004S-F07 | Fzd6 | FSFSKKYMT | 93 | SSIDGNGDHVFYA | 536 | CARPYYYDSSGYDPMGDYW | 801 | QASQDITNYLN | 945 | KASTLES | 1123 | CQQSYSAPYTF | 1248 |
| 004S-C08 | Fzd6 | FTVSSNYMN | 174 | SAIGTGGGTYYA | 502 | CAQGTYW | 632 | RASQSISSYLN | 996 | AASSLQS | 1071 | CQQSYSTPLTF | 1264 |
| 004S-F08 | Fzd6 | FTFDDYYMN | 107 | SAVSGNGGGTFYA | 511 | CARGGNYGSGDYW | 730 | RASQSIZWLA | 1000 | EASTLQS | 1094 | CQQTYTPPFTF | 1289 |
| 004S-G09 | Fzd6 | GTLNNHTLS | 219 | GRIIPIFGTANYA | 435 | CARDRRGYGMDVW | 692 | RASQAISNSLA | 955 | DASNLET | 1081 | CQQAYSFPWTF | 1216 |
| 004S-B10 | Fzd6 | FTFSDYYMS | 122 | SGINWNSAKIGYV | 514 | CARIGAGGAFDIW | 778 | RASQSISYLN | 996 | AASSLQS | 1071 | CQQSYSTPLTF | 1264 |
| 004S-H10 | Fzd6 | FIFSDYYMS | 84 | AVITSGGTFKYYA | 386 | CARNGIAAAEDYW | 793 | RASQSISTYLS | 999 | GASSLES | 1104 | CQQSYSPPFTF | 1254 |
| 004S-B11 | Fzd6 | FTFSSSWMH | 140 | SGISWNSGSIGYA | 522 | CARYSSGGSLDYW | 852 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 004S-D11 | Fzd6 | YZFZZZYMH | 309 | GRINPNSGGTNYA | 446 | CARARSSGWTDAFDIW | 648 | RASQSVSWLA | 1018 | AASTLQT | 1076 | CQQSYSTPTF | 1268 |
| 004S-F11 | Fzd6 | FTFSSYAMS | 141 | SSISGGGRHTYYA | 539 | CARPYSSRQGDYW | 800 | RASQSISSYLN | 996 | AASSLQS | 1071 | CQQSYSTPLTF | 1264 |
| 004S-Gil | Fzd6 | YIFTDYYMH | 278 | GWINPNSGGTNYA | 471 | CARDRPGFDPW | 687 | RASQSVSSYLA | 1019 | GASSRAT | 1107 | CQQYAISYTF | 1292 |
| 004S-812 | Fzd6 | FTFSSYWIH | 151 | SYISGDSGYTNYA | 566 | CAKGIRWFDPW | 613 | RASQSISSYLN | 996 | AASSLQS | 1071 | CQQSYSTPLTF | 1264 |
| 004S-C12 | Fzd6 | YIFTDYYMH | 278 | GWMNPNSGNTGYA | 490 | CASSHYAPGMDVW | 859 | RASQGISSYLA | 974 | RTSTLES | 1144 | CQQSYSTPWTF | 1270 |
| 004S-F12 | Fzd6 | FTVGNNYMS | 171 | SSITTTSTLYA | 547 | CARGKEGRYSNYEAAW | 741 | RASQSISSYLN | 996 | AASTLQT | 1076 | CQQSYSIPFTF | 1250 |
| 005S-B01 | Fzd7 | FTFRSYGMH | 116 | SLISGSGDNTNYA | 527 | CARREPLYSSRRGAFDIW | 807 | RASQSISYLN | 996 | AASSLQS | 1071 | CQQSYSTPLTF | 1264 |
| 005S-C01 | Fzd7 | FTFSYSMS | 147 | SAISGSGGSTYYA | 507 | CTRTIVGATPHYW | 914 | RASQGISNNLN | 969 | KASSLQS | 1121 | CQQSYLPYT | 1252 |
| 005S-F01 | Fzd7 | FTVSSNYMS | 175 | SAISGSGATTTYA | 505 | CAKGAGYGSGSWQAAW | 608 | RASQSVSSYLS | 1017 | GASSRAT | 1107 | CQQRYKSYTF | 1229 |
| 005S-B02 | Fzd8 | YSFTNYAMH | 280 | GRIIPIPGTAZYA | 436 | CARGTFLEWLLTNYGMDVW | 763 | RASQSISSYLN | 996 | AASSLQS | 1071 | CQQSYSTPLTF | 1264 |
| 005S-D02 | Fzd8 | GTFSSYVIS | 209 | GWIGPHNGNTNYA | 461 | CATGWPRYYYGMDVW | 868 | RASQSVSSNLA | 1014 | NTSNRAT | 1135 | CQHYNNWPFTF | 1201 |
| 005S-G02 | Fzd8 | YTFTSYYMH | 301 | GGIIPIPGTAZYA | 409 | CARLPYYDFWSGYYGGRTGFDYW | 786 | RASQSVSTNLA | 1020 | DASNRAT | 1084 | CQQRSNWPPQITF | 1227 |
| 005S-H02 | Fzd8 | YTFTYRYLH | 303 | GWINAGNGNTTYA | 465 | CARASLYDYVWGSYRHYYFDYW | 650 | QASQDISHYLN | 941 | AASSLQS | 1071 | CQQSYSTPLTF | 1264 |
| 005S-B03 | Fzd8 | GTFSSYAIS | 207 | GIINPSGGRTTYA | 421 | CATSFGGGWIVDTSLWYW | 872 | RASQSINSNLA | 989 | GASSRAT | 1107 | CQQYGSSPYT | 1305 |
| 005S-C03 | Fzd8 | GSFSGYAIS | 187 | GGIIPIPFGTANYA | 408 | CRVDAFDIW | 906 | RASQSVSSSYLS | 1017 | DTSNRAT | 1090 | CQQYGSSPIT | 1300 |
| 005S-E03 | Fzd8 | FTFTSSAVQ | 164 | GGIIPIPGTANYA | 408 | CARSSGWQNRFAFDIW | 820 | RTSQSISSYLN | 1047 | AASTSQS | 1077 | CQQSFSSWTF | 1234 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 005S-F03 | Fzd8 | YTFTYRYLH | 303 | GWINAGNGNTKYS | 464 | CATDLPVRKGFTYYDILTGSYGMDVW | 867 | RASQSISSYLN | 996 | AASSLQS | 1071 | CQQSYSTPLTF | 1264 |
| 005S-B04 | Fzd8 | YTFTNNFMH | 292 | GGIIPIFGTANHA | 407 | CARGLRYFDWPQGIYYYYGMDVW | 745 | QASHDINIALN | 936 | AASSLQS | 1071 | CQQSYSSPLTF | 1257 |
| 005S-C04 | Fzd8 | YTFTSYYMH | 301 | GRINPNSGGTNYA | 446 | CARGGLLFDYW | 728 | RASQSISSYLN | 996 | AASSLQS | 1071 | CQQSYSTPLTF | 1264 |
| 005S-D04 | Fzd8 | FTFSTYSMS | 159 | STIGTGGGTYYA | 552 | CARVGWLRFLDYW | 835 | RASQSISSYLN | 996 | AASSLQS | 1071 | CQQSYSTPLTF | 1264 |
| 005S-G04 | Fzd8 | GTFSSYAIS | 207 | GWMSPSSGNAGYA | 492 | CARNNFLRAFDIW | 794 | RASQSISSYLN | 996 | AASSLQS | 1071 | CQQSYSTPLTF | 1264 |
| 005S-A05 | Fzd8 | FAFSSYAMS | 81 | SRIDTDGSTTVYA | 529 | CARAPSYSSGVVYVRW | 644 | RASQSISSYLN | 996 | AASSLQS | 1071 | CQQSYSTPLTF | 1264 |
| 005S-C05 | Fzd8 | YTFTYYAMH | 304 | GIINPSGGSTSYA | 422 | CARELLPMTTVTSPFIW | 709 | RASQGISNNLN | 969 | RASSLQS | 1141 | CQQANSYPLTF | 1212 |
| 005S-E05 | Fzd8 | GTFSSYAIS | 207 | GGIIPIFGTANYA | 408 | CAIRAFDIW | 591 | RASQSISSYLN | 996 | AASSLQS | 1071 | CQQSYSTPLTF | 1264 |
| 005S-C06 | Fzd8 | ZTFSZYDMH | 311 | SSISSSHYKYYA | 542 | CARVRSKAVAGTLPKRLFDIW | 844 | RASQSVSSSYLS | 1017 | AASRAT | 1068 | CQQYSNWPFTF | 1316 |
| 005S-E06 | Fzd8 | YTFTSYYMH | 301 | GWMNPNSGNTGYA | 490 | CARGNPTSGHIVVVPAATFSDYW | 747 | QASQDISNRLN | 942 | SASRLQI | 1147 | CQQSYRTPRTF | 1246 |
| 005S-G06 | Fzd8 | GTFSZZTIS | 213 | GWMNPDSGKTGYA | 486 | CARWAFPIPNAFDIW | 486 | RASQSISSYLN | 996 | AASSLQS | 1071 | CQQSYSTPLTF | 1264 |
| 005S-H06 | Fzd8 | YTFTNNFMH | 292 | GGIFPIYGISTYA | 403 | CARDRPSSSWYAFDYW | 688 | RASQGISNNLN | 969 | DASTLQT | 1089 | CQQSFSAPITF | 1233 |
| 005S-A08 | Fzd9 | GTFSZYAIS | 212 | GGIIPIFGTANYA | 408 | CARGGLLRFGDGWGMGMDVW | 729 | RASQSISSKSLA | 995 | GASTRAT | 1111 | CQQYGIAPTF | 1299 |
| 005S-C08 | Fzd9 | YTFTDYHMH | 285 | GWINAGNGNTTYA | 465 | CARASSWLHYYYGMDVW | 652 | RASQSISSYLN | 996 | AASSLQS | 1071 | CQQSYSTPLTF | 1264 |
| 005S-E08 | Fzd9 | FIFSZYAMS | 85 | SSISAAGAYKYYA | 538 | CARRGYSSGWRDAFDIW | 808 | RASQSISSYLN | 996 | AASSLQS | 1071 | CQQSYSTPLTF | 1264 |
| 005S-F08 | Fzd9 | YTFTSYYMH | 301 | GWINAGNGNTTYA | 465 | CAKDVNYW | 607 | QASQGISNYLN | 947 | AASSLQS | 1071 | CQQTYSTPTTF | 1287 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 005S-H08 | Fzd9 | GTFSSYAIS | 207 | GRIIPILGTPNYA | 440 | CARDRLAFDYW | 686 | RASQSISSYLN | 996 | AASSLQS | 1071 | CQQSYSTPLTF | 1264 |
| 005S-A09 | Fzd9 | FAFSSHWMH | 80 | SAISVSGGTTFYA | 509 | CARWGKRLRGSPYYFDYW | 849 | RASQSIGSNLD | 983 | RASTLQS | 1143 | CQQSYSTPSF | 1267 |
| 005S-F09 | Fzd9 | FTFSIYGMH | 123 | SGISWNSGNIGYA | 521 | CARGPLPTKIGGHYMDVW | 749 | RASQSISSYLN | 996 | AASSLQS | 1071 | CQQSYSTPLTF | 1764 |
| 005S-B10 | Fzd9 | FTFSTXWMS | 154 | AVMYSGGTTYYA | 387 | CARLSYYYDSSGPKGDAFDIW | 788 | RASQGISNNLN | 969 | AASSLQS | 1071 | CQQGNNFPLTF | 1218 |
| 005S-C10 | Fzd9 | FSLSLSYGMH | 99 | SSISSSSSYIYYA | 543 | CARSGMVKWLRSFDYW | 814 | RASQDIGSFLA | 958 | AASSLQS | 1071 | CQKYNRAPFT | 1203 |
| 005S-E10 | Fzd9 | FTFTSSAMQ | 162 | GVINPGSGGTSYN | 459 | CARGYGDYVWGENYFDYW | 770 | RASQSISSYLN | 996 | AASSLQS | 1071 | CQQSYSTPLTF | 1264 |
| 005S-F10 | Fzd9 | YTLSNYGIS | 306 | GWISAYNGDTKYA | 475 | CARFDYFGGMDVW | 713 | RASQSISSYLN | 996 | AASSLQS | 1071 | CQQSYSTPLTF | 1264 |
| 005S-G10 | Fzd9 | YTFTRYAVH | 294 | GGIIPFFNTVNYA | 404 | CAADRSPYYYDSSGYYPDAFDIW | 576 | RASQGISNNLN | 969 | QASSLDS | 1138 | CQQSYNVPYTF | 1244 |
| 005S-A11 | Fzd9 | FTFSSYDMN | 142 | SGISWNSGYIGYA | 522 | CAKGSLLLGYYGMDVW | 617 | RASQSISNNLN | 990 | DASTLKR | 1088 | CQQSYNTPRTF | 1242 |
| 005S-B12 | Fzd9 | FTZSSYDMH | 176 | SSISGLGGSTYZA | 540 | CAREAGTTGGWFDPW | 702 | RASQSISSYLN | 996 | AASSLQS | 1071 | CQQSYSTPLTF | 1264 |
| 005S-D12 | Fzd9 | FTFSDHYMD | 118 | STIGPAGDTYVP | 551 | CARASTSGDYSLW | 653 | RASQSVSTSYLA | 1021 | GASTRAT | 1111 | CQQYGASPWTF | 1298 |
| 006S-B01 | Fzd10 | YTFTNYCTR | 293 | GLVCPSDGSTSYA | 428 | CARRTSASDIW | 812 | RASQSISSYLN | 996 | AASSLQS | 1071 | CQQSYSTPLTF | 1764 |
| 006S-C01 | Fzd10 | FTFTZSAVQ | 401 | GGFDPEDGETIYA | 401 | CTTDPLELPWYW | 917 | RASQGISSALA | 973 | SASNLQS | 1146 | CQQAISFPLTF | 1207 |
| 006S-E01 | Fzd10 | YTFTGYYMH | 288 | GIINPSSGRTDYA | 423 | CARDLTYYYDSSGHSPLGAFDIW | 678 | RASQSVTSSLA | 1022 | GASTRAT | 1111 | CQQYNDWPPTF | 1308 |
| 006S-G01 | Fzd10 | FTFSDFGMN | 117 | AGISGGGGSTDYA | 352 | CARDSDFWYYGMDVW | 694 | KSSQSVLYSSNNKNYLA | 934 | STNTRSS | 1151 | CQHRNFF | 1199 |
| 006S-B02 | Fzd10 | VSFSGYAMH | 276 | AYINSGSSEMNYA | 391 | CAREEWELFGMDVW | 704 | RASQSISSYLN | 996 | AASSLQS | 1071 | CQQSYSTPLTF | 1264 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 006S-G02 | Fzd10 | YTVTSYAMH | 308 | GGIIPIPFGTAKYA | 406 | CAKGGQWLYGMDVW | 610 | RASQSISSYLN | 996 | AASSLQS | 1071 | CQQSYSTPLTF | 1264 |
| 014S-A01 | Fzd1 | YTFTSYYMH | 301 | GWVSPSSGNTAYA | 495 | CARDEGAGVYYYMDVW | 663 | RASQSISSYLN | 996 | AASSLQS | 1071 | CQQSYSTPLTF | 1264 |
| 014S-C01 | Fzd2 | FTFSNYAMT | 130 | SAIGTGGGTYYA | 502 | CATAYRPGGLDVW | 866 | RSSQSLLHSDGKTYLY | 1032 | LGSNRAS | 1131 | CMQNTHWPLTR | 1186 |
| 014S-F01 | Fzd4 | FTFSSYAMH | 141 | SVISTSGDTVLYT | 559 | CARGGSSDVR | 735 | RASQSISSYLN | 996 | AASSLQS | 1071 | CQQSYSTPLTF | 1264 |
| 014S-H01 | Fzd4 | FTFSNYGMH | 131 | SYISSSSSTIYYA | 570 | CARAALGYCTGGVCPPVDYW | 634 | RASQGISNNLN | 969 | AASRLQS | 1067 | CQQSYSPPLTF | 1255 |
| 014S-C03 | Fzd7 | YTFTNNFMH | 292 | GIIZPGGGRTIYA | 426 | CAKGDYGALDYW | 609 | RASQSISSYLN | 996 | AASSLQS | 1071 | CQQSYSTPLTF | 1264 |
| 014S-D03 | Fzd7 | FNFSSYTMR | 87 | SVIYGGGNTNYA | 561 | CARGGSGGNLSYW | 733 | RASQSISSYLN | 996 | AASSLQS | 1071 | CQQSYSTPLTF | 1264 |
| 014S-F03 | Fzd8 | YTFTNNFMH | 292 | GGIIPLFGTANYA | 415 | CARLVVRGGYGMDVW | 790 | RASQSISSYLN | 996 | AASSLQS | 1071 | CQQSYSTPLTF | 1264 |
| 014S-A04 | Fzd8 | GTFSSYAIS | 207 | GWISSNGNTKYA | 482 | CARADDYYDSSGYYYGFDYW | 635 | RASQSISSYLN | 996 | AASSLQS | 1071 | CQQSYSTPLTF | 1264 |
| 014S-C04 | Fzd8 | FTFSSYTMN | 148 | SRINGDGSNTNYA | 530 | CARGWAGFDYW | 768 | RASQSISSYLN | 996 | AASSLQS | 1071 | CQQSYSTPLTF | 1264 |
| 014S-D04 | Fzd8 | HTFSGYHIH | 222 | GWINAGNGNTTYA | 465 | CARDLSPMVRGVISGMDVW | 676 | RASQSISSYLN | 996 | AASSLQS | 1071 | CQQSYSTPLTF | 1264 |
| 014S-E05 | Fzd8 | YTFTNNFMH | 292 | GIISPGGGRTIYA | 424 | CAKGDYGALDYW | 609 | RASQSISSYLN | 996 | AASSLQS | 1071 | CQQSYSTPLTF | 1264 |
| 014S-E06 | Fzd8 | FTFGNYDMN | 109 | SSLSWNSGTIVYA | 548 | CARDSSSGVVYASYYGMDVW | 695 | RASQSISRYLN | 993 | AASSLQS | 1071 | CLQHSYPFT | 1169 |
| 014S-F06 | Fzd10 | YTLITWYMX | 307 | GWMNPNSGNTAYA | 489 | CARGALGMDVW | 716 | QASQDISNYLN | 943 | AASSLHT | 1069 | CQESYSSPYTF | 1195 |
| 027S-C02 | Fzd5 | YTFTGHYMH | 287 | GWMNPNSGNTGYA | 490 | CARGTGGFDYW | 764 | RASQSISSYLN | 996 | AASSLQS | 1071 | CQQSYRTPYTF | 1271 |
| 027S-E03 | Fzd8 | YTFTGHYIH | 286 | GWMNPISGNTGYA | 487 | CARSTPFDPW | 822 | RASHDIGTFLA | 954 | AASTLQS | 1075 | CQQSYRTPYTF | 1247 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 027S-G03 | Fzd8 | YTFTHSYIH | 289 | GWINAKSGGTFYA | 466 | CARGDYDFWSGYHEYYYYGMDVW | 721 | QATQNIKKYLN | 948 | KASTLES | 1123 | CQQSYSTPLTF | 1264 |
| 027S-H03 | Fzd8 | YTFTSYYMH | 301 | GWINPNSGGTNYA | 471 | CARAPLDGSGSYVDW | 643 | RSSQSLLHSNGYNYLD | 1036 | LGSNRAS | 1131 | CMQALQTPQTF | 1176 |
| 027S-A04 | Fzd8 | YTFTNHFMH | 291 | GWISPNRGGTNYA | 478 | CARDCSGGSCYSHFDYW | 662 | RASQSISRSLA | 991 | AASNLQS | 1065 | CQQAYSFPQTF | 1215 |
| 027S-B04 | Fzd8 | FTVGSWYMS | 172 | SAIGTGGGTYA | 502 | CAKDITPYGDYSILSHW | 599 | RASQAISNYLN | 956 | AASSLQS | 1071 | CQQTFSPPLTF | 1275 |
| 027S-C04 | Fzd8 | YTFTSHWMH | 295 | GGIIPIPGTTNYA | 412 | CARDSSSWYSYYYYMDVW | 696 | RASQGINNYLA | 964 | QASNLES | 1137 | CQQTYSSPLTF | 1285 |
| 027S-D04 | Fzd8 | YTFTTYFMH | 302 | GWIYPNSGGTKYA | 485 | CTTDLRYDSSGPAAFDIW | 916 | QASQDIDNYLN | 937 | AASSLQS | 1071 | CQQSYSTPVTF | 1269 |
| 027S-E04 | Fzd8 | FTFSDHYMS | 119 | SGISGSGGTTYYA | 516 | CATYGDFGYFDLW | 875 | RASQGIRNDLG | 966 | AASTLQS | 1075 | CQQAYSFPWTF | 1216 |
| 027S-F05 | Fzd8 | GSFSTSVFG | 191 | GRIIPLFGTTNYA | 441 | CVKDRAWGFDYW | 924 | RASQGIRNDLA | 965 | AASSLQR | 1070 | CQQYSKPTF | 1251 |
| 027S-D05 | Fzd8 | YTFTSYYMH | 301 | GWINPKSGGTNYA | 467 | CARGGFVFDYW | 725 | QASQDISNYLN | 943 | ASSTLQT | 1078 | CQQSYSAPYTF | 1248 |
| 027S-E05 | Fzd8 | GTFSSYAIS | 207 | GMINPSGGSTTYA | 432 | CARQAGLHCSSTSCYLGNWFDPW | 802 | RASQGITKSLA | 975 | AASNLQL | 1064 | CQQYNTFPITF | 1314 |
| 027S-F05 | Fzd8 | GTFNRYGIS | 202 | GGIIPRLGATDYA | 417 | CAKGNWAFDIW | 616 | RASQSISTYLA | 998 | GASTRAT | 1111 | CQQYGSSPTF | 1303 |
| 027S-G05 | Fzd8 | GTFSSYAIS | 207 | GWISPYNGNTKYA | 479 | CARGVWTTPMGGGGNWFDPW | 766 | RASQSISSYLN | 996 | YASSLQN | 1155 | CQQSYSTPFTF | 1260 |
| 027S-H05 | Fzd8 | GTFGNYGIN | 198 | GWINPNSGGTNYA | 471 | CARETTDYYYGMDVW | 711 | RASQSIGTYLN | 986 | DASNLET | 1081 | CQQANSFPLTF | 1209 |
| 027S-A06 | Fzd8 | GTFSSYAIN | 206 | GVIDPSTGGTNYA | 457 | CARVLPGDSSGWVRGYYYYGMDVW | 838 | RASQGISNNLN | 969 | KASSLES | 1120 | CQQANSFPITF | 1208 |
| 027S-C06 | Fzd8 | GTFTSYPIS | 217 | GWINTYNGNTIYA | 473 | CARDLDSGFDLW | 673 | RASQGVGDYLA | 976 | DAS N LQS | 1082 | CQQHNAYPLTF | 1221 |
| 027S-D06 | Fzd8 | GTFSSYAIS | 207 | GWISAYNGHTNYA | 476 | CARGGYSVGTVFDYW | 739 | RASQDISSWLA | 961 | KASTLES | 1123 | CQQSYGAPLTF | 1239 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 027S-E06 | Fzd8 | YTFTKDYMH | 290 | GGIIPIFGTANYA | 408 | CARGLPPAAGGGYFQHW | 744 | RASQNVNDWLA | 980 | SASNLQS | 1146 | CQQSYSTPFTF | 1260 |
| 027S-F06 | Fzd8 | FTFSSYAMH | 141 | AVTWYDGSNKYYA | 389 | CAKDLVPYCSGGSCPPSGW | 602 | RASQSISYLNVA | 996 | GASNLQS | 1101 | CQQSYSTPLTF | 1264 |
| 027S-G06 | Fzd5 | YTFTDYYMH | 285 | GWMSPNSGNAGFA | 491 | CARGKSGSFDYW | 743 | RASQSVNNTYVA | 1009 | GTSTRAT | 1116 | CQQYDTSPPTF | 1296 |
| 027S-H06 | Fzd5 | YTFTGHYIH | 286 | GIINPSGGSTSYA | 422 | CARGFCSGGSCLWYGMDVW | 722 | RASQSISYLN | 996 | AASSLQS | 1071 | CQQSYTTPFTF | 1274 |
| 027S-A07 | Fzd5 | GTFGSYAIT | 199 | GGIIPIFGTANYA | 408 | CAKDNGWYFDLW | 603 | RASQSISTNVN | 997 | AASSLQS | 1071 | CQQSYSTPYTF | 1271 |
| 029S-B01 | Fzd1 | GTFSSYAIS | 207 | GRINPHNGNTNYA | 1352 | CARATRVSAAGTVHFQHW | 1363 | KSSQSVLHSSNKNYLA | 1389 | STNTRSS | 1151 | CQQYSTPFTF | 1433 |
| 029S-D01 | Fzd2 | YTFTRYYIH | 1344 | GWMNPNSGNTGYA | 490 | CARVRFLEEMDVW | 1385 | RASQSLSSWLA | 1403 | DASTLQS | 1412 | CQQAISFPLTF | 1207 |
| 029S-C02 | Fzd2 | GTFSSYGIS | 1329 | GIINPSGGSTSYA | 1350 | CARGDIVATMGMKKVDYYYMDVW | 1369 | RASQDISNNLN | 1391 | GASHLQT | 1414 | CQQANSFPVTF | 1210 |
| 029S-F02 | Fzd2 | YTFTRYYLH | 1345 | GWMNPNSGNTGYA | 490 | CARGIGYW | 1372 | RASQGISNYLA | 971 | AASRLQT | 1407 | CLQYNTYPWTF | 1420 |
| 029S-H02 | Fzd2 | GTFSTYAIS | 210 | GDIIPIFGSANYA | 1348 | CARELGLGWFDPW | 1367 | RSSQSLLHSNGYNYLD | 1036 | LGSSRAS | 1417 | CMQALQTPLTF | 1175 |
| 030S-A02 | Fzd7 | YTFTDYYMH | 285 | GWMNPNSGSTGYA | 1358 | CARGDINYGNFDYW | 1368 | RASQSISYLN | 996 | KASTLHN | 1415 | CQQAISFPLTF | 1207 |
| 030S-B02 | Fzd3 | YTFTDYYMH | 285 | GWMNPNSGNTGYA | 490 | CARQGGSYSMGLDPW | 1379 | RASQSITTYLN | 1402 | KTSSLQS | 1416 | CQQGDSFPYTF | 1422 |
| 029S-E03 | Fzd3 | YTFTGYYMH | 1342 | GWINPNSGNTGYA | 1354 | CARSYYGVIDAPDIW | 1383 | RASCISISSYLN | 996 | AASSLQT | 1408 | CQQSFRLPLTF | 1423 |
| 029S-G03 | Fzd3 | YTFTNYYMH | 1343 | GWMNPNSGNTGYA | 490 | CAREDDFWSGGGMDVW | 1365 | RASQSISYLN | 1400 | AASSLQS | 1071 | CQQSWRFPYTF | 1426 |
| 030S-E03 | Fzd3 | FTFSDYYMS | 122 | SAISGSGHSTYYA | 1359 | CAREGLRGWSIFDIW | 1366 | KSSQSVLYSSNKNYLA | 934 | WASTRES | 1418 | CQQYSTPPTF | 1434 |
| 029S-D05 | Fzd3 | YTFTDHYFH | 1338 | GWANPSSGNTGTA | 1353 | CARSRLRWDWYFDLW | 1382 | RASQTISSYLN | 1405 | DASNLET | 1081 | CQQSYSIPLTF | 1250 |

TABLE 1A-continued

Clone IDs and CDR sequences.

| Clone ID | Initial Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 030S-H03 | Fzd3 | FSFSSHAMS | 1327 | SAIGTGGGTYYA | 502 | CANPKHYW | 1361 | RASQGVSTYLA | 1396 | AASSLQS | 1071 | CQQYSSPQTF | 1432 |
| 029S-B06 | Fzd3 | YTFSRHYIH | 1337 | GWMNPNSGNTGYA | 490 | CARGGHTGYSSGWYNHW | 1370 | RASQSVSSWLA | 1404 | AASSLQS | 1071 | CQQAFRFPPTF | 1421 |
| 029S-E06 | Fzd3 | YWFTASYMH | 1347 | GWMKPDSGNTGYA | 1356 | CARRSSSWGWYFDLW | 1380 | RASQNINSWLA | 1397 | AASSLQS | 1071 | CQQYSFPLTF | 1431 |
| 029S-H06 | Fzd3 | YTFAKYYIH | 1335 | GWMNPNSGNTGYA | 490 | CARHKRHTPYAFDIW | 1378 | RASQSISYLN | 996 | AASSLQS | 1071 | CQQSHSTPLTF | 1424 |
| 029S-G07 | Fzd3 | YTFTDSYIH | 1339 | GWISAYNGNTNYA | 477 | CARGSGYFDLW | 1377 | RASQSISKWLA | 1401 | GASTLQS | 1109 | CQQAYSFPWTF | 1216 |
| 029S-H08 | Fzd3 | YTFTGHYMH | 1340 | GWMNPNSGNTGYA | 490 | CARVGDYDRFNWYFDLW | 1384 | RASRTVNFLA | 1406 | DASNLRT | 1411 | CQQSYSTPPTF | 1427 |
| 029S-F09 | Fzd3 | GTFSSYAIT | 1328 | GWISAYNGNTNYA | 477 | CARANRGLRKNYYYGMDVW | 1362 | RASQSIARYLN | 1398 | GASSLQS | 1105 | CQQSYNTPWTF | 1243 |
| 030S-F04 | Fzd3 | YTFTSSYIH | 1346 | GIINPSGGGAVYA | 1349 | CARWTTVVTGAAFDIW | 1386 | RASQGIRNDLN | 1393 | DASNLGT | 1410 | CQQSRIPPTF | 1425 |
| 029S-A10 | Fzd3 | YSFTGYYLH | 1333 | GWINPNSGGTNYA | 471 | CARDHGTMIAVAGTFDYYYMDVW | 1364 | RASQGISKYLA | 1394 | AASSLQS | 1071 | CQQSYSTPWTF | 1270 |
| 029S-B11 | Fzd3 | YTFNGYY | 1336 | GIVNPSGGGTNYA | 1351 | CARGGNYGRWLQPWYFDLW | 1371 | QASQDISNYLN | 943 | GASALRS | 1413 | CQQTKSFPLTF | 1429 |
| 029S-D11 | Fzd3 | HTFTSHYMH | 1331 | GWMNPNSANAGYA | 1357 | CARGLGYFDLW | 1374 | RASQDISRGLG | 1392 | AASTLYR | 1409 | CQQAYSFPWTF | 1216 |
| 030S-H05 | Fzd7 | YSFTNYYMH | 1334 | GWMNPNSGNTGYA | 490 | CARSPDFWSGEGYFDLW | 1381 | RASQSIGNYLN | 1399 | AASSLQS | 1071 | CQQANSFPLTF | 1209 |
| 030S-A06 | Fzd7 | YMFTGHDMH | 1332 | GRIIPILGIANYA | 438 | CARGIHGDYGLDYYYMDVW | 1373 | RASQAIGRRLA | 1390 | AASSLQS | 1071 | CQQDTYWTF | 1430 |
| 029S-C12 | Fzd7 | YTFTGYYMH | 1342 | GWMNPNSGNTGYA | 490 | CARGMEYW | 1375 | RASQGISSYLA | 974 | AASTLQS | 1075 | CLQYNTYPWTF | 1420 |
| 030S-C06 | Fzd7 | YTFTGYYIH | 1341 | GWMDPNSGYTGYA | 1355 | CARGPADFWSGYKNDYFDFW | 1376 | RASQGISSWLA | 1395 | DASSLQS | 1086 | CQQSYSTPYSF | 1428 |
| 4A12 | Fzd5 | GYTFTNYDIN | 1330 | WIYPRDGSTKYNEKFKG | 1360 | CVRSAWGPAY | 1387 | KASQDVGTAVA | 1388 | WASTRHT | 1419 | QQYSTYPLT | 1435 |

Table 1B provides clone IDs, the sequence identifier number of the antibody heavy chain fragment and/or light chain fragment, if present, for illustrative clones. In certain embodiments, the Fzd binding domain is an Fab or was derived from an Fab, so the heavy chain of Table 1B includes VH and CH1 sequence, but not CH2 or CH3 sequences. In certain embodiments, the Fzd binding domain is a VHH or sdAb® or was derived from a VHH or sdAb, so Table 1B includes the VHH domain. Table 1B also provides data demonstrating binding of these clones to various Fzd receptors. The Kd values were determined by BLI as described above. Blank entries denote that the binding to the specific Fzd receptor has not yet been determined. The entry of "n.b." indicates no binding. As shown in Table 1 B, a subset of antibody fragments exhibited mono-specificity for a single Fzd, or specificity for a subfamily of Fzd as determined by binding affinity in Octet BLI.

TABLE 1B

Clone IDs, Heavy Chain (HC) and Light Chain (LC) Seq ID Nos, and Binding Characteristics.

| Clone ID | HC SID NO | LC SID NO | Confirmed Binding | Kd (nM) | | | | | | | | | |
|---|---|---|---|---|---|---|---|---|---|---|---|---|---|
| | | | | Fz1 | Fz2 | Fz3 | Fz4 | Fz5 | Fz6 | Fz7 | Fz8 | Fz9 | Fz10 |
| 001S-B01 | 1 | 38 | Fzd1, 2, 7, 9 | ** | ** | n.b. | n.b. | n.b. | n.b. | ** | n.b. | * | n.b. |
| 001S-E02 | 2 | 39 | Fzd1, 2, 7 | * | ** | n.b. | n.b. | n.b. | n.b. | * | n.b. | n.b. | n.b. |
| 001S-G02 | 3 | 40 | Fzd1, 2, 7 | ** | ** | n.b. | n.b. | n.b. | n.b. | ** | n.b. | n.b. | n.b. |
| 001S-H02 | 4 | 41 | Fzd1, 2, 7 | ** | ** | n.b. | n.b. | n.b. | n.b. | ** | n.b. | n.b. | n.b. |
| 001S-A03 | 5 | 42 | Fzd1, 2, 7, 9 | * | ** | n.b. | n.b. | n.b. | n.b. | ** | n.b. | ** | n.b. |
| 001S-B03 | 6 | 43 | Fzd1, 2, 7 | * | * | n.b. | n.b. | n.b. | n.b. | * | n.b. | n.b. | n.b. |
| 004S-G06 | 7 | 44 | Fzd5, 8 | | | | | * | | | * | | |
| 002S-B01 | 8 | | Fzd1 | * | | | | | | | | | |
| 002S-C02 | 9 | | Fzd1 | * | | | | | | | | | |
| 002S-E02 | 10 | | Fzd1 | ** | | | | | | | | | |
| 002S-G02 | 11 | | Fzd1 | ** | | | | | | | | | |
| 002S-F03 | 12 | | Fzd1 | ** | | | | | | | | | |
| 002S-A04 | 13 | | Fzd1 | * | | | | | | | | | |
| 002S-B04 | 14 | | Fzd1 | ** | | | | | | | | | |
| 002S-D04 | 15 | | Fzd1 | ** | | | | | | | | | |
| 004S-H04 | 16 | 45 | Fzd 5 | | | | | ** | | | | | |
| 001S-A04 | 17 | 46 | Fzd1, 2, 5, 7, 8 | * | * | n.b. | n.b. | * | n.b. | * | * | n.b. | n.b. |
| 003S-E07 | 18 | 47 | Fzd2 | | ** | | | | | | | | |
| 003S-D10 | 19 | 48 | Fzd4 | n.b. | n.b. | * | n.b. | n.b. | | n.b. | n.b. | n.b. | |
| 004S-B08 | 20 | 49 | Fzd6 | n.b. | n.b. | | n.b. | n.b. | ** | | n.b. | n.b. | n.b. |
| 004S-D08 | 21 | 50 | Fzd6 | n.b. | n.b. | | n.b. | n.b. | ** | | n.b. | n.b. | n.b. |
| 004S-C09 | 22 | 51 | Fzd6 | n.b. | n.b. | | n.b. | n.b. | ** | | n.b. | n.b. | n.b. |
| 004S-F10 | 23 | 52 | Fzd6 | n.b. | n.b. | | n.b. | n.b. | ** | | n.b. | n.b. | n.b. |
| 004S-A11 | 24 | 53 | Fzd6 | n.b. | n.b. | | n.b. | n.b. | ** | | n.b. | n.b. | n.b. |
| 004S-A12 | 25 | 54 | Fzd6 | n.b. | n.b. | | n.b. | n.b. | ** | | n.b. | n.b. | n.b. |
| 005S-B07 | 26 | 55 | Fzd 9 | n.b. | n.b. | | n.b. | n.b. | n.b. | | n.b. | ** | n.b. |
| 005S-D08 | 27 | 56 | Fzd 9 | n.b. | n.b. | | n.b. | n.b. | n.b. | | n.b. | ** | n.b. |
| 005S-E09 | 28 | 57 | Fzd 9 | n.b. | n.b. | | n.b. | n.b. | n.b. | | n.b. | ** | n.b. |
| 005S-H10 | 29 | 58 | Fzd 9 | n.b. | n.b. | | n.b. | n.b. | n.b. | | n.b. | ** | n.b. |
| 005S-B11 | 30 | 59 | Fzd 9 | n.b. | n.b. | | n.b. | n.b. | n.b. | | n.b. | ** | n.b. |
| 005S-D11 | 31 | 60 | Fzd 9 | n.b. | n.b. | | n.b. | n.b. | n.b. | | n.b. | ** | n.b. |
| 014S-G02 | 32 | 61 | Fzd6 | n.b. | n.b. | | n.b. | n.b. | 414 | | n.b. | n.b. | n.b. |
| 014S-B04 | 33 | 62 | Fzd 8 | n.b. | n.b. | | n.b. | n.b. | n.b. | | ** | n.b. | n.b. |
| 014S-B06 | 34 | 63 | Fzd 9 | n.b. | n.b. | | n.b. | n.b. | n.b. | | ** | ** | n.b. |
| 014S-G06 | 35 | 64 | Fzd10 | n.b. | n.b. | | n.b. | n.b. | n.b. | | n.b. | n.b. | ** |
| 014S-A07 | 36 | 65 | Fzd10 | n.b. | n.b. | | n.b. | n.b. | n.b. | | n.b. | n.b. | ** |
| 017S-B09 | 37 | | Fzd8 | n.b. | n.b. | | n.b. | n.b. | n.b. | | * | n.b. | n.b. |
| 004S-D01 | 66 | 67 | Fzd4 | | | | * | | | | | | |
| 004S-E09 | 68 | 69 | Fzd6 | | | | | | | | | | |
| 004S-F09 | | | Fzd6 | | | | | | ** | | | | |
| 004S-H09 | | | Fzd6 | | | | | n.b. | ** | | n.b. | | n.b. |
| 004S-B10 | | | Fzd6 | | | | | | ** | | | | |
| 004S-C10 | | | Fzd6 | n.b. | n.b. | | n.b. | n.b. | ** | n.b. | n.b. | | n.b. |
| 004S-F10 | | | Fzd6 | n.b. | n.b. | | n.b. | n.b. | ** | | n.b. | n.b. | n.b. |
| 004S-G10 | | | Fzd6 | | | | n.b. | ** | | n.b. | | | |
| 004S-A11 | | | Fzd6 | n.b. | n.b. | | n.b. | n.b. | ** | | n.b. | n.b. | n.b. |
| 004S-B11 | | | n.b. | | | | | | n.b. | | | | |
| 004S-D11 | | | Fzd6 | n.b. | n.b. | n.b. | n.b. | n.b. | ** | n.b. | n.b. | n.b. | n.b. |
| 004S-E11 | | | n.b. | | | | | n.b. | n.b. | | n.b. | | n.b. |
| 004S-F11 | | | Fzd6 | | | | | | ** | | | | |
| 004S-G11 | | | Fzd6 | | | | | | * | | | | |
| 004S-A12 | | | Fzd6 | n.b. | n.b. | | n.b. | n.b. | ** | | n.b. | n.b. | n.b. |
| 004S-B12 | | | Fzd6 | | | | | | ** | | | | |
| 004S-C12 | | | n.b. | | | | | | | | | | |
| 004S-D12 | | | n.b. | | | | | | n.b. | | | | |
| 004S-F12 | | | n.b. | | | | | | | | | | |
| 004S-F12 | | | n.b. | n.b. | n.b. | | | | n.b. | | | | |
| 004S-G12 | | | n.b. | n.b. | n.b. | | | | n.b. | | | | |
| 005S-B02 | | | n.b. | | | | n.b. | | n.s. | | | | |
| 005S-C02 | | | n.b. | n.b. | n.b. | | n.b. | n.b. | | | n.b. | n.b. | n.b. |

TABLE 1B-continued

Clone IDs, Heavy Chain (HC) and Light Chain
(LC) Seq ID Nos, and Binding Characteristics.

| Clone ID | HC SID NO | LC SID NO | Confirmed Binding | Kd (nM) | | | | | | | | | |
|---|---|---|---|---|---|---|---|---|---|---|---|---|---|
| | | | | Fz1 | Fz2 | Fz3 | Fz4 | Fz5 | Fz6 | Fz7 | Fz8 | Fz9 | Fz10 |
| 005S-D02 | | | Fzd5, 8 | n.b. | n.b. | n.b. | n.b. | ** | n.b. | n.b. | ** | n.b. | n.b. |
| 005S-E02 | | | Fzd5, 8 | n.b. | n.b. | | n.b. | ** | n.b. | | ** | n.b. | n.b. |
| 005S-H02 | | | Fzd5, 8 | | | | | ** | | | ** | | |
| 005S-A03 | | | Fzd5, 8 | n.b. | n.b. | | n.b. | ** | n.b. | | ** | n.b. | n.b. |
| 005S-C03 | | | n.s. | | | | | | | | n.s. | | |
| 005S-E03 | | | n.s. | | | | | n.s. | | | n.s. | | |
| 005S-F03 | | | Fzd8 | | | | | | | | ** | | |
| 005S-B04 | | | Fzd5, 8 | | | | | ** | | | n.s. | | |
| 005S-F04 | | | n.b. | | | | n.b. | | | | n.b. | | n.b. |
| 005S-G04 | | | Fzd5, 8 | | | | | ** | | | ** | | |
| 005S-H04 | | | n.b. | | n.b. | n.b. | | n.b. | n.b. | n.b. | | n.b. | n.b. |
| 005S-E05 | | | n.b. | | | | | | | | n.b. | | |
| 005S-G05 | | | Fzd5, 8 | n.b. | n.b. | | n.b. | ** | n.b. | | ** | n.b. | n.b. |
| 005S-H05 | | | Fzd5, 8 | n.b. | ** | n.b. | * | n.b. | | * | n.b. | n.b. | |
| 005S-D06 | | | Fzd8 | n.b. | n.b. | | n.b. | n.b. | n.b. | | ** | n.b. | n.b. |
| 005S-F06 | | | n.b. | n.b. | n.b. | | n.b. | n.b. | n.b. | | n.b. | n.b. | n.b. |
| 005S-G06 | | | n.s. | | | | | n.s. | | | n.s. | | |
| 005S-A07 | | | Fzd9, 10 | n.b. | n.b. | | n.b. | n.b. | n.b. | | n.b. | * | ** |
| 005S-B07 | | | Fzd9 | n.b. | n.b. | | n.b. | n.b. | n.b. | | n.b. | ** | n.b. |
| 005S-A08 | | | Fzd9 | | | | | | | | | ** | n.b. |
| 005S-B08 | | | Fzd9 | n.b. | n.b. | | n.b. | n.b. | n.b. | | n.b. | ** | n.b. |
| 005S-D08 | | | Fzd9 | n.b. | n.b. | | n.b. | n.b. | n.b. | | n.b. | ** | n.b. |
| 005S-E08 | | | Fzd9 | | | | | | | | | ** | n.b. |
| 005S-F08 | | | n.b. | | | | | | | | | n.b. | n.b. |
| 005S-C09 | | | Fzd9 | n.b. | n.b. | | n.b. | n.b. | n.b. | | n.b. | ** | n.b. |
| 005S-D09 | | | Fzd9 | | | | | | | | | ** | |
| 005S-E09 | | | Fzd9 | n.b. | n.b. | | n.b. | n.b. | n.b. | | n.b. | ** | n.b. |
| 005S-F09 | | | Fzd9 | | | | | | | | | ** | n.b. |
| 005S-A10 | | | Fzd9 | | | | | | | | | ** | n.b. |
| 005S-B10 | | | Fzd9 | | | | | | | | | ** | n.b. |
| 005S-E10 | | | Fzd9 | | | | | | | | | ** | n.b. |
| 005S-H10 | | | Fzd9 | n.b. | n.b. | | n.b. | n.b. | n.b. | | n.b. | ** | n.b. |
| 005S-B11 | | | Fzd9 | n.b. | n.b. | | n.b. | n.b. | n.b. | | n.b. | ** | n.b. |
| 005S-D11 | | | Fzd9 | n.b. | n.b. | | n.b. | n.b. | n.b. | | n.b. | ** | n.b. |
| 005S-G11 | | | n.b. | | | | | | | | | n.b. | |
| 005S-H11 | | | n.b. | | | | | | | | | | n.b. |
| 005S-E12 | | | Fzd10 | n.b. | n.b. | | n.b. | n.b. | n.b. | | n.b. | n.b. | ** |
| 006S-A01 | | | Fzd10 | | | | | | | | | | ** |
| 006S-H01 | | | n.b. | | | | | | | | | | n.b. |
| 006S-A02 | | | Fzd10 | n.b. | n.b. | | n.b. | n.b. | n.b. | | n.b. | n.b. | ** |
| 006S-D02 | | | n.b. | | | | | | | | | n.b. | n.b. |
| 006S-H02 | | | Fzd10 | n.b. | n.b. | | n.b. | n.b. | n.b. | | n.b. | n.b. | ** |
| 006S-A03 | | | n.b. | | | | | | | | | | n.b. |
| 006S-B03 | | | n.b. | | | | | | | | | | n.b. |
| 006S-C03 | | | n.b. | | | | | | | | | | |
| 014S-A01 | | | Fzd1, 2, 7 | * | ** | | | | | * | | | |
| 014S-B02 | | | n.b. | n.b. | n.b. | | n.b. | n.b. | n.b. | | n.b. | n.b. | n.b. |
| 014S-G02 | | | Fzd6 | n.b. | n.b. | | n.b. | n.b. | 350 | | n.b. | n.b. | n.b. |
| 014S-B03 | | | n.b. | | | | | n.b. | | | | | |
| 014S-C03 | | | Fzd1, 2, 7 | ** | ** | | | | | ** | | | |
| 014S-A04 | | | n.b. | | | | | n.b. | | | n.b. | | |
| 014S-B04 | | | Fzd8 | n.b. | n.b. | | n.b. | n.b. | n.b. | | ** | n.b. | n.b. |
| 014S-B05 | | | Fzd5, 8 | n.b. | n.b. | | n.b. | ** | n.b. | | ** | n.b. | n.b. |
| 014S-B06 | | | Fzd9 | n.b. | n.b. | | n.b. | n.b. | n.b. | | n.b. | ** | n.b. |
| 014S-F06 | | | n.s. | | | | | | | | | | |
| 014S-G06 | | | Fzd10 | n.b. | n.b. | | n.b. | n.b. | n.b. | | n.b. | n.b. | ** |
| 014S-A07 | | | Fzd10 | n.b. | n.b. | | n.b. | n.b. | n.b. | | n.b. | n.b. | ** |
| 017S-E08 | | | Fzd8 | | | | | n.b. | | | ** | | |
| 017S-H08 | | | n.b. | | | | | n.b. | | | n.b. | | |
| 017S-A09 | | | n.b. | n.b. | n.b. | | n.b. | n.b. | n.b. | | n.b. | n.b. | n.b. |
| 017S-B09 | | | Fzd8 | n.b. | n.b. | | n.b. | n.b. | n.b. | | * | n.b. | n.b. |
| 018S-F06 | | | Fzd4 | n.b. | n.b. | | ** | n.b. | n.b. | | n.b. | n.b. | n.b. |
| 018S-H06 | | | n.b. | | | | | n.b. | | | n.b. | | |
| 018S-B07 | | | n.b. | n.b. | n.b. | | n.b. | n.b. | n.b. | | n.b. | n.b. | n.b. |
| 017S-A10 | | | n.b. | n.b. | n.b. | | n.b. | n.b. | n.b. | | n.b. | n.b. | n.b. |
| 017S-B10 | | | n.b. | n.b. | n.b. | | n.b. | n.b. | n.b. | | n.b. | n.b. | n.b. |
| 017S-D10 | | | n.b. | n.b. | n.b. | | n.b. | n.b. | n.b. | | n.b. | n.b. | n.b. |
| 018S-H08 | | | n.b. | n.b. | n.b. | | n.b. | n.b. | n.b. | | n.b. | n.b. | n.b. |
| 018S-B09 | | | Fzd5, 8 | n.b. | n.b. | | n.b. | ** | n.b. | | ** | n.b. | n.b. |
| 021S-A01 | | | n.b. | | n.b. | | | n.b. | | | n.b. | | n.b. |
| 021S-E02 | | | Fzd5, 8 | n.b. | n.b. | | n.b. | ** | n.b. | | ** | n.b. | n.b. |
| 021S-G02 | | | n.s. | | | | | | | | | | |

TABLE 1B-continued

Clone IDs, Heavy Chain (HC) and Light Chain
(LC) Seq ID Nos, and Binding Characteristics.

| Clone ID | HC SID NO | LC SID NO | Confirmed Binding | Kd (nM) Fz1 | Fz2 | Fz3 | Fz4 | Fz5 | Fz6 | Fz7 | Fz8 | Fz9 | Fz10 |
|---|---|---|---|---|---|---|---|---|---|---|---|---|---|
| 021S-A03 | | | n.b. | n.b. | | | n.b. | | | n.b. | | n.b. | |
| 029S-B01 | | | n.b. | n.b. | | | | | | | | | |
| 029S-D01 | | | Fzd1, 2, 7 | ** | ** | | | | | ** | | | |
| 029S-C02 | | | Fzd1, 2, 7 | ** | ** | | | | | ** | | | |
| 029S-H02 | | | Fzd1 | ** | n.b. | | | | | n.b. | | | |
| 030S-A02 | | | Fzd7 | | | | | | | ** | | | |
| 029S-E06 | | | Fzd2, 6, 3 | | | * | | | | | | | |
| 030S-F04 | | | Fzd3 | | | ** | | | | | | | |
| 030S-H05 | | | Fzd7 | | | | | | | ** | | | |
| 030S-A06 | | | Fzd1, 2, 5 | * | * | | | ** | | * | | | |
| 029S-C12 | | | Fzd7 | | | | | | | ** | | | |
| 030S-C06 | | | Fzd1 | ** | ** | ** | | | | | | | |
| 001S-A01 | | | Fzd1, 2, 7 | ** | ** | | | | | ** | | | |
| 001S-H01 | | | Fzd1, 2, 7 | ** | ** | | | | | * | | | |

* Indicates <100 nM; ** indicates 100-2000 nM

Example 2

Alanine-Scanning Mutation of an Anti-Fzd Antibody Fragment

One antibody fragment, clone 001S-A04, was selected for alanine-scanning mutagenesis of CDRs, and the respective Fzd1 binding affinities of the various mutants were determined by Octet BLI as described in Example 1. As shown in Table 2, a large number of mutants bound Fzd1 with a similar affinity as the wild type antibody fragment, demonstrating that the Fzd1 antibodies and antigen-binding fragments thereof can tolerate amino acid modifications within the CDRs.

TABLE 2

001S-A04 alanine-scanning mutant CDR sequences and $K_D$ (nM) to biotinylated-Fzdd1 CRD as determined by Octet BLI

| Clone ID | Kd (nM) | CDRH1 | SEQ ID No. | CDRH2 | SEQ ID No. | CDRH3 | SEQ ID No. | CDRL1 | SEQ ID No. | CDRL2 | SEQ ID No. | CDRL3 | SEQ ID No. |
|---|---|---|---|---|---|---|---|---|---|---|---|---|---|
| WT | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGRGIWVF | 1165 |
| VLL1A | * | YTFTSYGIS | 300 | GWISAYNGNTNYA | 477 | CASSKEKATYYYGMDVW | 860 | GLSSGSVSTNYYPS | 931 | YTNTRSS | 1057 | CALYLGRGIWVF | 1444 |
| VLL2A | * | YTFTSYGIS | 300 | GWISAYNGNTNYA | 477 | CASSKEKATYYYGMDVW | 860 | GLSSGSVSTNYYPS | 931 | YTNTRSS | 1057 | CLAYLGRGIWVF | 1445 |
| VLY3A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLALGRGIWVF | 1446 |
| VLL4A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYAGRGIWVF | 1447 |
| VLG5A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLARGIWVF | 1448 |
| VLR6A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGAGIWVF | 1449 |
| VLG7A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGRAIWVF | 1450 |
| VLI8A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGRGAWVF | 1451 |
| VLW9A | ** | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGRGIAVF | 1452 |
| VLV10A | * | YTFTSYGIS | 300 | GWISAYNGNTNYA | 477 | CASSKEKATYYYGMDVW | 860 | GLSSGSVSTNYYPS | 931 | YTNTRSS | 1057 | CLLYLGRGIWAF | 1453 |
| VHK2A | * | YTFTSYGIS | 300 | GWISAYNGNTNYA | 477 | CASSAEKATYYYGMDVW | 1436 | GLSSGSVSTNYYPS | 931 | YTNTRSS | 1057 | CLLYLGRGIWVF | 1165 |

TABLE 2-continued

001S-A04 alanine-scanning mutant CDR sequences and $K_D$ (nM) to biotinylated-Fzdd1 CRD as determined by Octet BLI

| Clone ID | Kd (nM) | CDRH1 | SEQ ID No. | CDRH2 | SEQ ID No. | CDRH3 | SEQ ID No. | CDRL1 | SEQ ID No. | CDRL2 | SEQ ID No. | CDRL3 | SEQ ID No. |
|---|---|---|---|---|---|---|---|---|---|---|---|---|---|
| VHK4A | * | YTFTSYGIS | 300 | GWISAYNGNTNYA | 477 | CASSKEAATYYYGMDVW | 1437 | GLSSGSVSTNYYPS | 931 | YTNTRSS | 1057 | CLLYLGRGIWVF | 1165 |
| VHT6A | ** | YTFTSYGIS | 300 | GWISAYNGNTNYA | 477 | CASSKEKAAYYYGMDVW | 1438 | GLSSGSVSTNYYPS | 931 | YTNTRSS | 1057 | CLLYLGRGIWVF | 1165 |
| VHY7A | ** | YTFTSYGIS | 300 | GWISAYNGNTNYA | 477 | CASSKEKATAYYGMDVW | 1439 | GLSSGSVSTNYYPS | 931 | YTNTRSS | 1057 | CLLYLGRGIWVF | 1165 |
| VHY8A | n.b. | YTFTSYGIS | 300 | GWISAYNGNTNYA | 477 | CASSKEKATYAYGMDVW | 1440 | GLSSGSVSTNYYPS | 931 | YTNTRSS | 1057 | CLLYLGRGIWVF | 1165 |
| VHY9A | ** | YTFTSYGIS | 300 | GWISAYNGNTNYA | 477 | CASSKEKATYYAGMDVW | 1441 | GLSSGSVSTNYYPS | 931 | YTNTRSS | 1057 | CLLYLGRGIWVF | 1165 |
| VHG10A | * | YTFTSYGIS | 300 | GWISAYNGNTNYA | 477 | CASSKEKATYYYAMDVW | 1442 | GLSSGSVSTNYYPS | 931 | YTNTRSS | 1057 | CLLYLGRGIWVF | 1165 |
| VHV13A | * | YTFTSYGIS | 300 | GWISAYNGNTNYA | 477 | CASSKEKATYYYGMDAW | 1443 | GLSSGSVSTNYYPS | 931 | YTNTRSS | 1057 | CLLYLGRGIWVF | 1165 |

\* Indicates ≤ 100;
\*\* indicates > 100
(n.b. indicates no binding observed).

Example 3

Crystal Structures of Anti-Fzd Antibody Fragments Bound to Fzd Extra-Cellular Domains Fzds are a class of GPCRs in which an extra-cellular Cys-rich domain (CRD) is connected to its 7-transmemberane helical domain and cytoplasmic tail through a linker region. Fzds have either one or two predicted -NxS/T-glycosylation motifs within their extra-cellular domain. To enable high-resolution structures, Fzds extra-cellular domains that contain two glycosylation motifs were truncated before second predicted -NxS/T-glycosylation motifs resulting constructs named CRD-Xtal. Sequence of each of 10 Fzd CRD-Xtal containing an eight-Histidine motif at their C-terminus are as follows:

hFzd1_Q9UP38_101-230
(SEQ ID NO: 1454)
QYNGERGISVPDHGYCQPISIPLCTDIAYNQTIMPNLLGHTNQEDAGLEV

HQFYPLVKVQCSAELKFFLCSMYAPVCTVLEQALPPCRSLCERARQGCEA

LMNKFGFQWPDTLKCEKFPVHGAGELCVGQGSHHHHHHHH hFzd2_Q14332_24-153
(SEQ ID NO: 1455)
QFHGEKGISIPDHGFCQPISIPLCTDIAYNQTIMPNLLGHTNQEDAGLEV

HQFYPLVKVQCSPELRFFLCSMYAPVCTVLEQAIPPCRSICERARQGCEA

LMNKFGFQWPERLRCEHFPRHGAEQICVGQHHHHHHHH hFzd3_Q9NPG1_23-148
(SEQ ID NO: 1456)
HSLFSCEPITLRMCQDLPYNTTFMPNLLNHYDQQTAALAMEPFHPMVNLD

CSRDFRPFLCALYAPICMEYGRVTLPCRRLCQRAYSECSKLMEMFGVPWP

EDMECSRFPDCDEPYPRLVDLNLAGEHHHHHHHH hFzd4_Q9ULV1_38-167
(SEQ ID NO: 1457)
GDEEERRCDPIRISMCQNLGYNVTKMPNLVGHELQTDAELQLTTFTPLIQ

YGCSSQLQFFLCSVYVPMCTEKINIPIGPCGGMCLSVKRRCEPVLKEFGF

AWPESLNCSKFPPQNDHNHMCMEGPGDEEVHHHHHHHH hFzd5_Q13467_27-152
(SEQ ID NO: 1458)
ASKAPVCQEITVPMCRGIGYNLTHMPNQFNHDTQDEAGLEVHQFWPLVEI

QCSPDLRFFLCSMYTPICLPDYHKPLPPCRSVCERAKAGCSPLMRQYGFA

WPERMSCDRLPVLGRDAEVLCMDYNRHHHHHHHH hFzd6_O60353_18-145
(SEQ ID NO: 1459)
HSLFTCEPITVPRCMKMAYNMTFFPNLMGHYDQSIAAVEMEHFLPLANLE

CSPNIETFLCKAFVPTCIEQIHVVPPCRKLCEKVYSDCKKLIDTFGIRWP

EELECDRLQYCDETVPVTFDPHTEFLGHHHHHHHH hFzd7_O75084_36-165
(SEQ ID NO: 1460)
HGEKGISVPDHGFCQPISIPLCTDIAYNQTILPNLLGHTNQEDAGLEVHQ

FYPLVKVQCSPELRFFLCSMYAPVCTVLDQAIPPCRSLCERARQGCEALM

NKFGFQWPERLRCENFPVHGAGEICVGQNTHHHHHHHH hFzd8_Q9H461_28-153
(SEQ ID NO: 1461)
ASAKELACQEITVPLCKGIGYNYTYMPNQFNHDTQDEAGLEVHQFWPLVE

IQCSPDLKFFLCSMYTPICLEDYKKPLPPCRSVCERAKAGCAPLMRQYGF

AWPDRMRCDRLPEQGNPDTLCMDYNRHHHHHHHH

-continued hFzd9_000144_23-159
(SEQ ID NO: 1462)
LEIGRFDPERGRGAAPCQAVEIPMCRGIGYNLTRMPNLLGHTSQGEAAAE

LAEFAPLVQYGCHSHLRFFLCSLYAPMCTDQVSTPIPACRPMCEQARLRC

APIMEQFNFGWPDSLDCARLPTRNDPHALCMEAPENAHHHHHHH hFzd10_Q9ULW2_21-154
(SEQ ID NO: 1463)
SSMDMERPGDGKCQPIEIPMCKDIGYNMTRMPNLMGHENQREAAIQLHEF

APLVEYGCHGHLRFFLCSLYAPMCTEQVSTPIPACRVMCEQARLKCSPIM

EQFNFKWPDSLDCRKLPNKNDPNYLCMEAPNNGHHHHHHHH

Example 4

Expression and Purification of Fzd CRD_Xtal Constructs

FreeStyle™ 293-F Cells (Thermofisher) stably expressing all Fzd CRD_Xtal protein constructs were created using lenti-viral technology. For large-scale expression, a frozen vial FreeStyle™ 293-F Cells expressing Fzd CRD_Xtal was thawed into 20 mL of FreeStyle (Thermofisher) media in the presence of 10 U penicillin and 10 µg of streptomycin (Lonza) per mL. Cells were expended on alternative days, until density of ~3.0×10⁶ cell/mL was reached at desired volumes, typically 6 to 10 L. At this stage, cells were allowed to grow continuously to higher density and, media was harvested by centrifugation at a viability of ~70%. Fzd CRD_Xtal proteins were purified from media by incubation with Ni-NTA resin (1 mL per L of culture; Qiagen) pre-equilibrated in HBS (20 mM HEPES pH 7.4, 150 mM NaCl), and eluted with 500 mM imidazole in HBS. Ni-NTA eluates were concentrated to 5m L, and further polished on a HiLoad 16/600 Superdex 200 pg column (GE Life Sciences) pre-equilibrated with HBS. Fractions near the main peak was further analyzed by SDS-Polyacrylamide Gel Electrophoresis (SDS-PAGE) to confirm the content. SDS-PAGE was performed using Tris-HCl 4-15% gel (Bio-Rad, Hercules, CA) under both reducing and non-reducing conditions. The samples were prepared in Laemmli sample buffer and heated at 100° C. for 5 min. Fractions containing Fzd CRD_Xtal were concentrated to ~2 mg/mL and frozen in the presence of 10% glycerol for storage at –80C until further use. Protein concentrations were determined using a NanoDrop Spectrophotometer (Thermo Scientific) by the direct UV A280 method. The relationship of absorbance to protein concentration is linear based on Beer-Lamber equation, $A=\varepsilon l c$; A is the absorbance value, c is the wavelength-dependent extinction coefficient, l is the path length in centimeters, and c is the protein concentration. The extinction coefficients of all produced proteins were estimated by their amino acid sequences.

Example 5

Expression and Purification of Fab Binders

Plasmids expressing light-chain and heavy-chain (with hexa-histidine tag at its C-terminus) of Fab binders of Fzd CRD_Xtal were co-transfected for co-expression in Expi293 cells, typically at 1000 mL scale, following the standard protocols from the manufacturer (Thermofisher). After 4 days of continuous cell growth, media were harvested by centrifugation, and bound to Complete-His resin (2.5 mL per 1 L culture; Roche) pre-equilibrated in PBS, and eluted under gravity-flow using 250 mM imidazole in PBS. Elutions containing Fab binders were concentrated to ~5m L, and further polished on a HiLoad 16/600 Superdex 200 pg column (GE Life Sciences) column pre-equilibrated with HBS. Fractions near main peak were further analyzed by SDS-Polyacrylamide Gel Electrophoresis (SDS-PAGE) to confirm the content. SDS-PAGE was performed using Tris-HCl 4-15% gel (Bio-Rad, Hercules, CA) under both reducing and non-reducing conditions. The samples were prepared in Laemmli sample buffer and heated at 100° C. for 5 min. Fractions containing Fzd CRD_Xtal were concentrated to ~3 mg/mL and frozen in the presence of 10% glycerol for storage at –80° C. until further use. Protein concentrations were determined using a NanoDrop Spectrophotometer (Thermo Scientific) by the direct UV A280 method. The relationship of absorbance to protein concentration is linear based on Beer-Lamber equation, $A=E$ c; A is the absorbance value, c is the wavelength-dependent extinction coefficient, I is the path length in centimeters, and c is the protein concentration. The extinction coefficients of all produced proteins were estimated by their amino acid sequences.

Example 6

Fzd: Fab Complex Formation, Crystallization, and Structure Determination

Purfied Fzd CRD_Xtal and Fab binders were mixed at 1.1:1 molar ratio (little excess of the smaller molecular weight protein), and incubated with carboxy-peptidase A and B at a w/w ratio of 100:1 for over-night at 4° C. Complex formation was confirmed by observation of a single-major peak on SuperdexS200 Increase (10/300 GL) column pre-equilibrated in HBS. Fractions containing complexes were further checked by SDS-PAGE, and concentrated to a range from 10 to 55 mg/mL for crystallization screens. Initial crystallization screen, using commercially available MCSG1, MCSG2, MCSG3, MCSG4, PACT (Molecular Dimensions), PEGs I, and PEGs II (Qiagen) screen, and optimization by grid-screens or microseed matrix screen [MMS; Microseed matrix screening for optimization in protein crystallization: what have we learned? D'Arcy, A., Bergfors, T., Cowan-Jacob S. W., and Marshd, M. Acta Cryst. F70, 1117-1126 (2014)]. were performed using Mosquito (TTP LabTech) liquid handler, and equilibrated at 18° C. inside an EchoTherm incubator (Torrey Pines Scientific). 96-well plate crystal screening experiments were periodically monitored manually via a DiscoveryV20 stereomicroscope (Zeiss), and crystals were frozen for data collection by plunging into liquid nitrogen in the presence of various cryo-protectants (typically 15 to 30% v/v of glycerol or ethyleneglycol). X-ray diffraction datasets were collected at the Berkeley Center for Structural Biology at the Advanced Light Source (ALS), Berkeley CA, and processed with XDS [Kabsch, W. XDS. Acta Cryst. D66, 125-132 (2010)], and xdsme [Legrand, P. XDSME: XDS Made Easier (2017) GitHub repository, https://github-.com/legrandp/xdsme DOI 10.5281/zenodo.837885]. programs. Structure of Fzd:Fab complexes were determined by molecular replacement method using Phaser with constant and variable domains of related Fabs are template [Phaser crystallographic software. A. J. McCoy, R. W. Grosse-Kunstleve, P. D. Adams, M. D. Winn, L. C. Storoni, and R. J. Read. J Appl Crystallogr 40, 658-674 (2007)], followed by refinement and validation by MolProbity as implemented in Phenix [PHENIX: a comprehensive Python-based system for macromolecular structure solution. P. D. Adams, P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. Acta Cryst. D66, 213-221 (2010); MolProbity: all-atom structure validation for macromolecular crystallography. V. B. Chen, W. B. Arendall, J. J. Headd, D. A. Keedy, R. M. Immormino, G. J. Kapral, L. W. Murray, J. S. Richardson, and D. C. Richardson. Acta Cryst. D66, 12-21 (2010)]. Crystallography models were manually inspected and built using COOT [Features and development of Coot. P. Emsley, B. Lohkamp, W. G. Scott, and K. Cowtan. Acta Cryst. D66, 486-501 (2010)]. Analyses of refined crystal structures, and image creations were performed using MOE (CCG) and PyMol (Schrodinger).

Example 7

Structure of Fzd1:1 RC07 Complex

Sequence of 1RC07 (001S-B03) Fab:

1RC07_Lchain
(SEQ ID NO: 1464)
SYVLTQPPSVSVSPGQTASITCSGDKVGHKYASVVYQQKPGQSPVLVIYE

DSQRPSGIPVRFSGSNSGNTATLTISGTQAMDEADYYCQAWDSSTDVVFG

GGTKLTVLGQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

1RC07_Hchain
(SEQ ID NO: 1465)
QVQLQQWGAGLLKPSETLSLTCAVSGASFSGHYVVTWIRQPPGKGLEWIG

EIDHTGSTNYEPSLRSRVTISVDTSKNQFSLNLKSVTAADTAVYYCARGG

QGGYDWGHYHGLDVWGQGTTVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCGSGSGHHHHHH

Diffraction quality crystals of Fzd1:1RC07 complex (concentration=28 mg/mL) grew in a crystallization condition containing 0.1 M lithium chloride, 0.1 M HEPES: NaOH, pH 7.5, and 25% (w/v) PEG 6000. Crystal was cryo-protected using 20% glycerol in the well-solution. Fzd1:1RC07 complex crystallized in the P21212 space group (a=65.79, b=192.21, c=44.79 Å) with one complex molecule per asymmetric unit. Structure of Fzd1: 1RC07 complex was determined at a resolution of 2.10 Å, and refined to $R_{cryst}$ and $R_{free}$ factors of 19.9% and 24.8%, respectively. In the crystal structure 101-114, 179-189, 203-207, and 217-230 stretch of residues of Fzd1 could not be modeled due to disordered electron density maps.

Overall structure of Fzd1:1RC07 complex is shown in FIG. 1 (A and B), which reveals that the heavy-chain CDR3 of 1RC07 binds closer to the lipid binding site as observed in the complex of Fzd8:Wnt8a complex [PDB Code: 4FOA; Janda, C. Y., Waghray, D., Levin, A. M., Thomas, C., Garcia, K. C. (2012) Science 337: 59-64]. During crystallographic model building a strong $mF_o$-$DF_c$ difference map electron density, at >10 was observed at the interface antigen Fzd1 and antibody 1RC07. This strong positive difference-density maps could satisfactorily be explained by modeling a Zinc ion, which was further confirmed by a strong anomalous difference map peak, at >15 calculated at 3.5 Å resolution FIG. 1 (C). This Zn2+ ion was bound by His107 (at 2.04 Å) and His109 (at 2.01 Å) from CDR H3-loop, and Glu49 (at 2.03 and 2.76 Å) of CDR L2-loop of 1RC07, and His151 (at 2.00 Å) of Fzd1 that is conserved in the sequences of Fzd2, Fzd7, Fzd5, Fzd8, and Fzd10.

Structure of the complex allow us to identify epitope of Fzd1 for 1RC07 with the following residue defining the core interaction-site on Fzd1 (5 Å cut-off):
Pro122, Leu148, His151, Gln152, Try154, Pro155, Leu156, Lys158, and Gln160.

In addition, following residues on Fzd1 could be identified as immediate-interaction site for 1RC07 (interaction distances >5.0 Å and <=8.0 Å):
Ser120, Ile121, Leu123, Cys124, Thr125, Asp126, Glu144, Gly147, Glu149, Val150, Phe153, Val157, Val159, Cys161, Cys198, Leu201, and Met202.

Structure of Fzd1:1RC07 complex also allow us to identify following residues on 1RC07 at less-than or equal to 5.0 Å from any atoms of Fzd1:
1RC07 Heavy Chain:
Tyr103, Trp105, Gly106, His107, and His109.
1RC07 Light Chain:
Val27, Gly28, His29, Lys30, Tyr31, Ala32, Tyr48, Glu49, Asp50, Ser51, Gln52, and Asn65.

Further, the structure of Fzd1:1RC07 complex reveals following residues on 1RC07 to be immediate-interaction site for Fzd1 with interaction distances >=5.0 Å and <=8.0 Å:
1RC07 Heavy Chain:
Gln100, Gly101, and Tyr108.
1RC07 Light Chain:
Lsy26, Ser33, Ile47, Arg53, Val59, Ser62, Gly63, Ser64, Asn65, Ser66, Gly67, Thr69, Ala70, Trp90, and Ser92.

Example 8

Structure of Fzd1:R2M9 Complex

Sequence of R2M9 (003S-E07) Fab:

R2M9_Lchain
(SEQ ID NO: 1466)
DIQMTQSPSSLSASVGDRVTITCRASQSISSYLNVVYQQKPGKAPKLLI

YAASSLQSGVPSRFSGSGSGTDFTLTISSLQPEDFATYYCQQSYRTPFT

FGPGTKVDIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

R2M9_Hchain
(SEQ ID NO: 1467)
QVQLVQSGAEVKKPGSSVKVSCKASGYTFTNNFMHVVVRQAPGQGLEVV

MGWINPNSGGTKYAQKFQGRVTITADESTSTAYMELSSLRSEDTAVYYC

ARSVGEVGATMLGIGVVVYWFDPWGQGTLVTVSSASTKGPSVFPLAPSS

KSTSGGTAALGCLVKDYFPEPVTVSWNSGALTSGVHTFPAVLQSSGLYS

LSSVVTVPSSSLGTQTYICNVNHKPSNTKVDKKVEPKSCGSGSGHHHHHH

Diffraction quality crystals of Fzd1:R2M9 complex (concentration=32 mg/mL) grew in a crystallization condition containing 0.1 M sodium formate, and 11% (w/v) PEG 3350. Crystal was cryo-protected using 26% glycerol in the well-solution. Fzd1:R2M9 complex crystallized in the P2₁ space group (a=50.57, b=160.60, c=88.97 Å, and)1=95.5° with two complex molecules per asymmetric unit. Structure of Fzd1: R2M9 complex was determined at a resolution of 2.60 Å, and refined to $R_{cryst}$ and $R_{free}$ factors of 23.1% and 26.3%, respectively.

Figure 2:
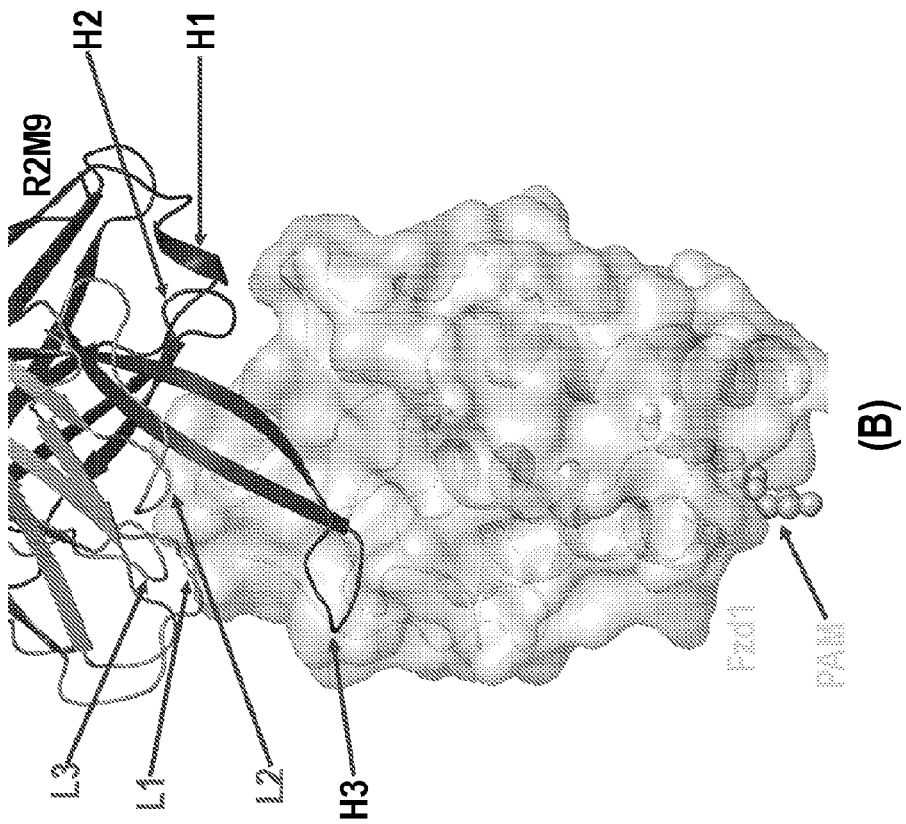
FIG. 2. (A) Overall structure of Fzd1:R2M9 complex. Molecular surface of Fzd1 is shown as light-gray transparent surface. Heavy- and Light-chains of R2M9 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd1:R2M9 interface with positions of CDR loops H1, H2, H3 of heavy-chain and L1, L2, and L3 of light-chain are marked.
Figure 2:
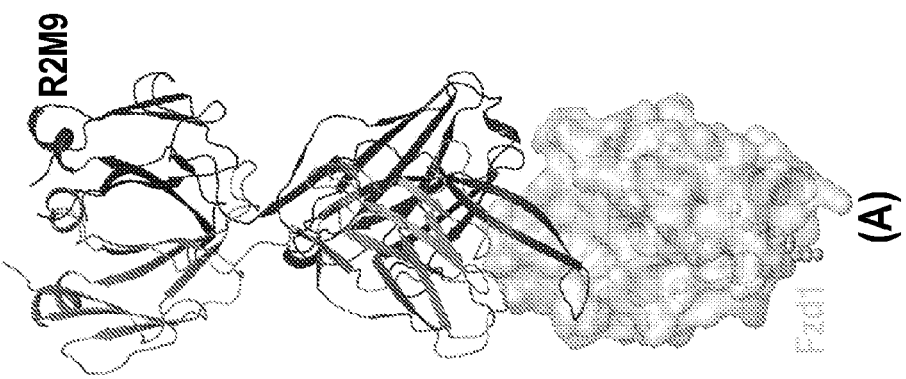

Overall structure of Fzd1: R2M9 complex is shown in FIG. 2 (A and B), which reveals that the R2M9 recognizes Fzd1 from a direction opposite to the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. Structure of the complex allow us to identify epitope of Fzd1 for R2M9 with the following residue defining the core interaction-site on Fzd1 (5 Å cut-off):

Tyr115, Ala128, Tyr129, Phe167, Val176, Thr178, Val179, Leu180, Glu181, Gln182, Leu184, Gly224, Leu226, Cys227, and Val228.

In addition, following residues on Fzd1 could be identified as immediate-interaction site for R2M9 (interaction distances >=5.0 Å and <=8.0 Å):

Cys116, Ile127, Asn130, Gln131, Ser171, Cys177, Ala183, Pro185, Cys187, His221, Ala223, Glu225, Gly229, and Gln230.

Crystal structure of Fzd1:R2M9 complex reveals that a molecule of glycerol, used as cryoprotectant during sample preparation, interacting with Ser95 of R2M9 CDR H3-loop is at distances less than 5 Å from Leu180, Gln182, Leu184, and Leu226 of Fzd1. Another glycerol molecule bound to Val108 of R2M9 CDR H3-loop is at distances less than 5 Å from Val176, Cys177, Thr178, and Val179 of Fzd1. It is possible to exploit these interactions towards structure-guided engineering of R2M9 to optimize its properties.

Structure of Fzd1: R2M9 complex also allow us to identify following residues on R2M9 at less-than or equal to 5.0 Å from any atoms of Fzd1:

R2M9 Heavy Chain:
Asn31, Phe33, His35, Trp50, Asn52, Lys58, Ser95, Gly97, Glu98, Val99, Leu104, Gly105, Ile106, Val108, and Tyr110.

R2M9 Light Chain:
Ser91, Tyr92, Arg93, Thr94 and Phe96.

Further, the structure of Fzd1: R2M9 complex reveals following residues on R2M9 to be immediate-interaction site for Fzd1 with interaction distances >5.0 Å and <=8.0 Å:

R2M9 Heavy Chain:
Thr30, Asn32, Met34, Trp47, Ile51, Asn53, Ser54, Gly56, Thr57, Tyr59, Val96, Gly100, Ala101, Thr102, Met103, Gly107, Trp109, Trp111, and Phe112.

R2M9 Light Chain:
Try32, Gln89, Gln90, and Pro95.

Example 9

Structure of Fzd4:003S-D10 Complex

Sequence of the 003S-D10 Fab:

003S-D10_Lchain
(SEQ ID NO: 1468)
DIQMTQSPSSLSASVGDRVTITCRASQGISSYLAVVYQQKPGKAPKLLIY

AASNLLGGVPSRFSGSGSGTDFTLTISSLQPEDFATYYCQQTYSTPWTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

003S-D10_Hchain
(SEQ ID NO: 1469)
EVQLVESGGGLVKPGGSLRLSCAASGFNFGIYSMTVVVRQAPGKGLEWIS

YISGDSGYTNYADSVKGRFTISRDDSKNTLYLQMNSLKTEDTAVYYCARV

GPGGWFDPWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCGSGSGHHHHHH

Diffraction quality crystals of Fzd4:003S-D10 (concentration=23 mg/mL) were obtained by MMS in MCSG1 screen, H4 condition containing 0.1 M Sodium Citrate: HCl, pH 5.6, 20% (v/v) PEG 4000, 20% (v/v) Isopropanol. Crystal was cryo-protected using 20% glycerol in well-solution. Fzd4:3SD10 crystallized in the P3121 space group (a=b=149.4 Å and c=91.9 Å) with one complex molecule per asymmetric unit. Structure of Fzd4:003S-D10 complex was determined at a resolution of 2.10 A, and refined to $R_{cryst}$ and $R_{free}$ factors of 18.5% and 21.6%, respectively.

Figure 3:
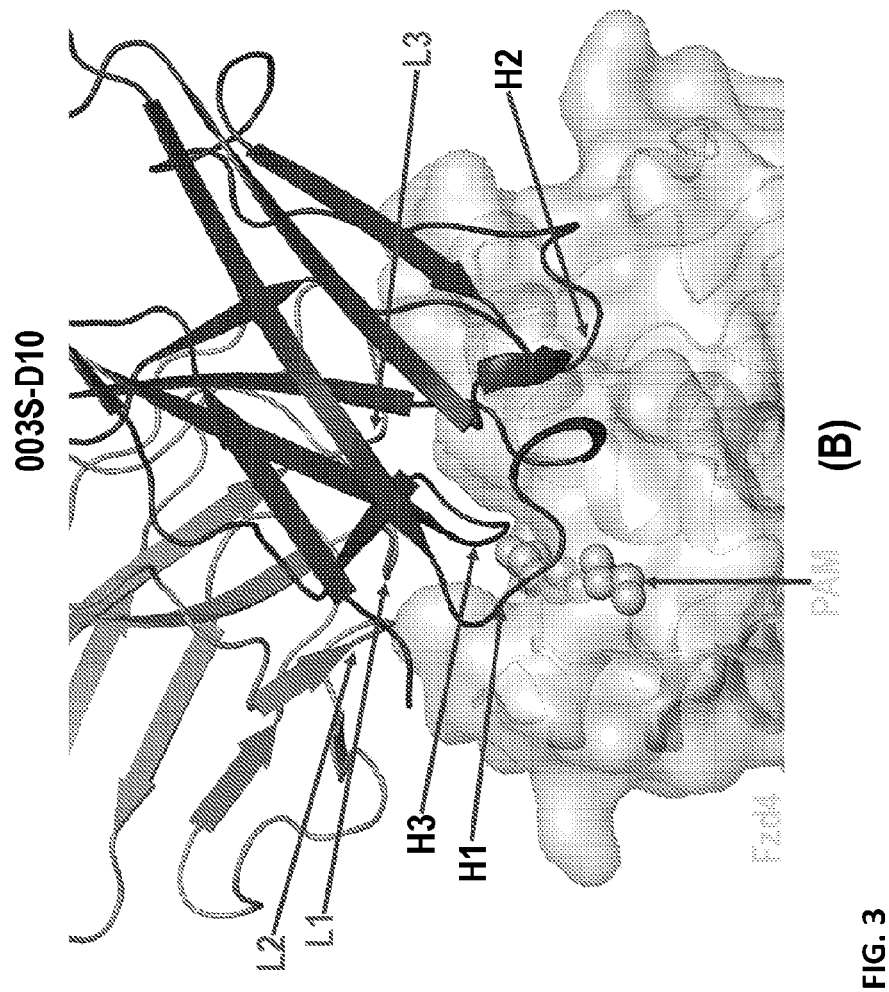
FIG. 3. (A) Overall structure of Fzd4:003S-D10 complex. Molecular surface of Fzd4 is shown as light-gray transparent surface. Heavy- and Light-chains of 3SD10 are colored in shades of darker- and light-black. The lipid (palmitoleic acid; PAM) as observed in the structure of Wnt8:Fzd8 (PDB code: 4F0A) is shown in light-gray spheres. (B) Close-up view of the Fzd4:3SD10 interface with positions of CRD loops marked.
Figure 3:
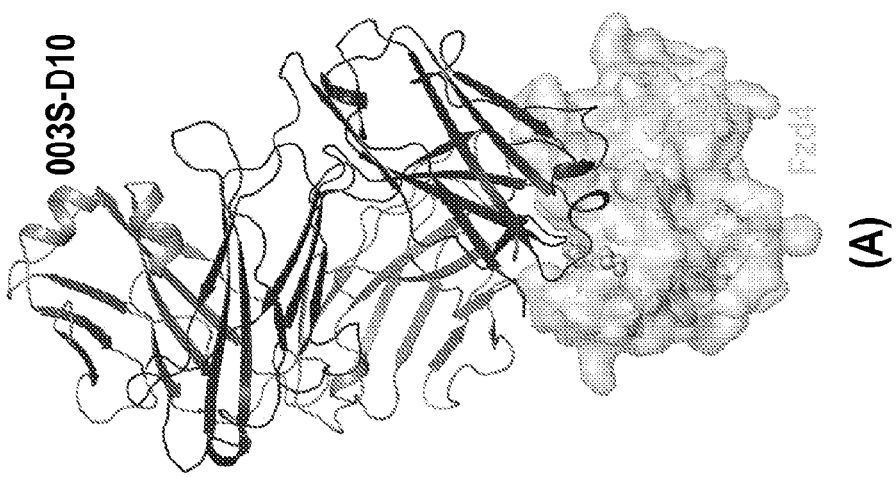

Overall structure of Fzd4:003S-D10 complex is show in FIG. 3 (A), which reveals that the heavy-chain CDR3 of 003S-D10 binds at the lipid binding site (FIG. 3 (B)) as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. Structure of the complex allow us to identify epitope of Fzd4 for 003S-D10 with the following residue defining the core interaction-site on Fzd4 (5 Å cut-off):

Val67, Gly68, His69, Thr73, Asp74, Glu76, Leu77, Gln78, Thr80, Thr81, Phe82, Thr83, Pro84, Leu85, Gln87, Tyr88, Tyr102, Leu132, Phe135, Gly136, Phe137, Ala138, and Ser142.

In addition, following residues on Fzd4 could be identified as immediate-interaction site (interaction distances >=5.0 Å and <=8.0 Å:

Ile50, Ser51, Met52, Pro64, Asn65, Leu66, Glu70, Leu71, Gln72, Ala75, Leu79, Ile86, Gly89, Leu94, Gln95, Leu98, Val101, Tyr102, Val131, Lys133, Glu134, Trp139, Pro140, Glu141, Leu143, and Lys147.

Structure of Fzd4: 003S-D10 also allow us to identify following residues on 003S-D10 at less-than or equal to 5.0 Å from any atoms of Fzd4:

003S-D10 heavy chain:
Gly30, Ile31, Tyr32, Ser33, Tyr50, Ser52, Gly53, Asp54, Tyr57, Asn59, Arg98, Val99, Gly100, Pro101, Gly102, Gly103, Trp104, and Asp106.

003S-D10 light chain:
Ser30, Tyr32, Leu46, Try49, Asn53, Leu55, Gly56, Thr91, Tyr92, Ser93, Thr94, and Trp96.

Further, the structure of Fzd4: 003S-D10 reveals following residues on 003S-D10 to be immediate-interaction site for Fzd4 with interaction distances >=5.0 Å and <=8.0 Å:

003S-D10 heavy chain:
Val2, Phe27, Asn28, Phe29, Met34, Trp47, Ile51, Ser55, Gly56, Thr58, Tyr60, Arg72, Asp74, Phe105, and Pro107.

003S-D10 light chain:
Ile2, Gln27, Gly28, Ile29, Ser31, Tyr36, Ile48, Ala50, Leu54, Ser67, Gln90, Pro95, and Thr97

Example 10

Structure of Fzd5:R2M3 Complex

Sequence of R2M3 (001S-A04) Fab:

>R2M3_Lchain
(SEQ ID NO: 1470)
QAVVLQEPSLSVSPGGTVTLTCGLSSGSVSTNYYPSVVYQQTPGQAPRTL

IYYTNTRSSDVPERFSGSIVGNKAALTITGAQPDDESVYFCLLYLGRGIV

VVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

>R2M3_Hchain
(SEQ ID NO: 1471)
EVQLVQSGAEVKKPGASVKVSCKASGYTFTSYGISVVVRQAPGQGLEVVM

GWISAYNGNTNYAQKLQGRVTMTTDTSTSTAYMELRSLRSDDTAVYYCAS

SKEKATYYYGMDVWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCGSGSGHHHHHH

Diffraction quality crystals of Fzd5:R2M3 complex (concentration=28 mg/mL) grew in a crystallization condition containing 0.1 M lithium chloride, 0.1 M HEPES: NaOH, pH 7.5, and 25% (w/v) PEG 6000. Crystal was cryo-protected using 20% glycerol in the well-solution. Fzd5: R2M3 complex crystallized in the P212121 space group (a=59.61 Å, b=69.29 Å, c=284.54 Å) with two complex molecules per asymmetric unit. Structure of Fzd5:R2M3 complex was determined at a resolution of 2.0 Å, and refined to $R_{cryst}$ and $R_{free}$ factors of 21.9% and 23.8%, respectively.

Figure 4:
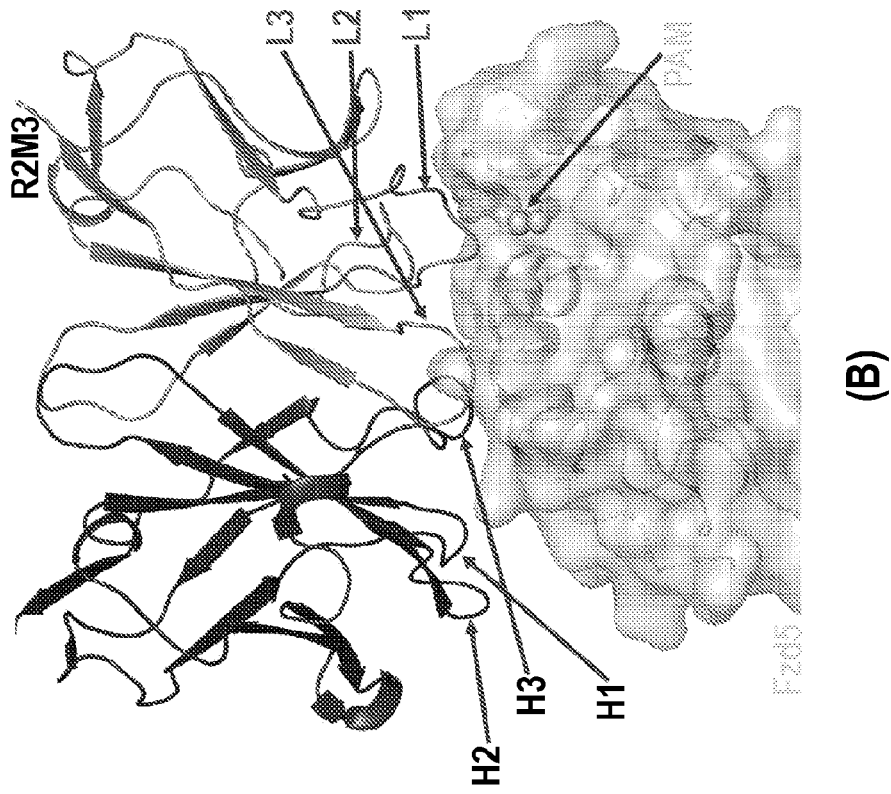
FIG. 4. (A) Overall structure of Fzd5:R2M3 complex. Molecular surface of Fzd5 is shown as light-gray transparent surface. Heavy- and Light-chains of R2M3 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd5:R2M3 interface with positions of CDR loops H1, H2, H3 of heavy-chain and L1, L2, and L3 of light-chain are marked.
Figure 4:
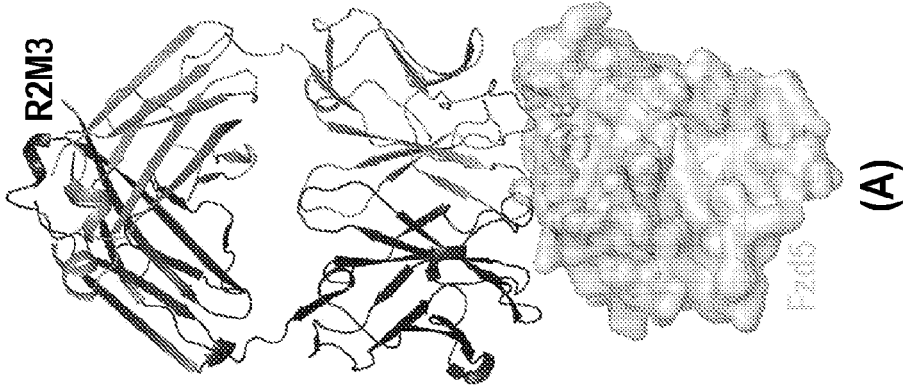

Overall structure of Fzd5:R2M3 complex is shown in FIG. 4 (A and B), which reveals that the R2M3 binds closer to the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. R2M3 binds to both Fzd 1, 2, 7 and Fzd 5,8 subfamilies of Fzds with wider specificity.

Structure of the complex allow us to identify epitope of Fzd5 for R2M3 with the following residue defining the core interaction-site on Fzd5 (5 Å cut-off):

Thr37, Val38, Pro39, Arg42, Asn56, His57, Asp58, Gln60, Asp61, Glu62, Gly64, Leu65, Glu66, His68, Gln69, Trp71, Pro72, Try123, and Gly124.

In addition, following residues on Fzd5 could be identified as immediate-interaction site for R2M3 (interaction distances >5.0 Å and <=8.0 Å):

Gln34, Glu35, Ile36, Met40, Cys41, Pro52, Asn53, Phe55, Thr59, Ala63, Val67, Phe70, Glu75, Tyr90, Met120, Arg121, Gln122, Phe125, Ala126, Pro128, and Glu129.

Structure of Fzd5:R2M3 complex also allow us to identify following residues on R2M3 at less-than or equal to 5.0 Å from any atoms of Fzd5:

R2M3 heavy chain: Ser31, Trp50, Tyr54, Asn55, Asn57, Lys102, Ile103, Thr104, Tyr105, and Tyr106.

R2M3 light chain: Thr31, Asn32, Tyr34, Tyr52, Asn54, Thr55, Tyr93, Gly95, Arg96, Gly97, and Trp99.

Further, the structure of Fzd5:R2M3 complex reveals following residues on R2M3 to be immediate-interaction site for Fzd5 with interaction distances >5.0 Å and <=8.0 Å:

R2M3 heavy chain: Phe29, Thr30, Tyr32, Gly33, Ile51, Ser52, Gly56, Thr58, Asn59, Glu101, Tyr107, and Gly108.

R2M3 light chain: Ser30, Tyr33, Pro35, Tyr51, Thr53, Gly66, Ser67, Ile68, Leu94, and Ile98.

Example 11

Structure of Fzd8:005S-H05 Complex

Sequence of 005S-H05 Fab:

>005S-H05_Lchain
(SEQ ID NO: 1472)
DIQMTQSPSSLSASVGDRVTITCRASQGISSALAVVYQQKPGKAPKLLI

YAASSLQSGVPSRFSGSGSGTDFTLTISSLQPEDFATYYCQQTYSMPIT

FGQGTRLEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

>005S-H05_Hchain
(SEQ ID NO: 1473)
QVQLVQSGAEVKKPGASVKVSCKASGYTFTSYYMHVVVRQAPGQGLEVV

MGRINPNSGGTNYAQKFQGRVTMTRDTSTSTVYMELSSLRSEDTAVYYC

ARVPDFWSGYLDYWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSGSGHHHHHH

Diffraction quality crystals of Fzd8: 005S-H05 complex (concentration=38 mg/mL) grew in a crystallization condition containing 0.2 M ammonium sulfate, 0.1 M HEPES: NaOH, pH 7.5, and 25% (w/v) PEG3350 Crystal was cryo-protected using 26% glycerol in the well-solution. Fzd8: 005S-H05 complex crystallized in the C2 space group (a=92.63 Å, b=60.38 Å, c=110.35 Å;)1=97.5° with two complex molecules per asymmetric unit. Structure of Fzd8: 005S-H05 complex was determined at a resolution of 1.65 Å, and refined to $R_{cryst}$ and $R_{free}$ factors of 16.8% and 18.6%, respectively.

Figure 5:
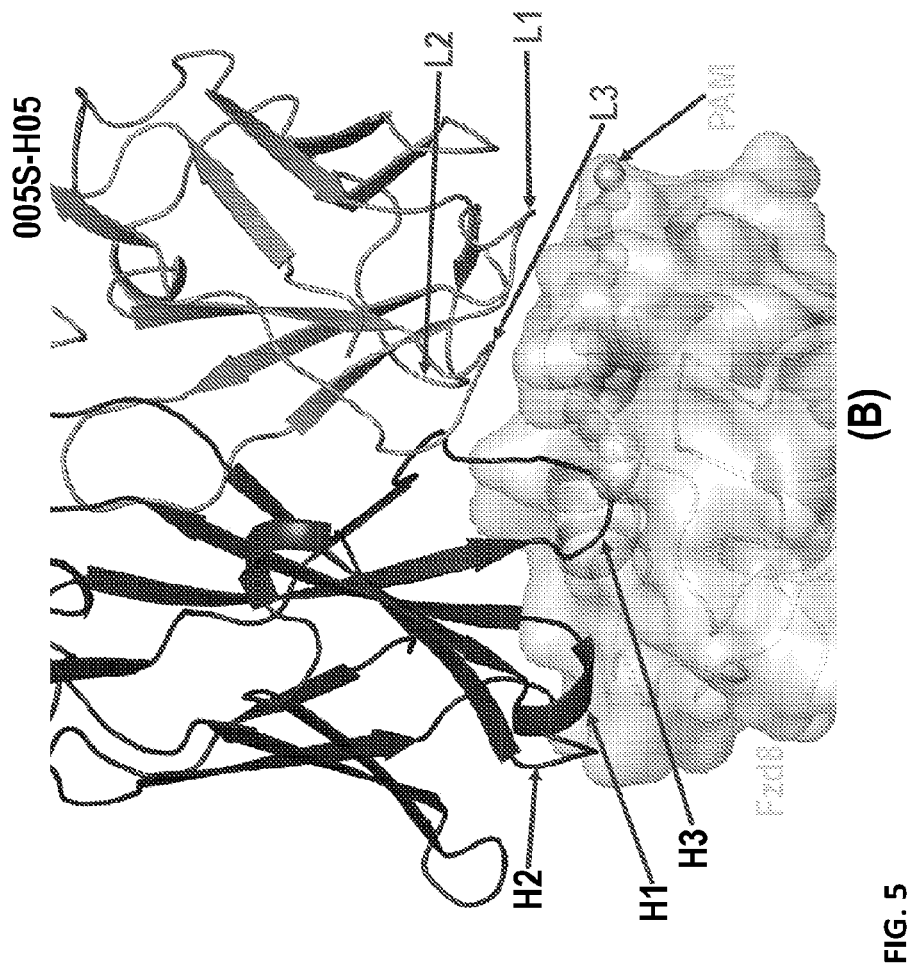
FIG. 5. (A) Overall structure of Fzd8:005S-H05 complex. Molecular surface of Fzd8 is shown as light-gray transparent surface. Heavy- and Light-chains of 005S-H05 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd8: 005S-H05 interface with positions of CDR loops H1, H2, H3 of heavy-chain and L1, L2, and L3 of light-chain are marked.
Figure 5:
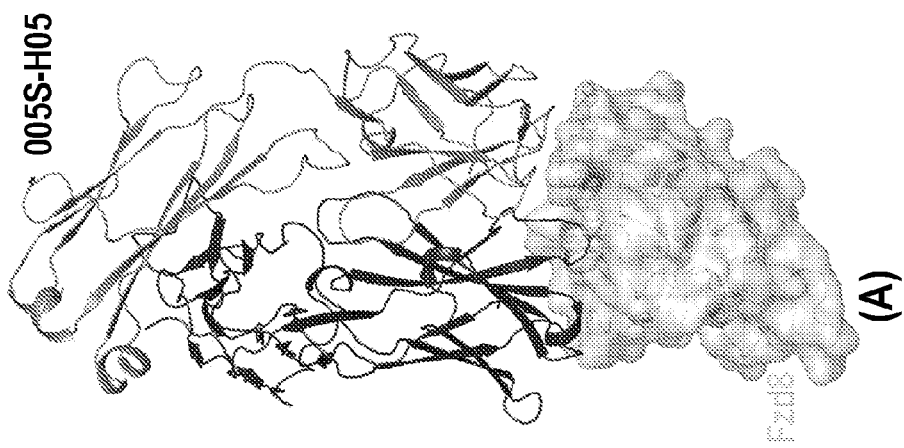

Overall structure of Fzd8: 005S-H05 complex is shown in FIG. 5 (A and B), which reveals that the Heavy-chain CDR3 of 005S-H05 inserts into the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. 005S-H05 binds to both Fzd 5 and Fzd 8 with subfamily specificity.

Structure of the complex allow us to identify epitope of Fzd8 for 005S-H05 with the following residue defining the core interaction-site on Fzd8 (5 Å cut-off):

Phe57, Asn58, Glu64, Leu67, Glu68, His70, Gln71, Phe72, Trp73, Pro74, Glu77, Try92, Arg123, Gln124, Try125, Gly126, Phe127, Ala128, Trp129, Pro130, Arg132, and Met133.

In addition, following residues on Fzd8 could be identified as immediate-interaction site for 005S-H05 (interaction distances >5.0 Å and <=8.0 Å):

Asn55, Gln56, His59, Asp60, Gly66, Val69, Leu75, Ile78, Leu88, Leu121, Met122, Asp131, and Arg137.

Structure of Fzd8: 005S-H05 complex also allow us to identify following residues on 005S-H05 at less-than or equal to 5.0 Å from any atoms of Fzd8:

005S-H05 heavy chain: Gly26, Try27, Thr28, Ser31, Tyr32, Pro100, Asp101, Phe102, Trp103, Ser104, Gly105, Tyr106, and Asp108.

005S-H05 light chain: Ile29, Ser30, Ser31, Ala32, Tyr49, Ala50, Ser52, Ser53, Leu54, Gln55, Ser56, Thr91, Tyr92, and Ser93.

Further, the structure of Fzd8: 005S-H05 complex reveals following residues on R2M3 to be immediate-interaction site for Fzd5 with interaction distances >5.0 Å and <=8.0 Å:

005S-H05 heavy chain: Gln1, Val2, Phe29, Thr30, Tyr33, Arg50, Asn52, Asn54, Arg98, Val99, Leu107, and Tyr109.

005S-H05 light chain: Ile2, Gly28, Leu33, Ala34, Leu46, Ala51, Gly57, Gly66, Ser67, Gly68, Phe71, Gln90, and Met94.

Example 12

Structure of Fzd5:004S-E05 Complex

Sequence of 004S-E05 Fab:

```
>004S-E05_Lchain
                                    (SEQ ID NO: 1474)
DIQMTQSPSSLSASVGDRVTITCRASQGISSALAVVYQQKPGKAPKLLI

YAASALQSGVPSRFSGSGSGTDFTLTISSLQPEDFATYYCQQTYSTPRT

FGPGTKVDIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

>004S-E05_Hchian
                                    (SEQ ID NO: 1475)
EVQLVESGGGLVQPGGSLRLSCAASGFTFSTYEMNVVVRQAPGKGLEVV

VSGVSWNGSRTHYVDSVKGRFTISRDNSKNTLYLQLNSLRAEDTAVYYC

ARGQSEKVVWSGLYGMDVWGQGTTVWSSASTKGPSVFPLAPSSKSTSGG

TAALGCLVKDYFPEPVTVSWNSGALTSGVHTFPAVLQSSGLYSLSSVVT

VPSSSLGTQTYICNVNHKPSNTKVDKKVEPKSCGSGSGHHHHHH
```

Diffraction quality crystals of Fzd5: 004S-E05 complex (concentration=30 mg/mL) grew in a crystallization condition containing 0.1 M Bis-Tris pH 5.7, and 24% (w/v) PEG3350. Crystal was cryo-protected using 33% ethyleneglycol in the well-solution. Fzd5: 004S-E05 complex crystallized in the P21212 space group (a=72.87 Å, b=192.35 Å, c=90.25 Å) with two complex molecules per asymmetric unit. Structure of Fzd5: 004S-E05 complex was determined at a resolution of 1.70 Å, and refined to $R_{cryst}$ and $R_{free}$ factors of 18.5% and 20.7%, respectively.

Figure 6:
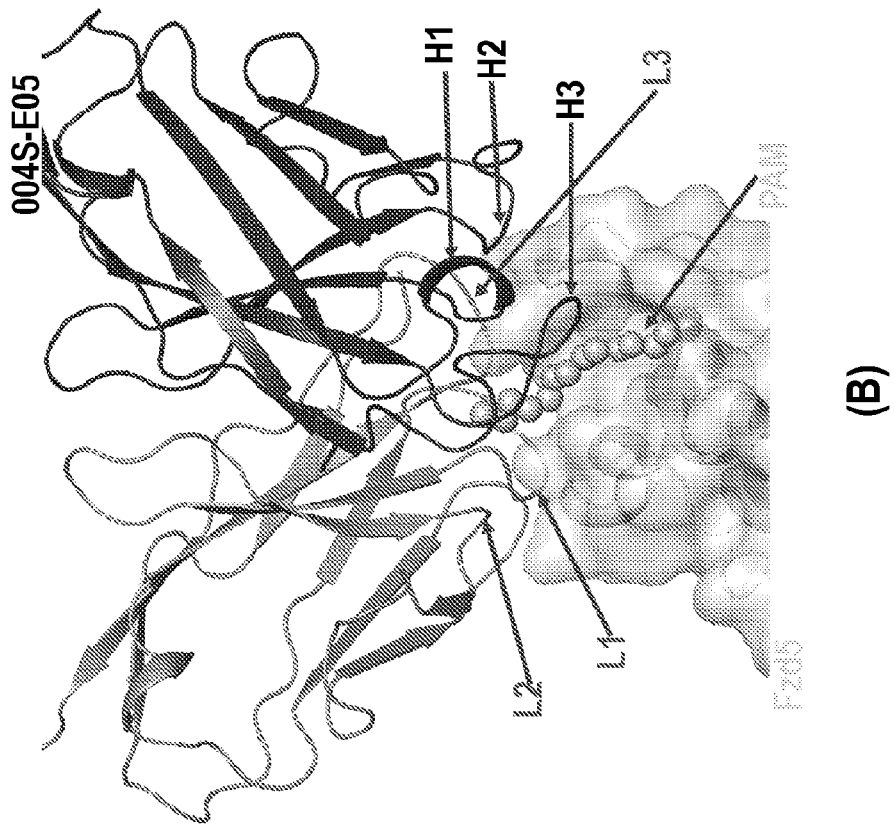
FIG. 6. (A) Overall structure of Fzd5:004S-E05 complex. Molecular surface of Fzd5 is shown as light-gray transparent surface. Heavy- and Light-chains of 004S-E05 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd5: 004S-E05 interface with positions of CDR loops H1, H2, H3 of heavy-chain and L1, L2, and L3 of light-chain are marked.
Figure 6:
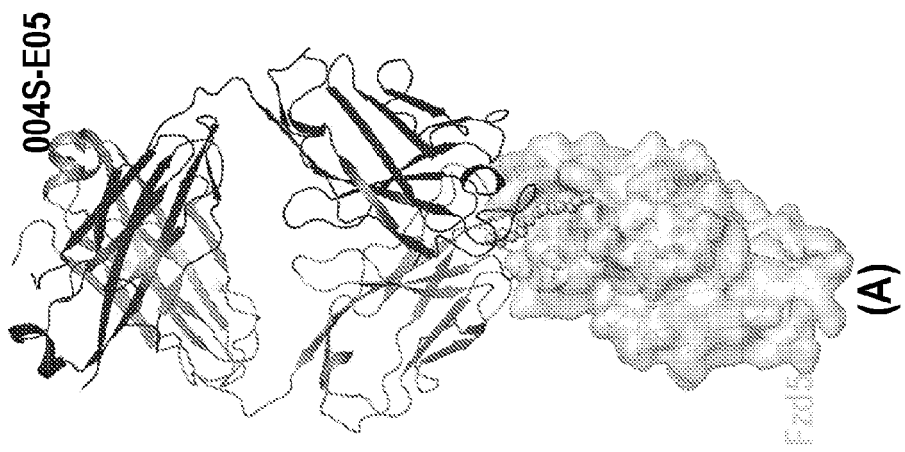

Overall structure of Fzd5: 004S-E05 complex is shown in FIG. 6 (A and B), which reveals that the CDR-H3 of 004S-E05 binds at the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. 004S-E050 binds to both Fzd 5 and Fzd 8 with bias towards the former. An ethyleneglycol, used as a cryoprotectant, bound Glu75 of Fzd5 interacts with Ala50, and Ala53 of the light-chain of 004S-E05.

Structure of the complex allow us to identify epitope of Fzd5 for 004S-E05 with the following residue defining the core interaction-site on Fzd5 (5 Å cut-off):

Gln69, Phe70, Trp71, Pro72, Leu73, Glu75, Ile76, Gln77, Cys78, Gly115, Pro118, Leu119, Met120, Arg121, Gln122, Try123, Gly124, and Phe125.

In addition, following residues on Fzd5 could be identified as immediate-interaction site for 004S-E05 (interaction distances >5.0 Å and <=8.0 Å):

Leu65, Glu66, Val67, His68, Val74, Ser79, Leu82, Cys116, Ser117, Ala126, and Pro128.

Structure of Fzd5: 004S-E05 complex also allow us to identify following residues on 004S-E05 at less-than or equal to 5.0 Å from any atoms of Fzd5:

004S-E05 heavy chain: Arg57, His59, Ser101, Trp104, Tryp105, Ser106, Gly107, Leu108, and Tyr109.

004S-E05 light chain: Ser30, Ser31, Ala32, Try49, Ala50, Ala53, Ser67, Thr91, Tyr92, Ser93, Thr94, and Arg96.

Further, the structure of Fzd5: 004S-E05 complex reveals following residues on R2M3 to be immediate-interaction site for Fzd5 with interaction distances >5.0 Å and <=8.0 Å:

004S-E05 heavy chain: Glu33, Ser52, Trp53, Ser56, His59, Gln100, Glu102, Lys103, and Gly110.

004S-E05 light chain: Ile2, Gln27, Gly28, Ile29, Leu33, Tyr49, Ala51, Ser52, Leu54, Gly66, Gly68, Phe71, Gln89, Gln90, Pro95, and Arg96.

Example 13

Structure of Fzd5:4A12 Complex

Sequence of 4A12 Fab:

```
>4A12_Lchain
                                    (SEQ ID NO: 1476)
DIVMTQSHKFMSTSVGDRVSITCKASQDVGTAVAVVYQQKPGQSPKLLIY

WASTRHTGVPDRFTGSGSGTDFTLTINNVQSEDLADYFCQQYSTYPLTFG

AGTKLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>4A12_Hchain
                                    (SEQ ID NO: 1477)
QVQLQQSGPELVKPGASVKLSCKASGYTFTNYDINVVVKQRPGQGLEWIG

WIYPRDGSTKYNEKFKGKATLTVDTSSSTAYMELHSLTSEDSAVYFCVRS

AWGFAYWGQGTLVTVSAASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCGSGSGHHHHHH
```

Diffraction quality crystals of Fzd5:4A12 complex (concentration=10 mg/mL), obtained by MMS, grew in a crystallization condition containing 0.2 M sodium chloride, 0.1 M Na2HPO4: Citric Acid, pH 4.2, and 20% (w/v) PEG8000. Crystal was cryo-protected using 25% ethyleneglycol in the well-solution. Fzd5:4A12 complex crystallized in the C2 space group (a=93.84 Å, b=60.07 Å, c=110.80 Å; ß=104.7°) with two complex molecules per asymmetric unit. Structure of Fzd5:4A12 complex was determined at a resolution of 1.75 Å, and refined to $R_{cryst}$ and $R_{free}$ factors of 17.7% and 21.6%, respectively.

Figure 7:
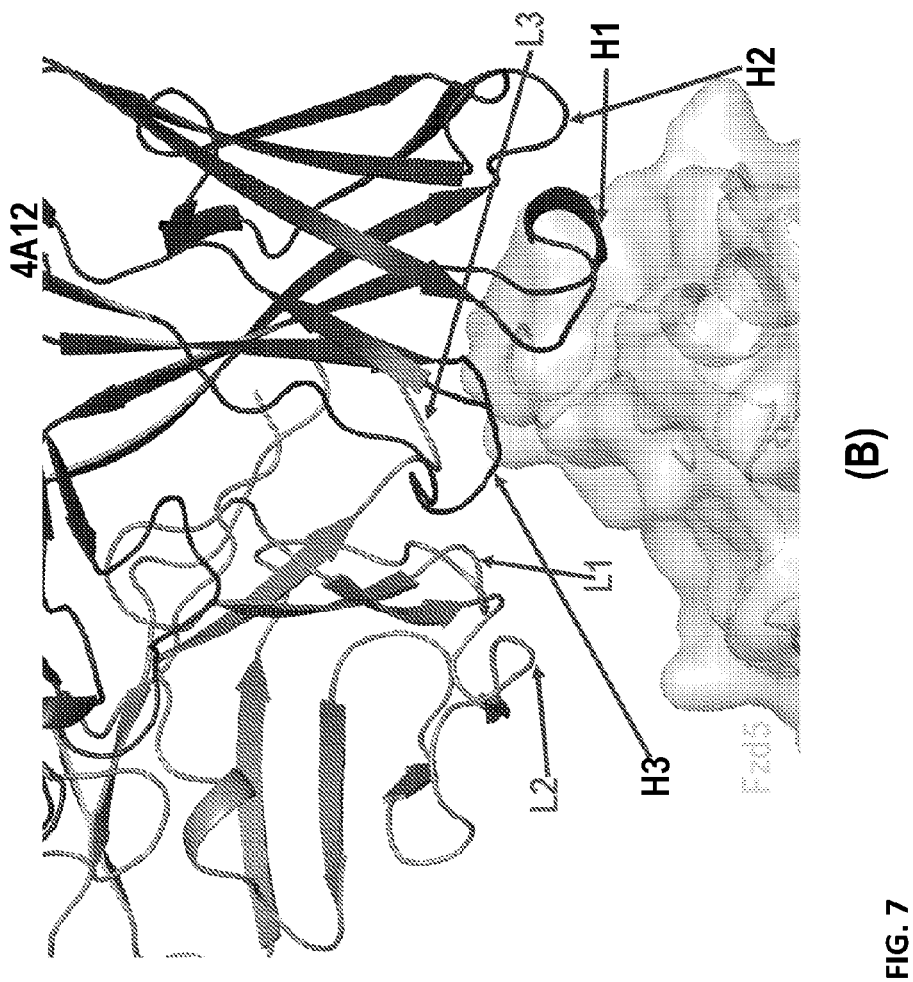
FIG. 7. (A) Overall structure of Fzd5:4A12 complex. Molecular-surface of Fzd5 is shown as light-gray transparent surface. Heavy- and Light-chains of 4A12 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd5:4A12 interface with positions of CDR loops H1, H2, H3 of heavy-chain and L1, L2, and L3 of light-chain are marked.
Figure 7:
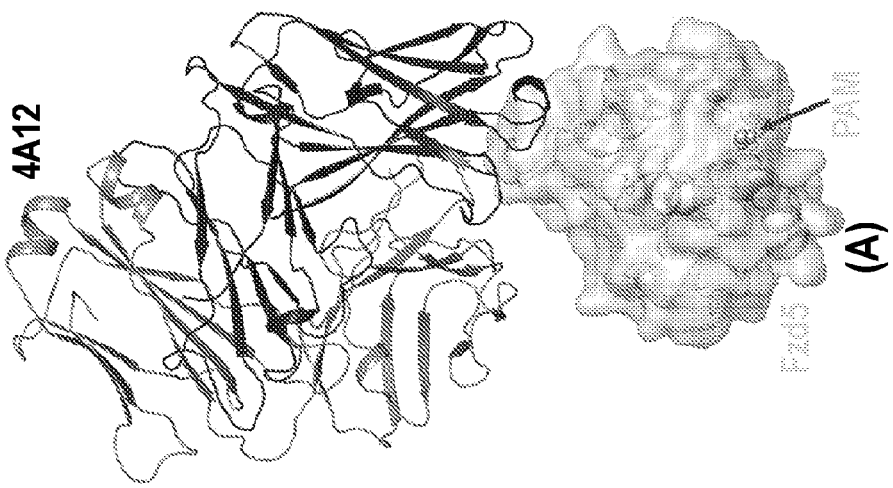

Overall structure of Fzd5:4A12 complex is shown in FIG. 7 (A and B), which reveals that the 4A12 binds opposite to the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64], and recognizes the c-terminal region of Fzd5. Electron density maps revealed a chloride ion, bound at the interface of Fzd5:4A12 complex, bound to Arg111 of Fzd5 also interacting with the main-chain amide-nitrogen of Thr28 and the side-chain amide group of Asn31 of the heavy-chain of 4A12.

Structure of the complex allow us to identify epitope of Fzd5 for 4A12 with the following residue defining the core interaction-site on Fzd5 (5 Å cut-off):

Cys105, Arg106, Ser107, Glu110, Arg111, Cys133, Asp134, Val138, Leu139, Gly140, Arg141, Asp142, Ala143, Val145, Leu146, Cys147, and Asp149.

In addition, following residues on Fzd5 could be identified as immediate-interaction site for 4A12 (interaction distances >5.0 Å and <=8.0 Å):

Asp81, Tyr98, Leu102, Pro103, Val108, Cys109, Ala112, Ala114, Ser132, Arg135, Leu136, Pro137, Glu144, and Met148.

Structure of Fzd5:4A12 complex also allow us to identify following residues on 4A12 at less-than or equal to 5.0 Å from any atoms of Fzd5:

4A12 heavy chain: Asn31, Tyr32, Asp33, Trp50, Tyr52, Arg54, Ser99, Ala100, and Trp101.

4A12 light chain: Ala32, Trp50, Tyr91, Ser92, and Tyr94.

Further, the structure of Fzd5:4A12 complex reveals following residues on 4A12 to be immediate-interaction site for Fzd5 with interaction distances >5.0 Å and <=8.0 Å:

4A12 heavy chain: Gly26, Tyr27, Thr28, Thr30, Ile34, Asp35, Trp47, Ile51, Pro53, Asp55, Ser57, Thr58, Lys59, Arg98, Gly102, Phe103, Ala104, and Tyr105.

4A12 light chain: Val29, Thr31, Tyr49, Gln89, Gln90, Thr93, and Leu96.

Example 14

Structure of Fzd9: 014S-B06 Complex

Sequence of 014S-B06 Fab:

014S-B06_Lchain
(SEQ ID NO: 1478)
DIQMTQSPSSLSASVGDRVTITCRASQSISSYLNVVYQQKPGKAPKLLI

YAASSLQSGVPSRFSGSGSGTDFTLTISSLQPEDFATYYCQQSYSTPLT

FGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

014S-B06_Hchain
(SEQ ID NO: 1479)
EVQLVQSGGGLVKPGGSLRLSCAASGFTFSSYSMNVVVRQAPGKGLEVV

VSYIENDGSITTYADSVKGRFTISRDDSKNTLYLQMNSLKTEDTAVYYC

ARAPYYYGSGSLFRLDYWGQGTLVTVSSASTKGPSVFPLAPSSKSTSGG

TAALGCLVKDYFPEPVTVSWNSGALTSGVHTFPAVLQSSGLYSLSSVVT

VPSSSLGTQTYICNVNHKPSNTKVDKKVEPKSCGSGSGHHHHHH

Diffraction quality crystals of Fzd9: 014S-B06 complex (concentration=31 mg/mL) grew in a crystallization condition containing 4% PEG 3350, 0.1M HEPES pH 7.5, and 0.2M lithium chloride. Crystal was cryo-protected using 27% glycerol in the well-solution. Fzd9: 014S-B06 crystallized in the P212121 space group (a=63.8 Å, b=81.4 Å, and c=160.5 Å) with one complex molecule per asymmetric unit. Structure of Fzd9: 014S-B06 complex was determined at a resolution of 1.95 Å, and refined to Rcryst and Rfree factors of 19.8% and 22.6%, respectively.

Figure 8:
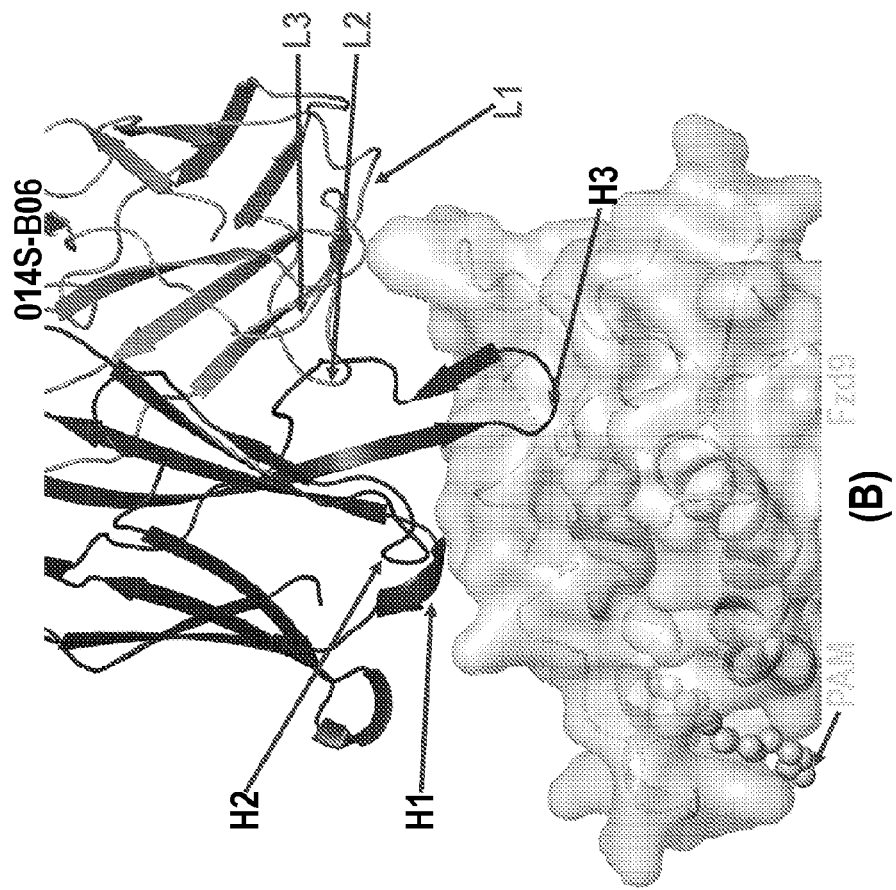
FIG. 8. (A) Overall structure of Fzd9:014S-B06 complex. Molecular surface of Fzd5 is shown as light-gray transparent surface. Heavy- and Light-chains of 014S-B06 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd5: 014S-B06 interface with positions of CDR loops H1, H2, H3 of heavy-chain and L1, L2, and L3 of light-chain are marked.
Figure 8:

Overall structure of Fzd9: 014S-B06 complex is shown in FIG. 8 (A and B), which reveals that the heavy-chain CDR3 of 014S-B06 binds away from the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64], and recognize the region closer to the C-terminus of Fzd9.

Structure of the complex allow us to identify epitope of Fzd9 for 014S-B06 with the following residue defining the core interaction-site on Fzd9 (5 Å cut-off):

Leu60, Leu61, Lue95, Thr106, Pro107, Pro109, Arg112, Arg119, Asp135, Ser136, Leu137, Asp138, Ala140, Arg141, Leu142, Pro143, Thr144, Asp147, Pro148, His149, and Ala150.

In addition, following residues on Fzd9 could be identified as immediate-interaction site for 014S-B06 (interaction distances >=5.0 Å and <=8.0 Å):

Asn59, Gly62, Phe91, Ser94, Pro98, Ser105, Ile108, Ala110, Trp133, Pro134, Asp138, Cys139, Arg145, Asn146, Leu151, and Cys152.

Structure of Fzd9: 014S-B06 complex also allow us to identify following residues on 3SD10 at less-than or equal to 5.0 Å from any atoms of Fzd4:

014S-B06 heavy chain:
Thr28, Ser30, Ser31, Tyr32, Asn53, Tyr101, Tyr102, Try103, Gly104, Ser105, Leu108, and Arg110.

014S-B06 light chain:
Ser31, Try32, Try49, Ala50, Ser53, and Ser91.

Further, the structure of Fzd9: 014S-B06 complex reveals following residues on 014S-B06 to be immediate-interaction site for Fzd9 with interaction distances >=5.0 Å and <=8.0 Å:

014S-B06 heavy chain:
Phe27, Phe29, Asp54, Arg72, Asp74, Asn77, Arg98, Ala99, Pro100, Gly106, Ser107, Phe109, and Asp112.

014S-B06 light chain:
Ile29, Ser30, Leu33, Asn34, Ala51, Ser52, and Tyr92.

Example 15

Structure of Fzd10: 005S-A07 Complex

Sequence of 005S-A07 Fab:

005S-A07_Lchain
(SEQ ID NO: 1480)
EIVLTQSPATLSVSPGERATLSCRASQSVSRNLAVVYQQKPGQAPRLL

IYGASTRATGIPARFSGSGSGTEFTLTISSLQSEDFAVYYCQQRSNWP

ITFGQGTRLEIKRTVAAPSVFIFPPSDEQLKSGTASVVCLLNNFYPRE

AKVQWKVDNALQSGNSQESVTEQDSKDSTYSLSSTLTLSKADYEKHKV

YACEVTHQGLSSPVTKSFNRGEC

005S-A07_Hchain
(SEQ ID NO: 1481)
QVQLVQSGAEVKKPGSSVKVSCKASGFTFTGSAVQVVVRQAPGQGLEV

VVGGILPIYGTTKYAQKFQGRVTITADESTSTAYMELSSLRSEDTAVY

YCARGARLYGFDYWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKKVEPKSCGSGSGHHHHHH

Diffraction quality crystals of Fzd10: 005S-A07 complex (concentration=37 mg/mL) grew in a crystallization condition containing 0.2 M ammonium sulfate, 0.1 M sodium citrate:HCl pH 5.6, and 25% (w/v) PEG 4000. Crystal was cryo-protected using 20% glycerol in the well-solution. Fzd10: 005S-A07 complex crystallized in the H32 space group (a=b=138.2 Å, and c=190.6 Å) with one complex molecule per asymmetric unit. Structure of Fzd10: 005S-A07 complex was determined at a resolution of 2.40 Å, and refined to Rcryst and Rfree factors of 20.6% and 25.0%, respectively.

Figure 9:
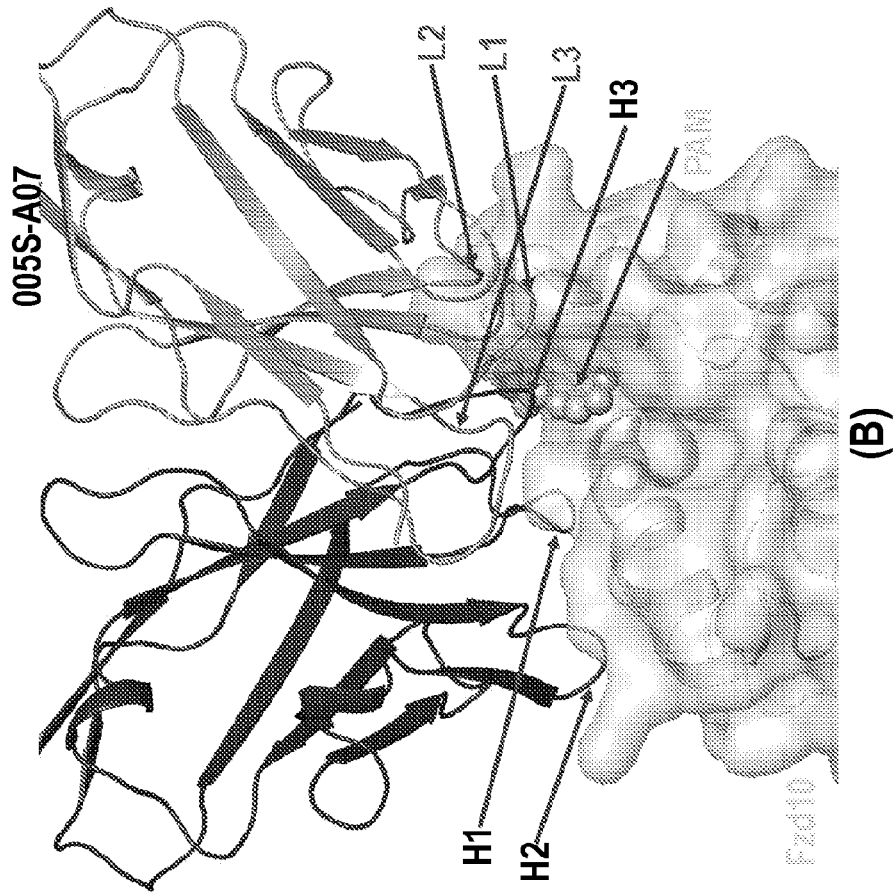
FIG. 9. (A) Overall structure of Fzd10:005S-A07 complex. Molecular surface of Fzd5 is shown as light-gray transparent surface. Heavy- and Light-chains of 005S-A07 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd10: 005S-A07 interface with positions of CDR loops H1, H2, H3 of heavy-chain and L1, L2, and L3 of light-chain are marked.

Overall structure of Fzd10: 005S-A07 complex FIG. 9 (A and B), reveals that the 005S-A07 binds to Fzd10 at the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64]. Interestingly, crystal structure of Fzd10: 005S-A07 showed potential binding sites for two sulfate-ions (SO42-) at the antigen-Fab interface, that could be helpful in further structure-guided engineering of 005S-A07 to optimize its properties. Structure of the complex allow us to identify epitope on Fzd10 for 005S-A07 with the following residue defining the core interaction-site on Fzd10 (5 Å cut-off):

Pro40, Met41, Ile66, Gln67, His69, Glu70, Phe71, Ala72, Pro73, Val75, Glu76, Tyr77, Arg84, Met121, Glu122, Gln123, Phe124, Asn125, Phe126, Lys127, Pro129, and Asp130.

In addition, following residues on Fzd10 could be identified as immediate-interaction site for 005S-A07 (interaction distances >=5.0 Å and <=8.0 Å):

Ile39, Cys42, Lys43, Arg62, Glu63, Ala65, Ile66, Leu68, Leu74, Gly78, Cys88, Tyr91, Ser118, Pro119,Ile120, Trp128, Ser131, and Leu132.

Structure of Fzd10: 005S-A07 complex also allow us to identify following residues on 005S-A07 at less-than or equal to 5.0 Å from any atoms of Fzd4:

005S-A07 heavy chain:
Thr28, Thr30, Gly31, Ser32, Leu52,Ile54, Tyr55, Thr57, Lys59, Arg98, Ala100, Arg101, Leu102, Tyr103, Gly104, and Asp106.

005S-A07 light chain:
Arg33, Asn34, Leu48, Tyr51, Gly52, Ala57, Thr58, and Trp96.

Further, the structure of Fzd10: 005S-A07 complex reveals following residues on 005S-A07 to be immediate-interaction site for Fzd9 with interaction distances >=5.0 Å and <=8.0 Å:

005S-A07 heavy chain:
Phe27, Phe29, Ala33, Gln35, Pro53, Gly56, Thr58, Gly99, Phe105, and Tyr107.

005S-A07 light chain:
Val31, Ser32, Leu35, Leu49, Ile50, Ala53, Thr55, Arg56, Gly59, Ile60, Arg93, Ser94, Asn95, and Ile98.

Example 16

Structure of Fzd10:005S-E12 Complex

Sequence of 005S-E12 Fab:

005S-E12_Lchain
(SEQ ID NO: 1482)
DIQMTQSPSSLSASVGDRVTITCRASQSVGRVVMAVVYQQKPGKAPKLLI

YAASSLQSGVPSRFSGSGSGTDFTLTISSLQPEDFATYYCQQANTFPFTF

GPGTKVDIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC

005S-E12_Hchain
(SEQ ID NO: 1483)
QVQLVQSGAEVKKPGASVKVSCKASGYIFTDYYMHVVVRQAPGQGLEVVM

GVIFPVYPTPDYAQKFQGRVTMTRDTSTSTVYMELSSLRSEDTAVYYCAR

GGSTGYYGMDVWGQGTTVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCGSGSGHHHHHH

Diffraction quality crystals of Fzd10: 005S-E12 complex (concentration=34 mg/mL) were obtained by MSS in a crystallization condition containing 0.1 M Bis-Tris Propane: HCl, pH 7, and 2.5 M ammonium sulfate. Crystal was cryo-protected using 1.7M sodium malonate pH 7.0 in the well-solution. Fzd10: 005S-E12 complex crystallized in the P312 space group (a=b=90.4 Å, and c=185.1 Å) with one complex molecule per asymmetric unit. Structure of Fzd10: 005S-E12 complex was determined at a resolution of 2.50 Å, and refined to Rcryst and Rfree factors of 20.1% and 24.4%, respectively.

Figure 10:
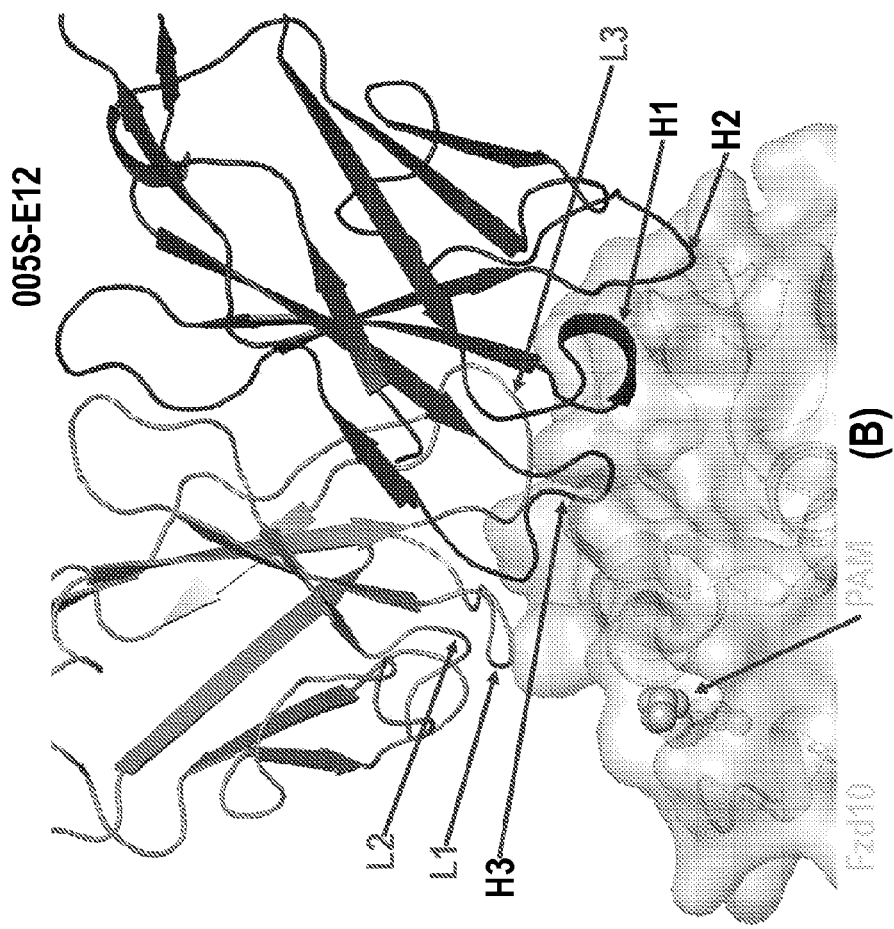
FIG. 10. (A) Overall structure of Fzd10:005S-E12 complex. Molecular surface of Fzd5 is shown as light-gray transparent surface. Heavy- and Light-chains of 005S-E12 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd10: 005S-E12 interface with positions of CDR loops H1, H2, H3 of heavy-chain and L1, L2, and L3 of light-chain are marked.
Figure 10:
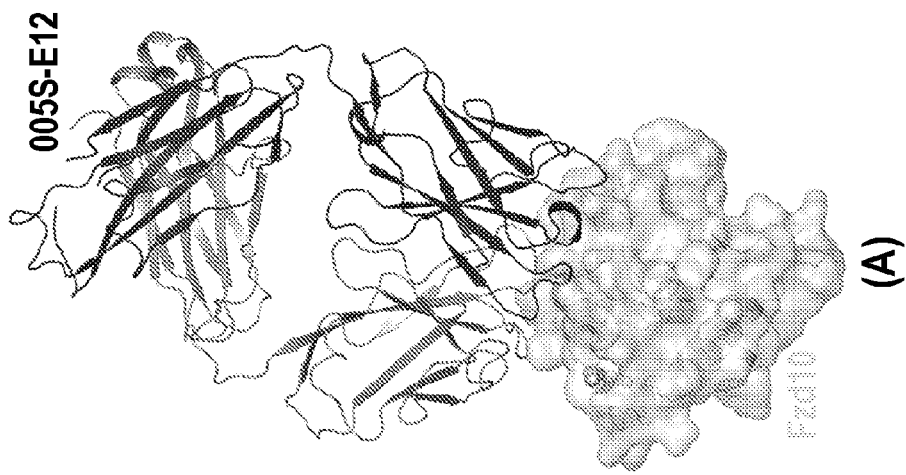

Overall structure of Fzd10: 005S-E12 complex FIG. 10 (A and B), reveals that the 005S-E12 binds to Fzd10 adjacent to the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64], and recognize the tail and helix at the N-terminal region of Fzd10. Structure of the complex allow us to identify epitope on Fzd10 for 005S-E12 with the following residue defining the core interaction-site on Fzd10 (5 Å cut-off):

Ile37, Glu38, Ile39, Pro40, Met41, Cys42, Lys43, Asp44, Ile45, Gly46, Asn48, Gln61, Arg62, Glu63, Ala65, Ile66, Leu68, His69, Ala72, Pro73, Val75, Glu76, and Arg84.

In addition, following residues on Fzd10 could be identified as immediate-interaction site for 005S-E12 (interaction distances >=5.0 Å and <=8.0 Å):

Glu35, Pro36, Tyr47, Asn60, Gln61, Ala64, Gln67, Glu70, Phe71, Leu74, Tyr77, and Phe124.

Structure of Fzd10: 005S-E12 complex also allow us to identify following residues on 005S-E12 at less-than or equal to 5.0 Å from any atoms of Fzd4:

005S-E12 heavy chain:
Tyr33, Phe52, Pro53, Val54, Tyr55, Thr57, Asp59, Gly100, Ser101, Thr102, Gly103, Tyr104, and Tyr105.

005S-E12 light chain:
Ile2, Gln27, Ser28, Val29, Gly30, Arg31, Trp32, Ala50, Ala91, Asn92, Thr93, Phe94, and Phe96.

Further, the structure of Fzd10: 005S-E12 complex reveals following residues on 005S-E12 to be immediate-interaction site for Fzd9 with interaction distances >=5.0 Å and <=8.0 Å:

005S-E12 heavy chain:
Thr30, Asp31, Tyr32, His35, Trp47, Val50, Ile51, Pro56, Pro58, Tyr60, Gln62, Arg72, Gly99, and Gly106.

005S-E12 light chain:
Asp1, Ala25, Ser26, Met33, Tyr49, Ala51, Ser52, Ser53, Ser67, Gly68, Thr69, Gln90, and Pro95.

Example 17

Structure of Fzd3:029S-E03 Complex

Sequence of 029S-E03 Fab:

>029S-E03_Lchain
(SEQ ID NO: 1484)
DIQMTQSPSSLSASVGDRVTITCRASQSISSYLNVVYQQKPGKAPKLLI

YAASSLQTGVPSRFSGSGSGTDFTLTISSLQPEDFATYYCQQSFRLPLT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

>029S-E03_Hchain
(SEQ ID NO: 1485)
QVQLVQSGAEVKKPGASVKVSCKASGYTFTGYYMHVVVRQAPGQGLEVV

MGWINPNSGNTGYAQKFQGRVTMTRDTSTSTVYMELSSLRSEDTAVYYC

ARSYYGVIDAFDIWGQGTMVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSGSGHHHHHH

Diffraction quality crystals of Fzd3: 029S-E03 complex (concentration=25 mg/mL) grew in a crystallization condition containing 0.2 M Trimethylamine N-Oxide, 0.1 M Tris: HCl, pH 8.5, and 20% (w/v) PEG 2000 MME. Crystal was cryo-protected using 20% glycerol in the well-solution. Fzd3: 029S-E03 crystallized in the P21 space group (a=69.60 Å, b=145.50 Å, and c=104.31 Å; 11=101.8°) with one complex molecule per asymmetric unit. Structure of Fzd3: 029S-E03 complex was determined at a resolution of 2.40 Å, and refinement is in progress with $R_{cryst}$ and $R_{free}$ factors of 24.4% and 31.8%, respectively.

Figure 11:
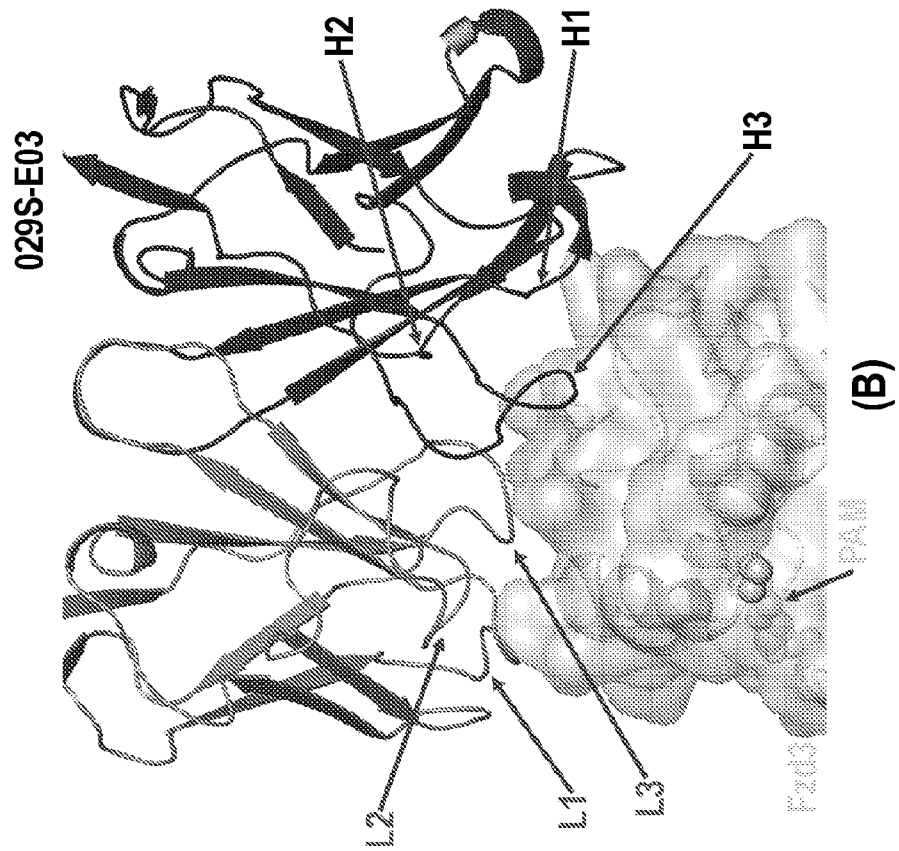
FIG. 11. (A) Overall structure of Fzd3:029S-E03 complex. Molecular surface of Fzd5 is shown as light-gray transparent surface. Heavy- and Light-chains of 029S-E03 are colored in shades of darker- and lighter-black, respectively. The lipid (palmitoleic acid; PAM) as observed in the structure of Wnt8:Fzd8 (PDB code: 4F0A) is shown in light-gray spheres. (B) Close-up view of the Fzd3: 029S-E03 interface with positions of CDR loops H1, H2, H3 of heavy-chain and L1, L2, and L3 of light-chain are marked.
Figure 11:
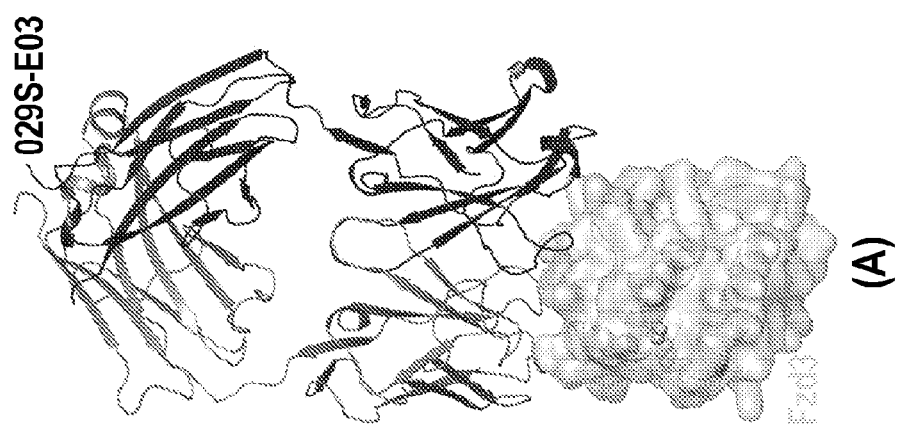

029S-E03 is a mono-specific binder of Fzd3, and does not show detectable binding to other Fzds. Overall structure of Fzd3: 029S-E03 complex is shown in FIG. 11 (A and B), which reveals that the heavy-chain CDR3 of 029S-E03 binds adjacent to the lipid binding site as observed in the complex of Fzd8:Wnt8a complex [PDB Code: 4F0A; Janda, C. Y., Waghray, D., Levin, A. M., Thomas, C., Garcia, K. C. (2012) Science 337: 59-64], and recognize the region closer to the N-terminus of Fzd3.

Structure of the complex allow us to identify epitope of Fzd3 for 029S-E03 with the following residue defining the core interaction-site on Fzd3 (5 Å cut-off):

Pro30, Ile31, Thr32, Leu33, Arg34, Gln37, Asp38, Leu39, Gln55, Gln66, Ala59, Leu60, Glu63, His66, and Asn70.

In addition, following residues on Fzd3 could be identified as immediate-interaction site for 029S-E03 (interaction distances >=5.0 Å and <=8.0 Å):

Gln29, Met35, Cys36, Pro40, Tyr41, Asn42, Thr43, Asp54, Thr57, Ala58, Ala61, Met62, Pro67, Val69, Leu71, Asp72, and Arg78.

Structure of Fzd3: 029S-E03 complex also allow us to identify following residues on 3SD10 at less-than or equal to 5.0 Å from any atoms of Fzd3:

029S-E03 heavy chain: Tyr33, Trp50, Asn52, Ser55, Asn57, Gln62, Tyr101, Val103, Ile104, and Asp105.

029S-E03 light chain: Ile2, Gln27, Ser28, Ser30, Tyr32, Ser91, Phe92, Arg93, and Leu94.

Further, the structure of Fzd3: 029S-E03 complex reveals following residues on 029S-E03 to be immediate-interaction site for Fzd3 with interaction distances >=5.0 Å and <=8.0 Å:

029S-E03 heavy chain: Trp47, Ile51, Pro53, Asn54, Gly56, Thr58, Gly59, Tyr60, Gln65, Ser99, Tyr100, Gly102, and Ala06.

029S-E03 light chain: Asp1, Ser26, Ile29, Ser31, Leu33, Asn34, Gly68, Gln90, Pro95, and Leu96.

TABLE 3

Summary of Binding Characteristics of Antigen Binding proteins as determined by co-crystal structures

| Antigen Binding Protein | Antigen | Interaction site on Fzd (<5 angstroms) | Interaction site on Fzd (5-8 angstroms) |
|---|---|---|---|
| 1RC07 (Binds to Fzd1, Fzd2, and Fzd7) | Fzd1 | Pro122, Leu148, His151, Gln152, Tyr154, Pro155, Leu156, Lys158, and Gln160. | Ser120, Ile121, Leu123, Cys124, Thr125, Asp126, Glu144, Gly147, Glu149, Val150, Phe153, Val157, Val159, Cys161, Cys198, Leu201, and Met202. |
| | Fzd2 / Fzd7 | P45/P55, L71/L81, H74/84, Y77/87, P78/88, L79/89, K81/91, and Q83/93. | S43/S53, I44/I54, L46/56, C47/57, T48/58, D49/59, E67/77, G70/80, E72/82, V73/83, F76/86, V80/90, V82/92, C84/94, C121/131, L124/134, and M125/135. |
| R2M9 (Binds to Fzd1, Fzd2, and Fzd7) | Fzd1 | Tyr115, Ala128, Tyr129, Phe167, Val176, Thr178, Val179, Leu180, Glu181, Gln182, Leu184, Gly224, Leu226, Cys227, and Val228. | Cys116, Ile127, Asn130, Gln131, Ser171, Cys177, Ala183, Pro185, Cys187, His221, Ala223, Glu225, Gly229, and Gln230. |
| | Fzd2 / Fzd7 | F38/48, A51/61, Y52/62, F90/100, V99/109, T101/111, V102/112, L103/113, E104/D114, Q105/115, I107/117, E147/G157, I149/159, C150/160, and V151/161. | C39/49, I50/60, N53/63, Q54/64, C100/110, A106/116, P108/118, C110/120, H144/154, A146/156, Q148/E158, G152/G162, and Q153/163. |

TABLE 3-continued

Summary of Binding Characteristics of Antigen Binding proteins as determined by co-crystal structures

| Antigen Binding Protein | Antigen | Interaction site on Fzd (<5 angstroms) | Interaction site on Fzd (5-8 angstroms) |
|---|---|---|---|
| 003S-D10 (Binds only to Fzd4, mono4) | Fzd4 | Val67, Gly68, His69, Thr73, Asp74, Glu76, Leu77, Gln78, Thr80, Thr81, Phe82, Thr83, Pro84, Leu85, Gln87, Tyr88, Tyr102, Leu132, Phe135, Gly136, Phe137, Ala138, and Ser142. | Ile50, Ser51, Met52, Pro64, Asn65, Leu66, Glu70, Leu71, Gln72, Ala75, Leu79, Ile86, Gly89, Leu94, Gln95, Leu98, Val101, Tyr102, Val131, Lys133, Glu134, Trp139, Pro140, Glu141, Leu143, and Lys147. |
| R2M3 (Binds to Fzd1, Fzd2, Fzd7, Fzd5, and Fzd8) | Fzd5 | Thr37, Val38, Pro39, Arg42, Asn56, His57, Asp58, Gln60, Asp61, Glu62, Gly64, Leu65, Glu66, His68, Gln69, Trp71, Pro72, Tyr123, and Gly124 | Gln34, Glu35, Ile36, Met40, Cys41, Pro52, Asn53, Phe55, Thr59, Ala63, Val67, Phe70, Glu75, Tyr90, Met120, Arg121, Gln122, Phe125, Ala126, Pro128, and Glu129. |
|  | Fzd8 / Fzd1 / Fzd2 / Fzd7 | T39/S120/43/53, V40/I121/44/54, P41/122/45/55, K44/T125/49, 59, N58/G139/62/72, H59/140/63/73, D60/T141/64/74, Q62/143/66/76, D63/E144/67/77, E64/D145/68/78/, G66/147/70/80, L67/148/71/81, E68/149/72/82, H70/151/74/84, Q71/152/75/85, W73/Y154/77/87, P74/155/78/88, Y125/F205/128/138, and G126/206/129/139, | Q36/117/40/50, E37/P118/41/51, I38/119/42/52, L42/125/46/56, C43/124/47/57, P54/136/58/68, N55/136/59/69, F57/L137/60/70, T61/N142/65/75, A65/146/69/79, V69/150/73/83, F72/153/76/86, E77/K158/81/91, Y92/173/96/106, M122/202/125/135, R123/N203/126/136, Q124/K204/127/137, F127/207/130/140, A128/Q208/131/141, P130/210/133/143, and D131/211/E134/144 |
| 005S-H05 (Binds to Fzd5 and Fzd8 in biased manner; also binds to Fzd1, Fzd2, and Fzd7 | Fzd8 | Phe57, Asn58, Glu64, Leu67, Glu68, His70, Gln71, Phe72, Trp73, Pro74, Glu77, Tyr92, Arg123, Gln124, Tyr125, Gly126, Phe127, Ala128, Trp129, Pro130, Arg132, and Met133. | Asn55, Gln56, His59, Asp60, Gly66, Val69, Leu75, Ile78, Leu88, Leu121, Met122, Asp131, and Arg137. |
|  | Fzd5 / Fzd1 / Fzd2 / Fzd7 | F55/L138/61/71, N56/G139/62/72, E62/D145/68/78/, E66/149/72/82, H68/151/74/84, Q69/152/75/85, F70/153/76/86, W71/Y154/77/87, P72/155/78/88, E75/K158/81/91, Y90/173/96/106, R121/N203/126/136, Q122/K204/127/137, Y123/F205/128/138, G124/206/129/139, F125/207/130/140, A126/Q208/131/141, W127/209/132/142, P128/210/133/143, R130/T211/R135/145, and M131/L212/136/146. | N53/136/59/69, Q54/L137/60/70, H57/140/63/73, D58/T141/64/74, G64/147/70/80, V67/150/73/83, L73/156/79/89, I76/V159/82/92, L86/169/92/102, L119/201/124/134, M120/202/125/135, E129/D211/E134/144, and R135/K217/H140/N150. |
| 004S-E05 (Binds preferentially to Fzd5) | Fzd5 | Gln69, Phe70, Trp71, Pro72, Leu73, Glu75, Ile76, Gln77, Cys78, Gly115, Pro118, Leu119, Met120, Arg121, Gln122, Tyr123, Gly124, and Phe125. | Leu65, Glu66, Val67, His68, Val74, Ser79, Leu82, Cys116, Ser117, Ala126, and Pro128. |
|  | Fzd8 | Q71, F72, W73, P74, L75, E77, I78, G117, P120, L121, M122, R123, Q124, Y125 G126, and F127. | L67, E68, V69, H70, V76, S81, L84, C118, A119, A128, and P130. |

TABLE 3-continued

Summary of Binding Characteristics of Antigen Binding proteins as determined by co-crystal structures

| Antigen Binding Protein | Antigen | Interaction site on Fzd (<5 angstroms) | Interaction site on Fzd (5-8 angstroms) |
|---|---|---|---|
| 4A12 (Binds only to Fzd5, mono5) | Fzd5 | Cys105, Arg106, Ser107, Glu110, Arg111, Cys133, Asp134, Val138, Leu139, Gly140, Arg141, Asp142, Ala143, Val145, Leu146, Cys147, and Asp149. | Asp81, Tyr98, Leu102, Pro103, Val108, Cys109, Ala112, Ala114, Ser132, Arg135, Leu136, Pro137, Glu144, and Met148. |
| 014S-B06 (Binds only to Fzd9, mono9) | Fzd9 | Leu60, Leu61, Lue95, Thr106, Pro107, Pro109, Arg112, Arg119, Asp135, Ser136, Leu137, Asp138, Ala140, Arg141, Leu142, Pro143, Thr144, Asp147, Pro148, His149, and Ala150. | Asn59, Gly62, Phe91, Ser94, Pro98, Ser105, Ile108, Ala110, Trp133, Pro134, Asp138, Cys139, Arg145, Asn146, Leu151, and Cys152. |
| 005S-A07 (Binds to both Fzd9 and Fzd10) | Fzd10 | Pro40, Met41, Ile66, Gln67, His69, Glu70, Phe71, Ala72, Pro73, Val75, Glu76, Tyr77, Arg84, Met121, Glu122, Gln123, Phe124, Asn125, Phe126, Lys127, Pro129, and Asp130. | Ile39, Cys42, Lys43, Arg62, Glu63, Ala65, Leu68, Leu74, Gly78, Cys88, Tyr91, Ser118, Pro119, Ile120, Trp128, Ser131, and Leu132. |
| | Fzd9 | P45, M46, A71, E72, A74, E75, F76, A77, P78, V80, M126, E127, Q128, F129, N130, F131, G132, P134, and D135. | I44, C47, R48, G67, E68, A70, L73, L79, G83, C93, Y96, A123, P124, I125, W133, S136, and L138. |
| 005S-E12 (Binds only to Fzd10, mono10) | Fzd10 | Ile37, Glu38, Ile39, Pro40, Met41, Cys42, Lys43, Asp44, Ile45, Gly46, Asn48, Gln61, Arg62, Glu63, Ala65, Ile66, Leu68, His69, Ala72, Pro73, Val75, Glu76, and Arg84. | Glu35, Pro36, Tyr47, Asn60, Gln61, Ala64, Gln67, Glu70, Phe71, Leu74, Tyr77, and Phe124. |
| 029S-E03 (Binds only to Fzd3, mono3) | Fzd3 | Pro30, Ile31, Thr32, Leu33, Arg34, Gln37, Asp38, Leu39, Gln55, Gln66, Ala59, Leu60, Glu63, His66, and Asn70. | Gln29, Met35, Cys36, Pro40, Tyr41, Asn42, Thr43, Asp54, Thr57, Ala58, Ala61, Met62, Pro67, Val69, Leu71, Asp72, and Arg78. |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that binds to Frizzled 5 and Frizzled 8, comprising:
   a heavy chain variable region comprising CDRH1, CDRH2 and CDRH3 sequences set forth as SEQ ID NOs: 218, 410, and 861, respectively; and
   a light chain variable region comprising CDRL1, CDRL2 and CDRL3 sequences set forth as SEQ ID NOs: 996, 1071, and 1264, respectively.

2. The isolated antibody, or antigen-binding fragment thereof, of claim 1, comprising a heavy chain variable region comprising an amino acid sequence having at least 90% identity to the amino acid sequence set forth in SEQ ID NO:7 and a light chain variable region comprising an amino acid sequence having at least 90% identity to the amino acid sequence set forth in SEQ ID NO:44.

3. The isolated antibody, or antigen-binding fragment thereof, of claim 1, wherein the antibody, or antigen-binding fragment thereof, is humanized.

4. The isolated antibody, or antigen-binding fragment thereof, of claim 1, wherein the antibody, or antigen-binding fragment thereof, is an IgG antibody, a single chain antibody, a scFv, a univalent antibody lacking a hinge region, a Fab or a Fab' fragment, or a minibody.

5. A pharmaceutical composition comprising a physiologically acceptable excipient, diluent, or carrier, and the isolated antibody, or antigen-binding fragment thereof, according to claim 1.

6. The isolated antibody, or antigen-binding fragment thereof, of claim 1, comprising a heavy chain variable region comprising an amino acid sequence having at least 95% identity to the amino acid sequence set forth in SEQ ID NO:7 and a light chain variable region comprising an amino acid sequence having at least 95% identity to the amino acid sequence set forth in SEQ ID NO:44.

7. The isolated antibody, or antigen-binding fragment thereof, of claim 1, comprising a heavy chain variable region comprising an amino acid sequence having at least 98% identity to the amino acid sequence set forth in SEQ ID NO:7 and a light chain variable region comprising an amino acid sequence having at least 98% identity to the amino acid sequence set forth in SEQ ID NO:44.

8. A pharmaceutical composition comprising a physiologically acceptable excipient, diluent, or carrier, and the isolated antibody, or antigen-binding fragment thereof, according to claim 7.

* * * * *

SEQUENCE LISTING

```
<160> NUMBER OF SEQ ID NOS: 1485

<210> SEQ ID NO 1
<211> LENGTH: 227
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 1

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
```

```
                20                  25                  30
Gly Tyr Ser Trp Ser Trp Ile Arg Gln Pro Gly Lys Gly Leu Glu
            35                  40                  45

Trp Ile Gly Ser Ile Tyr His Ser Gly Ser Thr Tyr Tyr Asn Pro Ser
 50                  55                  60

Leu Lys Ser Arg Leu Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Phe Tyr Tyr Asp Ile Leu Thr Gly Tyr Ser Tyr Phe Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Val Glu Pro
210                 215                 220

Lys Ser Cys
225

<210> SEQ ID NO 2
<211> LENGTH: 223
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 2

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Gly Asn
             20                  25                  30

Asn Tyr Tyr Trp Gly Trp Ile Arg Gln Pro Pro Gly Lys Gly Leu Glu
             35                  40                  45

Trp Ile Gly Ser Ile Tyr Phe Thr Gly Gly Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Met Leu Ile Thr Asp Ala Phe Asp Ile Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220
```

<210> SEQ ID NO 3
<211> LENGTH: 224
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 3

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ala Ile Ser Gly Thr
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Thr Gly Asn Thr Tyr Tyr Asn Pro Ser
    50                  55                  60

Leu Lys Ser Arg Leu Thr Val Ser Val Asp Thr Ser Lys Asn Gln Phe
65                  70                  75                  80

Ser Leu Asn Leu Asn Ser Val Thr Ala Ala Asp Thr Ala Thr Tyr Tyr
            85                  90                  95

Cys Ala Arg Ile Gly Ile Ala Val Ala Ala Pro Val Asp His Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220
```

<210> SEQ ID NO 4
<211> LENGTH: 223
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
            85                  90                  95

Cys Ala Arg Ala Thr Tyr Gly Gly Asp Ala Phe Asp Ile Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
    210                 215                 220

<210> SEQ ID NO 5
<211> LENGTH: 230
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 5

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Arg Asp Tyr Asp Ser Ser Gly Tyr Tyr Asp
            100                 105                 110

Tyr Phe Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
130                 135                 140

-continued

```
Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys
225                 230

<210> SEQ ID NO 6
<211> LENGTH: 227
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Ser Gly Ala Ser Phe Ser Gly His
            20                  25                  30

Tyr Trp Thr Trp Ile Arg Gln Pro Pro Gly Lys Gly Leu Glu Trp Ile
        35                  40                  45

Gly Glu Ile Asp His Thr Gly Ser Thr Asn Tyr Glu Pro Ser Leu Arg
    50                  55                  60

Ser Arg Val Thr Ile Ser Val Asp Thr Ser Lys Asn Gln Phe Ser Leu
65                  70                  75                  80

Asn Leu Lys Ser Val Thr Ala Ala Asp Thr Ala Val Tyr Tyr Cys Ala
                85                  90                  95

Arg Gly Gly Gln Gly Gly Tyr Asp Trp Gly His Tyr His Gly Leu Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 7
<211> LENGTH: 225
<212> TYPE: PRT
```

```
<213> ORGANISM: Artificial Sequence
<220> FEATURE:
<223> OTHER INFORMATION: Made in Lab - Synthesized variable heavy chain
      sequence

<400> SEQUENCE: 7

Glu Val Gln Leu Leu Gln Ser Gly Ala Glu Val Lys Lys Pro Gly Ser
1               5                   10                  15

Ser Val Lys Val Ser Cys Lys Ala Ser Gly Gly Thr Phe Thr Tyr Arg
            20                  25                  30

Tyr Leu His Trp Val Arg Gln Ala Pro Gly Gln Gly Leu Glu Trp Met
        35                  40                  45

Gly Gly Ile Ile Pro Ile Phe Gly Thr Gly Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Met Val Arg Val Pro Tyr Tyr Gly Met Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220
Cys
225

<210> SEQ ID NO 8
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Thr Ala Ser Gly Ser Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Gly Gly Ser Thr Phe Tyr Ser Gly Ser Val
    50                  55                  60

Lys Gly Arg Phe Thr Ile Ser Arg Asp Ser Ala Lys Asn Thr Val His
65                  70                  75                  80

Leu Gln Met Asp Ser Leu Ile Pro Glu Asp Thr Ala Val Tyr Tyr Cys
```

```
                        85                  90                  95

Ala Ala Gly Pro Ile Ala Arg Trp Tyr Arg Gly Asp Met Asp Tyr Trp
            100                 105                 110

Gly Lys Gly Thr Leu Val Thr Val Ser Ser
        115                 120
```

<210> SEQ ID NO 9
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 9

```
Asp Val Gln Leu Val Glu Ser Gly Gly Gly Leu Val Gln Thr Gly Gly
1               5                   10                  15

Ser Leu Arg Leu Ser Cys Val Ala Ser Gly Arg Thr Phe Arg Ala Tyr
            20                  25                  30

Ala Met Gly Trp Phe Arg Gln Ala Pro Gly Lys Glu Arg Glu Phe Val
        35                  40                  45

Ser Ala Ile Ser Trp Ser Gly Gly Ser Thr Tyr Tyr Ala Gly Ser Val
    50                  55                  60

Lys Gly Arg Phe Thr Ile Ser Arg Asp Ser Ala Lys Asn Thr Val His
65                  70                  75                  80

Leu Gln Met Asp Ser Leu Ile Pro Glu Asp Thr Ala Val Tyr Tyr Cys
                85                  90                  95

Ala Ala Gly Pro Ile Ala Arg Trp Tyr Arg Gly Asp Met Asp Tyr Trp
            100                 105                 110

Gly Lys Gly Thr Leu Val Thr Val Ser Ser
        115                 120
```

<210> SEQ ID NO 10
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 10

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Glu Tyr
            20                  25                  30

Ala Met Thr Trp Val Arg Gln Ser Pro Gly Lys Arg Leu Glu Trp Val
        35                  40                  45

Ser Gly Ile Ser Arg Asp Gly Arg Thr Ser Tyr Ser Asp Ser Leu
    50                  55                  60

Lys Gly Arg Phe Thr Ile Ser Arg Asp Asn Ala Lys Asn Thr Leu Tyr
65                  70                  75                  80

Leu Gln Met Asn Asn Leu Thr Pro Glu Asp Thr Ala Val Tyr Tyr Cys
                85                  90                  95

Ala Pro Arg Val Leu Val Thr Ala Pro Ser Gly Gly Met Asp Tyr Trp
            100                 105                 110

Gly Lys Gly Thr Gln Val Thr Val Ser Ser
        115                 120
```

```
<210> SEQ ID NO 11
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 11

Ala Val Gln Leu Val Asp Ser Gly Gly Gly Leu Met Gln Ala Gly Gly
1               5                   10                  15

Ser Leu Arg Leu Ser Cys Ala Ala Ser Gly Arg Thr Phe Gly Thr Trp
            20                  25                  30

Ala Met Gly Trp Phe Arg Gln Ala Pro Gly Lys Glu Arg Glu Phe Val
        35                  40                  45

Ala Ala Ile Ser Tyr Asn Gly Phe Ser Thr Tyr Tyr Ser Asp Ala Val
    50                  55                  60

Lys Gly Arg Phe Thr Ile Ser Arg Asp Asn Ala Lys Asn Thr Met Tyr
65                  70                  75                  80

Leu Gln Met Asp Ser Leu Ile Pro Glu Asp Thr Ala Val Tyr Tyr Cys
                85                  90                  95

Ala Ala Gly Pro Ile Ala Arg Trp Tyr Arg Gly Asp Met Asp Tyr Trp
            100                 105                 110

Gly Lys Gly Thr Gln Val Thr Val Ser Ser
        115                 120

<210> SEQ ID NO 12
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 12

Ala Val Gln Leu Val Glu Ser Gly Gly Gly Leu Val Gln Ala Gly Gly
1               5                   10                  15

Pro Leu Arg Leu Ser Cys Ala Ala Ser Gly Arg Thr Ser Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Pro Ile Pro Glu Asp Thr Ala Val Tyr Tyr Cys
                85                  90                  95

Ala Ala Gly Pro Ile Ala Arg Trp Tyr Arg Gly Asp Met Asp Tyr Trp
            100                 105                 110

Gly Lys Gly Thr Leu Val Thr Val Ser Ser
        115                 120

<210> SEQ ID NO 13
<211> LENGTH: 122
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 13
```

Ala Val Gln Leu Val Glu Ser Gly Gly Gly Leu Val Gln Ala Gly
1               5                   10                  15

Ser Leu Arg Leu Ser Cys Thr Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Gly Arg Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Ala Tyr Tyr Cys
                85                  90                  95

Ala Ala Gly Pro Ile Ala Arg Trp Tyr Arg Gly Asp Met Asp Tyr Trp
            100                 105                 110

Gly Lys Gly Thr Leu Val Thr Val Ser Ser
            115                 120

<210> SEQ ID NO 14
<211> LENGTH: 124
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 14

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Pro Asn Tyr Ser Trp Phe Met Pro Ser Ser Ser Arg Leu
            100                 105                 110

Ile Trp Gly Gln Gly Thr Leu Val Thr Val Ser Ser
            115                 120

<210> SEQ ID NO 15
<211> LENGTH: 124
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 15

Gln Val Lys Leu Glu Glu Ser Gly Gly Gly Leu Val Gln Ala Gly Gly
1               5                   10                  15

Ser Leu Arg Leu Ser Cys Ala Ala Ser Gly Gly Thr Ser Ser Thr Tyr
            20                  25                  30

Ala Met Gly Trp Phe Arg Gln Ala Pro Gly Lys Glu Arg Glu Phe Val
            35                  40                  45

```
Ala Ala Ile Asn Arg Ser Gly Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Asn Pro Glu Asp Thr Ala Val Tyr Tyr Cys
                85                  90                  95

Ala Ala Val Phe Leu Ser Arg Asn Tyr Glu Ile Gln Glu Tyr Tyr Arg
            100                 105                 110

Tyr Gln Gly Gln Gly Thr Gln Val Thr Val Ser Ser
            115                 120
```

<210> SEQ ID NO 16
<211> LENGTH: 224
<212> TYPE: PRT
<213> ORGANISM: Artificial Sequence
<220> FEATURE:
<223> OTHER INFORMATION: Made in Lab - Synthesized variable heavy chain sequence

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Thr Tyr Asn Gly Ala Thr Asn Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Gly Arg Phe Gly Glu Gly Met Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 17
<211> LENGTH: 225
<212> TYPE: PRT
<213> ORGANISM: Artificial Sequence
<220> FEATURE:
<223> OTHER INFORMATION: Made in Lab - Synthesized variable heavy chain sequence

<400> SEQUENCE: 17

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Ser Lys Glu Lys Ala Thr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
210                 215                 220

Cys
225

<210> SEQ ID NO 18
<211> LENGTH: 232
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Asn
            20                  25                  30

Phe Met His Trp Val Arg Gln Ala Pro Gly Gln Gly Leu Glu Trp Met
            35                  40                  45

Gly Trp Ile Asn Pro Asn Ser Gly Gly Thr Lys Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Glu Val Gly Ala Thr Met Leu Gly Ile Gly Val
            100                 105                 110

Trp Tyr Trp Phe Asp Pro Trp Gly Gln Gly Thr Leu Val Thr Val Ser
```

```
                115                 120                 125
Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Gln
                195                 200                 205

Thr Tyr Ile Cys Asn Val Asn His Lys Pro Ser Asn Thr Lys Val Asp
210                 215                 220

Lys Lys Val Glu Pro Lys Ser Cys
225                 230

<210> SEQ ID NO 19
<211> LENGTH: 221
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Phe Gly Ile Tyr
                20                  25                  30

Ser Met Thr Trp Val Arg Gln Ala Pro Gly Lys Gly Leu Glu Trp Ile
                35                  40                  45

Ser Tyr Ile Ser Gly Asp Ser Gly Tyr Thr Asn Tyr Ala Asp Ser Val
                50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Val Gly Pro Gly Gly Trp Phe Asp Pro Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys
                210                 215                 220

<210> SEQ ID NO 20
<211> LENGTH: 226
```

```
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
                20                  25                  30

Phe Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Gln Asn Tyr Tyr Gly Ser Gly Ser Tyr Pro Gly Phe Asp Tyr
                100                 105                 110

Trp Gly Gln Gly Thr Leu Val Asn Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225

<210> SEQ ID NO 21
<211> LENGTH: 223
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Thr His Asp Ser Ser Gly Tyr Tyr Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220
```

<210> SEQ ID NO 22
<211> LENGTH: 221
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Phe Met His Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Arg Gly Tyr Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

```
<210> SEQ ID NO 23
<211> LENGTH: 218
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ser Trp Val Arg Gln Ala Pro Gly Lys Gly Leu Glu Trp Val
        35                  40                  45

Ala Leu Val Gly Tyr Asp Gly Ser Gln Gln Phe Tyr Gly Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Asn Thr Gly Ile Pro Met Leu Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
    210                 215

<210> SEQ ID NO 24
<211> LENGTH: 223
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Glu Ser Val Asn Asn Tyr Tyr Tyr Met Asp Val Trp Gly Lys
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
            210                 215                 220

<210> SEQ ID NO 25
<211> LENGTH: 228
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Phe Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Tyr Ser Ser Gly Trp Tyr Arg Gly Asp Ala Phe
            100                 105                 110

Asp Ile Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu

Pro Lys Ser Cys
225

<210> SEQ ID NO 26
<211> LENGTH: 227
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Gln Gln Trp Leu Thr Gly Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 27
<211> LENGTH: 225
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser His
            20                  25                  30

Trp Met His Trp Val Arg Gln Ala Pro Gly Lys Gly Leu Glu Trp Val

```
                35                  40                  45
Ser Ala Ile Asp Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gln Leu Gly Trp Ala His Trp Tyr Phe Asp Leu Trp
                100                 105                 110

Gly Arg Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys
225

<210> SEQ ID NO 28
<211> LENGTH: 227
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 28

Glu Val Gln Leu Val Gln Ser Gly Gly Gly Leu Val Gln Pro Gly Gly
  1               5                  10                  15

Ser Leu Arg Leu Ser Cys Ala Ala Ser Gly Phe Asn Leu Arg Arg Tyr
                 20                  25                  30

Asn Met Asn Trp Val Arg Gln Ala Pro Gly Lys Gly Leu Glu Trp Val
                 35                  40                  45

Ser Arg Ile Ser Asn Ser Gly Ser Leu Val Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Asp Ser Ser Gly Tyr Tyr Arg Tyr Asp Ala Phe Asp
                100                 105                 110

Ile Trp Gly Gln Gly Thr Met Val Thr Val Ser Ser Ala Ser Thr Lys
                115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
145                 150                 155                 160
```

```
Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
        210                 215                 220

Lys Ser Cys
225

<210> SEQ ID NO 29
<211> LENGTH: 221
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Thr Ser
            20                  25                  30

Ser Ile Ser Trp Val Arg Gln Ala Pro Gly Gln Gly Leu Glu Trp Val
        35                  40                  45

Gly Arg Ile Ile Pro Val Leu Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Trp Arg Ser Ser Phe Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 30
<211> LENGTH: 223
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 30
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Ala Gly Asp Trp Gly Leu Tyr Gly Met Asp Val Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys
    210                 215                 220

<210> SEQ ID NO 31
<211> LENGTH: 230
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Phe Met His Trp Val Arg Gln Ala Pro Gly Gln Gly Leu Glu Trp Met
        35                  40                  45

Gly Trp Ile Asn Pro Asn Ser Gly Asp Thr Lys Phe Ala Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Asn Tyr Asp Ile Leu Thr Gly Tyr Ile Arg Pro Asp
                100                 105                 110

Ala Phe Asp Ile Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
            130                 135                 140
```

```
Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
210                 215                 220

Val Glu Pro Lys Ser Cys
225             230
```

<210> SEQ ID NO 32
<211> LENGTH: 224
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Asn Trp Val Arg Gln Ala Pro Gly Gln Gly Leu Glu Trp Met
        35                  40                  45

Gly Ile Ile Ser Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Asp Tyr Gly Asp Leu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220
```

<210> SEQ ID NO 33
<211> LENGTH: 228
<212> TYPE: PRT
<213> ORGANISM: Artificial Sequence
<220> FEATURE:
<223> OTHER INFORMATION: Made in Lab - Synthesized variable heavy chain -continued sequence

<400> SEQUENCE: 33

Gln Val Gln Leu Val Gln Ser Gly Ala Glu Val Lys Pro Gly Ala
1               5                   10                  15

Ser Val Lys Val Ser Cys Lys Ala Ser Gly Tyr Ile Phe Thr Asp Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Arg Tyr Asp Phe Trp Ser Gly His Trp Tyr Phe
            100                 105                 110

Asp Leu Trp Gly Arg Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 34
<211> LENGTH: 227
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 34

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Glu Asn Asp Gly Ser Ile Thr Thr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Ala Pro Tyr Tyr Tyr Gly Ser Gly Ser Leu Phe Arg Leu Asp

```
              100                 105                 110
Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 35
<211> LENGTH: 219
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Ala Gly Gly Thr Tyr Tyr Ala Asp Ser Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Asp Ala Tyr Asn Trp Phe Asp Pro Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215
```

```
<210> SEQ ID NO 36
<211> LENGTH: 222
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Gln Met Ser Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Glu Gly Ser Tyr Tyr Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 37
<211> LENGTH: 116
<212> TYPE: PRT
<213> ORGANISM: Artificial Sequence
<220> FEATURE:
<223> OTHER INFORMATION: Made in Lab - Synthesized variable heavy chain
      sequence

<400> SEQUENCE: 37

Ala Val Gln Gln Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Ser Trp Phe Arg Gln Ala Pro Gly Lys Lys Arg Glu Leu Val
        35                  40                  45

Ala Asp Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Ile Tyr Leu
65                  70                  75                  80
```

```
Gln Met Asn Ser Leu Lys Pro Glu Asp Thr Ala Val Tyr Phe Cys Asn
            85                  90                  95

Ala Val Thr Tyr Asn Gly Tyr Thr Ile Trp Gly Gln Gly Thr Gln Val
            100                 105                 110

Thr Val Ser Ser
        115
```

<210> SEQ ID NO 38
<211> LENGTH: 220
<212> TYPE: PRT
<213> ORGANISM: Artificial Sequence
<220> FEATURE:
<223> OTHER INFORMATION: Made in Lab - Synthesized variable light chain sequence

<400> SEQUENCE: 38

```
Asp Ile Val Met Thr His Thr Pro Leu Ser Leu Ser Val Thr Pro Gly
1               5                   10                  15

Glu Pro Ala Ser Ile Ser Cys Arg Ser Ser Arg Ser Leu Leu Asp Thr
            20                  25                  30

Asp Asp Gly Asn Thr Tyr Leu Asp Trp Tyr Leu Gln Lys Pro Gly Gln
        35                  40                  45

Ser Pro Gln Leu Leu Ile His Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ser Ile Gln Leu Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 39
<211> LENGTH: 219
<212> TYPE: PRT
<213> ORGANISM: Artificial Sequence
<220> FEATURE:
<223> OTHER INFORMATION: Made in Lab - Synthesized variable light chain sequence

<400> SEQUENCE: 39

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 40
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 40

Glu Ile Val Leu Thr Gln Ser Pro Ala Thr Leu Ser Leu Ser Pro Gly
1                5                  10                  15

Glu Gly Ala Thr Leu Ser Cys Arg Ala Ser Gln Ser Val Gly Thr Tyr
            20                  25                  30

Leu Thr Trp Tyr Arg Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ala Gly Thr Asp Phe Thr Leu Lys Ile Ser Arg Val Glu Ala
65                  70                  75                  80

Glu Asp Val Gly Val Tyr Tyr Cys Met Gln Ala Thr Gln Phe Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 217
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 41

```
Gln Ser Val Val Thr Gln Pro Pro Ser Val Ser Gly Ala Pro Gly Gln
1               5                   10                  15

Arg Val Thr Ile Ser Cys Thr Arg Ser Ser Ser Asn Ile Gly Ala Gly
            20                  25                  30

Tyr Asp Val His Trp Tyr Gln Gln His Pro Gly Thr Ala Pro Lys Leu
        35                  40                  45

Leu Ile Phe Gly Asn Ser Ile Arg Pro Ser Gly Val Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Gly Thr Trp Asp Ser Ser
                85                  90                  95

Leu Ser Ala Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 42
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 42

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Ser Ile Ser Ser Tyr
            20                  25                  30
```

```
Phe Asn Trp Tyr Gln Gln Lys Pro Gly Lys Ala Pro Lys Leu Leu Ile
                 35                  40                  45

Tyr Ala Ala Ser Ser Leu Gln Ser Gly Val Pro Ser Arg Phe Ser Gly
             50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asp Thr Phe Pro Pro
                         85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 43
<211> LENGTH: 213
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 43

Ser Tyr Val Leu Thr Gln Pro Pro Ser Val Ser Val Ser Pro Gly Gln
 1               5                  10                  15

Thr Ala Ser Ile Thr Cys Ser Gly Asp Lys Val Gly His Lys Tyr Ala
                 20                  25                  30

Ser Trp Tyr Gln Gln Lys Pro Gly Gln Ser Pro Val Leu Val Ile Tyr
                 35                  40                  45

Glu Asp Ser Gln Arg Pro Ser Gly Ile Pro Val Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Asp Val
                 85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
```

165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 44
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
            20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 46
<211> LENGTH: 216
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 46

Gln Ala Val Val Leu Gln Glu Pro Ser Leu Ser Val Ser Pro Gly Gly
 1               5                  10                  15

Thr Val Thr Leu Thr Cys Gly Leu Ser Ser Gly Ser Val Ser Thr Asn
            20                  25                  30

Tyr Tyr Pro Ser Trp Tyr Gln Gln Thr Pro Gly Gln Ala Pro Arg Thr
            35                  40                  45

Leu Ile Tyr Tyr Thr Asn Thr Arg Ser Ser Asp Val Pro Glu Arg Phe
            50                  55                  60

Ser Gly Ser Ile Val Gly Asn Lys Ala Ala Leu Thr Ile Thr Gly Ala
 65                  70                  75                  80

Gln Pro Asp Asp Glu Ser Val Tyr Phe Cys Leu Leu Tyr Leu Gly Arg
            85                  90                  95

Gly Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160
```

```
Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 47
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 48

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Leu Gly Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 50
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 51
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 51

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 52
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175
Ser Thr Leu Thr Leu Ser Lys Ala Asp Tyr Glu Lys His Lys Val Tyr
                    180                 185                 190
Ala Cys Glu Val Thr His Gln Gly Leu Ser Ser Pro Val Thr Lys Ser
                    195                 200                 205
Phe Asn Arg Gly Glu Cys
            210

<210> SEQ ID NO 53
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 53

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 54
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 54

Asp Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Ser Ile Ser Ser Tyr
                20                  25                 30

Leu Asn Trp Tyr Gln Gln Lys Pro Gly Lys Ala Pro Lys Leu Leu Ile
                35                  40                 45

Tyr Ala Ala Ser Ser Leu Gln Ser Gly Val Pro Ser Arg Phe Ser Gly
                50                  55                 60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                 95

Thr Phe Gly Gly Gly Thr Lys Val Glu Ile Lys Arg Thr Val Ala Ala
                100                 105                110

Pro Ser Val Phe Ile Phe Pro Pro Ser Asp Glu Gln Leu Lys Ser Gly
                115                 120                125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
                180                 185                190

Ala Cys Glu Val Thr His Gln Gly Leu Ser Ser Pro Val Thr Lys Ser
                195                 200                205

Phe Asn Arg Gly Glu Cys
                210
```

<210> SEQ ID NO 55
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 55

```
Asp Ile Gln Met Thr Gln Ser Pro Ser Ser Leu Ser Ala Ser Val Gly
1               5                   10                 15

Asp Arg Val Thr Ile Thr Cys Arg Ala Ser Gln Gly Ile Ser Ser Ala
                20                  25                 30

Leu Ala Trp Tyr Gln Gln Lys Pro Gly Lys Ala Pro Lys Leu Leu Ile
                35                  40                 45

Tyr Gly Ala Ser Thr Leu Gln Ser Gly Val Pro Ser Arg Phe Ser Gly
                50                  55                 60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                 95

Thr Phe Gly Pro Gly Thr Lys Val Asp Ile Lys Arg Thr Val Ala Ala
                100                 105                110

Pro Ser Val Phe Ile Phe Pro Pro Ser Asp Glu Gln Leu Lys Ser Gly
                115                 120                125

Thr Ala Ser Val Val Cys Leu Leu Asn Asn Phe Tyr Pro Arg Glu Ala
130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 57
```

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Arg Asn Asn Trp Leu Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 58

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ser Trp Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Thr Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 60

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Leu Arg Ser Lys
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Asn Ser Pro Trp
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 61
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Ala Thr Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn Ser Tyr Pro Pro
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 62
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 63
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 64
<211> LENGTH: 214
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 65
<211> LENGTH: 216
<212> TYPE: PRT
<213> ORGANISM: Artificial Sequence
<220> FEATURE:
<223> OTHER INFORMATION: Made in Lab - Synthesized variable light chain
      sequence

<400> SEQUENCE: 65

Glu Ile Val Leu Thr Gln Ser Pro Ala Thr Leu Ser Val Ser Pro Gly
1               5                   10                  15
Glu Arg Ala Thr Leu Ser Cys Arg Ala Ser Gln Asn Ile Gly Ser Arg
            20                  25                  30
Leu Ala Trp Tyr Gln Gln Lys Pro Gly Gln Ala Pro Arg Leu Leu Ile
        35                  40                  45
Tyr Gly Ala Ser Asn Arg Ala Ser Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn His Trp Pro Pro
                85                  90                  95
Leu Phe Thr Phe Gly Pro Gly Thr Lys Val Asp Ile Lys Arg Thr Val
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
    130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
        195                 200                 205
Lys Ser Phe Asn Arg Gly Glu Cys
    210                 215

<210> SEQ ID NO 66
<211> LENGTH: 120
<212> TYPE: PRT
<213> ORGANISM: Artificial Sequence
<220> FEATURE:
<223> OTHER INFORMATION: Made in Lab - 004S-D01 Heavy Chain
```

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Ala Thr Gly Phe Gly Thr Val Val Phe Asp Tyr Trp Gly Gln
            100                 105                 110

Gly Thr Leu Val Thr Val Ser Ser
        115                 120

<210> SEQ ID NO 67
<211> LENGTH: 107
<212> TYPE: PRT
<213> ORGANISM: Artificial Sequence
<220> FEATURE:
<223> OTHER INFORMATION: Made in Lab - 004S-D01 Light Chain

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 68
<211> LENGTH: 119
<212> TYPE: PRT
<213> ORGANISM: Artificial Sequence
<220> FEATURE:
<223> OTHER INFORMATION: Made in Lab - 004S-E09 Heavy Chain

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Ser Asn Tyr
            20                  25                  30

Val Ile Ser Trp Val Arg Gln Ala Pro Gly Gln Gly Leu Glu Trp Met
        35                  40                  45

Gly Arg Ile Ser Ala Tyr Asn Gly Tyr Lys Ser Tyr Ala Gln Asn Phe
    50                  55                  60

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Ser Gly Tyr Val Gly Trp Phe Asp Pro Trp Gly Gln Gly
            100                 105                 110

Thr Leu Val Thr Val Ser Ser
            115
```

```
<210> SEQ ID NO 69
<211> LENGTH: 107
<212> TYPE: PRT
<213> ORGANISM: Artificial Sequence
<220> FEATURE:
<223> OTHER INFORMATION: Made in Lab - 004S-E09 Light Chain

<400> SEQUENCE: 69
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105
```

```
<210> SEQ ID NO 70
<211> LENGTH: 90
<212> TYPE: PRT
<213> ORGANISM: Homo sapiens

<400> SEQUENCE: 70
```

```
Lys Met Tyr His Thr Lys Gly Gln Glu Gly Ser Val Cys Leu Arg Ser
 1               5                  10                  15

Ser Asp Cys Ala Ser Gly Leu Cys Cys Ala Arg His Phe Trp Ser Lys
             20                  25                  30

Ile Cys Lys Pro Val Leu Lys Glu Gly Gln Val Cys Thr Lys His Arg
         35                  40                  45

Arg Lys Gly Ser His Gly Leu Glu Ile Phe Gln Arg Cys Tyr Cys Gly
 50                  55                  60

Glu Gly Leu Ser Cys Arg Ile Gln Lys Asp His His Gln Ala Ser Asn
 65                  70                  75                  80

Ser Ser Arg Leu His Thr Cys Gln Arg His
                 85                  90
```

```
<210> SEQ ID NO 71
<211> LENGTH: 88
<212> TYPE: PRT
<213> ORGANISM: Homo sapiens

<400> SEQUENCE: 71
```

```
Lys Met Ser His Ile Lys Gly His Glu Gly Asp Pro Cys Leu Arg Ser
 1               5                  10                  15
```

```
Ser Asp Cys Ile Glu Gly Phe Cys Cys Ala Arg His Phe Trp Thr Lys
            20                  25                  30
Ile Cys Lys Pro Val Leu His Gln Gly Glu Val Cys Thr Lys Gln Arg
            35                  40                  45
Lys Lys Gly Ser His Gly Leu Glu Ile Phe Gln Arg Cys Asp Cys Ala
50              55                  60
Lys Gly Leu Ser Cys Lys Val Trp Asp Ala Thr Tyr Ser Ser Lys
65              70                  75                  80
Ala Arg Leu His Val Cys Gln Lys
                85

<210> SEQ ID NO 72
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 72

Ala Ser Phe Ser Gly His Tyr Trp Thr
1               5

<210> SEQ ID NO 73
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 73

Ala Ser Val Ser Ser Asn Ser Ala Ala Trp Asn
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 74

Asp Ser Val Ser Ser Asn Ser Ala Ala Trp Asn
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 75

Asp Ser Val Ser Ser Asn Ser Ala Thr Trp Asn
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthesized molecular recognition unit - heavy
```

```
                      CDR1

<400> SEQUENCE: 76

Asp Ser Val Ser Ser Asn Ser Gly Ala Trp Asn
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 77

Asp Thr Phe Ser Asn Tyr Val Ile Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 78

Asp Thr Phe Ser Asn Tyr Val Leu Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 79

Phe Ala Phe Asp Asp Tyr Ala Met His
1               5

<210> SEQ ID NO 80
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 80

Phe Ala Phe Ser Ser His Trp Met His
1               5

<210> SEQ ID NO 81
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 81

Phe Ala Phe Ser Ser Tyr Ala Met Ser
1               5

<210> SEQ ID NO 82
```

```
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 82

Phe Ala Val Ser Ser Ser Tyr Met Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 83

Phe Phe Phe Ser Gly Tyr Trp Met Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 84

Phe Ile Phe Ser Asp Tyr Tyr Met Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 85

Phe Ile Phe Ser Glx Tyr Ala Met Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 86

Phe Asn Phe Gly Ile Tyr Ser Met Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 87
```

```
Phe Asn Phe Ser Ser Tyr Thr Met Arg
1               5

<210> SEQ ID NO 88
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 88

Phe Asn Ile Arg Arg Glx Asn Met Glx
1               5

<210> SEQ ID NO 89
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 89

Phe Asn Leu Arg Arg Tyr Asn Met Asn
1               5

<210> SEQ ID NO 90
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 90

Phe Pro Phe Ser Thr Phe Ser Met Asn
1               5

<210> SEQ ID NO 91
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 91

Phe Arg Phe Ile Ser His Pro Ile His
1               5

<210> SEQ ID NO 92
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 92

Phe Ser Phe Arg Ser Tyr Ser Met Ser
1               5

<210> SEQ ID NO 93
<211> LENGTH: 9
<212> TYPE: PRT
<213> ORGANISM: Artificial Sequence
<220> FEATURE:
```

```
<223> OTHER INFORMATION: Synthesized molecular recognition unit - heavy
     CDR1

<400> SEQUENCE: 93

Phe Ser Phe Ser Lys Lys Tyr Met Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 94

Phe Ser Phe Ser Arg Tyr Gly Met Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 95

Phe Ser Phe Ser Ser Thr Ala Met Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 96

Phe Ser Phe Ser Ser Tyr Gly Met His
1               5

<210> SEQ ID NO 97
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 97

Phe Ser Phe Ser Ser Tyr Gly Met Ser
1               5

<210> SEQ ID NO 98
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 98

Phe Ser Phe Ser Thr Tyr Thr Met Ser
1               5
```

```
<210> SEQ ID NO 99
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 99

Phe Ser Leu Ser Ser Tyr Gly Met His
1               5

<210> SEQ ID NO 100
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 100

Phe Ser Val Gly Ser Asn Tyr Met Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 101

Phe Ser Val Ser Ser Asn Tyr Met Asn
1               5

<210> SEQ ID NO 102
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 102

Phe Thr Phe Ala Asp Tyr Gly Met His
1               5

<210> SEQ ID NO 103
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 103

Phe Thr Phe Ala Asn Tyr Ala Met His
1               5

<210> SEQ ID NO 104
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 104
```

```
Phe Thr Phe Ala Asn Tyr Ala Met Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 105

Phe Thr Phe Asp Asp Tyr Ala Met His
1               5

<210> SEQ ID NO 106
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 106

Phe Thr Phe Asp Asp Tyr Gly Met His
1               5

<210> SEQ ID NO 107
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 107

Phe Thr Phe Asp Asp Tyr Tyr Met Asn
1               5

<210> SEQ ID NO 108
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 108

Phe Thr Phe Asp His Asn Pro Met Asn
1               5

<210> SEQ ID NO 109
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 109

Phe Thr Phe Gly Asn Tyr Asp Met Asn
1               5

<210> SEQ ID NO 110
<211> LENGTH: 9
<212> TYPE: PRT
<213> ORGANISM: Artificial Sequence
```

```
<220> FEATURE:
<223> OTHER INFORMATION: Synthesized molecular recognition unit - heavy
      CDR1

<400> SEQUENCE: 110

Phe Thr Phe Gly Thr Tyr Trp Val Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 111

Phe Thr Phe Asn Arg His Ala Leu Ser
1               5

<210> SEQ ID NO 112
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 112

Phe Thr Phe Arg Asp Tyr Ala Met Asn
1               5

<210> SEQ ID NO 113
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 113

Phe Thr Phe Arg Glu Tyr Ala Met Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 114

Phe Thr Phe Arg Met Tyr Gly Met His
1               5

<210> SEQ ID NO 115
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 115

Phe Thr Phe Arg Asn Ser Ala Met His
1               5
```

```
<210> SEQ ID NO 116
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 116

Phe Thr Phe Arg Ser Tyr Gly Met His
1               5

<210> SEQ ID NO 117
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 117

Phe Thr Phe Ser Asp Phe Gly Met Asn
1               5

<210> SEQ ID NO 118
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 118

Phe Thr Phe Ser Asp His Tyr Met Asp
1               5

<210> SEQ ID NO 119
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 119

Phe Thr Phe Ser Asp His Tyr Met Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 120

Phe Thr Phe Ser Asp Ser Tyr Met Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

```
<400> SEQUENCE: 121

Phe Thr Phe Ser Asp Tyr Gly Met His
1               5

<210> SEQ ID NO 122
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 122

Phe Thr Phe Ser Asp Tyr Tyr Met Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 123

Phe Thr Phe Ser Ile Tyr Gly Met His
1               5

<210> SEQ ID NO 124
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 124

Phe Thr Phe Ser Asn Ala Gln Met Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 125

Phe Thr Phe Ser Asn Ala Trp Met Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 126

Phe Thr Phe Ser Asn His Tyr Met Ser
1               5

<210> SEQ ID NO 127
<211> LENGTH: 9
<212> TYPE: PRT
```

<213> ORGANISM: Artificial Sequence
<220> FEATURE:
<223> OTHER INFORMATION: Synthesized molecular recognition unit - heavy
      CDR1

<400> SEQUENCE: 127

Phe Thr Phe Ser Asn His Tyr Thr Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 128

Phe Thr Phe Ser Asn Ser Asp Met Asn
1               5

<210> SEQ ID NO 129
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 129

Phe Thr Phe Ser Asn Tyr Ala Met His
1               5

<210> SEQ ID NO 130
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 130

Phe Thr Phe Ser Asn Tyr Ala Met Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 131

Phe Thr Phe Ser Asn Tyr Gly Met His
1               5

<210> SEQ ID NO 132
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 132

Phe Thr Phe Ser Asn Tyr Tyr Thr Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 133

Phe Thr Phe Ser Arg Tyr Ala Met His
1               5

<210> SEQ ID NO 134
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 134

Phe Thr Phe Ser Arg Tyr Ala Met Ser
1               5

<210> SEQ ID NO 135
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 135

Phe Thr Phe Ser Ser Phe Gly Met His
1               5

<210> SEQ ID NO 136
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 136

Phe Thr Phe Ser Ser His Ser Thr His
1               5

<210> SEQ ID NO 137
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 137

Phe Thr Phe Ser Ser Asn Ala Met His
1               5

<210> SEQ ID NO 138
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 138

Phe Thr Phe Ser Ser Ser Ala Met His
1               5

<210> SEQ ID NO 139
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 139

Phe Thr Phe Ser Ser Ser Asn Met Asn
1               5

<210> SEQ ID NO 140
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 140

Phe Thr Phe Ser Ser Ser Trp Met His
1               5

<210> SEQ ID NO 141
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 141

Phe Thr Phe Ser Ser Tyr Ala Met Ser
1               5

<210> SEQ ID NO 142
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 142

Phe Thr Phe Ser Ser Tyr Asp Met Asn
1               5

<210> SEQ ID NO 143
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 143

Phe Thr Phe Ser Ser Tyr Gly Met His
1               5

<210> SEQ ID NO 144
<211> LENGTH: 9

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 144

Phe Thr Phe Ser Ser Tyr Gly Met Ser
1               5

<210> SEQ ID NO 145
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 145

Phe Thr Phe Ser Ser Tyr Asn Met Asn
1               5

<210> SEQ ID NO 146
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 146

Phe Thr Phe Ser Ser Tyr Ser Met Asn
1               5

<210> SEQ ID NO 147
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 147

Phe Thr Phe Ser Ser Tyr Ser Met Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 148

Phe Thr Phe Ser Ser Tyr Thr Met Asn
1               5

<210> SEQ ID NO 149
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 149

Phe Thr Phe Ser Ser Tyr Thr Met Ser
```

```
1               5

<210> SEQ ID NO 150
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 150

Phe Thr Phe Ser Ser Tyr Val Met Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 151

Phe Thr Phe Ser Ser Tyr Trp Ile His
1               5

<210> SEQ ID NO 152
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 152

Phe Thr Phe Ser Ser Tyr Trp Met His
1               5

<210> SEQ ID NO 153
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 153

Phe Thr Phe Ser Ser Glx Glx Met His
1               5

<210> SEQ ID NO 154
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
<220> FEATURE:
<221> NAME/KEY: misc_feature
<222> LOCATION: (6)..(6)
<223> OTHER INFORMATION: Xaa can be any naturally occurring amino acid

<400> SEQUENCE: 154

Phe Thr Phe Ser Thr Xaa Trp Met Ser
1               5

<210> SEQ ID NO 155
<211> LENGTH: 9
```

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 155

Phe Thr Phe Ser Thr Tyr Ala Met His
1               5

<210> SEQ ID NO 156
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 156

Phe Thr Phe Ser Thr Tyr Glu Met Asn
1               5

<210> SEQ ID NO 157
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 157

Phe Thr Phe Ser Thr Tyr Gly Met His
1               5

<210> SEQ ID NO 158
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 158

Phe Thr Phe Ser Thr Tyr Ser Met Ile
1               5

<210> SEQ ID NO 159
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 159

Phe Thr Phe Ser Thr Tyr Ser Met Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 160

Phe Thr Phe Thr Gly Ser Ala Val Gln
```

<210> SEQ ID NO 161
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 161

Phe Thr Phe Thr Asn Tyr Ala Met Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 162

Phe Thr Phe Thr Ser Ser Ala Met Gln
1               5

<210> SEQ ID NO 163
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 163

Phe Thr Phe Thr Ser Ser Ala Thr Gln
1               5

<210> SEQ ID NO 164
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 164

Phe Thr Phe Thr Ser Ser Ala Val Gln
1               5

<210> SEQ ID NO 165
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 165

Phe Thr Phe Thr Ser Tyr Ala Met His
1               5

<210> SEQ ID NO 166
<211> LENGTH: 9
<212> TYPE: PRT
<213> ORGANISM: Artificial Sequence
<220> FEATURE:
<223> OTHER INFORMATION: Synthesized molecular recognition unit - heavy

CDR1

<400> SEQUENCE: 166

Phe Thr Phe Thr Glx Ser Ala Val Gln
1               5

<210> SEQ ID NO 167
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 167

Phe Thr Phe Glx Glx Ser Glx Val Gln
1               5

<210> SEQ ID NO 168
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 168

Phe Thr Leu Asp Tyr Tyr Ala Ile Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 169

Phe Thr Leu Ser Ser His His Met Asn
1               5

<210> SEQ ID NO 170
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 170

Phe Thr Leu Ser Thr Tyr Asn Met Asn
1               5

<210> SEQ ID NO 171
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 171

Phe Thr Val Gly Asn Asn Tyr Met Ser
1               5

<210> SEQ ID NO 172

```
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 172

Phe Thr Val Gly Ser Trp Tyr Met Ser
1               5

<210> SEQ ID NO 173
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 173

Phe Thr Val Ser Ser His Ser Met Gly
1               5

<210> SEQ ID NO 174
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 174

Phe Thr Val Ser Ser Asn Tyr Met Asn
1               5

<210> SEQ ID NO 175
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 175

Phe Thr Val Ser Ser Asn Tyr Met Ser
1               5

<210> SEQ ID NO 176
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 176

Phe Thr Glx Ser Ser Tyr Asp Met His
1               5

<210> SEQ ID NO 177
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 177
```

```
Phe Thr Glx Ser Ser Tyr Ser Met Asn
1               5
```

<210> SEQ ID NO 178
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 178

```
Gly Ala Phe Ser Thr Ser Ser Ile Ser
1               5
```

<210> SEQ ID NO 179
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 179

```
Gly Ala Ile Ser Gly Thr Ser Tyr Phe Trp Gly
1               5                   10
```

<210> SEQ ID NO 180
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 180

```
Gly Asp Phe Thr Asn Tyr Ala Met Ala
1               5
```

<210> SEQ ID NO 181
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 181

```
Gly Phe Phe Ser Ser Phe Thr Met Gly
1               5
```

<210> SEQ ID NO 182
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 182

```
Gly Phe Thr Phe Ser Asp His Tyr
1               5
```

<210> SEQ ID NO 183
<211> LENGTH: 9
<212> TYPE: PRT
<213> ORGANISM: Artificial Sequence
<220> FEATURE:

<223> OTHER INFORMATION: Synthesized molecular recognition unit - heavy
      CDR1

<400> SEQUENCE: 183

Gly Asn Phe Lys Asn Tyr Gly Ile Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 184

Gly Pro Phe Asn Leu Phe Ala Met Gly
1               5

<210> SEQ ID NO 185
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 185

Gly Pro Phe Asn Leu Leu Ala Met Gly
1               5

<210> SEQ ID NO 186
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 186

Gly Ser Phe Ser Gly Tyr Ala Ile Asn
1               5

<210> SEQ ID NO 187
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 187

Gly Ser Phe Ser Gly Tyr Ala Ile Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 188

Gly Ser Phe Ser Gly Tyr Tyr Trp His
1               5

```
<210> SEQ ID NO 189
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 189

Gly Ser Phe Ser Gly Tyr Tyr Trp Ser
1               5

<210> SEQ ID NO 190
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 190

Gly Ser Phe Ser Asn Tyr Ala Ile Ser
1               5

<210> SEQ ID NO 191
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 191

Gly Ser Phe Ser Thr Ser Val Phe Gly
1               5

<210> SEQ ID NO 192
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 192

Gly Ser Ile Ser Gly Asn Asn Tyr Tyr Trp Gly
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 193

Gly Ser Ile Ser Gly Asn Asn Tyr Tyr Glx Gly
1               5                   10

<210> SEQ ID NO 194
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 194
```

```
Gly Ser Ile Ser Asn Tyr Tyr Trp Ser
1               5

<210> SEQ ID NO 195
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 195

Gly Ser Ile Ser Ser Gly Gly Tyr Ser Trp Ser
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 196

Gly Ser Ile Ser Ser Gly Gly Tyr Tyr Trp Ser
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 197

Gly Ser Ile Ser Ser Ser Ser Tyr Tyr Trp Gly
1               5                   10

<210> SEQ ID NO 198
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 198

Gly Thr Phe Gly Asn Tyr Gly Ile Asn
1               5

<210> SEQ ID NO 199
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 199

Gly Thr Phe Gly Ser Tyr Ala Ile Thr
1               5

<210> SEQ ID NO 200
<211> LENGTH: 9
<212> TYPE: PRT
<213> ORGANISM: Artificial Sequence
```

```
<220> FEATURE:
<223> OTHER INFORMATION: Synthesized molecular recognition unit - heavy
      CDR1

<400> SEQUENCE: 200

Gly Thr Phe Gly Ser Tyr Ala Val Gly
1               5

<210> SEQ ID NO 201
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 201

Gly Thr Phe Asn Arg Tyr Ala Ile Thr
1               5

<210> SEQ ID NO 202
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 202

Gly Thr Phe Asn Arg Tyr Gly Ile Ser
1               5

<210> SEQ ID NO 203
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 203

Gly Thr Phe Asn Ser Tyr Ala Ile Ala
1               5

<210> SEQ ID NO 204
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 204

Gly Thr Phe Arg Ser Tyr Ala Ile Asn
1               5

<210> SEQ ID NO 205
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 205

Gly Thr Phe Ser Ser Asn Val Ile Ser
1               5
```

<210> SEQ ID NO 206
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 206

Gly Thr Phe Ser Ser Tyr Ala Ile Asn
1               5

<210> SEQ ID NO 207
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 207

Gly Thr Phe Ser Ser Tyr Ala Ile Ser
1               5

<210> SEQ ID NO 208
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 208

Gly Thr Phe Ser Ser Tyr Thr Ile Ser
1               5

<210> SEQ ID NO 209
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 209

Gly Thr Phe Ser Ser Tyr Val Ile Ser
1               5

<210> SEQ ID NO 210
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 210

Gly Thr Phe Ser Thr Tyr Ala Ile Ser
1               5

<210> SEQ ID NO 211
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

```
<400> SEQUENCE: 211

Gly Thr Phe Ser Thr Tyr Ala Met Gly
1               5

<210> SEQ ID NO 212
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 212

Gly Thr Phe Ser Glx Tyr Ala Ile Ser
1               5

<210> SEQ ID NO 213
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 213

Gly Thr Phe Ser Glx Glx Thr Ile Ser
1               5

<210> SEQ ID NO 214
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 214

Gly Thr Phe Thr Asn Asn Phe Met His
1               5

<210> SEQ ID NO 215
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 215

Gly Thr Phe Thr Arg Asn Ser Ile Ser
1               5

<210> SEQ ID NO 216
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 216

Gly Thr Phe Thr Ser Tyr Ala Ile Ser
1               5

<210> SEQ ID NO 217
<211> LENGTH: 9
<212> TYPE: PRT
```

```
<213> ORGANISM: Artificial Sequence
<220> FEATURE:
<223> OTHER INFORMATION: Synthesized molecular recognition unit - heavy
      CDR1

<400> SEQUENCE: 217

Gly Thr Phe Thr Ser Tyr Pro Ile Ser
1               5

<210> SEQ ID NO 218
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 218

Gly Thr Phe Thr Tyr Arg Tyr Leu His
1               5

<210> SEQ ID NO 219
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 219

Gly Thr Leu Asn Asn His Thr Leu Ser
1               5

<210> SEQ ID NO 220
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 220

Gly Thr Ser Ser Thr Tyr Ala Met Gly
1               5

<210> SEQ ID NO 221
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 221

His Asp Phe Ser Ser Thr Tyr Gly Val Gly
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 222

His Thr Phe Ser Gly Tyr His Ile His
1               5
```

<210> SEQ ID NO 223
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 223

Ile Ile Phe Ser Pro Asn Asp Met Gly
1               5

<210> SEQ ID NO 224
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 224

Ile Lys Ser Met Phe Asp Met Asn Phe Met Gly
1               5                   10

<210> SEQ ID NO 225
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 225

Ile Thr Phe Gly Phe Asp Ser Val Gly
1               5

<210> SEQ ID NO 226
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 226

Ile Thr Phe Ser Phe Asn Ser Val Gly
1               5

<210> SEQ ID NO 227
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 227

Leu Ala Phe Asn Gly Tyr Thr Met Gly
1               5

<210> SEQ ID NO 228
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 228

Leu Ala Ile Asp Asp Tyr Tyr Met Val
1               5

<210> SEQ ID NO 229
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 229

Leu Thr Phe Ser Asp Tyr Thr Val Gly
1               5

<210> SEQ ID NO 230
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 230

Leu Thr Phe Ser Ile Tyr Ala Met His
1               5

<210> SEQ ID NO 231
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 231

Leu Thr Phe Ser Thr Tyr Gly Met Gly
1               5

<210> SEQ ID NO 232
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 232

Leu Thr Ile Asp Asp Tyr Tyr Met Val
1               5

<210> SEQ ID NO 233
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 233

Leu Thr Ile Asp Asp Tyr Tyr Val Val
1               5

<210> SEQ ID NO 234
<211> LENGTH: 9

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 234

Leu Thr Val Ser Thr Asn Phe Met Ser
1               5

<210> SEQ ID NO 235
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 235

Asn Phe Phe Ser Asn Tyr Pro Leu Gly
1               5

<210> SEQ ID NO 236
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 236

Asn Ile Phe Arg Ile Tyr Ala Ile Ala
1               5

<210> SEQ ID NO 237
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 237

Gln Thr Phe Thr Ala Tyr Ala Met Gly
1               5

<210> SEQ ID NO 238
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 238

Arg Ala Phe Ser Asn Tyr Ala Met Gly
1               5

<210> SEQ ID NO 239
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 239

Arg Ala Phe Thr Asp Asn Val Met Ala
```

```
<210> SEQ ID NO 240
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 240

Arg Ile Phe Ser Ser Tyr Ala Gln Ala
1               5

<210> SEQ ID NO 241
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 241

Arg Met Phe Ser Asn Tyr Ala Met Gly
1               5

<210> SEQ ID NO 242
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 242

Arg Arg Phe Thr Thr Tyr Gly Met Gly
1               5

<210> SEQ ID NO 243
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 243

Arg Ser Phe Arg Thr Asn Ala Leu Gly
1               5

<210> SEQ ID NO 244
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 244

Arg Ser Phe Ser Ile Tyr Asn Thr Ala
1               5

<210> SEQ ID NO 245
<211> LENGTH: 9
<212> TYPE: PRT
<213> ORGANISM: Artificial Sequence
<220> FEATURE:
<223> OTHER INFORMATION: Synthesized molecular recognition unit - heavy
```

```
                          CDR1

<400> SEQUENCE: 245

Arg Ser Phe Ser Asn Tyr Arg Val Ala
1               5

<210> SEQ ID NO 246
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 246

Arg Ser Phe Ser Thr Tyr Pro Met Gly
1               5

<210> SEQ ID NO 247
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 247

Arg Thr Asp Gly Gly Tyr Val Met Gly
1               5

<210> SEQ ID NO 248
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 248

Arg Thr Asp Gly Met Gln Ala Met Gly
1               5

<210> SEQ ID NO 249
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 249

Arg Thr Phe Gly Ser Tyr Ala Met Gly
1               5

<210> SEQ ID NO 250
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 250

Arg Thr Phe Gly Thr Trp Ala Met Gly
1               5

<210> SEQ ID NO 251
```

```
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 251

Arg Thr Phe Asn Arg His Val Met Gly
1               5

<210> SEQ ID NO 252
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 252

Arg Thr Phe Arg Ala Tyr Ala Met Gly
1               5

<210> SEQ ID NO 253
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 253

Arg Thr Phe Ser Glu Tyr Ala Met Gly
1               5

<210> SEQ ID NO 254
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 254

Arg Thr Phe Ser Asn Tyr Val Met Gly
1               5

<210> SEQ ID NO 255
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 255

Arg Thr Phe Ser Ser Ala Ala Met Gly
1               5

<210> SEQ ID NO 256
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 256
```

```
Arg Thr Phe Ser Ser Phe Val Met Gly
1               5

<210> SEQ ID NO 257
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 257

Arg Thr Phe Ser Ser Tyr Ala Met Gly
1               5

<210> SEQ ID NO 258
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 258

Arg Thr Phe Ser Ser Tyr Ser Leu Ala
1               5

<210> SEQ ID NO 259
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 259

Arg Thr Phe Ser Thr Tyr Gly Met Gly
1               5

<210> SEQ ID NO 260
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 260

Arg Thr Phe Ser Trp Tyr Ser Met Gly
1               5

<210> SEQ ID NO 261
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 261

Arg Thr Leu Ser Ser Tyr Val Val Gly
1               5

<210> SEQ ID NO 262
<211> LENGTH: 9
<212> TYPE: PRT
<213> ORGANISM: Artificial Sequence
<220> FEATURE:
```

<223> OTHER INFORMATION: Synthesized molecular recognition unit - heavy
     CDR1

<400> SEQUENCE: 262

Arg Thr Ser Asp Leu Tyr Thr Met Gly
1               5

<210> SEQ ID NO 263
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 263

Arg Thr Ser Ser Ser Tyr Ala Met Gly
1               5

<210> SEQ ID NO 264
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 264

Arg Val Phe Ser Ser Tyr Ala Gln Ala
1               5

<210> SEQ ID NO 265
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 265

Ser Ala Phe Ser Asn Tyr Ala Met Gly
1               5

<210> SEQ ID NO 266
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 266

Ser Ile Asp Ser Ile Asn Ala Met Ala
1               5

<210> SEQ ID NO 267
<211> LENGTH: 9
<212> TYPE: PRT
<213> ORGANISM: Artificial Sequence
<220> FEATURE:
<223> OTHER INFORMATION: Synthesized molecular recognition unit - heavy
     CDR1

<400> SEQUENCE: 267

Ser Ile Phe Ser Ile Asn Ala Met Gly
1               5

```
<210> SEQ ID NO 268
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 268

Ser Ile Phe Ser Ile Tyr Ala Met Gly
1               5

<210> SEQ ID NO 269
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 269

Ser Ile Phe Ser Ser Asn Thr Ile Tyr
1               5

<210> SEQ ID NO 270
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 270

Ser Leu Phe Arg Leu Asn Gly Met Gly
1               5

<210> SEQ ID NO 271
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 271

Ser Thr Phe Ser Asn Tyr Ala Met Gly
1               5

<210> SEQ ID NO 272
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 272

Ser Thr Phe Ser Thr Tyr Ala Met Gly
1               5

<210> SEQ ID NO 273
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 273
```

```
Ser Thr Phe Thr Asn Ala Trp Met Ser
1               5

<210> SEQ ID NO 274
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 274

Ser Val Val Asn Phe Val Val Met Gly
1               5

<210> SEQ ID NO 275
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 275

Thr Thr Leu Asn Lys Tyr Ala Ile Ser
1               5

<210> SEQ ID NO 276
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 276

Val Ser Phe Ser Gly Tyr Ala Met His
1               5

<210> SEQ ID NO 277
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 277

Tyr Asp Phe Thr Thr Tyr Gly Ile His
1               5

<210> SEQ ID NO 278
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 278

Tyr Ile Phe Thr Asp Tyr Tyr Met His
1               5

<210> SEQ ID NO 279
<211> LENGTH: 9
<212> TYPE: PRT
<213> ORGANISM: Artificial Sequence
```

```
<220> FEATURE:
<223> OTHER INFORMATION: Synthesized molecular recognition unit - heavy
      CDR1

<400> SEQUENCE: 279

Tyr Ile Phe Thr Gly Tyr Tyr Met His
1               5

<210> SEQ ID NO 280
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 280

Tyr Ser Phe Thr Asn Tyr Ala Met His
1               5

<210> SEQ ID NO 281
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 281

Tyr Ser Phe Thr Thr Tyr Gly Met Asn
1               5

<210> SEQ ID NO 282
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 282

Tyr Thr Phe Ala Ser Tyr Asp Ile His
1               5

<210> SEQ ID NO 283
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 283

Tyr Thr Phe Ala Ser Tyr Gly Met His
1               5

<210> SEQ ID NO 284
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 284

Tyr Thr Phe Ser Gly Tyr Tyr Leu His
1               5
```

<210> SEQ ID NO 285
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 285

Tyr Thr Phe Thr Asp Tyr Tyr Met His
1               5

<210> SEQ ID NO 286
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 286

Tyr Thr Phe Thr Gly His Tyr Ile His
1               5

<210> SEQ ID NO 287
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 287

Tyr Thr Phe Thr Gly His Tyr Met His
1               5

<210> SEQ ID NO 288
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 288

Tyr Thr Phe Thr Gly Tyr Tyr Met His
1               5

<210> SEQ ID NO 289
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 289

Tyr Thr Phe Thr His Ser Tyr Ile His
1               5

<210> SEQ ID NO 290
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

```
<400> SEQUENCE: 290

Tyr Thr Phe Thr Lys Asp Tyr Met His
1               5

<210> SEQ ID NO 291
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 291

Tyr Thr Phe Thr Asn His Phe Met His
1               5

<210> SEQ ID NO 292
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 292

Tyr Thr Phe Thr Asn Asn Phe Met His
1               5

<210> SEQ ID NO 293
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 293

Tyr Thr Phe Thr Asn Tyr Cys Thr Arg
1               5

<210> SEQ ID NO 294
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 294

Tyr Thr Phe Thr Arg Tyr Ala Val His
1               5

<210> SEQ ID NO 295
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 295

Tyr Thr Phe Thr Ser His Trp Met His
1               5

<210> SEQ ID NO 296
<211> LENGTH: 9
<212> TYPE: PRT
```

<213> ORGANISM: Artificial Sequence
<220> FEATURE:
<223> OTHER INFORMATION: Synthesized molecular recognition unit - heavy CDR1

<400> SEQUENCE: 296

Tyr Thr Phe Thr Ser Ser Ala Ile His
1               5

<210> SEQ ID NO 297
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 297

Tyr Thr Phe Thr Ser Tyr Ala Ile Ser
1               5

<210> SEQ ID NO 298
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 298

Tyr Thr Phe Thr Ser Tyr Ala Met His
1               5

<210> SEQ ID NO 299
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 299

Tyr Thr Phe Thr Ser Tyr Asp Ile Asn
1               5

<210> SEQ ID NO 300
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 300

Tyr Thr Phe Thr Ser Tyr Gly Ile Ser
1               5

<210> SEQ ID NO 301
<211> LENGTH: 9
<212> TYPE: PRT
<213> ORGANISM: Artificial Sequence
<220> FEATURE:
<223> OTHER INFORMATION: Synthesized molecular recognition unit - heavy CDR1

<400> SEQUENCE: 301

Tyr Thr Phe Thr Ser Tyr Tyr Met His
1               5

```
<210> SEQ ID NO 302
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 302

Tyr Thr Phe Thr Thr Tyr Phe Met His
1               5

<210> SEQ ID NO 303
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 303

Tyr Thr Phe Thr Tyr Arg Tyr Leu His
1               5

<210> SEQ ID NO 304
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 304

Tyr Thr Phe Thr Tyr Tyr Ala Met His
1               5

<210> SEQ ID NO 305
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 305

Tyr Thr Ile Thr Thr Tyr Ala Ile His
1               5

<210> SEQ ID NO 306
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 306

Tyr Thr Leu Ser Asn Tyr Gly Ile Ser
1               5

<210> SEQ ID NO 307
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 307

Tyr Thr Leu Thr Thr Trp Tyr Met Xaa
1               5

<210> SEQ ID NO 308
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 308

Tyr Thr Val Thr Ser Tyr Ala Met His
1               5

<210> SEQ ID NO 309
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 309

Tyr Glx Phe Glx Glx Glx Tyr Met His
1               5

<210> SEQ ID NO 310
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 310

Glx Ser Val Ser Ser Asn Tyr Met Ser
1               5

<210> SEQ ID NO 311
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 311

Glx Thr Phe Ser Glx Tyr Asp Met His
1               5

<210> SEQ ID NO 312
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 312

Glx Glx Glx Thr Asp Tyr Tyr Glx Gln
1               5
```

<210> SEQ ID NO 313
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 313

Ala Ala Ile Gly Tyr Lys Val Lys Trp Asn Gly Glu Arg Thr Tyr Tyr
1               5                   10                  15

Leu

<210> SEQ ID NO 314
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 314

Ala Ala Ile Asn Arg Ser Gly Gly Ser Thr Tyr Tyr Ala
1               5                   10

<210> SEQ ID NO 315
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 315

Ala Ala Ile Asn Trp Ser Gly Asp Ser Ala Tyr Tyr Ala
1               5                   10

<210> SEQ ID NO 316
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 316

Ala Ala Ile Asn Trp Ser Gly Arg Ser Thr Val Tyr Ala
1               5                   10

<210> SEQ ID NO 317
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 317

Ala Ala Ile Ser Gly Ser Gly Glu Asn Thr Tyr Tyr Ala
1               5                   10

<210> SEQ ID NO 318
<211> LENGTH: 13
<212> TYPE: PRT
<213> ORGANISM: Artificial Sequence
<220> FEATURE:

```
<223> OTHER INFORMATION: Synthesized molecular recognition unit - heavy
      CDR2

<400> SEQUENCE: 318

Ala Ala Ile Ser Arg Asn Gly Val Tyr Thr Arg Phe Ala
1               5                   10

<210> SEQ ID NO 319
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 319

Ala Ala Ile Ser Ser Gly Gly Ser Gly Thr Tyr Tyr Ser
1               5                   10

<210> SEQ ID NO 320
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 320

Ala Ala Ile Ser Trp Gly Gly Gly Ser Thr Phe Tyr Ser
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 321

Ala Ala Ile Ser Trp Met Ser Asn Thr Tyr Tyr Ala
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 322

Ala Ala Ile Ser Trp Arg Gly Thr Asn Ile Ala
1               5                   10

<210> SEQ ID NO 323
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 323

Ala Ala Ile Ser Trp Ser Asp Asn Thr Tyr Tyr Ala
1               5                   10
```

-continued

```
<210> SEQ ID NO 324
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 324

Ala Ala Ile Ser Trp Ser Gly Asp Ser Thr Tyr Tyr Ala
1               5                   10

<210> SEQ ID NO 325
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 325

Ala Ala Ile Ser Trp Ser Gly Asp Ser Thr Tyr Tyr Leu
1               5                   10

<210> SEQ ID NO 326
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 326

Ala Ala Ile Ser Trp Ser Gly Gly Ser Thr His Tyr Ala
1               5                   10

<210> SEQ ID NO 327
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 327

Ala Ala Ile Ser Trp Ser Gly Gly Ser Thr Tyr Tyr Ala
1               5                   10

<210> SEQ ID NO 328
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 328

Ala Ala Ile Ser Trp Ser Gly Arg Ser Thr Tyr Tyr Ala
1               5                   10

<210> SEQ ID NO 329
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 329
```

Ala Ala Ile Ser Trp Ser Gly Ser Ala Thr His Tyr Ala
1               5                   10

<210> SEQ ID NO 330
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 330

Ala Ala Ile Ser Trp Ser Gly Ser Thr Ala Tyr Tyr Ala
1               5                   10

<210> SEQ ID NO 331
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 331

Ala Ala Ile Ser Trp Thr Gly Gly Ser Thr Tyr Tyr Ala
1               5                   10

<210> SEQ ID NO 332
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 332

Ala Ala Ile Ser Tyr Asp Glu Ser Asn Lys Phe Tyr Ala
1               5                   10

<210> SEQ ID NO 333
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 333

Ala Ala Ile Ser Tyr Asn Gly Phe Ser Thr Tyr Tyr Ser
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 334

Ala Ala Ile Thr Ser Gly Gly Ser Thr Asn Tyr Ala
1               5                   10

<210> SEQ ID NO 335
<211> LENGTH: 13
<212> TYPE: PRT
<213> ORGANISM: Artificial Sequence

```
<220> FEATURE:
<223> OTHER INFORMATION: Synthesized molecular recognition unit - heavy
      CDR2

<400> SEQUENCE: 335

Ala Ala Ile Thr Trp Ser Gly Ala Arg Thr Tyr Tyr Ala
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 336

Ala Ala Leu Thr Gly Gln Arg Thr Thr Asn Tyr Ala
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 337

Ala Ala Leu Thr Ser Gly Gly Ile Thr Tyr His Ala
1               5                   10

<210> SEQ ID NO 338
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 338

Ala Ala Val Asn Trp Arg Gly Asp Gly Thr Tyr Tyr Ser
1               5                   10

<210> SEQ ID NO 339
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 339

Ala Ala Val Asn Trp Ser Gly Gly Ser Thr Tyr Tyr Ala
1               5                   10

<210> SEQ ID NO 340
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 340

Ala Ala Val Ser Ala Ser Gly Ala Asn Thr Tyr Tyr Ala
1               5                   10
```

<210> SEQ ID NO 341
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 341

Ala Ala Val Ser Ala Ser Gly Gly Tyr Thr Trp Tyr Ala
1               5                   10

<210> SEQ ID NO 342
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 342

Ala Ala Val Ser Trp Ser Gly Val Ser Thr Tyr Tyr Pro
1               5                   10

<210> SEQ ID NO 343
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 343

Ala Ala Val Thr Ala Ser Gly Gly Tyr Ala Trp Tyr Ala
1               5                   10

<210> SEQ ID NO 344
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 344

Ala Ala Val Thr Trp Arg Ala Gly Ser Thr Tyr Tyr Ala
1               5                   10

<210> SEQ ID NO 345
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 345

Ala Ala Val Thr Trp Arg Ser Gly Ser Thr Tyr Tyr Ala
1               5                   10

<210> SEQ ID NO 346
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

```
<400> SEQUENCE: 346

Ala Asp Ile Thr Ser Gly Gly Ser Thr Asn Tyr Ala
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 347

Ala Phe Ile Thr Arg Gly Gly Thr Thr Arg Tyr Gly
1               5                   10

<210> SEQ ID NO 348
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 348

Ala Gly Ile Ala Ser Asp Ser Thr Thr Phe Tyr Ala
1               5                   10

<210> SEQ ID NO 349
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 349

Ala Gly Ile Gly Trp Asp Ser Thr Asn Ile Gly Tyr Ala
1               5                   10

<210> SEQ ID NO 350
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 350

Ala Gly Ile Asn Trp Asn Gly Gly Ser Val Val Tyr Ala
1               5                   10

<210> SEQ ID NO 351
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 351

Ala Gly Ile Ser Ala Ser Gly Gly Ser Thr Tyr Tyr Ala
1               5                   10

<210> SEQ ID NO 352
<211> LENGTH: 13
<212> TYPE: PRT
```

```
<213> ORGANISM: Artificial Sequence
<220> FEATURE:
<223> OTHER INFORMATION: Synthesized molecular recognition unit - heavy
      CDR2

<400> SEQUENCE: 352

Ala Gly Ile Ser Gly Gly Gly Ser Thr Asp Tyr Ala
1               5                   10

<210> SEQ ID NO 353
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 353

Ala Gly Ile Ser Gly Ser Gly Lys Thr Thr Phe Tyr Ala
1               5                   10

<210> SEQ ID NO 354
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 354

Ala Gly Ile Ser Arg Thr Gly Gly Asn Thr Gly Tyr Ala
1               5                   10

<210> SEQ ID NO 355
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 355

Ala Gly Ile Ser Trp Asn Ser Gly Thr Ile Asp Tyr Ala
1               5                   10

<210> SEQ ID NO 356
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 356

Ala Gly Val Ser Ile Asp Ala Asn Lys Lys Tyr Tyr Ala
1               5                   10

<210> SEQ ID NO 357
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 357

Ala Ile Val Ser Tyr Asp Gly Thr Tyr Lys Tyr Tyr Ser
1               5                   10
```

```
<210> SEQ ID NO 358
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 358

Ala Leu Ile Ser Leu Ser Gly Ala Ser Thr Tyr Tyr Ala
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 359

Ala Leu Ile Ser Ser Gly Gly Ser Thr Ser Tyr Ala
1               5                   10

<210> SEQ ID NO 360
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 360

Ala Leu Ile Ser Ser Asn Gly Asp His Lys Tyr Tyr Thr
1               5                   10

<210> SEQ ID NO 361
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 361

Ala Leu Ile Ser Tyr Asp Gly Gly Asn Lys Tyr Tyr Ala
1               5                   10

<210> SEQ ID NO 362
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 362

Ala Leu Ile Ser Tyr Asp Gly Gly Thr Lys Tyr Tyr Ala
1               5                   10

<210> SEQ ID NO 363
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2
```

<400> SEQUENCE: 363

Ala Leu Ile Ser Tyr Asp Gly Ser His Thr Tyr Tyr Ala
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 364

Ala Leu Ile Thr Thr Ser Gly Asn Thr Asn Tyr Ala
1               5                   10

<210> SEQ ID NO 365
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 365

Ala Leu Met Ser Pro Asp Gly Thr Ile Ile Tyr Tyr Ala
1               5                   10

<210> SEQ ID NO 366
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 366

Ala Leu Thr Ser Tyr Asp Gly Ser Lys Lys Phe Tyr Ala
1               5                   10

<210> SEQ ID NO 367
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 367

Ala Leu Val Gly Tyr Asp Gly Ser Gln Gln Phe Tyr Gly
1               5                   10

<210> SEQ ID NO 368
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 368

Ala Asn Ile Lys Gln Asp Gly Ser Glu Lys Tyr Tyr Val
1               5                   10

<210> SEQ ID NO 369
<211> LENGTH: 13

```
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 369

Ala Gln Ile Ser Trp Thr Gly Gly Ser Thr Asp Tyr Ala
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 370

Ala Ser Ile Pro Ser Asp Gly Thr Thr Phe Tyr Ala
1               5                   10

<210> SEQ ID NO 371
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 371

Ala Ser Ile Thr Trp Asn Gly Arg Tyr Thr Tyr Tyr Ala
1               5                   10

<210> SEQ ID NO 372
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 372

Ala Ser Ile Trp Phe Asp Gly Ser Asn Gln Asp Tyr Ala
1               5                   10

<210> SEQ ID NO 373
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 373

Ala Ser Ser Thr Gly Gly Gly Val Phe Glu Asn Tyr Ala
1               5                   10

<210> SEQ ID NO 374
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 374

Ala Thr Ile Gln Ser Gly Gly Arg Thr Asn Tyr Ala
```

```
<210> SEQ ID NO 375
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 375

Ala Thr Ile Ser Gly Gly Gly Gly Ser Thr Phe Asp Asp
1               5                   10

<210> SEQ ID NO 376
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 376

Ala Thr Ile Ser Thr Arg Gly Thr Thr His Tyr Ala
1               5                   10

<210> SEQ ID NO 377
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 377

Ala Thr Ile Ser Trp Gly Gly Thr Asn Ile Ala
1               5                   10

<210> SEQ ID NO 378
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 378

Ala Thr Val Thr Trp Arg Thr Gly Thr Thr Tyr Tyr Ala
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 379

Ala Val Phe Ile Ala Gly Tyr Gly Ala Tyr Tyr Ala
1               5                   10

<210> SEQ ID NO 380
<211> LENGTH: 12
<212> TYPE: PRT
<213> ORGANISM: Artificial Sequence
<220> FEATURE:
<223> OTHER INFORMATION: Synthesized molecular recognition unit - heavy
```

CDR2

<400> SEQUENCE: 380

Ala Val Phe Asn Ala Gly Tyr Arg Ala Tyr Tyr Ala
1               5                   10

<210> SEQ ID NO 381
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 381

Ala Val Ile Ser Arg Ser Gly Gly Asn Thr Tyr Tyr Thr
1               5                   10

<210> SEQ ID NO 382
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 382

Ala Val Ile Ser Ser Asp Gly Asn Asn Lys Tyr Tyr Thr
1               5                   10

<210> SEQ ID NO 383
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 383

Ala Val Ile Ser Tyr Asp Gly Ser Asn Glu Tyr Tyr Ala
1               5                   10

<210> SEQ ID NO 384
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 384

Ala Val Ile Ser Tyr Asp Gly Ser Asn Lys Tyr Tyr Ala
1               5                   10

<210> SEQ ID NO 385
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 385

Ala Val Ile Ser Tyr Asp Gly Ser Asn Arg Glx Tyr Ala
1               5                   10

<210> SEQ ID NO 386

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 386

Ala Val Ile Thr Ser Gly Gly Thr Phe Lys Tyr Tyr Ala
1               5                   10

<210> SEQ ID NO 387
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 387

Ala Val Met Tyr Ser Gly Gly Thr Thr Tyr Tyr Ala
1               5                   10

<210> SEQ ID NO 388
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 388

Ala Val Ser Trp Ser Val Gly Met Thr Tyr Tyr Ala
1               5                   10

<210> SEQ ID NO 389
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 389

Ala Val Thr Trp Tyr Asp Gly Ser Asn Lys Tyr Tyr Ala
1               5                   10

<210> SEQ ID NO 390
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 390

Ala Val Val Ala Thr Gly Gly Ala Thr Asn Tyr Ala
1               5                   10

<210> SEQ ID NO 391
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 391
```

Ala Tyr Ile Asn Ser Gly Ser Ser Glu Met Asn Tyr Ala
1               5                   10

<210> SEQ ID NO 392
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 392

Ala Tyr Ile Asn Ser Arg Gly Ser Leu Met Tyr Tyr Ala
1               5                   10

<210> SEQ ID NO 393
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 393

Gly Ala Ile Ser Arg Thr Gly Ser Gly Thr Phe Tyr Ala
1               5                   10

<210> SEQ ID NO 394
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 394

Gly Ala Ile Thr Trp Ser Leu Gly Ile Ala Phe Tyr Ala
1               5                   10

<210> SEQ ID NO 395
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 395

Gly Ala Ile Thr Trp Ser Leu Gly Ser Ala Phe Tyr Ala
1               5                   10

<210> SEQ ID NO 396
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 396

Gly Glu Ile Asp His Thr Gly Ser Thr Asn Tyr Glu
1               5                   10

<210> SEQ ID NO 397
<211> LENGTH: 12
<212> TYPE: PRT
<213> ORGANISM: Artificial Sequence
<220> FEATURE:

```
<223> OTHER INFORMATION: Synthesized molecular recognition unit - heavy
      CDR2

<400> SEQUENCE: 397

Gly Glu Ile Asp Arg Ser Gly Asp Thr Asn Tyr Asn
1               5                   10

<210> SEQ ID NO 398
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 398

Gly Glu Ile Asn His Ser Gly Ser Thr Asn Tyr Asn
1               5                   10

<210> SEQ ID NO 399
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 399

Gly Phe Ile Arg Ser Lys Ala Tyr Gly Gly Thr Thr Glu Tyr Ala
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 400

Gly Phe Ile Arg Ser Lys Asp Tyr Gly Gly Thr Thr Glu Tyr Ala
1               5                   10                  15

<210> SEQ ID NO 401
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 401

Gly Gly Phe Asp Pro Glu Asp Gly Glu Thr Ile Tyr Ala
1               5                   10

<210> SEQ ID NO 402
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 402

Gly Gly Ile Phe Pro Ile Phe Gly Thr Ala Asn Tyr Ala
1               5                   10
```

```
<210> SEQ ID NO 403
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 403

Gly Gly Ile Phe Pro Ile Tyr Gly Ile Ser Thr Tyr Ala
1               5                   10

<210> SEQ ID NO 404
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 404

Gly Gly Ile Ile Pro Phe Phe Asn Thr Val Asn Tyr Ala
1               5                   10

<210> SEQ ID NO 405
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 405

Gly Gly Ile Ile Pro Ile Phe Gly Ile Ala Asn Tyr Ala
1               5                   10

<210> SEQ ID NO 406
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 406

Gly Gly Ile Ile Pro Ile Phe Gly Thr Ala Lys Tyr Ala
1               5                   10

<210> SEQ ID NO 407
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 407

Gly Gly Ile Ile Pro Ile Phe Gly Thr Ala Asn His Ala
1               5                   10

<210> SEQ ID NO 408
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 408
```

```
Gly Gly Ile Ile Pro Ile Phe Gly Thr Ala Asn Tyr Ala
1               5                   10

<210> SEQ ID NO 409
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 409

Gly Gly Ile Ile Pro Ile Phe Gly Thr Ala Glx Tyr Ala
1               5                   10

<210> SEQ ID NO 410
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 410

Gly Gly Ile Ile Pro Ile Phe Gly Thr Gly Asn Tyr Ala
1               5                   10

<210> SEQ ID NO 411
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 411

Gly Gly Ile Ile Pro Ile Phe Gly Thr Pro His Tyr Ala
1               5                   10

<210> SEQ ID NO 412
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 412

Gly Gly Ile Ile Pro Ile Phe Gly Thr Thr Asn Tyr Ala
1               5                   10

<210> SEQ ID NO 413
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 413

Gly Gly Ile Ile Pro Ile Leu Gly Ile Ala Asn Tyr Ala
1               5                   10

<210> SEQ ID NO 414
<211> LENGTH: 13
<212> TYPE: PRT
<213> ORGANISM: Artificial Sequence
```

```
<220> FEATURE:
<223> OTHER INFORMATION: Synthesized molecular recognition unit - heavy
      CDR2

<400> SEQUENCE: 414

Gly Gly Ile Ile Pro Ile Ser Gly Lys Thr Asp Tyr Ala
1               5                   10

<210> SEQ ID NO 415
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 415

Gly Gly Ile Ile Pro Leu Phe Gly Thr Ala Asn Tyr Ala
1               5                   10

<210> SEQ ID NO 416
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 416

Gly Gly Ile Ile Pro Leu Phe Gly Thr Thr Asp Tyr Ala
1               5                   10

<210> SEQ ID NO 417
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 417

Gly Gly Ile Ile Pro Arg Leu Gly Ala Thr Asp Tyr Ala
1               5                   10

<210> SEQ ID NO 418
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 418

Gly Gly Ile Leu Pro Ile Tyr Gly Thr Thr Lys Tyr Ala
1               5                   10

<210> SEQ ID NO 419
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 419

Gly Gly Met Asn Glx Asn Arg Gly Asn Thr Gly Tyr Ala
1               5                   10
```

-continued

<210> SEQ ID NO 420
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 420

Gly Gly Val Ile Pro Ala Phe Gly Ala Thr Asp Tyr Ser
1               5                   10

<210> SEQ ID NO 421
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 421

Gly Ile Ile Asn Pro Ser Gly Gly Arg Thr Thr Tyr Ala
1               5                   10

<210> SEQ ID NO 422
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 422

Gly Ile Ile Asn Pro Ser Gly Gly Ser Thr Ser Tyr Ala
1               5                   10

<210> SEQ ID NO 423
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 423

Gly Ile Ile Asn Pro Ser Ser Gly Arg Thr Asp Tyr Ala
1               5                   10

<210> SEQ ID NO 424
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 424

Gly Ile Ile Ser Pro Gly Gly Gly Arg Thr Ile Tyr Ala
1               5                   10

<210> SEQ ID NO 425
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

```
<400> SEQUENCE: 425

Gly Ile Ile Ser Pro Ser Gly Gly Ser Thr Ser Tyr Ala
1               5                   10

<210> SEQ ID NO 426
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 426

Gly Ile Ile Glx Pro Gly Gly Gly Arg Thr Ile Tyr Ala
1               5                   10

<210> SEQ ID NO 427
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 427

Gly Leu Ile Ser Arg Asn Ala Gly Asn Thr Leu Tyr Ala
1               5                   10

<210> SEQ ID NO 428
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 428

Gly Leu Val Cys Pro Ser Asp Gly Ser Thr Ser Tyr Ala
1               5                   10

<210> SEQ ID NO 429
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 429

Gly Leu Val Asp Pro Glu Asp Gly Glu Thr Ile Tyr Ala
1               5                   10

<210> SEQ ID NO 430
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 430

Gly Met Ile Ile Pro Phe Leu Gly Ile Thr Asn Tyr Ala
1               5                   10

<210> SEQ ID NO 431
<211> LENGTH: 13
<212> TYPE: PRT
```

```
<213> ORGANISM: Artificial Sequence
<220> FEATURE:
<223> OTHER INFORMATION: Synthesized molecular recognition unit - heavy
      CDR2

<400> SEQUENCE: 431

Gly Met Ile Asn Pro Ile Gly Gly Ser Ile Asn Tyr Ala
1               5                   10

<210> SEQ ID NO 432
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 432

Gly Met Ile Asn Pro Ser Gly Gly Ser Thr Thr Tyr Ala
1               5                   10

<210> SEQ ID NO 433
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 433

Gly Arg Ala Tyr Tyr Lys Ser Arg Trp Tyr Tyr Asp Tyr Ala
1               5                   10

<210> SEQ ID NO 434
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 434

Gly Arg Ile Ile Pro Ala Leu Gly Thr Ala Asn Tyr Ala
1               5                   10

<210> SEQ ID NO 435
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 435

Gly Arg Ile Ile Pro Ile Phe Gly Thr Ala Asn Tyr Ala
1               5                   10

<210> SEQ ID NO 436
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 436

Gly Arg Ile Ile Pro Ile Phe Gly Thr Ala Glx Tyr Ala
1               5                   10
```

<210> SEQ ID NO 437
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 437

Gly Arg Ile Ile Pro Ile Phe Gly Thr Val Asn Tyr Ala
1               5                   10

<210> SEQ ID NO 438
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 438

Gly Arg Ile Ile Pro Ile Leu Gly Ile Ala Asn Tyr Ala
1               5                   10

<210> SEQ ID NO 439
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 439

Gly Arg Ile Ile Pro Ile Leu Gly Ser Ala Asn Tyr Ala
1               5                   10

<210> SEQ ID NO 440
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 440

Gly Arg Ile Ile Pro Ile Leu Gly Thr Pro Asn Tyr Ala
1               5                   10

<210> SEQ ID NO 441
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 441

Gly Arg Ile Ile Pro Leu Phe Gly Thr Thr Asn Tyr Ala
1               5                   10

<210> SEQ ID NO 442
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 442

Gly Arg Ile Ile Pro Thr Val Gly Thr Ala Asn Tyr Ala
1               5                   10

<210> SEQ ID NO 443
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 443

Gly Arg Ile Ile Pro Val Leu Gly Thr Ala Asn Tyr Ala
1               5                   10

<210> SEQ ID NO 444
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 444

Gly Arg Ile Lys Ser Lys Ala Asn Gly Gly Thr Thr Asp Tyr Ala
1               5                   10                  15

<210> SEQ ID NO 445
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 445

Gly Arg Ile Lys Ser Lys Ala Tyr Gly Gly Thr Thr Glu Tyr Ala
1               5                   10                  15

<210> SEQ ID NO 446
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 446

Gly Arg Ile Asn Pro Asn Ser Gly Gly Thr Asn Tyr Ala
1               5                   10

<210> SEQ ID NO 447
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 447

Gly Arg Ile Ser Ala Tyr Asn Gly Tyr Lys Ser Tyr Ala
1               5                   10

<210> SEQ ID NO 448
<211> LENGTH: 13

```
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 448

Gly Arg Ile Thr Pro Val Val Gly Val Thr Asn Tyr Ala
1               5                   10

<210> SEQ ID NO 449
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 449

Gly Arg Ile Val Pro Ala Ile Gly Phe Thr Gln Tyr Ala
1               5                   10

<210> SEQ ID NO 450
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 450

Gly Arg Ile Val Pro Ile Val Asp Val Val Lys Tyr Ala
1               5                   10

<210> SEQ ID NO 451
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 451

Gly Arg Thr Tyr Tyr Arg Ser Lys Trp Tyr Asn Asp Tyr Ala
1               5                   10

<210> SEQ ID NO 452
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 452

Gly Arg Thr Tyr Tyr Arg Ser Lys Tyr Tyr Asn Gly Tyr Ala
1               5                   10

<210> SEQ ID NO 453
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 453

Gly Arg Val Ile Pro Ile Leu Gly Val Thr Asn Tyr Ala
```

```
1               5                   10
```

<210> SEQ ID NO 454
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 454

```
Gly Ser Ile Tyr Phe Thr Gly Gly Thr Tyr Tyr Asn
1               5                   10
```

<210> SEQ ID NO 455
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 455

```
Gly Ser Ile Tyr Tyr Thr Gly Asn Thr Tyr Tyr Asn
1               5                   10
```

<210> SEQ ID NO 456
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 456

```
Gly Thr Val Thr Pro Ile Leu Gly Thr Ala Asn Tyr Ala
1               5                   10
```

<210> SEQ ID NO 457
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 457

```
Gly Val Ile Asp Pro Ser Thr Gly Gly Thr Asn Tyr Ala
1               5                   10
```

<210> SEQ ID NO 458
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 458

```
Gly Val Ile Phe Pro Val Tyr Pro Thr Pro Asp Tyr Ala
1               5                   10
```

<210> SEQ ID NO 459
<211> LENGTH: 13
<212> TYPE: PRT
<213> ORGANISM: Artificial Sequence
<220> FEATURE:
<223> OTHER INFORMATION: Synthesized molecular recognition unit - heavy

```
            CDR2

<400> SEQUENCE: 459

Gly Val Ile Asn Pro Gly Ser Gly Gly Thr Ser Tyr Asn
1               5                   10

<210> SEQ ID NO 460
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 460

Gly Val Ile Ser Lys Asp Gly Asp Asn Lys Tyr Tyr Ala
1               5                   10

<210> SEQ ID NO 461
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 461

Gly Trp Ile Gly Pro His Asn Gly Asn Thr Asn Tyr Ala
1               5                   10

<210> SEQ ID NO 462
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 462

Gly Trp Ile Asn Ala Asp Thr Gly Asp Thr Ala Tyr Ser
1               5                   10

<210> SEQ ID NO 463
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 463

Gly Trp Ile Asn Ala Gly Asn Gly Asn Thr Lys Tyr Ala
1               5                   10

<210> SEQ ID NO 464
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 464

Gly Trp Ile Asn Ala Gly Asn Gly Asn Thr Lys Tyr Ser
1               5                   10

<210> SEQ ID NO 465
```

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 465

Gly Trp Ile Asn Ala Gly Asn Gly Asn Thr Thr Tyr Ala
1               5                   10

<210> SEQ ID NO 466
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 466

Gly Trp Ile Asn Ala Lys Ser Gly Gly Thr Phe Tyr Ala
1               5                   10

<210> SEQ ID NO 467
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 467

Gly Trp Ile Asn Pro Lys Ser Gly Gly Thr Asn Tyr Ala
1               5                   10

<210> SEQ ID NO 468
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 468

Gly Trp Ile Asn Pro Asn Ser Gly Asp Thr Lys Phe Ala
1               5                   10

<210> SEQ ID NO 469
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 469

Gly Trp Ile Asn Pro Asn Ser Gly Gly Thr Ile Tyr Ala
1               5                   10

<210> SEQ ID NO 470
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 470
```

Gly Trp Ile Asn Pro Asn Ser Gly Gly Thr Lys Tyr Ala
1               5                   10

<210> SEQ ID NO 471
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 471

Gly Trp Ile Asn Pro Asn Ser Gly Gly Thr Asn Tyr Ala
1               5                   10

<210> SEQ ID NO 472
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 472

Gly Trp Ile Asn Ser Gly Asn Gly Asn Thr Lys Tyr Ser
1               5                   10

<210> SEQ ID NO 473
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 473

Gly Trp Ile Asn Thr Tyr Asn Gly Asn Thr Ile Tyr Ala
1               5                   10

<210> SEQ ID NO 474
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 474

Gly Trp Ile Asn Thr Tyr Asn Gly Asn Thr Asn Tyr Pro
1               5                   10

<210> SEQ ID NO 475
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 475

Gly Trp Ile Ser Ala Tyr Asn Gly Asp Thr Lys Tyr Ala
1               5                   10

<210> SEQ ID NO 476
<211> LENGTH: 13
<212> TYPE: PRT
<213> ORGANISM: Artificial Sequence
<220> FEATURE:

<223> OTHER INFORMATION: Synthesized molecular recognition unit - heavy
      CDR2

<400> SEQUENCE: 476

Gly Trp Ile Ser Ala Tyr Asn Gly His Thr Asn Tyr Ala
1               5                   10

<210> SEQ ID NO 477
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 477

Gly Trp Ile Ser Ala Tyr Asn Gly Asn Thr Asn Tyr Ala
1               5                   10

<210> SEQ ID NO 478
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 478

Gly Trp Ile Ser Pro Asn Arg Gly Gly Thr Asn Tyr Ala
1               5                   10

<210> SEQ ID NO 479
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 479

Gly Trp Ile Ser Pro Tyr Asn Gly Asn Thr Lys Tyr Ala
1               5                   10

<210> SEQ ID NO 480
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 480

Gly Trp Ile Ser Pro Tyr Asn Gly Asn Thr Asn Tyr Ala
1               5                   10

<210> SEQ ID NO 481
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 481

Gly Trp Ile Ser Pro Tyr Asn Gly Tyr Thr Lys Tyr Ala
1               5                   10

```
<210> SEQ ID NO 482
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 482

Gly Trp Ile Ser Ser Phe Asn Gly Asn Thr Lys Tyr Ala
1               5                   10

<210> SEQ ID NO 483
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 483

Gly Trp Ile Ser Thr Phe Asn Asp Asn Thr Asn Tyr Ala
1               5                   10

<210> SEQ ID NO 484
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 484

Gly Trp Ile Ser Thr Tyr Asn Gly Ala Thr Asn Tyr Ala
1               5                   10

<210> SEQ ID NO 485
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 485

Gly Trp Ile Tyr Pro Asn Ser Gly Gly Thr Lys Tyr Ala
1               5                   10

<210> SEQ ID NO 486
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 486

Gly Trp Met Asn Pro Asp Ser Gly Lys Thr Gly Tyr Ala
1               5                   10

<210> SEQ ID NO 487
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 487
```

Gly Trp Met Asn Pro Ile Ser Gly Asn Thr Gly Tyr Ala
1               5                   10

<210> SEQ ID NO 488
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 488

Gly Trp Met Asn Pro Asn Asn Gly Asn Thr Thr Tyr Ala
1               5                   10

<210> SEQ ID NO 489
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 489

Gly Trp Met Asn Pro Asn Ser Gly Asn Thr Ala Tyr Ala
1               5                   10

<210> SEQ ID NO 490
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 490

Gly Trp Met Asn Pro Asn Ser Gly Asn Thr Gly Tyr Ala
1               5                   10

<210> SEQ ID NO 491
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 491

Gly Trp Met Ser Pro Asn Ser Gly Asn Ala Gly Phe Ala
1               5                   10

<210> SEQ ID NO 492
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 492

Gly Trp Met Ser Pro Ser Ser Gly Asn Ala Gly Tyr Ala
1               5                   10

<210> SEQ ID NO 493
<211> LENGTH: 13
<212> TYPE: PRT
<213> ORGANISM: Artificial Sequence

```
<220> FEATURE:
<223> OTHER INFORMATION: Synthesized molecular recognition unit - heavy
      CDR2

<400> SEQUENCE: 493

Gly Trp Val Asn Pro Thr Thr Gly Asn Thr Gly Tyr Ala
1               5                   10

<210> SEQ ID NO 494
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 494

Gly Trp Val Ser Pro Asn Thr Gly Asn Thr Val Tyr Ala
1               5                   10

<210> SEQ ID NO 495
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 495

Gly Trp Val Ser Pro Ser Ser Gly Asn Thr Ala Tyr Ala
1               5                   10

<210> SEQ ID NO 496
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 496

Gly Tyr Ile Tyr Tyr Ser Gly Ser Thr Tyr Tyr Asn
1               5                   10

<210> SEQ ID NO 497
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 497

Pro Arg Ile Pro Ser Asp Ser Thr Thr Phe Tyr Ala
1               5                   10

<210> SEQ ID NO 498
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 498

Ser Ala Ile Asp Gly Ala Gly Arg Thr Tyr Tyr Thr
1               5                   10
```

<210> SEQ ID NO 499
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 499

Ser Ala Ile Asp Gly Ser Gly Gly Ser Thr Tyr Tyr Ala
1               5                   10

<210> SEQ ID NO 500
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 500

Ser Ala Ile Gly Ala Gly Gly Gly Thr Tyr Tyr Ala
1               5                   10

<210> SEQ ID NO 501
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 501

Ser Ala Ile Gly Thr Gly Gly Asp Thr Tyr Tyr Ala
1               5                   10

<210> SEQ ID NO 502
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 502

Ser Ala Ile Gly Thr Gly Gly Gly Thr Tyr Tyr Ala
1               5                   10

<210> SEQ ID NO 503
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 503

Ser Ala Ile Ser Ala Ser Gly Asp Ser Thr Phe Tyr Ala
1               5                   10

<210> SEQ ID NO 504
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

-continued

<400> SEQUENCE: 504

Ser Ala Ile Ser Gly Asp Gly Ala Leu Thr Tyr Tyr Ala
1               5                   10

<210> SEQ ID NO 505
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 505

Ser Ala Ile Ser Gly Ser Gly Ala Thr Thr Tyr Tyr Ala
1               5                   10

<210> SEQ ID NO 506
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 506

Ser Ala Ile Ser Gly Ser Gly Phe Thr Tyr Tyr Ala
1               5                   10

<210> SEQ ID NO 507
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 507

Ser Ala Ile Ser Gly Ser Gly Gly Ser Thr Tyr Tyr Ala
1               5                   10

<210> SEQ ID NO 508
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 508

Ser Ala Ile Ser Asn Ser Gly Gly Ser Thr Tyr Tyr Ala
1               5                   10

<210> SEQ ID NO 509
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 509

Ser Ala Ile Ser Val Ser Gly Gly Thr Thr Phe Tyr Ala
1               5                   10

<210> SEQ ID NO 510
<211> LENGTH: 13
<212> TYPE: PRT

<213> ORGANISM: Artificial Sequence
<220> FEATURE:
<223> OTHER INFORMATION: Synthesized molecular recognition unit - heavy
      CDR2

<400> SEQUENCE: 510

Ser Ala Ile Ser Trp Ser Gly Gly Ser Thr Tyr Tyr Ala
1               5                   10

<210> SEQ ID NO 511
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 511

Ser Ala Val Ser Gly Asn Gly Gly Gly Thr Phe Tyr Ala
1               5                   10

<210> SEQ ID NO 512
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 512

Ser Gly Ile Gly Val Gly Gly Gly Thr Tyr Tyr Ala
1               5                   10

<210> SEQ ID NO 513
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 513

Ser Gly Ile Asn Trp Asn Gly Gly Ser Thr Gly Tyr Ala
1               5                   10

<210> SEQ ID NO 514
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 514

Ser Gly Ile Asn Trp Asn Ser Ala Lys Ile Gly Tyr Val
1               5                   10

<210> SEQ ID NO 515
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 515

Ser Gly Ile Ser Gly Ser Gly Gly Ser Thr Tyr Tyr Ala
1               5                   10

```
<210> SEQ ID NO 516
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 516

Ser Gly Ile Ser Gly Ser Gly Gly Thr Thr Tyr Tyr Ala
1               5                   10

<210> SEQ ID NO 517
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 517

Ser Gly Ile Ser Gly Ser Gly Arg Ser Thr Tyr Tyr Ala
1               5                   10

<210> SEQ ID NO 518
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 518

Ser Gly Ile Ser Gly Ser Gly Ser Ser Thr Tyr Tyr Ala
1               5                   10

<210> SEQ ID NO 519
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 519

Ser Gly Ile Ser Gly Ser Gly Thr Thr Tyr Tyr Arg
1               5                   10

<210> SEQ ID NO 520
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 520

Ser Gly Ile Ser Arg Asp Gly Gly Arg Thr Ser Tyr Ser
1               5                   10

<210> SEQ ID NO 521
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2
```

<400> SEQUENCE: 521

Ser Gly Ile Ser Trp Asn Ser Gly Asn Ile Gly Tyr Ala
1               5                   10

<210> SEQ ID NO 522
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 522

Ser Gly Ile Ser Trp Asn Ser Gly Ser Ile Gly Tyr Ala
1               5                   10

<210> SEQ ID NO 523
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 523

Ser Gly Ile Thr Gly Ser Gly Gly Arg Thr Phe Tyr Ala
1               5                   10

<210> SEQ ID NO 524
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 524

Ser Gly Val Gly Gly Ser Gly Gly Ser Thr Glx Tyr Ala
1               5                   10

<210> SEQ ID NO 525
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 525

Ser Gly Val Ser Trp Asn Gly Ser Arg Thr His Tyr Val
1               5                   10

<210> SEQ ID NO 526
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 526

Ser His Ile Ser Ser Gly Gly Ala Thr Ile Asp Tyr Ala
1               5                   10

<210> SEQ ID NO 527
<211> LENGTH: 13

```
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 527

Ser Leu Ile Ser Gly Ser Gly Asp Asn Thr Asn Tyr Ala
1               5                   10

<210> SEQ ID NO 528
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 528

Ser Leu Val Ser Phe Asp Gly Ser Lys Glu His Tyr Ala
1               5                   10

<210> SEQ ID NO 529
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 529

Ser Arg Ile Asp Thr Asp Gly Ser Thr Thr Val Tyr Ala
1               5                   10

<210> SEQ ID NO 530
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 530

Ser Arg Ile Asn Gly Asp Gly Ser Asn Thr Asn Tyr Ala
1               5                   10

<210> SEQ ID NO 531
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 531

Ser Arg Ile Asn Gly Asp Gly Ser Ser Thr Arg Tyr Ala
1               5                   10

<210> SEQ ID NO 532
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 532

Ser Arg Ile Asn Ser Asp Gly Ser Thr Ile Ser Tyr Ala
```

```
<210> SEQ ID NO 533
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 533

Ser Arg Ile Asn Tyr Asp Gly Ser Ala Thr Thr Tyr Ala
1               5                   10

<210> SEQ ID NO 534
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 534

Ser Arg Ile Ser Asn Ser Gly Ser Leu Val Tyr Tyr Ala
1               5                   10

<210> SEQ ID NO 535
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 535

Ser Arg Ile Ser Pro Asp Gly Arg Thr Thr Thr Tyr Ala
1               5                   10

<210> SEQ ID NO 536
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 536

Ser Ser Ile Asp Gly Asn Gly Asp His Val Phe Tyr Ala
1               5                   10

<210> SEQ ID NO 537
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 537

Ser Ser Ile Asn Asn Ser Ser Arg Thr Val Phe Tyr Ala
1               5                   10

<210> SEQ ID NO 538
<211> LENGTH: 13
<212> TYPE: PRT
<213> ORGANISM: Artificial Sequence
<220> FEATURE:
<223> OTHER INFORMATION: Synthesized molecular recognition unit - heavy
```

CDR2

<400> SEQUENCE: 538

Ser Ser Ile Ser Ala Ala Gly Ala Tyr Lys Tyr Tyr Ala
1               5                   10

<210> SEQ ID NO 539
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 539

Ser Ser Ile Ser Gly Gly Gly Arg His Thr Tyr Tyr Ala
1               5                   10

<210> SEQ ID NO 540
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 540

Ser Ser Ile Ser Gly Leu Gly Gly Ser Thr Tyr Glx Ala
1               5                   10

<210> SEQ ID NO 541
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 541

Ser Ser Ile Ser Ser Gly Asn Ser Tyr Ile Tyr Tyr Ala
1               5                   10

<210> SEQ ID NO 542
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 542

Ser Ser Ile Ser Ser Ser Ser His Tyr Lys Tyr Tyr Ala
1               5                   10

<210> SEQ ID NO 543
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 543

Ser Ser Ile Ser Ser Ser Ser Ser Tyr Ile Tyr Tyr Ala
1               5                   10

<210> SEQ ID NO 544

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 544

Ser Ser Ile Ser Thr Ser Gly Gly Ser Thr Tyr Tyr Ala
1               5                   10

<210> SEQ ID NO 545
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 545

Ser Ser Ile Ser Trp Asn Ser Gly Arg Val Asp Tyr Ala
1               5                   10

<210> SEQ ID NO 546
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 546

Ser Ser Ile Thr Arg Thr Pro Ser Gly Gly Thr Thr Glu Tyr Ala
1               5                   10                  15

<210> SEQ ID NO 547
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 547

Ser Ser Ile Thr Thr Thr Ser Thr Leu Tyr Ala
1               5                   10

<210> SEQ ID NO 548
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 548

Ser Ser Leu Ser Trp Asn Ser Gly Thr Ile Val Tyr Ala
1               5                   10

<210> SEQ ID NO 549
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 549
```

Ser Ser Thr Ser Gly Ser Gly Gly Asn Ser Lys Tyr Ser
1               5                   10

<210> SEQ ID NO 550
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 550

Ser Thr Ile Ala Gly Ser Gly Gly Arg Thr Tyr Tyr Ser
1               5                   10

<210> SEQ ID NO 551
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 551

Ser Thr Ile Gly Pro Ala Gly Asp Thr Tyr Tyr Pro
1               5                   10

<210> SEQ ID NO 552
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 552

Ser Thr Ile Gly Thr Gly Gly Thr Tyr Tyr Ala
1               5                   10

<210> SEQ ID NO 553
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 553

Ser Thr Ile Ser Gly Gly Gly Ser Thr Tyr Tyr Ala
1               5                   10

<210> SEQ ID NO 554
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 554

Ser Thr Ile Ser Gly Ser Gly Gly Ser Thr Tyr Tyr Ser
1               5                   10

<210> SEQ ID NO 555
<211> LENGTH: 13
<212> TYPE: PRT
<213> ORGANISM: Artificial Sequence
<220> FEATURE:

<223> OTHER INFORMATION: Synthesized molecular recognition unit - heavy
      CDR2

<400> SEQUENCE: 555

Ser Thr Ile Ser Gly Ser Gly Val Ser Thr Phe Tyr Ala
1               5                   10

<210> SEQ ID NO 556
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 556

Ser Thr Ile Ser Pro Ser Gly Leu Tyr Ile Tyr Gln Ala
1               5                   10

<210> SEQ ID NO 557
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 557

Ser Thr Ile Ser Ser Ser Gly Gly Arg Thr Phe Tyr Ala
1               5                   10

<210> SEQ ID NO 558
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 558

Ser Val Ile Ser Ser Gly Gly Ser Pro Tyr Tyr Ala
1               5                   10

<210> SEQ ID NO 559
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 559

Ser Val Ile Ser Thr Ser Gly Asp Thr Val Leu Tyr Thr
1               5                   10

<210> SEQ ID NO 560
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 560

Ser Val Ile Ser Thr Ser Gly Gly Thr Val Leu Tyr Thr
1               5                   10

```
<210> SEQ ID NO 561
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 561

Ser Val Ile Tyr Gly Gly Gly Asn Thr Asn Tyr Ala
1               5                   10

<210> SEQ ID NO 562
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 562

Ser Tyr Ile Glu Asn Asp Gly Ser Ile Thr Thr Tyr Ala
1               5                   10

<210> SEQ ID NO 563
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 563

Ser Tyr Ile Gly Thr Ser Asp Gly Thr Thr Tyr Tyr Ala
1               5                   10

<210> SEQ ID NO 564
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 564

Ser Tyr Ile Ser Ala Gly Asp Gly Phe Thr Tyr Tyr Ala
1               5                   10

<210> SEQ ID NO 565
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 565

Ser Tyr Ile Ser Gly Ala Gly Gly Ser Thr Glu Tyr Ala
1               5                   10

<210> SEQ ID NO 566
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 566
```

```
Ser Tyr Ile Ser Gly Asp Ser Gly Tyr Thr Asn Tyr Ala
1               5                   10
```

<210> SEQ ID NO 567
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 567

```
Ser Tyr Ile Ser Ser Gly Ser Tyr Thr Ile Tyr Tyr Ser
1               5                   10
```

<210> SEQ ID NO 568
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 568

```
Ser Tyr Ile Ser Ser Ser Gly Ser Ile Thr His Tyr Ala
1               5                   10
```

<210> SEQ ID NO 569
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 569

```
Ser Tyr Ile Ser Ser Ser Ser Ala Ile Tyr Tyr Ala
1               5                   10
```

<210> SEQ ID NO 570
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 570

```
Ser Tyr Ile Ser Ser Ser Ser Thr Ile Tyr Tyr Ala
1               5                   10
```

<210> SEQ ID NO 571
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 571

```
Ser Tyr Ile Ser Thr Ser Asp Gly Ser Thr Tyr Tyr Ala
1               5                   10
```

<210> SEQ ID NO 572
<211> LENGTH: 13
<212> TYPE: PRT
<213> ORGANISM: Artificial Sequence

```
<220> FEATURE:
<223> OTHER INFORMATION: Synthesized molecular recognition unit - heavy
      CDR2

<400> SEQUENCE: 572

Ser Tyr Ser Ser Gly Asn Ser Gly Tyr Thr Asn Tyr Ala
1               5                   10

<210> SEQ ID NO 573
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 573

Thr Val Ile Ser Gly Ser Gly Gly Ser Thr Tyr Tyr Ala
1               5                   10

<210> SEQ ID NO 574
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 574

Thr Val Ile Ser Gly Ser Gly Gly Ser Thr Tyr Tyr Ser
1               5                   10

<210> SEQ ID NO 575
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 575

Cys Ala Ala Ala Ser Ser Leu Thr Ser Thr Pro Tyr Asp Leu Trp
1               5                   10                  15

<210> SEQ ID NO 576
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 576

Cys Ala Ala Asp Arg Ser Pro Tyr Tyr Tyr Asp Ser Ser Gly Tyr Tyr
1               5                   10                  15

Pro Asp Ala Phe Asp Ile Trp
            20

<210> SEQ ID NO 577
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 577
```

Cys Ala Ala Gly Phe Pro Thr Val Phe Val Val Asp Gly Glu Tyr Asp
1               5                   10                  15

Tyr Trp

<210> SEQ ID NO 578
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 578

Cys Ala Ala Gly Pro Ile Ala Arg Trp Tyr Arg Gly Asp Met Asp Tyr
1               5                   10                  15

Trp

<210> SEQ ID NO 579
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 579

Cys Ala Ala Gly Pro Asn Tyr Ser Trp Phe Met Pro Ser Ser Ser Arg
1               5                   10                  15

Leu Ile Trp

<210> SEQ ID NO 580
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 580

Cys Ala Ala Gly Pro Thr Leu Pro Phe Arg Tyr Trp
1               5                   10

<210> SEQ ID NO 581
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 581

Cys Ala Ala Gly Val Thr Gly Ser Trp Arg Tyr Trp
1               5                   10

<210> SEQ ID NO 582
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 582

Cys Ala Ala Pro Asp Val Val Val Thr Ala Asp Gly Tyr Tyr Trp
1               5                   10                  15

<210> SEQ ID NO 583
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 583

Cys Ala Ala Pro Asp Tyr Trp
1               5

<210> SEQ ID NO 584
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 584

Cys Ala Ala Pro Gln Ser Pro Asn Met Tyr Ile Arg Thr Asp Gln Leu
1               5                   10                  15

Trp Trp Tyr Lys Tyr Trp
            20

<210> SEQ ID NO 585
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 585

Cys Ala Ala Gln Lys Pro Tyr Tyr Asn Gly His Phe Tyr Ala Asp Asp
1               5                   10                  15

Lys His Tyr Asp His Trp
            20

<210> SEQ ID NO 586
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 586

Cys Ala Ala Val Phe Leu Ser Arg Asn Tyr Glu Ile Gln Glu Tyr Tyr
1               5                   10                  15

Arg Tyr Gln

<210> SEQ ID NO 587
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 587

Cys Ala Asp Gly Ser Gly Thr Ser His Arg
1               5                   10

```
<210> SEQ ID NO 588
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 588

Cys Ala Glu Ser Leu Thr Ser Thr Ala Asp Trp
1               5                   10

<210> SEQ ID NO 589
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 589

Cys Ala Gly Gly Glu Val Tyr Glu Leu
1               5

<210> SEQ ID NO 590
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 590

Cys Ala His Ser Asp Phe Phe Ser Gly Leu Ser Phe Gly Asp Trp
1               5                   10                  15

<210> SEQ ID NO 591
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 591

Cys Ala Ile Arg Ala Phe Asp Ile Trp
1               5

<210> SEQ ID NO 592
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 592

Cys Ala Lys Ala Gly Asp Trp Gly Leu Tyr Gly Met Asp Val Trp
1               5                   10                  15

<210> SEQ ID NO 593
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 593
```

Cys Ala Lys Ala Gly Gln Gln Leu Asp Trp
1               5                   10

<210> SEQ ID NO 594
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 594

Cys Ala Lys Ala Ser Thr Pro Met Val Gln Gly Ala Pro Asp Tyr Trp
1               5                   10                  15

<210> SEQ ID NO 595
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 595

Cys Ala Lys Asp Gly Val Val Arg
1               5

<210> SEQ ID NO 596
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 596

Cys Ala Lys Asp Gly Tyr Trp
1               5

<210> SEQ ID NO 597
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 597

Cys Ala Lys Asp His Leu Ala Val Ala Asp Ala His Gly Arg
1               5                   10

<210> SEQ ID NO 598
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 598

Cys Ala Lys Asp Ile Gly Ser Ser Trp Tyr Tyr Tyr Met Asp Val Trp
1               5                   10                  15

<210> SEQ ID NO 599
<211> LENGTH: 17
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 599

Cys Ala Lys Asp Ile Thr Pro Tyr Gly Asp Tyr Ser Ile Leu Ser His
1               5                   10                  15

Trp

<210> SEQ ID NO 600
<211> LENGTH: 17
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 600

Cys Ala Lys Asp Lys Val Pro Tyr Ser Tyr Gly Pro Asn Phe Asp Tyr
1               5                   10                  15

Trp

<210> SEQ ID NO 601
<211> LENGTH: 16
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 601

Cys Ala Lys Asp Leu Val Pro Trp Gly Ser Ser Ala Phe Asn Ile Trp
1               5                   10                  15

<210> SEQ ID NO 602
<211> LENGTH: 19
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 602

Cys Ala Lys Asp Leu Val Pro Tyr Cys Ser Gly Gly Ser Cys Pro Pro
1               5                   10                  15

Ser Gly Trp

<210> SEQ ID NO 603
<211> LENGTH: 12
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 603

Cys Ala Lys Asp Asn Gly Trp Tyr Phe Asp Leu Trp
1               5                   10

<210> SEQ ID NO 604
<211> LENGTH: 15
<212> TYPE: PRT
<213> ORGANISM: Artificial Sequence
<220> FEATURE:
<223> OTHER INFORMATION: Synthesized molecular recognition unit - heavy CDR3

```
<400> SEQUENCE: 604

Cys Ala Lys Asp Arg Gly Asn Tyr Gly Asp Tyr Leu Asp Tyr Trp
1               5                   10                  15

<210> SEQ ID NO 605
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 605

Cys Ala Lys Asp Arg Gly Tyr Ser Ser Gly Trp Tyr Leu Asp Tyr Trp
1               5                   10                  15

<210> SEQ ID NO 606
<211> LENGTH: 25
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 606

Cys Ala Lys Asp Ser Ile Gly Arg Arg Gly Arg Gly Ala Pro Gln Pro
1               5                   10                  15

Tyr Tyr Tyr Tyr Gly Met Asp Val Trp
            20                  25

<210> SEQ ID NO 607
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 607

Cys Ala Lys Asp Val Asn Tyr Trp
1               5

<210> SEQ ID NO 608
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 608

Cys Ala Lys Gly Ala Gly Tyr Gly Ser Gly Ser Trp Gln Ala Ala Trp
1               5                   10                  15

<210> SEQ ID NO 609
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 609

Cys Ala Lys Gly Asp Tyr Gly Ala Leu Asp Tyr Trp
1               5                   10
```

<210> SEQ ID NO 610
<211> LENGTH: 14
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 610

Cys Ala Lys Gly Gly Gln Trp Leu Tyr Gly Met Asp Val Trp
1               5                   10

<210> SEQ ID NO 611
<211> LENGTH: 16
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 611

Cys Ala Lys Gly Gly Arg Asp Gly Tyr Lys Gly Tyr Phe Asp Tyr Trp
1               5                   10                  15

<210> SEQ ID NO 612
<211> LENGTH: 13
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 612

Cys Ala Lys Gly Gly Trp Arg Ser Ser Phe Asp Pro Trp
1               5                   10

<210> SEQ ID NO 613
<211> LENGTH: 11
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 613

Cys Ala Lys Gly Ile Arg Trp Phe Asp Pro Trp
1               5                   10

<210> SEQ ID NO 614
<211> LENGTH: 15
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 614

Cys Ala Lys Gly Ile Val Gly Asp Tyr Gly Ala Phe Asp Ile Trp
1               5                   10                  15

<210> SEQ ID NO 615
<211> LENGTH: 12
<212> TYPE: PRT
<213> ORGANISM: Artificial Sequence
<220> FEATURE:
<223> OTHER INFORMATION: Synthesized molecular recognition unit - heavy CDR3

```
<400> SEQUENCE: 615

Cys Ala Lys Gly Leu Trp Gly Pro Leu Leu Asn Trp
1               5                   10

<210> SEQ ID NO 616
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 616

Cys Ala Lys Gly Asn Trp Ala Phe Asp Ile Trp
1               5                   10

<210> SEQ ID NO 617
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 617

Cys Ala Lys Gly Ser Leu Leu Leu Gly Tyr Tyr Gly Met Asp Val Trp
1               5                   10                  15

<210> SEQ ID NO 618
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 618

Cys Ala Lys Gly Ser Val Phe Gly Leu Lys Ala Gly Gly Tyr Ala Asp
1               5                   10                  15

Tyr Trp

<210> SEQ ID NO 619
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 619

Cys Ala Lys Gly Ser Tyr Tyr Tyr Asp Asn Ser Gly Tyr Tyr Trp Asp
1               5                   10                  15

Ala Phe Asp Ile Trp
            20

<210> SEQ ID NO 620
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 620

Cys Ala Lys Gly Ser Tyr Tyr Tyr Asp Ser Ser Gly Tyr Tyr Trp Asp
1               5                   10                  15
```

Ala Phe Asp Ile Trp
            20

<210> SEQ ID NO 621
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 621

Cys Ala Lys Leu Gly Gly Ser Ser Trp Leu Arg Glu Tyr Asp Tyr Trp
1               5                   10                  15

<210> SEQ ID NO 622
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 622

Cys Ala Lys Pro Gly Ile Ala Ala Ala Gly Thr Asn Asn Trp Phe Asp
1               5                   10                  15

Pro Trp

<210> SEQ ID NO 623
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 623

Cys Ala Lys Thr Gly Arg Gly Tyr Ala Phe Asp Ile Trp
1               5                   10

<210> SEQ ID NO 624
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 624

Cys Ala Lys Thr Lys Leu Pro Ile Trp
1               5

<210> SEQ ID NO 625
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 625

Cys Ala Lys Thr Leu Val Thr Ser His Ala Leu His Ile Trp
1               5                   10

<210> SEQ ID NO 626
<211> LENGTH: 16

```
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 626

Cys Ala Lys Trp His Ile Gly Ala Thr Gly Asn Trp Phe Asp Pro Trp
1               5                   10                  15

<210> SEQ ID NO 627
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 627

Cys Ala Leu Leu Val Gly Ala Ala Arg Gly Ile Ser Tyr Tyr Tyr Tyr
1               5                   10                  15

Tyr Gly Met Asp Val Trp
            20

<210> SEQ ID NO 628
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 628

Cys Ala Leu Ser Ser Ser Trp Tyr Gly Gly Phe Asp Tyr Trp
1               5                   10

<210> SEQ ID NO 629
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 629

Cys Ala Asn Gly Ser Tyr Ala Gln His Leu Trp
1               5                   10

<210> SEQ ID NO 630
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 630

Cys Ala Pro Asn Glu Ser Gly Asn Val Asp Tyr Trp
1               5                   10

<210> SEQ ID NO 631
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 631

Cys Ala Pro Arg Val Leu Val Thr Ala Pro Ser Gly Gly Met Asp Tyr
1               5                   10                  15

Trp

<210> SEQ ID NO 632
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 632

Cys Ala Gln Gly Thr Tyr Trp
1               5

<210> SEQ ID NO 633
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 633

Cys Ala Arg Ala Ala Ala Gly Ser Tyr Gly Gly Gly Tyr Trp
1               5                   10

<210> SEQ ID NO 634
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 634

Cys Ala Arg Ala Ala Leu Gly Tyr Cys Thr Gly Gly Val Cys Pro Pro
1               5                   10                  15

Val Asp Tyr Trp
            20

<210> SEQ ID NO 635
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 635

Cys Ala Arg Ala Asp Asp Tyr Tyr Asp Ser Ser Gly Tyr Tyr Tyr Gly
1               5                   10                  15

Phe Asp Tyr Trp
            20

<210> SEQ ID NO 636
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 636
```

```
Cys Ala Arg Ala Gly Asp Ser Pro Asp Tyr Trp
1               5                   10
```

<210> SEQ ID NO 637
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 637

```
Cys Ala Arg Ala Gly Ser Gly Tyr Tyr Asn Phe Asp Tyr Trp
1               5                   10
```

<210> SEQ ID NO 638
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 638

```
Cys Ala Arg Ala Gly Val Ala Thr Ile Ala Phe Asp Tyr Trp
1               5                   10
```

<210> SEQ ID NO 639
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 639

```
Cys Ala Arg Ala Ile Pro Gly Asp Tyr Asp Tyr Trp
1               5                   10
```

<210> SEQ ID NO 640
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 640

```
Cys Ala Arg Ala Ile Val Gly Ala Thr Gly Leu Asn Arg Phe Lys Ala
1               5                   10                  15

Phe Asp Ile Trp
            20
```

<210> SEQ ID NO 641
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 641

```
Cys Ala Arg Ala Lys Gly Ser Gly Trp Tyr Val Gly Ser Ala Phe Asp
1               5                   10                  15

Ile Trp
```

<210> SEQ ID NO 642
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 642

Cys Ala Arg Ala Met Trp Ser Tyr Gly Gln Gln Asn Ala Phe Asp Ile
1               5                   10                  15

Trp

<210> SEQ ID NO 643
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 643

Cys Ala Arg Ala Pro Leu Asp Gly Ser Gly Ser Tyr Tyr Val Asp Trp
1               5                   10                  15

<210> SEQ ID NO 644
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 644

Cys Ala Arg Ala Pro Ser Tyr Ser Ser Gly Trp Tyr Val Arg Trp
1               5                   10                  15

<210> SEQ ID NO 645
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 645

Cys Ala Arg Ala Pro Tyr Tyr Tyr Gly Ser Gly Ser Leu Phe Arg Leu
1               5                   10                  15

Asp Tyr Trp

<210> SEQ ID NO 646
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 646

Cys Ala Arg Ala Arg Gly Gly Asp Ser Pro Leu Ser Leu
1               5                   10

<210> SEQ ID NO 647
<211> LENGTH: 19
<212> TYPE: PRT
<213> ORGANISM: Artificial Sequence

```
<220> FEATURE:
<223> OTHER INFORMATION: Synthesized molecular recognition unit - heavy
      CDR3

<400> SEQUENCE: 647

Cys Ala Arg Ala Arg Leu Leu Gly Gly Tyr Tyr Thr Pro Asp Arg Met
1               5                   10                  15

Asp Val Trp

<210> SEQ ID NO 648
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 648

Cys Ala Arg Ala Arg Ser Ser Gly Trp Thr Asp Ala Phe Asp Ile Trp
1               5                   10                  15

<210> SEQ ID NO 649
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 649

Cys Ala Arg Ala Ser Ala Trp Thr Pro Tyr Gly Ala Phe Asp Ile Trp
1               5                   10                  15

<210> SEQ ID NO 650
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 650

Cys Ala Arg Ala Ser Leu Tyr Tyr Asp Tyr Val Trp Gly Ser Tyr Arg
1               5                   10                  15

His Tyr Tyr Phe Asp Tyr Trp
            20

<210> SEQ ID NO 651
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 651

Cys Ala Arg Ala Ser Arg Ile Asp Gly Gly Trp Pro Ile Ile Asp His
1               5                   10                  15

Leu

<210> SEQ ID NO 652
<211> LENGTH: 18
<212> TYPE: PRT
<213> ORGANISM: Artificial Sequence
<220> FEATURE:
<223> OTHER INFORMATION: Synthesized molecular recognition unit - heavy
```

CDR3

<400> SEQUENCE: 652

Cys Ala Arg Ala Ser Ser Trp Tyr Leu His Tyr Tyr Gly Met Asp
1               5                   10                  15

Val Trp

<210> SEQ ID NO 653
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 653

Cys Ala Arg Ala Ser Thr Ser Gly Asp Tyr Ser Leu Trp
1               5                   10

<210> SEQ ID NO 654
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 654

Cys Ala Arg Ala Thr Gly Phe Gly Thr Val Val Phe Asp Tyr Trp
1               5                   10                  15

<210> SEQ ID NO 655
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 655

Cys Ala Arg Ala Thr Gln Glu Leu Leu Leu Pro Tyr Gly Met Asp Val
1               5                   10                  15

Trp

<210> SEQ ID NO 656
<211> LENGTH: 26
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 656

Cys Ala Arg Ala Thr Ser Leu Gly Arg Arg Tyr Cys Ser Ser Thr Ser
1               5                   10                  15

Cys Tyr Pro Arg Asp Ala Phe Asp Ile Trp
            20                  25

<210> SEQ ID NO 657
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

-continued

<400> SEQUENCE: 657

Cys Ala Arg Ala Thr Tyr Gly Gly Asp Ala Phe Asp Ile Trp
1               5                   10

<210> SEQ ID NO 658
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 658

Cys Ala Arg Ala Trp Lys Gly Leu Trp Phe Gly Glu Gly Thr Phe Asp
1               5                   10                  15

Tyr Trp

<210> SEQ ID NO 659
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 659

Cys Ala Arg Asp Ala Asp Ser Ser Gly Tyr Tyr Arg Tyr Asp Ala Phe
1               5                   10                  15

Asp Ile Trp

<210> SEQ ID NO 660
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 660

Cys Ala Arg Asp Ala Tyr Asn Trp Phe Asp Pro Arg
1               5                   10

<210> SEQ ID NO 661
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 661

Cys Ala Arg Asp Ala Tyr Asn Trp Phe Asp Pro Trp
1               5                   10

<210> SEQ ID NO 662
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 662

Cys Ala Arg Asp Cys Ser Gly Gly Ser Cys Tyr Ser His Phe Asp Tyr
1               5                   10                  15

Trp

<210> SEQ ID NO 663
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 663

Cys Ala Arg Asp Glu Gly Ala Gly Tyr Tyr Tyr Tyr Met Asp Val
1               5                   10                  15

Trp

<210> SEQ ID NO 664
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 664

Cys Ala Arg Asp Gly Gly Asp Tyr Gly Met Asp Val Trp
1               5                   10

<210> SEQ ID NO 665
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 665

Cys Ala Arg Asp Gly Gly Tyr Trp
1               5

<210> SEQ ID NO 666
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 666

Cys Ala Arg Asp Gly Ile Trp Asp Ile Phe Asp Tyr Trp
1               5                   10

<210> SEQ ID NO 667
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 667

Cys Ala Arg Asp Gly Ser Ser Gly Trp Tyr Ser Pro Asn Ala Phe Asp
1               5                   10                  15

Ile Trp

<210> SEQ ID NO 668
<211> LENGTH: 7

```
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 668

Cys Ala Arg Asp Gly Ser Trp
1               5

<210> SEQ ID NO 669
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 669

Cys Ala Arg Asp Gly Thr Pro Phe Tyr Ser Gly Ser Tyr Tyr Gly Ser
1               5                   10                  15

Trp

<210> SEQ ID NO 670
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 670

Cys Ala Arg Asp Gly Val Glu
1               5

<210> SEQ ID NO 671
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 671

Cys Ala Arg Asp His Gly Ser Ser Trp Tyr Gln Asn Thr Asp Ala Phe
1               5                   10                  15

Asp Ile Trp

<210> SEQ ID NO 672
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 672

Cys Ala Arg Asp Ile Thr Gly Ala Asp Gly Met Asp Val Trp
1               5                   10

<210> SEQ ID NO 673
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 673

Cys Ala Arg Asp Leu Asp Ser Gly Phe Asp Leu Trp
1               5                   10

<210> SEQ ID NO 674
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 674

Cys Ala Arg Asp Leu Met Val Gly Arg Asn Lys Leu Asp Tyr Trp
1               5                   10                  15

<210> SEQ ID NO 675
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 675

Cys Ala Arg Asp Leu Arg Phe Tyr Ser Ser Ser Trp Arg Arg Val Gly
1               5                   10                  15

Met Asp Val Trp
            20

<210> SEQ ID NO 676
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 676

Cys Ala Arg Asp Leu Ser Pro Met Val Arg Gly Val Ile Ser Gly Met
1               5                   10                  15

Asp Val Trp

<210> SEQ ID NO 677
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 677

Cys Ala Arg Asp Leu Thr Pro Phe Thr Gln Gln Gln Leu Val Leu Gly
1               5                   10                  15

Leu Leu

<210> SEQ ID NO 678
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 678
```

```
Cys Ala Arg Asp Leu Thr Tyr Tyr Asp Ser Ser Gly His Ser Pro
1               5                   10                  15

Leu Gly Ala Phe Asp Ile Trp
            20

<210> SEQ ID NO 679
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 679

Cys Ala Arg Asp Leu Val Ala Ala Arg Pro Ser Asn Trp Asp Tyr Trp
1               5                   10                  15

<210> SEQ ID NO 680
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 680

Cys Ala Arg Asp Asn Gly Tyr Cys Ser Gly Gly Ser Cys Tyr Ala Thr
1               5                   10                  15

Tyr Tyr Gly Met Asp Val Arg
            20

<210> SEQ ID NO 681
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 681

Cys Ala Arg Asp Pro Ile Met Phe Gly Asp Gln Pro Gly Trp Phe Asp
1               5                   10                  15

Pro Trp

<210> SEQ ID NO 682
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 682

Cys Ala Arg Asp Gln Asn Asp Ser Trp Tyr Arg Ser Asp Tyr Trp
1               5                   10                  15

<210> SEQ ID NO 683
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 683
```

```
Cys Ala Arg Asp Arg Asp Ile Val Val Val Pro Ala Gln Arg Gly Glu
1               5                   10                  15

Gly Gly Phe Asp Pro Trp
            20
```

<210> SEQ ID NO 684
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 684

```
Cys Ala Arg Asp Arg Asp Tyr Trp
1               5
```

<210> SEQ ID NO 685
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 685

```
Cys Ala Arg Asp Arg Phe Asp Asn Trp Phe Asp Pro Trp
1               5                   10
```

<210> SEQ ID NO 686
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 686

```
Cys Ala Arg Asp Arg Leu Ala Phe Asp Tyr Trp
1               5                   10
```

<210> SEQ ID NO 687
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 687

```
Cys Ala Arg Asp Arg Pro Gly Phe Asp Pro Trp
1               5                   10
```

<210> SEQ ID NO 688
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 688

```
Cys Ala Arg Asp Arg Pro Ser Ser Ser Trp Tyr Ala Phe Asp Tyr Trp
1               5                   10                  15
```

<210> SEQ ID NO 689
<211> LENGTH: 16

```
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 689

Cys Ala Arg Asp Arg Pro Thr Ser Ser Trp Tyr Ala Phe Asp Tyr Trp
1               5                   10                  15

<210> SEQ ID NO 690
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 690

Cys Ala Arg Asp Arg Pro Tyr Ser Ser Gly Trp Tyr Tyr Pro Ala Phe
1               5                   10                  15

Asp Ile Trp

<210> SEQ ID NO 691
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 691

Cys Ala Arg Asp Arg Gln Leu Gly Trp Ala His Trp Tyr Phe Asp Leu
1               5                   10                  15

Trp

<210> SEQ ID NO 692
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 692

Cys Ala Arg Asp Arg Arg Gly Tyr Gly Met Asp Val Trp
1               5                   10

<210> SEQ ID NO 693
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 693

Cys Ala Arg Asp Arg Val Thr Leu Arg Gly Tyr Ser Tyr Gly Thr
1               5                   10                  15

Asp Ala Phe Asp Ile Trp
            20

<210> SEQ ID NO 694
<211> LENGTH: 16
<212> TYPE: PRT
<213> ORGANISM: Artificial Sequence
```

```
<220> FEATURE:
<223> OTHER INFORMATION: Synthesized molecular recognition unit - heavy
      CDR3

<400> SEQUENCE: 694

Cys Ala Arg Asp Ser Asp Phe Trp Tyr Tyr Tyr Gly Met Asp Val Trp
1               5                   10                  15

<210> SEQ ID NO 695
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 695

Cys Ala Arg Asp Ser Ser Ser Gly Trp Tyr Ala Ser Tyr Tyr Gly Met
1               5                   10                  15

Asp Val Trp

<210> SEQ ID NO 696
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 696

Cys Ala Arg Asp Ser Ser Ser Trp Tyr Ser Tyr Tyr Tyr Tyr Met
1               5                   10                  15

Asp Val Trp

<210> SEQ ID NO 697
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 697

Cys Ala Arg Asp Ser Tyr Pro Tyr Gly Met Asp Val Trp
1               5                   10

<210> SEQ ID NO 698
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 698

Cys Ala Arg Asp Thr Cys Ser Ser Thr Ser Cys Ser Pro Asp Tyr Trp
1               5                   10                  15

<210> SEQ ID NO 699
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 699
```

```
Cys Ala Arg Asp Val Cys Ser Gly Gly Ser Cys Ser Pro Asp Val Trp
1               5                   10                  15

<210> SEQ ID NO 700
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 700

Cys Ala Arg Asp Val Met Asp Val Trp
1               5

<210> SEQ ID NO 701
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 701

Cys Ala Arg Asp Val Pro Lys Leu Val Thr Arg Gly Val Ala Tyr Gly
1               5                   10                  15

Met Asp Val Trp
            20

<210> SEQ ID NO 702
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 702

Cys Ala Arg Glu Ala Gly Thr Thr Gly Gly Trp Phe Asp Pro Trp
1               5                   10                  15

<210> SEQ ID NO 703
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 703

Cys Ala Arg Glu Ala Asn Tyr Asp Ile Leu Thr Gly Tyr Ile Arg Pro
1               5                   10                  15

Asp Ala Phe Asp Ile Trp
            20

<210> SEQ ID NO 704
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 704

Cys Ala Arg Glu Glu Trp Glu Leu Phe Gly Met Asp Val Trp
1               5                   10
```

<210> SEQ ID NO 705
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 705

Cys Ala Arg Glu Gly Arg Ser Arg Val Tyr Gly Gly Asn Ser Phe Asp
1               5                   10                  15

Tyr Trp

<210> SEQ ID NO 706
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 706

Cys Ala Arg Glu Gly Ser Tyr Tyr Asp Trp Tyr Phe Asp Leu Trp
1               5                   10                  15

<210> SEQ ID NO 707
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 707

Cys Ala Arg Glu Gly Trp Phe Gly Glu Ser Pro Phe Gly Met Asp Val
1               5                   10                  15

Trp

<210> SEQ ID NO 708
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 708

Cys Ala Arg Glu Gly Tyr Asp Phe Trp Ser Gly Pro Tyr Ala Phe Asp
1               5                   10                  15

Ile Trp

<210> SEQ ID NO 709
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 709

Cys Ala Arg Glu Leu Leu Pro Met Thr Thr Val Thr Ser Pro Phe Ile
1               5                   10                  15

Trp

<210> SEQ ID NO 710
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 710

Cys Ala Arg Glu Ser Val Asn Asn Tyr Tyr Tyr Met Asp Val Trp
1               5                   10                  15

<210> SEQ ID NO 711
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 711

Cys Ala Arg Glu Thr Thr Asp Tyr Tyr Tyr Gly Met Asp Val Trp
1               5                   10                  15

<210> SEQ ID NO 712
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 712

Cys Ala Arg Glu Tyr Leu Gly Ser Phe Asp Ile Trp
1               5                   10

<210> SEQ ID NO 713
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 713

Cys Ala Arg Phe Asp Tyr Phe Gly Gly Met Asp Val Trp
1               5                   10

<210> SEQ ID NO 714
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 714

Cys Ala Arg Phe Tyr Tyr Asp Ile Leu Asn Gly Tyr Ser Tyr Phe Asp
1               5                   10                  15

Tyr Trp

<210> SEQ ID NO 715
<211> LENGTH: 18
<212> TYPE: PRT
<213> ORGANISM: Artificial Sequence
<220> FEATURE:
<223> OTHER INFORMATION: Synthesized molecular recognition unit - heavy

CDR3

<400> SEQUENCE: 715

Cys Ala Arg Phe Tyr Tyr Asp Ile Leu Thr Gly Tyr Ser Tyr Phe Asp
1               5                   10                  15
Tyr Trp

<210> SEQ ID NO 716
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 716

Cys Ala Arg Gly Ala Leu Gly Met Asp Val Trp
1               5                   10

<210> SEQ ID NO 717
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 717

Cys Ala Arg Gly Ala Arg Leu Asp Tyr Trp
1               5                   10

<210> SEQ ID NO 718
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 718

Cys Ala Arg Gly Ala Arg Leu Tyr Gly Cys Asp Tyr Trp
1               5                   10

<210> SEQ ID NO 719
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 719

Cys Ala Arg Gly Ala Arg Leu Tyr Gly Phe Asp Tyr Trp
1               5                   10

<210> SEQ ID NO 720
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 720

Cys Ala Arg Gly Asp Ser Gly Ser Tyr Arg Asp Tyr Trp
1               5                   10

<210> SEQ ID NO 721
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 721

Cys Ala Arg Gly Asp Tyr Asp Phe Trp Ser Gly Tyr His Glu Tyr Tyr
1               5                   10                  15

Tyr Tyr Gly Met Asp Val Trp
            20

<210> SEQ ID NO 722
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 722

Cys Ala Arg Gly Phe Cys Ser Gly Gly Ser Cys Leu Trp Tyr Gly Met
1               5                   10                  15

Asp Val Trp

<210> SEQ ID NO 723
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 723

Cys Ala Arg Gly Gly Ala Gly Arg Phe Gly Glu Gly Met Asp Val Trp
1               5                   10                  15

<210> SEQ ID NO 724
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 724

Cys Ala Arg Gly Gly Glu Tyr Ser Ser Gly Trp Thr Tyr Tyr Tyr Tyr
1               5                   10                  15

Tyr Gly Met Asp Val Trp
            20

<210> SEQ ID NO 725
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 725

Cys Ala Arg Gly Gly Phe Val Phe Asp Tyr Trp
1               5                   10

```
<210> SEQ ID NO 726
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 726

Cys Ala Arg Gly Gly Gly Tyr Ser Ser Ser Trp
1               5                   10

<210> SEQ ID NO 727
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 727

Cys Ala Arg Gly Gly Leu Asp Gly Pro Ile Asp Tyr Arg
1               5                   10

<210> SEQ ID NO 728
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 728

Cys Ala Arg Gly Gly Leu Leu Phe Asp Tyr Trp
1               5                   10

<210> SEQ ID NO 729
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 729

Cys Ala Arg Gly Gly Leu Leu Arg Phe Gly Asp Gly Trp Gly Met Gly
1               5                   10                  15

Met Asp Val Trp
            20

<210> SEQ ID NO 730
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 730

Cys Ala Arg Gly Gly Asn Tyr Gly Ser Gly Asp Tyr Trp
1               5                   10

<210> SEQ ID NO 731
<211> LENGTH: 18
<212> TYPE: PRT
<213> ORGANISM: Artificial Sequence
<220> FEATURE:
<223> OTHER INFORMATION: Synthesized molecular recognition unit - heavy
```

```
                  CDR3

<400> SEQUENCE: 731

Cys Ala Arg Gly Gly Pro Ile His Tyr Tyr Tyr Tyr Tyr Met Asp
1               5                   10                  15

Val Trp

<210> SEQ ID NO 732
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 732

Cys Ala Arg Gly Gly Gln Gly Gly Tyr Asp Trp Gly His Tyr His Gly
1               5                   10                  15

Leu Asp Val Trp
            20

<210> SEQ ID NO 733
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 733

Cys Ala Arg Gly Gly Ser Gly Gly Asn Leu Ser Tyr Trp
1               5                   10

<210> SEQ ID NO 734
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 734

Cys Ala Arg Gly Gly Ser Arg Tyr Asp Phe Trp Ser Gly His Trp Tyr
1               5                   10                  15

Phe Asp Leu Trp
            20

<210> SEQ ID NO 735
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 735

Cys Ala Arg Gly Gly Ser Ser Asp Val Arg
1               5                   10

<210> SEQ ID NO 736
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3
```

<400> SEQUENCE: 736

Cys Ala Arg Gly Gly Ser Thr Gly Tyr Tyr Gly Met Asp Val Trp
1               5                   10                  15

<210> SEQ ID NO 737
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 737

Cys Ala Arg Gly Gly Trp Arg Pro Asp Tyr Tyr Gly Ser Gly Ser Tyr
1               5                   10                  15

Tyr Ser Phe Asp Tyr Trp
            20

<210> SEQ ID NO 738
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 738

Cys Ala Arg Gly Gly Trp Thr Asn Tyr Gly Gly Asn Leu Asp Tyr Trp
1               5                   10                  15

<210> SEQ ID NO 739
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 739

Cys Ala Arg Gly Gly Tyr Ser Tyr Gly Thr Val Phe Asp Tyr Trp
1               5                   10                  15

<210> SEQ ID NO 740
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 740

Cys Ala Arg Gly Gly Tyr Tyr Tyr Gly Met Asp Val Trp
1               5                   10

<210> SEQ ID NO 741
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 741

Cys Ala Arg Gly Lys Glu Gly Arg Tyr Ser Asn Tyr Glu Ala Ala Trp
1               5                   10                  15

<210> SEQ ID NO 742
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 742

Cys Ala Arg Gly Lys Gly Tyr Ser Tyr Gly Tyr Gly Lys Asp Trp Phe
1               5                   10                  15

Asp Pro Trp

<210> SEQ ID NO 743
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 743

Cys Ala Arg Gly Lys Ser Gly Ser Phe Asp Tyr Trp
1               5                   10

<210> SEQ ID NO 744
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 744

Cys Ala Arg Gly Leu Pro Pro Ala Ala Gly Gly Gly Gly Tyr Phe Gln
1               5                   10                  15

His Trp

<210> SEQ ID NO 745
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 745

Cys Ala Arg Gly Leu Arg Tyr Phe Asp Trp Pro Gln Gly Ile Tyr Tyr
1               5                   10                  15

Tyr Tyr Gly Met Asp Val Trp
                20

<210> SEQ ID NO 746
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 746

Cys Ala Arg Gly Leu Val Ile Ala Thr Asn Trp Phe Asp Pro Trp
1               5                   10                  15

<210> SEQ ID NO 747

```
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 747

Cys Ala Arg Gly Asn Pro Thr Ser Gly His Ile Val Val Pro Ala
1               5                   10                  15

Ala Thr Phe Ser Asp Tyr Trp
            20

<210> SEQ ID NO 748
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 748

Cys Ala Arg Gly Pro Lys Thr Met Trp Glu Asp Arg Pro Asp Tyr Trp
1               5                   10                  15

<210> SEQ ID NO 749
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 749

Cys Ala Arg Gly Pro Leu Pro Thr Lys Ile Gly Gly His Tyr Met Asp
1               5                   10                  15

Val Trp

<210> SEQ ID NO 750
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 750

Cys Ala Arg Gly Pro Arg Asp Ser Gly Tyr Tyr Pro Gly Gly Ala Phe
1               5                   10                  15

Asp Ile Trp

<210> SEQ ID NO 751
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 751

Cys Ala Arg Gly Pro Ser His Gln His Thr Phe Asp Ile Trp
1               5                   10

<210> SEQ ID NO 752
<211> LENGTH: 20
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 752

Cys Ala Arg Gly Gln Gly Tyr Ser Ser Gly Trp Tyr Arg Gly Asp Ala
1               5                   10                  15

Phe Asp Ile Trp
            20

<210> SEQ ID NO 753
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 753

Cys Ala Arg Gly Gln Ser Glu Lys Trp Trp Ser Gly Leu Tyr Gly Met
1               5                   10                  15

Asp Val Trp

<210> SEQ ID NO 754
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 754

Cys Ala Arg Gly Arg Gly Gln Gln Trp Leu Thr Gly Tyr Tyr Gly Met
1               5                   10                  15

Asp Val Trp

<210> SEQ ID NO 755
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 755

Cys Ala Arg Gly Arg Arg Leu Val Arg Phe Thr Val Thr Ser Ala Phe
1               5                   10                  15

Asp Ile Trp

<210> SEQ ID NO 756
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 756

Cys Ala Arg Gly Arg Val Trp Ser Ser Arg Asp Tyr Trp
1               5                   10

<210> SEQ ID NO 757
<211> LENGTH: 14
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 757

Cys Ala Arg Gly Ser Gly Ile Ala Ala Ser Gly Ser Tyr Trp
1               5                   10

<210> SEQ ID NO 758
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 758

Cys Ala Arg Gly Ser Gly Tyr Asp Phe Phe Asp Tyr Gly Met Asp Val
1               5                   10                  15

Trp

<210> SEQ ID NO 759
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 759

Cys Ala Arg Gly Ser Ser Gly Tyr Tyr Val Ala Trp
1               5                   10

<210> SEQ ID NO 760
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 760

Cys Ala Arg Gly Ser Ser Ser Trp Tyr Asp Trp
1               5                   10

<210> SEQ ID NO 761
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 761

Cys Ala Arg Gly Ser Tyr Trp
1               5

<210> SEQ ID NO 762
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 762
```

-continued

Cys Ala Arg Gly Thr Phe Asp Trp Leu Leu Ser Pro Ser Tyr Asp Tyr
1               5                   10                  15

Trp

<210> SEQ ID NO 763
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 763

Cys Ala Arg Gly Thr Phe Leu Glu Trp Leu Leu Thr Asn Tyr Gly Met
1               5                   10                  15

Asp Val Trp

<210> SEQ ID NO 764
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 764

Cys Ala Arg Gly Thr Gly Gly Phe Asp Tyr Trp
1               5                   10

<210> SEQ ID NO 765
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 765

Cys Ala Arg Gly Val Val Gly Ser Gly Ala Phe Asp Ile Trp
1               5                   10

<210> SEQ ID NO 766
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 766

Cys Ala Arg Gly Val Trp Thr Thr Pro Met Gly Gly Gly Gly Asn Trp
1               5                   10                  15

Phe Asp Pro Trp
            20

<210> SEQ ID NO 767
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 767

Cys Ala Arg Gly Val Tyr Pro Tyr Ser Ser Lys His Lys Pro Ser Tyr
1               5                   10                  15

Tyr Tyr Tyr Gly Met Asp Val Trp
            20

<210> SEQ ID NO 768
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 768

Cys Ala Arg Gly Trp Ala Gly Phe Asp Tyr Trp
1               5                   10

<210> SEQ ID NO 769
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 769

Cys Ala Arg Gly Trp Thr Thr Ile Ser Ser Leu Gly Val Trp
1               5                   10

<210> SEQ ID NO 770
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 770

Cys Ala Arg Gly Tyr Gly Asp Tyr Val Trp Gly Glu Asn Tyr Phe Asp
1               5                   10                  15

Tyr Trp

<210> SEQ ID NO 771
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 771

Cys Ala Arg Gly Tyr Tyr Tyr Gly Met Asp Val Trp
1               5                   10

<210> SEQ ID NO 772
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 772

Cys Ala Arg His Ala Gly Phe Tyr Gly Leu Ala Asp Tyr Phe Asp Tyr
1               5                   10                  15

Trp

```
<210> SEQ ID NO 773
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 773

Cys Ala Arg His Gly Arg Ile Ala Ala Asp Ile Trp
1               5                   10

<210> SEQ ID NO 774
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 774

Cys Ala Arg His Asn Pro Gly Tyr Met Gly Tyr Tyr Gly Met Asp
1               5                   10                  15

Val Trp

<210> SEQ ID NO 775
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 775

Cys Ala Arg His Val Tyr Gly Ser Gly Thr Tyr Asn Asn Trp Phe Asp
1               5                   10                  15

Pro Trp

<210> SEQ ID NO 776
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 776

Cys Ala Arg His Tyr Tyr Gly Ser Gly Asn Tyr Arg Asp Trp
1               5                   10

<210> SEQ ID NO 777
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 777

Cys Ala Arg His Tyr Tyr Gly Ser Gly Ser Tyr Pro Asp Trp
1               5                   10

<210> SEQ ID NO 778
<211> LENGTH: 13
<212> TYPE: PRT
<213> ORGANISM: Artificial Sequence
<220> FEATURE:
```

```
<223> OTHER INFORMATION: Synthesized molecular recognition unit - heavy
      CDR3

<400> SEQUENCE: 778

Cys Ala Arg Ile Gly Ala Gly Gly Ala Phe Asp Ile Trp
1               5                   10

<210> SEQ ID NO 779
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 779

Cys Ala Arg Ile Gly Ile Ala Val Ala Ala Pro Val Asp His Trp
1               5                   10                  15

<210> SEQ ID NO 780
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 780

Cys Ala Arg Ile Pro Lys Pro Arg Gly Tyr Ser Tyr Gly Asp Asn Gly
1               5                   10                  15

Ser Trp

<210> SEQ ID NO 781
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 781

Cys Ala Arg Lys Val Lys Gly Tyr Cys Ser Gly Gly Ser Cys Tyr Gly
1               5                   10                  15

Tyr Trp

<210> SEQ ID NO 782
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 782

Cys Ala Arg Leu Ala Phe Asp Ile Trp
1               5

<210> SEQ ID NO 783
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 783
```

Cys Ala Arg Leu Asp Pro Gly Tyr Tyr Tyr Gly Met Asp Val Trp
1               5                   10                  15

<210> SEQ ID NO 784
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 784

Cys Ala Arg Leu Gly Ser Thr Pro Asp Tyr Trp
1               5                   10

<210> SEQ ID NO 785
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 785

Cys Ala Arg Leu Pro Arg Arg Ser Gly Lys Gly Ser Ala Phe Asp Ile
1               5                   10                  15

Trp

<210> SEQ ID NO 786
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 786

Cys Ala Arg Leu Pro Tyr Tyr Asp Phe Trp Ser Gly Tyr Tyr Gly Gly
1               5                   10                  15

Arg Thr Gly Phe Asp Tyr Trp
            20

<210> SEQ ID NO 787
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 787

Cys Ala Arg Leu Ser Val Trp Lys Trp Glu Gln Val Thr Asn Trp Phe
1               5                   10                  15

Asp Pro Trp

<210> SEQ ID NO 788
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 788

Cys Ala Arg Leu Ser Tyr Tyr Asp Ser Ser Gly Pro Lys Gly Asp
1               5                   10                  15

Ala Phe Asp Ile Trp
            20

<210> SEQ ID NO 789
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 789

Cys Ala Arg Leu Thr Gly Gly Ala Val Ala Gly Thr His Arg Asp Tyr
1               5                   10                  15

Trp

<210> SEQ ID NO 790
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 790

Cys Ala Arg Leu Val Val Arg Gly Gly Tyr Gly Met Asp Val Trp
1               5                   10                  15

<210> SEQ ID NO 791
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 791

Cys Ala Arg Met Lys Asp Trp Phe Gly Ala Phe Asp Ile Trp
1               5                   10

<210> SEQ ID NO 792
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 792

Cys Ala Arg Met Ser Ser Asp Tyr Tyr Asp Ser Ser Gly Tyr Tyr Arg
1               5                   10                  15

Arg Gly Met Asp Val Trp
            20

<210> SEQ ID NO 793
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 793

Cys Ala Arg Asn Gly Ile Ala Ala Ala Glu Asp Tyr Trp
1               5                   10

<210> SEQ ID NO 794
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 794

Cys Ala Arg Asn Asn Phe Leu Arg Ala Phe Asp Ile Trp
1               5                   10

<210> SEQ ID NO 795
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 795

Cys Ala Arg Asn Val Glu Gly Ala Thr Ser Phe Pro Glu Phe Asp Tyr
1               5                   10                  15

Trp

<210> SEQ ID NO 796
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 796

Cys Ala Arg Pro Ala Gly Ser Ala Gln Asn Trp Phe Asp Pro Trp
1               5                   10                  15

<210> SEQ ID NO 797
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 797

Cys Ala Arg Pro Ile Val Gly Ala Thr Ala Phe Asp Ile Trp
1               5                   10

<210> SEQ ID NO 798
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 798

Cys Ala Arg Pro Ser Thr Thr Gly Thr Lys Ala Phe Asp Ile Trp
1               5                   10                  15

<210> SEQ ID NO 799
<211> LENGTH: 14
<212> TYPE: PRT
<213> ORGANISM: Artificial Sequence
<220> FEATURE:
<223> OTHER INFORMATION: Synthesized molecular recognition unit - heavy

```
                          CDR3

<400> SEQUENCE: 799

Cys Ala Arg Pro Ser Thr Thr Ser Phe Gly Met Asp Val Trp
1               5                   10

<210> SEQ ID NO 800
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 800

Cys Ala Arg Pro Tyr Ser Ser Ser Arg Gln Gly Asp Tyr Trp
1               5                   10

<210> SEQ ID NO 801
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 801

Cys Ala Arg Pro Tyr Tyr Tyr Asp Ser Ser Gly Tyr Asp Pro Met Gly
1               5                   10                  15

Asp Tyr Trp

<210> SEQ ID NO 802
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 802

Cys Ala Arg Gln Ala Gly Leu His Cys Ser Ser Thr Ser Cys Tyr Leu
1               5                   10                  15

Gly Asn Trp Phe Asp Pro Trp
            20

<210> SEQ ID NO 803
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 803

Cys Ala Arg Gln Ile Gly Trp Glu Leu Met Pro Asp Ile Trp
1               5                   10

<210> SEQ ID NO 804
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 804
```

Cys Ala Arg Gln Thr Arg Gly Gly Thr Thr Asp Gly Trp
1               5                   10

<210> SEQ ID NO 805
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 805

Cys Ala Arg Gln Tyr Cys Ser Gly Gly Ser Cys Tyr Pro Asp Ala Phe
1               5                   10                  15

Asp Ile Arg

<210> SEQ ID NO 806
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 806

Cys Ala Arg Gln Tyr Tyr Phe Asp Tyr Trp
1               5                   10

<210> SEQ ID NO 807
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 807

Cys Ala Arg Arg Glu Pro Leu Tyr Ser Ser Arg Arg Gly Ala Phe Asp
1               5                   10                  15

Ile Trp

<210> SEQ ID NO 808
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 808

Cys Ala Arg Arg Gly Tyr Ser Ser Gly Trp Arg Asp Ala Phe Asp Ile
1               5                   10                  15

Trp

<210> SEQ ID NO 809
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 809

Cys Ala Arg Arg Leu Ile Ala Val Ala Gly Ala Glu Phe Asp Pro Trp
1               5                   10                  15

<210> SEQ ID NO 810
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 810

Cys Ala Arg Arg Ser Gly Tyr Ser Gly Ser Val Tyr Tyr Tyr Gly
1               5                   10                  15
Met Asp Val Trp
            20

<210> SEQ ID NO 811
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 811

Cys Ala Arg Arg Thr Ala Val Ala Gly Thr Ile Asp Tyr Trp
1               5                   10

<210> SEQ ID NO 812
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 812

Cys Ala Arg Arg Thr Ser Ala Ser Asp Ile Trp
1               5                   10

<210> SEQ ID NO 813
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 813

Cys Ala Arg Ser Ala Val Ala Gly Ala Phe Asp Ile Trp
1               5                   10

<210> SEQ ID NO 814
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 814

Cys Ala Arg Ser Gly Met Val Lys Trp Leu Arg Ser Phe Asp Tyr Trp
1               5                   10                  15

<210> SEQ ID NO 815
<211> LENGTH: 19
<212> TYPE: PRT
<213> ORGANISM: Artificial Sequence
<220> FEATURE:

<223> OTHER INFORMATION: Synthesized molecular recognition unit - heavy
     CDR3

<400> SEQUENCE: 815

Cys Ala Arg Ser Gly Pro Ala Ala Met Val Tyr Tyr Tyr Gly Met
1               5                   10                  15

Asp Val Trp

<210> SEQ ID NO 816
<211> LENGTH: 15
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 816

Cys Ala Arg Ser Gly Tyr Asn Arg Arg Gly Tyr Phe Asp Tyr Trp
1               5                   10                  15

<210> SEQ ID NO 817
<211> LENGTH: 14
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 817

Cys Ala Arg Ser Pro Arg Trp Tyr Asp Ala Phe Asp Ile Trp
1               5                   10

<210> SEQ ID NO 818
<211> LENGTH: 14
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 818

Cys Ala Arg Ser Gln Ala Thr Gly Glu Arg Phe Asp Tyr Trp
1               5                   10

<210> SEQ ID NO 819
<211> LENGTH: 13
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 819

Cys Ala Arg Ser Ser Asp Leu Arg Ile Phe Asp Tyr Trp
1               5                   10

<210> SEQ ID NO 820
<211> LENGTH: 16
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 820

Cys Ala Arg Ser Ser Gly Trp Gln Asn Arg Phe Ala Phe Asp Ile Trp
1               5                   10                  15

```
<210> SEQ ID NO 821
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 821

Cys Ala Arg Ser Ser Gly Tyr Val Gly Trp Phe Asp Pro Trp
1               5                   10

<210> SEQ ID NO 822
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 822

Cys Ala Arg Ser Thr Pro Phe Asp Pro Trp
1               5                   10

<210> SEQ ID NO 823
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 823

Cys Ala Arg Ser Val Gly Glu Val Gly Ala Thr Met Leu Gly Ile Gly
1               5                   10                  15

Val Trp Tyr Trp Phe Asp Pro Trp
            20

<210> SEQ ID NO 824
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 824

Cys Ala Arg Ser Tyr Tyr Asp Ser Ser Gly Tyr Pro Arg Lys Asp Ala
1               5                   10                  15

Phe Asp Ile Trp
            20

<210> SEQ ID NO 825
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 825

Cys Ala Arg Thr Gly Arg Gly Tyr Tyr Gly Met Asp Val Trp
1               5                   10

<210> SEQ ID NO 826
```

```
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 826

Cys Ala Arg Thr Leu Thr Thr Pro Pro Tyr Tyr Tyr Gly Met Asp Val
1               5                   10                  15

Trp

<210> SEQ ID NO 827
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 827

Cys Ala Arg Thr Tyr Leu Lys Ala Phe Asp Ile Trp
1               5                   10

<210> SEQ ID NO 828
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 828

Cys Ala Arg Thr Tyr Arg Ile Val Gly Ala Thr Pro Arg Tyr Tyr Tyr
1               5                   10                  15

Tyr Gly Met Asp Val Trp
            20

<210> SEQ ID NO 829
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 829

Cys Ala Arg Val Ala Thr Gly Asn Ala Phe Asp Ile Trp
1               5                   10

<210> SEQ ID NO 830
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 830

Cys Ala Arg Val Asp Gly Ser Gly Tyr Tyr Gly Ile Asp Tyr Trp
1               5                   10                  15

<210> SEQ ID NO 831
<211> LENGTH: 11
<212> TYPE: PRT
<213> ORGANISM: Artificial Sequence
<220> FEATURE:
```

```
<223> OTHER INFORMATION: Synthesized molecular recognition unit - heavy
     CDR3

<400> SEQUENCE: 831

Cys Ala Arg Val Phe Pro Leu His Asp Tyr Trp
1               5                   10

<210> SEQ ID NO 832
<211> LENGTH: 15
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 832

Cys Ala Arg Val Gly Ala Thr Ser Ala Gly Gly Met Asp Val Trp
1               5                   10                  15

<210> SEQ ID NO 833
<211> LENGTH: 13
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 833

Cys Ala Arg Val Gly Pro Gly Gly Trp Phe Asp Pro Trp
1               5                   10

<210> SEQ ID NO 834
<211> LENGTH: 13
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 834

Cys Ala Arg Val Gly Arg Gly Tyr Ser Phe Asp Tyr Trp
1               5                   10

<210> SEQ ID NO 835
<211> LENGTH: 13
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 835

Cys Ala Arg Val Gly Trp Leu Arg Phe Leu Asp Tyr Trp
1               5                   10

<210> SEQ ID NO 836
<211> LENGTH: 16
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 836

Cys Ala Arg Val Ile Phe Ser Thr Val Thr Thr Thr Asn Asp Ile Trp
1               5                   10                  15
```

```
<210> SEQ ID NO 837
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 837

Cys Ala Arg Val Lys Trp Glu Leu Ala Ile Asp Tyr Trp
1               5                   10

<210> SEQ ID NO 838
<211> LENGTH: 25
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 838

Cys Ala Arg Val Leu Pro Gly Asp Ser Ser Gly Trp Tyr Arg Gly Tyr
1               5                   10                  15

Tyr Tyr Tyr Tyr Gly Met Asp Val Trp
            20                  25

<210> SEQ ID NO 839
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 839

Cys Ala Arg Val Met Leu Ile Thr Asp Ala Phe Asp Ile Trp
1               5                   10

<210> SEQ ID NO 840
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 840

Cys Ala Arg Val Pro Asp Phe Trp Ser Gly Tyr Leu Asp Tyr Trp
1               5                   10                  15

<210> SEQ ID NO 841
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 841

Cys Ala Arg Val Pro Thr Ser Pro Tyr Asp Ile Leu Thr Gly Pro Phe
1               5                   10                  15

Asp Tyr Trp

<210> SEQ ID NO 842
<211> LENGTH: 20
<212> TYPE: PRT
<213> ORGANISM: Artificial Sequence
```

<220> FEATURE:
<223> OTHER INFORMATION: Synthesized molecular recognition unit - heavy CDR3

<400> SEQUENCE: 842

Cys Ala Arg Val Arg Ala Arg Arg Phe Leu Val Ser Asp Arg Ser Ala
1               5                   10                  15

Phe Asp Ile Trp
            20

<210> SEQ ID NO 843
<211> LENGTH: 21
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 843

Cys Ala Arg Val Arg Asp Tyr Tyr Asp Ser Ser Gly Tyr Tyr Tyr Asp
1               5                   10                  15

Tyr Phe Asp Tyr Trp
            20

<210> SEQ ID NO 844
<211> LENGTH: 21
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 844

Cys Ala Arg Val Arg Ser Lys Ala Val Ala Gly Thr Leu Pro Lys Arg
1               5                   10                  15

Leu Phe Asp Ile Trp
            20

<210> SEQ ID NO 845
<211> LENGTH: 13
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 845

Cys Ala Arg Val Ser Arg Gly Phe Ala Phe Asp Tyr Trp
1               5                   10

<210> SEQ ID NO 846
<211> LENGTH: 16
<212> TYPE: PRT
<213> ORGANISM: Artificial Sequence
<220> FEATURE:
<223> OTHER INFORMATION: Synthesized molecular recognition unit - heavy CDR3

<400> SEQUENCE: 846

Cys Ala Arg Val Thr Leu Gly Ala Ser Val Asp Ala Phe Asp Ile Trp
1               5                   10                  15

<210> SEQ ID NO 847
<211> LENGTH: 15
<212> TYPE: PRT
<213> ORGANISM: Artificial Sequence

```
<220> FEATURE:
<223> OTHER INFORMATION: Synthesized molecular recognition unit - heavy
      CDR3

<400> SEQUENCE: 847

Cys Ala Arg Trp Ala Phe Pro Ile Pro Asn Ala Phe Asp Ile Trp
1               5                   10                  15

<210> SEQ ID NO 848
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 848

Cys Ala Arg Trp Gly Asp Tyr Gly Asp Leu Tyr Tyr Phe Asp Tyr Trp
1               5                   10                  15

<210> SEQ ID NO 849
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 849

Cys Ala Arg Trp Gly Lys Arg Leu Arg Gly Ser Pro Tyr Tyr Phe Asp
1               5                   10                  15

Tyr Trp

<210> SEQ ID NO 850
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 850

Cys Ala Arg Trp Lys Asn Tyr Phe Asp Pro Trp
1               5                   10

<210> SEQ ID NO 851
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 851

Cys Ala Arg Tyr Gly Asp Tyr Gly Asp Tyr Trp
1               5                   10

<210> SEQ ID NO 852
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 852

Cys Ala Arg Tyr Ser Ser Gly Gly Ser Leu Asp Tyr Trp
```

<210> SEQ ID NO 853
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 853

Cys Ala Ser Asp Pro Val Thr Ala Ala Thr Arg
1               5                   10

<210> SEQ ID NO 854
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 854

Cys Ala Ser Gly Leu Gly Tyr Phe Asp Tyr Trp
1               5                   10

<210> SEQ ID NO 855
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 855

Cys Ala Ser Lys Thr Thr Ile Asn Ser Gly Trp Ser Arg Glu Tyr His
1               5                   10                  15

Tyr Trp

<210> SEQ ID NO 856
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 856

Cys Ala Ser Pro Thr Gly Met Thr Thr Asn Phe Asp Tyr Trp
1               5                   10

<210> SEQ ID NO 857
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 857

Cys Ala Ser Pro Thr Val Thr Arg Arg
1               5

<210> SEQ ID NO 858
<211> LENGTH: 18
<212> TYPE: PRT
<213> ORGANISM: Artificial Sequence

```
<220> FEATURE:
<223> OTHER INFORMATION: Synthesized molecular recognition unit - heavy
      CDR3

<400> SEQUENCE: 858

Cys Ala Ser Gln Asn Tyr Tyr Gly Ser Gly Ser Tyr Pro Gly Phe Asp
1               5                   10                  15

Tyr Trp

<210> SEQ ID NO 859
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 859

Cys Ala Ser Ser His Tyr Ala Pro Gly Met Asp Val Trp
1               5                   10

<210> SEQ ID NO 860
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 860

Cys Ala Ser Ser Lys Glu Lys Ala Thr Tyr Tyr Tyr Gly Met Asp Val
1               5                   10                  15

Trp

<210> SEQ ID NO 861
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 861

Cys Ala Ser Ser Met Val Arg Val Pro Tyr Tyr Tyr Gly Met Asp Val
1               5                   10                  15

Trp

<210> SEQ ID NO 862
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 862

Cys Ala Ser Ser Arg Asp Gly Tyr Asn Arg Leu Ala Phe Asp Ile Trp
1               5                   10                  15

<210> SEQ ID NO 863
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 863

Cys Ala Ser Ser Ser Asp Tyr Gly Asp Tyr Leu Lys Glu Pro Asn Tyr
1               5                   10                  15

Gly Met Asp Val Trp
            20

<210> SEQ ID NO 864
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 864

Cys Ala Ser Thr Asp Pro Ser Ser Gly Leu Asp Tyr Trp
1               5                   10

<210> SEQ ID NO 865
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 865

Cys Ala Thr Ala Ser Gly Asp Phe Asp Tyr Trp
1               5                   10

<210> SEQ ID NO 866
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 866

Cys Ala Thr Ala Tyr Arg Arg Pro Gly Gly Leu Asp Val Trp
1               5                   10

<210> SEQ ID NO 867
<211> LENGTH: 26
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 867

Cys Ala Thr Asp Leu Pro Val Arg Lys Gly Phe Thr Tyr Tyr Asp Ile
1               5                   10                  15

Leu Thr Gly Ser Tyr Gly Met Asp Val Trp
            20                  25

<210> SEQ ID NO 868
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 868
```

-continued

Cys Ala Thr Gly Trp Pro Arg Tyr Tyr Tyr Gly Met Asp Val Trp
1               5                   10                  15

<210> SEQ ID NO 869
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 869

Cys Ala Thr Gly Tyr Tyr Tyr Asp Tyr Tyr Phe Asp Tyr Trp
1               5                   10

<210> SEQ ID NO 870
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 870

Cys Ala Thr His Asp Ser Ser Gly Tyr Tyr Ser Phe Asp Tyr Trp
1               5                   10                  15

<210> SEQ ID NO 871
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 871

Cys Ala Thr Leu Thr Pro Tyr Gly Thr Val Ala Ser Tyr
1               5                   10

<210> SEQ ID NO 872
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 872

Cys Ala Thr Ser Phe Gly Gly Gly Trp Ile Val Val Asp Thr Ser Leu
1               5                   10                  15

Trp Tyr Trp

<210> SEQ ID NO 873
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 873

Cys Ala Thr Thr Gln Gly Val Tyr Ser Ser Ser Trp Tyr Gly Gly Gly
1               5                   10                  15

Arg Ala Phe Asp Ile Trp
            20

```
<210> SEQ ID NO 874
<211> LENGTH: 25
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 874

Cys Ala Thr Val Gln Thr Asn Tyr Tyr Asp Ser Ser Gly Arg Phe Ser
1               5                   10                  15

Tyr Arg Ala His Tyr Phe Asp Tyr Trp
            20                  25

<210> SEQ ID NO 875
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 875

Cys Ala Thr Tyr Gly Asp Phe Gly Tyr Phe Asp Leu Trp
1               5                   10

<210> SEQ ID NO 876
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 876

Cys Glu Val His Asn Phe Gly Ala Thr Tyr Trp
1               5                   10

<210> SEQ ID NO 877
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 877

Cys His Phe Gly Val Ala Ser Val Gly Leu Asn Tyr Trp
1               5                   10

<210> SEQ ID NO 878
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 878

Cys Ile Gly Val Thr Tyr Asn Gly Tyr Thr Ile Gly
1               5                   10

<210> SEQ ID NO 879
<211> LENGTH: 11
<212> TYPE: PRT
<213> ORGANISM: Artificial Sequence
<220> FEATURE:
<223> OTHER INFORMATION: Synthesized molecular recognition unit - heavy
```

CDR3

<400> SEQUENCE: 879

Cys Lys Val His Asn Phe Glu Ala Thr Tyr Trp
1               5                   10

<210> SEQ ID NO 880
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 880

Cys Lys Val His Asn Phe Gly Ala Thr Tyr Trp
1               5                   10

<210> SEQ ID NO 881
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 881

Cys Asn Ala Asp Ser Leu Arg Gly Ile Asp Tyr Trp
1               5                   10

<210> SEQ ID NO 882
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 882

Cys Asn Ala Asp Tyr Gly Thr Trp Tyr Gly Ile Gly Trp
1               5                   10

<210> SEQ ID NO 883
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 883

Cys Asn Ala Gly Ala Pro Ala Trp Thr Tyr Arg Met Gly Thr Tyr Tyr
1               5                   10                  15

Pro Gln Phe Gly Ser Trp
            20

<210> SEQ ID NO 884
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 884

Cys Asn Ala Leu Ala Pro Gly Val Arg Gly Ser Trp
1               5                   10

```
<210> SEQ ID NO 885
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 885

Cys Asn Ala Arg Leu Asp Ala Val Tyr Gly His Ser Arg Tyr Asp Ser
1               5                   10                  15

Trp

<210> SEQ ID NO 886
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 886

Cys Asn Ala Arg Leu Ser Phe Ala Gly Gly Met Gly Tyr Trp
1               5                   10

<210> SEQ ID NO 887
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 887

Cys Asn Ala Val Cys Lys Phe Gly Thr Thr His Trp
1               5                   10

<210> SEQ ID NO 888
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 888

Cys Asn Ala Val Asn Gly Arg Leu Asn Tyr Trp
1               5                   10

<210> SEQ ID NO 889
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 889

Cys Asn Ala Val Ser Thr Asp Trp Thr Arg Asp Tyr Trp
1               5                   10

<210> SEQ ID NO 890
<211> LENGTH: 12
<212> TYPE: PRT
<213> ORGANISM: Artificial Sequence
<220> FEATURE:
```

-continued

<223> OTHER INFORMATION: Synthesized molecular recognition unit - heavy
     CDR3

<400> SEQUENCE: 890

Cys Asn Ala Val Thr Tyr Asn Gly Tyr Ser Ile Trp
1               5                   10

<210> SEQ ID NO 891
<211> LENGTH: 12
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 891

Cys Asn Ala Val Thr Tyr Asn Gly Tyr Thr Ile Trp
1               5                   10

<210> SEQ ID NO 892
<211> LENGTH: 12
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 892

Cys Asn Ala Val Trp Lys Phe Gly Thr Thr His Trp
1               5                   10

<210> SEQ ID NO 893
<211> LENGTH: 18
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 893

Cys Asn Ala Trp Val Leu Val Ala Gly Ser Arg Gly Thr Ser Ala Asp
1               5                   10                  15

Tyr Trp

<210> SEQ ID NO 894
<211> LENGTH: 12
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 894

Cys Asn Gly Val Thr Tyr Asn Gly Tyr Thr Ile Trp
1               5                   10

<210> SEQ ID NO 895
<211> LENGTH: 11
<212> TYPE: PRT
<213> ORGANISM: Artificial Sequence
<220> FEATURE:
<223> OTHER INFORMATION: Synthesized molecular recognition unit - heavy
     CDR3

<400> SEQUENCE: 895

Cys Asn Leu Ala Gln Arg Gly Glu Thr Tyr Trp
1               5                   10

```
<210> SEQ ID NO 896
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 896

Cys Asn Met Gly Leu Gly Tyr Ser Glu Tyr Arg Pro Leu Gly Tyr Trp
1               5                   10                  15

<210> SEQ ID NO 897
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 897

Cys Asn Met Arg Gly Asn Trp Tyr Arg Glu Gly Arg Pro Ala Glu Phe
1               5                   10                  15

Leu Ser Trp

<210> SEQ ID NO 898
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 898

Cys Asn Arg Val Gly Ser Arg Glu Tyr Ser Tyr Trp
1               5                   10

<210> SEQ ID NO 899
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 899

Cys Asn Ser Phe Pro Leu Arg Leu His Asp Trp
1               5                   10

<210> SEQ ID NO 900
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 900

Cys Asn Thr Gly Ile Pro Met Leu Tyr Trp
1               5                   10

<210> SEQ ID NO 901
<211> LENGTH: 15
<212> TYPE: PRT
<213> ORGANISM: Artificial Sequence
<220> FEATURE:
```

```
<223> OTHER INFORMATION: Synthesized molecular recognition unit - heavy
      CDR3

<400> SEQUENCE: 901

Cys Asn Thr Val Thr Tyr Asn Ala Gly Cys Tyr Lys Lys Tyr Trp
1               5                   10                  15

<210> SEQ ID NO 902
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 902

Cys Asn Thr Val Thr Tyr Thr Gly Gly Ser Tyr Lys Asn Tyr Trp
1               5                   10                  15

<210> SEQ ID NO 903
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 903

Cys Asn Val Ile Thr Ile Val Arg Gly Met Gly Pro Arg Ala Tyr Trp
1               5                   10                  15

<210> SEQ ID NO 904
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 904

Cys Asn Val Leu Ala Gln Asn Asp Gly Asp Tyr Arg Thr Tyr Gly
1               5                   10                  15

<210> SEQ ID NO 905
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 905

Cys Asn Val Leu Ala Gln Asn Asp Gly Asp Tyr Arg Thr Tyr Trp
1               5                   10                  15

<210> SEQ ID NO 906
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 906

Cys Arg Val Asp Ala Phe Asp Ile Trp
1               5
```

```
<210> SEQ ID NO 907
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 907

Cys Ser Ala Asp Lys Leu Asp Tyr Leu Asp Asp Gln Pro Phe Lys Thr
1               5                   10                  15

Trp Asp Tyr Trp
            20

<210> SEQ ID NO 908
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 908

Cys Thr Asp Glu Glu Ser Trp
1               5

<210> SEQ ID NO 909
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 909

Cys Thr Ile Leu Pro Ala Ala Ala Ala Gly Thr Tyr Tyr Tyr Tyr Gly
1               5                   10                  15

Met Asp Val Trp
            20

<210> SEQ ID NO 910
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 910

Cys Thr Arg Asp Leu Tyr Gly Gly Tyr Arg Asp Tyr Trp
1               5                   10

<210> SEQ ID NO 911
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 911

Cys Thr Arg Gly Asn Trp Asn Val Gly Leu Ala Asn Trp
1               5                   10

<210> SEQ ID NO 912
<211> LENGTH: 13
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 912

Cys Thr Arg Gly Ser Arg Ile Gly Trp Phe Asp Pro Trp
1               5                   10

<210> SEQ ID NO 913
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 913

Cys Thr Arg Pro Tyr Asp Ala Phe Asp Ile Trp
1               5                   10

<210> SEQ ID NO 914
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 914

Cys Thr Arg Thr Ile Val Gly Ala Thr Pro His Tyr Trp
1               5                   10

<210> SEQ ID NO 915
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 915

Cys Thr Ser Ser Phe Leu Thr Gly Ser Gln Pro Ser Gly Tyr Trp
1               5                   10                  15

<210> SEQ ID NO 916
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 916

Cys Thr Thr Asp Leu Arg Tyr Asp Ser Ser Gly Pro Ala Ala Phe Asp
1               5                   10                  15

Ile Trp

<210> SEQ ID NO 917
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 917
```

Cys Thr Thr Asp Pro Leu Glu Leu Pro Trp Tyr Trp
1               5                   10

<210> SEQ ID NO 918
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 918

Cys Thr Thr Asp Arg Arg Tyr Ser Thr Tyr Phe Asp Leu Trp
1               5                   10

<210> SEQ ID NO 919
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 919

Cys Thr Thr Gly Leu Phe Pro Tyr Tyr Arg Tyr Asn Trp Asn Asn Asp
1               5                   10                  15

Ala Phe Asp Ile Trp
            20

<210> SEQ ID NO 920
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 920

Cys Thr Thr Pro Asn Tyr Tyr Asp Ser Arg
1               5                   10

<210> SEQ ID NO 921
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 921

Cys Thr Thr Arg Thr Tyr Asp Ser Ser Gly Tyr Tyr Glu Thr Gln Asn
1               5                   10                  15

Tyr Tyr Met Asp Val Trp
            20

<210> SEQ ID NO 922
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 922

Cys Thr Thr Thr Glu Tyr Ser Ser Ser Pro Asp Tyr Tyr Tyr Gly Met
1               5                   10                  15

```
<210> SEQ ID NO 923
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 923

Cys Thr Thr Thr Thr Val Thr Thr Ser Trp
1               5                   10

<210> SEQ ID NO 924
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 924

Cys Val Lys Asp Arg Ala Trp Gly Phe Asp Tyr Trp
1               5                   10

<210> SEQ ID NO 925
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 925

Cys Val Lys Phe Gly Met Asn Leu Gly Tyr Ser Gly Tyr Asp Tyr Trp
1               5                   10                  15

<210> SEQ ID NO 926
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 926

Cys Val Arg Asp Leu Arg Pro Ser Gly Asp Leu Asn Phe Asp Tyr Trp
1               5                   10                  15

<210> SEQ ID NO 927
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 927

Cys Trp Gly Gly Ser Tyr Tyr Gly Asp Tyr Trp
1               5                   10

<210> SEQ ID NO 928
<211> LENGTH: 18
<212> TYPE: PRT
<213> ORGANISM: Artificial Sequence
<220> FEATURE:
<223> OTHER INFORMATION: Synthesized molecular recognition unit - heavy
```

```
                        CDR3

<400> SEQUENCE: 928

Cys Trp Thr Gly Leu Leu Trp Phe Gly Glu Ser Thr Asp Ala Phe Asp
1               5                   10                  15

Ile Trp

<210> SEQ ID NO 929
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 929

Cys Tyr Leu Glu Gly Pro Leu Asp Val Tyr Trp
1               5                   10

<210> SEQ ID NO 930
<211> LENGTH: 6
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 930

Pro Arg Leu Asp Tyr Trp
1               5

<210> SEQ ID NO 931
<211> LENGTH: 14
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 931

Gly Leu Ser Ser Gly Ser Val Ser Thr Asn Tyr Tyr Pro Ser
1               5                   10

<210> SEQ ID NO 932
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 932

Lys Ser Ser Gln Ser Leu Leu His Ser Asp Gly Lys Thr Tyr Leu Tyr
1               5                   10                  15

<210> SEQ ID NO 933
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 933

Lys Ser Ser Gln Ser Leu Leu His Ser Asp Gly Tyr Thr Tyr Leu Tyr
1               5                   10                  15
```

<210> SEQ ID NO 934
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 934

Lys Ser Ser Gln Ser Val Leu Tyr Ser Ser Asn Asn Lys Asn Tyr Leu
1               5                   10                  15

Ala

<210> SEQ ID NO 935
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 935

Gln Ala Asn Gln Asp Ile Ser Asn Tyr Leu Asn
1               5                   10

<210> SEQ ID NO 936
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 936

Gln Ala Ser His Asp Ile Asn Ile Ala Leu Asn
1               5                   10

<210> SEQ ID NO 937
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 937

Gln Ala Ser Gln Asp Ile Asp Asn Tyr Leu Asn
1               5                   10

<210> SEQ ID NO 938
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 938

Gln Ala Ser Gln Asp Ile Gly Lys Tyr Leu Asn
1               5                   10

<210> SEQ ID NO 939
<211> LENGTH: 11
<212> TYPE: PRT
<213> ORGANISM: Artificial Sequence
<220> FEATURE:
<223> OTHER INFORMATION: Synthesized molecular recognition unit - light

CDR1

<400> SEQUENCE: 939

Gln Ala Ser Gln Asp Ile Gly Asn Tyr Leu Asn
1               5                   10

<210> SEQ ID NO 940
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 940

Gln Ala Ser Gln Asp Ile Arg Asn Tyr Leu Asn
1               5                   10

<210> SEQ ID NO 941
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 941

Gln Ala Ser Gln Asp Ile Ser His Tyr Leu Asn
1               5                   10

<210> SEQ ID NO 942
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 942

Gln Ala Ser Gln Asp Ile Ser Asn Arg Leu Asn
1               5                   10

<210> SEQ ID NO 943
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 943

Gln Ala Ser Gln Asp Ile Ser Asn Tyr Leu Asn
1               5                   10

<210> SEQ ID NO 944
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 944

Gln Ala Ser Gln Asp Ile Ser Ser Tyr Leu Asn
1               5                   10

<210> SEQ ID NO 945

```
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 945

Gln Ala Ser Gln Asp Ile Thr Asn Tyr Leu Asn
1               5                   10

<210> SEQ ID NO 946
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 946

Gln Ala Ser Gln Gly Ile Ser Asn Asn Leu Asn
1               5                   10

<210> SEQ ID NO 947
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 947

Gln Ala Ser Gln Gly Ile Ser Asn Tyr Leu Asn
1               5                   10

<210> SEQ ID NO 948
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 948

Gln Ala Thr Gln Asn Ile Lys Lys Tyr Leu Asn
1               5                   10

<210> SEQ ID NO 949
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 949

Gln Gly Asp Ser Leu Arg Thr Tyr Tyr Ala Ser
1               5                   10

<210> SEQ ID NO 950
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 950
```

```
Gln Thr Ser Gln Asp Ile Asn Asn Asn Leu Asn
1               5                   10
```

<210> SEQ ID NO 951
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 951

```
Arg Ala Ile Gln Ser Ile Ser Ser Tyr Leu Asn
1               5                   10
```

<210> SEQ ID NO 952
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 952

```
Arg Ala Ser Glu Ser Val Ser Ser Asn Leu Ala
1               5                   10
```

<210> SEQ ID NO 953
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 953

```
Arg Ala Ser Glu Ser Val Ser Ser Ser Ser Phe Ala
1               5                   10
```

<210> SEQ ID NO 954
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 954

```
Arg Ala Ser His Asp Ile Gly Thr Phe Leu Ala
1               5                   10
```

<210> SEQ ID NO 955
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 955

```
Arg Ala Ser Gln Ala Ile Ser Asn Ser Leu Ala
1               5                   10
```

<210> SEQ ID NO 956
<211> LENGTH: 11
<212> TYPE: PRT
<213> ORGANISM: Artificial Sequence
<220> FEATURE:

<223> OTHER INFORMATION: Synthesized molecular recognition unit - light
      CDR1

<400> SEQUENCE: 956

Arg Ala Ser Gln Ala Ile Ser Asn Tyr Leu Asn
1               5                   10

<210> SEQ ID NO 957
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 957

Arg Ala Ser Gln Ala Ile Ser Ser Tyr Leu Ala
1               5                   10

<210> SEQ ID NO 958
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 958

Arg Ala Ser Gln Asp Ile Gly Ser Phe Leu Ala
1               5                   10

<210> SEQ ID NO 959
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 959

Arg Ala Ser Gln Asp Ile Arg Asp Glu Leu Ala
1               5                   10

<210> SEQ ID NO 960
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 960

Arg Ala Ser Gln Asp Ile Arg Ser Ala Leu Ala
1               5                   10

<210> SEQ ID NO 961
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 961

Arg Ala Ser Gln Asp Ile Ser Ser Trp Leu Ala
1               5                   10

```
<210> SEQ ID NO 962
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 962

Arg Ala Ser Gln Asp Ile Ser Ser Tyr Leu Ala
1               5                   10

<210> SEQ ID NO 963
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 963

Arg Ala Ser Gln Asp Val Asp Thr Trp Leu Ala
1               5                   10

<210> SEQ ID NO 964
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 964

Arg Ala Ser Gln Gly Ile Asn Asn Tyr Leu Ala
1               5                   10

<210> SEQ ID NO 965
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 965

Arg Ala Ser Gln Gly Ile Arg Asn Asp Leu Ala
1               5                   10

<210> SEQ ID NO 966
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 966

Arg Ala Ser Gln Gly Ile Arg Asn Asp Leu Gly
1               5                   10

<210> SEQ ID NO 967
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 967
```

Arg Ala Ser Gln Gly Ile Arg Ser Asp Leu Ala
1               5                   10

<210> SEQ ID NO 968
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 968

Arg Ala Ser Gln Gly Ile Ser Asn Asn Ile Asn
1               5                   10

<210> SEQ ID NO 969
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 969

Arg Ala Ser Gln Gly Ile Ser Asn Asn Leu Asn
1               5                   10

<210> SEQ ID NO 970
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 970

Arg Ala Ser Gln Gly Ile Ser Asn Trp Leu Ala
1               5                   10

<210> SEQ ID NO 971
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 971

Arg Ala Ser Gln Gly Ile Ser Asn Tyr Leu Ala
1               5                   10

<210> SEQ ID NO 972
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 972

Arg Ala Ser Gln Gly Ile Ser Arg Thr Leu Glx
1               5                   10

<210> SEQ ID NO 973
<211> LENGTH: 11
<212> TYPE: PRT
<213> ORGANISM: Artificial Sequence

```
<220> FEATURE:
<223> OTHER INFORMATION: Synthesized molecular recognition unit - light
      CDR1

<400> SEQUENCE: 973

Arg Ala Ser Gln Gly Ile Ser Ser Ala Leu Ala
1               5                   10

<210> SEQ ID NO 974
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 974

Arg Ala Ser Gln Gly Ile Ser Ser Tyr Leu Ala
1               5                   10

<210> SEQ ID NO 975
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 975

Arg Ala Ser Gln Gly Ile Thr Lys Ser Leu Ala
1               5                   10

<210> SEQ ID NO 976
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 976

Arg Ala Ser Gln Gly Val Gly Asp Tyr Leu Ala
1               5                   10

<210> SEQ ID NO 977
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 977

Arg Ala Ser Gln Gly Val Ser Thr Glx Leu Ser
1               5                   10

<210> SEQ ID NO 978
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 978

Arg Ala Ser Gln Asn Ile Gly Ser Arg Leu Ala
1               5                   10
```

<210> SEQ ID NO 979
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 979

Arg Ala Ser Gln Asn Ile Asn Asn Tyr Leu Ala
1               5                   10

<210> SEQ ID NO 980
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 980

Arg Ala Ser Gln Asn Val Asn Asp Trp Leu Ala
1               5                   10

<210> SEQ ID NO 981
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 981

Arg Ala Ser Gln Arg Val Gly Asn Asn Leu Ala
1               5                   10

<210> SEQ ID NO 982
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 982

Arg Ala Ser Gln Ser Ile Gly Arg Trp Leu Ala
1               5                   10

<210> SEQ ID NO 983
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 983

Arg Ala Ser Gln Ser Ile Gly Ser Asn Leu Asp
1               5                   10

<210> SEQ ID NO 984
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

```
<400> SEQUENCE: 984

Arg Ala Ser Gln Ser Ile Gly Ser Asn Leu Asn
1               5                   10

<210> SEQ ID NO 985
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 985

Arg Ala Ser Gln Ser Ile Gly Ser Ser Leu His
1               5                   10

<210> SEQ ID NO 986
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 986

Arg Ala Ser Gln Ser Ile Gly Thr Tyr Leu Asn
1               5                   10

<210> SEQ ID NO 987
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 987

Arg Ala Ser Gln Ser Ile Asn Arg Asn Tyr Leu Gly
1               5                   10

<210> SEQ ID NO 988
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 988

Arg Ala Ser Gln Ser Ile Asn Arg Trp Leu Ala
1               5                   10

<210> SEQ ID NO 989
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 989

Arg Ala Ser Gln Ser Ile Asn Ser Asn Leu Ala
1               5                   10

<210> SEQ ID NO 990
<211> LENGTH: 11
<212> TYPE: PRT
```

-continued

```
<213> ORGANISM: Artificial Sequence
<220> FEATURE:
<223> OTHER INFORMATION: Synthesized molecular recognition unit - light
      CDR1

<400> SEQUENCE: 990

Arg Ala Ser Gln Ser Ile Ser Asn Asn Leu Asn
1               5                   10

<210> SEQ ID NO 991
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 991

Arg Ala Ser Gln Ser Ile Ser Arg Ser Leu Ala
1               5                   10

<210> SEQ ID NO 992
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 992

Arg Ala Ser Gln Ser Ile Ser Arg Trp Leu Ala
1               5                   10

<210> SEQ ID NO 993
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 993

Arg Ala Ser Gln Ser Ile Ser Arg Tyr Leu Asn
1               5                   10

<210> SEQ ID NO 994
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 994

Arg Ala Ser Gln Ser Ile Ser Ser His Glx Asn
1               5                   10

<210> SEQ ID NO 995
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 995

Arg Ala Ser Gln Ser Ile Ser Ser Lys Ser Leu Ala
1               5                   10
```

<210> SEQ ID NO 996
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 996

Arg Ala Ser Gln Ser Ile Ser Ser Tyr Leu Asn
1               5                   10

<210> SEQ ID NO 997
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 997

Arg Ala Ser Gln Ser Ile Ser Thr Asn Val Asn
1               5                   10

<210> SEQ ID NO 998
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 998

Arg Ala Ser Gln Ser Ile Ser Thr Tyr Leu Ala
1               5                   10

<210> SEQ ID NO 999
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 999

Arg Ala Ser Gln Ser Ile Ser Thr Tyr Leu Ser
1               5                   10

<210> SEQ ID NO 1000
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 1000

Arg Ala Ser Gln Ser Ile Ser Glx Trp Leu Ala
1               5                   10

<210> SEQ ID NO 1001
<211> LENGTH: 11
<212> TYPE: PRT
<213> ORGANISM: Artificial Sequence
<220> FEATURE:
<223> OTHER INFORMATION: Synthesized molecular recognition unit - light CDR1

<400> SEQUENCE: 1001

Arg Ala Ser Gln Ser Ile Ser Glx Tyr Glx Asn
1               5                   10

<210> SEQ ID NO 1002
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1002

Arg Ala Ser Gln Ser Ile Val Ser Tyr Leu Asn
1               5                   10

<210> SEQ ID NO 1003
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1003

Arg Ala Ser Gln Ser Ile Glx Glx Tyr Glx Asn
1               5                   10

<210> SEQ ID NO 1004
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1004

Arg Ala Ser Gln Ser Leu Arg Ser Lys Leu Ala
1               5                   10

<210> SEQ ID NO 1005
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1005

Arg Ala Ser Gln Ser Val Gly Arg Trp Met Ala
1               5                   10

<210> SEQ ID NO 1006
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1006

Arg Ala Ser Gln Ser Val Gly Ser Asn Leu Ala
1               5                   10

<210> SEQ ID NO 1007
<211> LENGTH: 11

```
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1007

Arg Ala Ser Gln Ser Val Gly Ser Tyr Leu Ala
1               5                   10

<210> SEQ ID NO 1008
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1008

Arg Ala Ser Gln Ser Val Gly Thr Tyr Leu Thr
1               5                   10

<210> SEQ ID NO 1009
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1009

Arg Ala Ser Gln Ser Val Asn Asn Thr Tyr Val Ala
1               5                   10

<210> SEQ ID NO 1010
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1010

Arg Ala Ser Gln Ser Val Ser Gly Tyr Leu Ala
1               5                   10

<210> SEQ ID NO 1011
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1011

Arg Ala Ser Gln Ser Val Ser Arg Lys Leu Ala
1               5                   10

<210> SEQ ID NO 1012
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1012

Arg Ala Ser Gln Ser Val Ser Arg Asn Leu Ala
```

```
1               5                   10
```

<210> SEQ ID NO 1013
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1013

```
Arg Ala Ser Gln Ser Val Ser Ser Asp Leu Ala
1               5                   10
```

<210> SEQ ID NO 1014
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1014

```
Arg Ala Ser Gln Ser Val Ser Ser Asn Leu Ala
1               5                   10
```

<210> SEQ ID NO 1015
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1015

```
Arg Ala Ser Gln Ser Val Ser Ser Asn Gln Leu Ala
1               5                   10
```

<210> SEQ ID NO 1016
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1016

```
Arg Ala Ser Gln Ser Val Ser Ser Asn Tyr Leu Ser
1               5                   10
```

<210> SEQ ID NO 1017
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1017

```
Arg Ala Ser Gln Ser Val Ser Ser Ser Tyr Leu Ser
1               5                   10
```

<210> SEQ ID NO 1018
<211> LENGTH: 11
<212> TYPE: PRT
<213> ORGANISM: Artificial Sequence
<220> FEATURE:
<223> OTHER INFORMATION: Synthesized molecular recognition unit - light

CDR1

<400> SEQUENCE: 1018

Arg Ala Ser Gln Ser Val Ser Ser Trp Leu Ala
1               5                   10

<210> SEQ ID NO 1019
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1019

Arg Ala Ser Gln Ser Val Ser Ser Tyr Leu Ala
1               5                   10

<210> SEQ ID NO 1020
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1020

Arg Ala Ser Gln Ser Val Ser Thr Asn Leu Ala
1               5                   10

<210> SEQ ID NO 1021
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1021

Arg Ala Ser Gln Ser Val Ser Thr Ser Tyr Leu Ala
1               5                   10

<210> SEQ ID NO 1022
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1022

Arg Ala Ser Gln Ser Val Thr Ser Ser Leu Ala
1               5                   10

<210> SEQ ID NO 1023
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1023

Arg Ala Ser Gln Thr Ile Asn Asn Gln Leu Ala
1               5                   10

<210> SEQ ID NO 1024

```
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1024

Arg Ala Ser Gln Thr Ile Ser Arg Tyr Leu Asn
1               5                   10

<210> SEQ ID NO 1025
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1025

Arg Ala Ser Gln Glx Val Ser Arg Glx Glx Ala
1               5                   10

<210> SEQ ID NO 1026
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1026

Arg Ala Ser Arg Ser Ile Ser Ser Tyr Phe Asn
1               5                   10

<210> SEQ ID NO 1027
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1027

Arg Ala Thr Gln Thr Ile Ser Thr Tyr Leu Asn
1               5                   10

<210> SEQ ID NO 1028
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1028

Arg Ser Ser Glu Ser Leu Leu His Ser Asp Gly Lys Thr Tyr Leu Tyr
1               5                   10                  15

<210> SEQ ID NO 1029
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1029
```

```
Arg Ser Ser Gln Asn Ile Phe Gln Ser Leu Asn
1               5                   10

<210> SEQ ID NO 1030
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1030

Arg Ser Ser Gln Asn Val Ser Ser Tyr Leu Ala
1               5                   10

<210> SEQ ID NO 1031
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1031

Arg Ser Ser Gln Ser Leu Leu Asp Ser Asp Asp Gly Asn Thr Tyr Leu
1               5                   10                  15

Asp

<210> SEQ ID NO 1032
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1032

Arg Ser Ser Gln Ser Leu Leu His Ser Asp Gly Lys Thr Tyr Leu Tyr
1               5                   10                  15

<210> SEQ ID NO 1033
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1033

Arg Ser Ser Gln Ser Leu Leu His Ser Asp Gly Tyr Thr Tyr Leu Tyr
1               5                   10                  15

<210> SEQ ID NO 1034
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1034

Arg Ser Ser Gln Ser Leu Leu His Ser Asn Gly Phe Asn Tyr Val Asp
1               5                   10                  15

<210> SEQ ID NO 1035
<211> LENGTH: 16
<212> TYPE: PRT
```

```
<213> ORGANISM: Artificial Sequence
<220> FEATURE:
<223> OTHER INFORMATION: Synthesized molecular recognition unit - light
      CDR1

<400> SEQUENCE: 1035

Arg Ser Ser Gln Ser Leu Leu His Ser Asn Gly Asn Thr Tyr Leu Asp
1               5                   10                  15

<210> SEQ ID NO 1036
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1036

Arg Ser Ser Gln Ser Leu Leu His Ser Asn Gly Tyr Asn Tyr Leu Asp
1               5                   10                  15

<210> SEQ ID NO 1037
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1037

Arg Ser Ser Gln Ser Leu Leu Arg Arg Asn Gly His Asn Tyr Val Asp
1               5                   10                  15

<210> SEQ ID NO 1038
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1038

Arg Ser Ser Gln Ser Leu Val His Ser Asp Gly Asn Thr Tyr Leu Ser
1               5                   10                  15

<210> SEQ ID NO 1039
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1039

Arg Ser Ser Gln Tyr Leu Ser Ser Ala Tyr Leu Ala
1               5                   10

<210> SEQ ID NO 1040
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1040

Arg Ser Ser Arg Ser Leu Leu Asp Thr Asp Asp Gly Asn Thr Tyr Leu
1               5                   10                  15
```

Asp

<210> SEQ ID NO 1041
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1041

Arg Ser Ser Arg Ser Leu Leu His Ser Asp Gly Lys Thr Tyr Leu Tyr
1               5                   10                  15

<210> SEQ ID NO 1042
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1042

Arg Ser Ser Arg Ser Leu Leu His Ser Asn Gly Asn Thr Tyr Leu Gln
1               5                   10                  15

<210> SEQ ID NO 1043
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1043

Arg Ser Ser Arg Ser Leu Leu His Ser Asn Gly Asn Thr Tyr Leu Arg
1               5                   10                  15

<210> SEQ ID NO 1044
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1044

Arg Ser Ser Arg Ser Leu Leu His Thr Asn Gly Tyr Asn Tyr Leu Asp
1               5                   10                  15

<210> SEQ ID NO 1045
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1045

Arg Ser Ser Arg Ser Leu Leu His Thr Ser Gly Tyr Asn Tyr Leu Asp
1               5                   10                  15

<210> SEQ ID NO 1046
<211> LENGTH: 12
<212> TYPE: PRT
<213> ORGANISM: Artificial Sequence
<220> FEATURE:

<223> OTHER INFORMATION: Synthesized molecular recognition unit - light
      CDR1

<400> SEQUENCE: 1046

Arg Thr Ser Glu Arg Ser Ser Ile Ser Ser Phe Ala
1               5                   10

<210> SEQ ID NO 1047
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1047

Arg Thr Ser Gln Ser Ile Ser Ser Tyr Leu Asn
1               5                   10

<210> SEQ ID NO 1048
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1048

Arg Thr Ser Gln Ser Val Ser Ser Asn Leu Ala
1               5                   10

<210> SEQ ID NO 1049
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1049

Arg Val Ser Gln Gly Ile Ser Ser Ala Leu Ala
1               5                   10

<210> SEQ ID NO 1050
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1050

Ser Gly Asp Lys Val Gly His Lys Tyr Ala Ser
1               5                   10

<210> SEQ ID NO 1051
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1051

Ser Gly Asn Thr Leu Gly Ser His Tyr Val Ser
1               5                   10

```
<210> SEQ ID NO 1052
<211> LENGTH: 13
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1052

Ser Gly Ser Ser Ser Asn Ile Gly Ser His Thr Val Ser
1               5                   10

<210> SEQ ID NO 1053
<211> LENGTH: 14
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1053

Ser Gly Thr Ser Ser Asn Ile Gly Ala Gly Tyr Asp Val His
1               5                   10

<210> SEQ ID NO 1054
<211> LENGTH: 14
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1054

Thr Gly Ser Ser Ser Asn Ile Gly Ala Gly Phe Gly Val His
1               5                   10

<210> SEQ ID NO 1055
<211> LENGTH: 14
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1055

Thr Gly Thr Ser Ser Asp Val Gly Gly Tyr Asn Ser Val Ser
1               5                   10

<210> SEQ ID NO 1056
<211> LENGTH: 13
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1056

Thr Arg Ser Ser Gly Ser Ile Ala Ser Asn Tyr Val Gln
1               5                   10

<210> SEQ ID NO 1057
<211> LENGTH: 14
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1057
```

Thr Arg Ser Ser Asn Ile Gly Ala Gly Tyr Asp Val His
1               5                   10

<210> SEQ ID NO 1058
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1058

Thr Ser Ser Gln Ser Leu Leu His Ser Asp Gly Lys Thr Tyr Leu Tyr
1               5                   10                  15

<210> SEQ ID NO 1059
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1059

Glx Ala Cys Leu Arg Ile Ile Ser Tyr Leu Asn
1               5                   10

<210> SEQ ID NO 1060
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1060

Glx Pro Glx Gln Thr Glx Glx Ser His Leu Asn
1               5                   10

<210> SEQ ID NO 1061
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1061

Ala Ala Ser Ala Leu Gln Ser
1               5

<210> SEQ ID NO 1062
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1062

Ala Ala Ser Asn Leu Glu Thr
1               5

<210> SEQ ID NO 1063
<211> LENGTH: 7
<212> TYPE: PRT
<213> ORGANISM: Artificial Sequence -continued

```
<220> FEATURE:
<223> OTHER INFORMATION: Synthesized molecular recognition unit - light
      CDR2

<400> SEQUENCE: 1063

Ala Ala Ser Asn Leu Leu Gly
1               5

<210> SEQ ID NO 1064
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1064

Ala Ala Ser Asn Leu Gln Leu
1               5

<210> SEQ ID NO 1065
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1065

Ala Ala Ser Asn Leu Gln Ser
1               5

<210> SEQ ID NO 1066
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1066

Ala Ala Ser Arg Leu Glu Ser
1               5

<210> SEQ ID NO 1067
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1067

Ala Ala Ser Arg Leu Gln Ser
1               5

<210> SEQ ID NO 1068
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1068

Ala Ala Ser Arg Arg Ala Thr
1               5
```

<210> SEQ ID NO 1069
<211> LENGTH: 7
<212> TYPE: PRT
<213> ORGANISM: Artificial Sequence
<220> FEATURE:
<223> OTHER INFORMATION: Synthesized molecular recognition unit - light CDR2

<400> SEQUENCE: 1069

Ala Ala Ser Ser Leu His Thr
1               5

<210> SEQ ID NO 1070
<211> LENGTH: 7
<212> TYPE: PRT
<213> ORGANISM: Artificial Sequence
<220> FEATURE:
<223> OTHER INFORMATION: Synthesized molecular recognition unit - light CDR2

<400> SEQUENCE: 1070

Ala Ala Ser Ser Leu Gln Arg
1               5

<210> SEQ ID NO 1071
<211> LENGTH: 7
<212> TYPE: PRT
<213> ORGANISM: Artificial Sequence
<220> FEATURE:
<223> OTHER INFORMATION: Synthesized molecular recognition unit - light CDR2

<400> SEQUENCE: 1071

Ala Ala Ser Ser Leu Gln Ser
1               5

<210> SEQ ID NO 1072
<211> LENGTH: 7
<212> TYPE: PRT
<213> ORGANISM: Artificial Sequence
<220> FEATURE:
<223> OTHER INFORMATION: Synthesized molecular recognition unit - light CDR2

<400> SEQUENCE: 1072

Ala Ala Ser Ser Arg Val Thr
1               5

<210> SEQ ID NO 1073
<211> LENGTH: 7
<212> TYPE: PRT
<213> ORGANISM: Artificial Sequence
<220> FEATURE:
<223> OTHER INFORMATION: Synthesized molecular recognition unit - light CDR2

<400> SEQUENCE: 1073

Ala Ala Ser Thr Leu Glu Ser
1               5

<210> SEQ ID NO 1074
<211> LENGTH: 7
<212> TYPE: PRT
<213> ORGANISM: Artificial Sequence
<220> FEATURE:
<223> OTHER INFORMATION: Synthesized molecular recognition unit - light CDR2

```
<400> SEQUENCE: 1074

Ala Ala Ser Thr Leu Glu Thr
1               5

<210> SEQ ID NO 1075
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1075

Ala Ala Ser Thr Leu Gln Ser
1               5

<210> SEQ ID NO 1076
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1076

Ala Ala Ser Thr Leu Gln Thr
1               5

<210> SEQ ID NO 1077
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1077

Ala Ala Ser Thr Ser Gln Ser
1               5

<210> SEQ ID NO 1078
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1078

Ala Ser Ser Thr Leu Gln Thr
1               5

<210> SEQ ID NO 1079
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1079

Ala Thr Ser Thr Leu Gln Ser
1               5

<210> SEQ ID NO 1080
<211> LENGTH: 7
<212> TYPE: PRT
```

```
<213> ORGANISM: Artificial Sequence
<220> FEATURE:
<223> OTHER INFORMATION: Synthesized molecular recognition unit - light
      CDR2

<400> SEQUENCE: 1080

Asp Ala Ser Ile Arg Ala Thr
1               5

<210> SEQ ID NO 1081
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1081

Asp Ala Ser Asn Leu Glu Thr
1               5

<210> SEQ ID NO 1082
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1082

Asp Ala Ser Asn Leu Gln Ser
1               5

<210> SEQ ID NO 1083
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1083

Asp Ala Ser Asn Arg Ala Ser
1               5

<210> SEQ ID NO 1084
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1084

Asp Ala Ser Asn Arg Ala Thr
1               5

<210> SEQ ID NO 1085
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1085

Asp Ala Ser Ser Leu Glu Ser
1               5
```

<210> SEQ ID NO 1086
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1086

Asp Ala Ser Ser Leu Gln Ser
1               5

<210> SEQ ID NO 1087
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1087

Asp Ala Ser Thr Leu Glu Thr
1               5

<210> SEQ ID NO 1088
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1088

Asp Ala Ser Thr Leu Lys Arg
1               5

<210> SEQ ID NO 1089
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1089

Asp Ala Ser Thr Leu Gln Thr
1               5

<210> SEQ ID NO 1090
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1090

Asp Thr Ser Asn Arg Ala Thr
1               5

<210> SEQ ID NO 1091
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

```
<400> SEQUENCE: 1091

Asp Val Ser Asn Leu Glu Arg
1               5

<210> SEQ ID NO 1092
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1092

Asp Val Thr Lys Arg Pro Ser
1               5

<210> SEQ ID NO 1093
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1093

Glu Ala Ser Ser Val Ala Ser
1               5

<210> SEQ ID NO 1094
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1094

Glu Ala Ser Thr Leu Gln Ser
1               5

<210> SEQ ID NO 1095
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1095

Glu Asp Ser Gln Arg Pro Ser
1               5

<210> SEQ ID NO 1096
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1096

Glu Asn Asp Lys Arg Pro Ser
1               5

<210> SEQ ID NO 1097
<211> LENGTH: 7
```

```
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1097

Glu Val Ser Ser Leu Gln Gly
1               5

<210> SEQ ID NO 1098
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1098

Glu Val Ser Ser Val Gln Gly
1               5

<210> SEQ ID NO 1099
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1099

Phe Ala Ser Ser Leu Gln Ser
1               5

<210> SEQ ID NO 1100
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1100

Phe Gly Ser Tyr Arg Ala Ser
1               5

<210> SEQ ID NO 1101
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1101

Gly Ala Ser Asn Leu Gln Ser
1               5

<210> SEQ ID NO 1102
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1102

Gly Ala Ser Asn Arg Ala Ser
```

-continued

```
1               5

<210> SEQ ID NO 1103
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1103

Gly Ala Ser Asn Arg Pro Thr
1               5

<210> SEQ ID NO 1104
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1104

Gly Ala Ser Ser Leu Glu Ser
1               5

<210> SEQ ID NO 1105
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1105

Gly Ala Ser Ser Leu Gln Ser
1               5

<210> SEQ ID NO 1106
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1106

Gly Ala Ser Ser Arg Ala Pro
1               5

<210> SEQ ID NO 1107
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1107

Gly Ala Ser Ser Arg Ala Thr
1               5

<210> SEQ ID NO 1108
<211> LENGTH: 7
<212> TYPE: PRT
<213> ORGANISM: Artificial Sequence
<220> FEATURE:
<223> OTHER INFORMATION: Synthesized molecular recognition unit - light
```

-continued

CDR2

<400> SEQUENCE: 1108

Gly Ala Ser Thr Leu Gln Arg
1               5

<210> SEQ ID NO 1109
<211> LENGTH: 7
<212> TYPE: PRT
<213> ORGANISM: Artificial Sequence
<220> FEATURE:
<223> OTHER INFORMATION: Synthesized molecular recognition unit - light
    CDR2

<400> SEQUENCE: 1109

Gly Ala Ser Thr Leu Gln Ser
1               5

<210> SEQ ID NO 1110
<211> LENGTH: 7
<212> TYPE: PRT
<213> ORGANISM: Artificial Sequence
<220> FEATURE:
<223> OTHER INFORMATION: Synthesized molecular recognition unit - light
    CDR2

<400> SEQUENCE: 1110

Gly Ala Ser Thr Arg Ala Ala
1               5

<210> SEQ ID NO 1111
<211> LENGTH: 7
<212> TYPE: PRT
<213> ORGANISM: Artificial Sequence
<220> FEATURE:
<223> OTHER INFORMATION: Synthesized molecular recognition unit - light
    CDR2

<400> SEQUENCE: 1111

Gly Ala Ser Thr Arg Ala Thr
1               5

<210> SEQ ID NO 1112
<211> LENGTH: 7
<212> TYPE: PRT
<213> ORGANISM: Artificial Sequence
<220> FEATURE:
<223> OTHER INFORMATION: Synthesized molecular recognition unit - light
    CDR2

<400> SEQUENCE: 1112

Gly Ala Ser Thr Val Glu Ser
1               5

<210> SEQ ID NO 1113
<211> LENGTH: 7
<212> TYPE: PRT
<213> ORGANISM: Artificial Sequence
<220> FEATURE:
<223> OTHER INFORMATION: Synthesized molecular recognition unit - light
    CDR2

<400> SEQUENCE: 1113

Gly Asn Asn Asn Arg Pro Ser
1               5

<210> SEQ ID NO 1114

```
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1114

Gly Asn Ser Ile Arg Pro Ser
1               5

<210> SEQ ID NO 1115
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1115

Gly Ser Ser Asn Arg Ala Ala
1               5

<210> SEQ ID NO 1116
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1116

Gly Thr Ser Thr Arg Ala Thr
1               5

<210> SEQ ID NO 1117
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1117

Gly Val Ser Asn Arg Ala Thr
1               5

<210> SEQ ID NO 1118
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1118

Lys Ala Ser Asn Leu Glu Thr
1               5

<210> SEQ ID NO 1119
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1119
```

Lys Ala Ser Ser Leu Glu Asn
1               5

<210> SEQ ID NO 1120
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1120

Lys Ala Ser Ser Leu Glu Ser
1               5

<210> SEQ ID NO 1121
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1121

Lys Ala Ser Ser Leu Gln Ser
1               5

<210> SEQ ID NO 1122
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1122

Lys Ala Ser Thr Leu Asp Thr
1               5

<210> SEQ ID NO 1123
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1123

Lys Ala Ser Thr Leu Glu Ser
1               5

<210> SEQ ID NO 1124
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1124

Lys Ile Ser Asn Arg Phe Ser
1               5

<210> SEQ ID NO 1125
<211> LENGTH: 7
<212> TYPE: PRT
<213> ORGANISM: Artificial Sequence
<220> FEATURE:

```
<223> OTHER INFORMATION: Synthesized molecular recognition unit - light
      CDR2

<400> SEQUENCE: 1125

Leu Ala Ser Arg Arg Ala Ser
1               5

<210> SEQ ID NO 1126
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1126

Leu Gly Phe Asn Arg Ala Ser
1               5

<210> SEQ ID NO 1127
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1127

Leu Gly Ser Asp Arg Ala Ser
1               5

<210> SEQ ID NO 1128
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1128

Leu Gly Ser Asp Arg Thr Ser
1               5

<210> SEQ ID NO 1129
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1129

Leu Gly Ser His Arg Ala Ser
1               5

<210> SEQ ID NO 1130
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1130

Leu Gly Ser Lys Arg Ala Ser
1               5
```

```
<210> SEQ ID NO 1131
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1131

Leu Gly Ser Asn Arg Ala Ser
1               5

<210> SEQ ID NO 1132
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1132

Met Gly Ser Asn Arg Ala Pro
1               5

<210> SEQ ID NO 1133
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1133

Met Gly Ser Tyr Arg Ala Ser
1               5

<210> SEQ ID NO 1134
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1134

Met Leu Ser Ser Arg Ala Pro
1               5

<210> SEQ ID NO 1135
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1135

Asn Thr Ser Asn Arg Ala Thr
1               5

<210> SEQ ID NO 1136
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1136
```

```
Pro Ala Ser Ser Leu Gln Ser
1               5

<210> SEQ ID NO 1137
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1137

Gln Ala Ser Asn Leu Glu Ser
1               5

<210> SEQ ID NO 1138
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1138

Gln Ala Ser Ser Leu Asp Ser
1               5

<210> SEQ ID NO 1139
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1139

Gln Ala Ser Ser Leu Ile Ser
1               5

<210> SEQ ID NO 1140
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1140

Gln Asp Ser Lys Arg Pro Ser
1               5

<210> SEQ ID NO 1141
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1141

Arg Ala Ser Ser Leu Gln Ser
1               5

<210> SEQ ID NO 1142
<211> LENGTH: 7
<212> TYPE: PRT
<213> ORGANISM: Artificial Sequence
```

```
<220> FEATURE:
<223> OTHER INFORMATION: Synthesized molecular recognition unit - light
      CDR2

<400> SEQUENCE: 1142

Arg Ala Ser Thr Leu Glu Ser
1               5

<210> SEQ ID NO 1143
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1143

Arg Ala Ser Thr Leu Gln Ser
1               5

<210> SEQ ID NO 1144
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1144

Arg Thr Ser Thr Leu Glu Ser
1               5

<210> SEQ ID NO 1145
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1145

Arg Val Ser Ser Arg Phe Ser
1               5

<210> SEQ ID NO 1146
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1146

Ser Ala Ser Asn Leu Gln Ser
1               5

<210> SEQ ID NO 1147
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1147

Ser Ala Ser Arg Leu Gln Ile
1               5
```

<210> SEQ ID NO 1148
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1148

Ser Ala Ser Ser Leu Gln Ser
1               5

<210> SEQ ID NO 1149
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1149

Ser Asp Arg Asn Arg Pro Ser
1               5

<210> SEQ ID NO 1150
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1150

Ser Asn Tyr Gln Arg Pro Ser
1               5

<210> SEQ ID NO 1151
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1151

Ser Thr Asn Thr Arg Ser Ser
1               5

<210> SEQ ID NO 1152
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1152

Thr Ala Ser Ser Leu Gln Ser
1               5

<210> SEQ ID NO 1153
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

```
<400> SEQUENCE: 1153

Thr Leu Ser His Arg Ala Ser
1               5

<210> SEQ ID NO 1154
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1154

Tyr Ala Ser Gln Ser Val Ser
1               5

<210> SEQ ID NO 1155
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1155

Tyr Ala Ser Ser Leu Gln Asn
1               5

<210> SEQ ID NO 1156
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1156

Tyr Ala Ser Ser Leu Gln Ser
1               5

<210> SEQ ID NO 1157
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1157

Tyr Thr Asn Thr Arg Ser Ser
1               5

<210> SEQ ID NO 1158
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1158

Glx Ala Ser Ser Leu Gln Ser
1               5

<210> SEQ ID NO 1159
<211> LENGTH: 14
<212> TYPE: PRT
```

```
<213> ORGANISM: Artificial Sequence
<220> FEATURE:
<223> OTHER INFORMATION: Synthesized molecular recognition unit - light
      CDR3

<400> SEQUENCE: 1159

Cys Ala Ala Trp Asp Gly Ser Leu Phe Gly His Trp Val Phe
1               5                   10

<210> SEQ ID NO 1160
<211> LENGTH: 9
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1160

Cys Phe Ser Tyr Ala Gly Ser Arg Phe
1               5

<210> SEQ ID NO 1161
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1161

Cys Gly Thr Trp Asp Ser Ser Leu Ser Ala Trp Val Phe
1               5                   10

<210> SEQ ID NO 1162
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1162

Cys His Gln Ser Gly Arg Val Pro Val Thr Phe
1               5                   10

<210> SEQ ID NO 1163
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1163

Cys His Gln Ser Tyr Ser Ile Pro Arg Thr Phe
1               5                   10

<210> SEQ ID NO 1164
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1164

Cys Ile Gln Asn Thr His Trp Pro Leu Thr Arg
1               5                   10
```

<210> SEQ ID NO 1165
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1165

Cys Leu Leu Tyr Leu Gly Arg Gly Ile Trp Val Phe
1               5                   10

<210> SEQ ID NO 1166
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1166

Cys Leu Gln Asp Tyr Asn Tyr Pro Phe Thr Phe
1               5                   10

<210> SEQ ID NO 1167
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1167

Cys Leu Gln Asp Tyr Ser Tyr Pro Arg Thr Phe
1               5                   10

<210> SEQ ID NO 1168
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1168

Cys Leu Gln Asp Tyr Ser Tyr Pro Tyr Thr Phe
1               5                   10

<210> SEQ ID NO 1169
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1169

Cys Leu Gln His His Ser Tyr Pro Phe Thr Phe
1               5                   10

<210> SEQ ID NO 1170
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

```
<400> SEQUENCE: 1170

Cys Leu Gln His Lys Ser Phe Pro Thr Phe
1               5                   10

<210> SEQ ID NO 1171
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1171

Cys Leu Gln His Asn Gly Tyr Pro Ile Thr Phe
1               5                   10

<210> SEQ ID NO 1172
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1172

Cys Leu Gln His Asn Ser Leu Pro Phe Thr Phe
1               5                   10

<210> SEQ ID NO 1173
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1173

Cys Met His Gly Leu His Pro Pro Phe Thr Phe
1               5                   10

<210> SEQ ID NO 1174
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1174

Cys Met Gln Ala Leu Gln Ile Pro Pro Thr Phe
1               5                   10

<210> SEQ ID NO 1175
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1175

Cys Met Gln Ala Leu Gln Thr Pro Leu Thr Phe
1               5                   10

<210> SEQ ID NO 1176
<211> LENGTH: 11
```

```
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1176

Cys Met Gln Ala Leu Gln Thr Pro Gln Thr Phe
1               5                   10

<210> SEQ ID NO 1177
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1177

Cys Met Gln Ala Thr Gln Phe Pro His Thr Phe
1               5                   10

<210> SEQ ID NO 1178
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1178

Cys Met Gln Ala Thr Gln Phe Pro Leu Thr Phe
1               5                   10

<210> SEQ ID NO 1179
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1179

Cys Met Gln Gly Leu Gln Thr Pro His Thr Phe
1               5                   10

<210> SEQ ID NO 1180
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1180

Cys Met Gln Gly Leu Gln Thr Pro Trp Thr Phe
1               5                   10

<210> SEQ ID NO 1181
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1181

Cys Met Gln Gly Thr His Trp Pro Leu Thr Phe
```

```
1               5                   10

<210> SEQ ID NO 1182
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1182

Cys Met Gln Gly Thr His Trp Pro Tyr Thr Phe
1               5                   10

<210> SEQ ID NO 1183
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1183

Cys Met Gln Gly Thr Arg Trp Pro Thr Phe
1               5                   10

<210> SEQ ID NO 1184
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1184

Cys Met Gln Asn Leu Gln Thr Pro Trp Thr Phe
1               5                   10

<210> SEQ ID NO 1185
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1185

Cys Met Gln Asn Thr His Trp Pro Leu Thr Leu
1               5                   10

<210> SEQ ID NO 1186
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1186

Cys Met Gln Asn Thr His Trp Pro Leu Thr Arg
1               5                   10

<210> SEQ ID NO 1187
<211> LENGTH: 11
<212> TYPE: PRT
<213> ORGANISM: Artificial Sequence
<220> FEATURE:
<223> OTHER INFORMATION: Synthesized molecular recognition unit - light
```

```
                            CDR3

<400> SEQUENCE: 1187

Cys Met Gln Arg Leu Glu Phe Pro Tyr Thr Phe
1               5                   10

<210> SEQ ID NO 1188
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1188

Cys Met Gln Ser Ile Gln Leu Pro Trp Thr Phe
1               5                   10

<210> SEQ ID NO 1189
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1189

Cys Met Gln Ser Leu Gln Ser Pro Leu Thr Phe
1               5                   10

<210> SEQ ID NO 1190
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1190

Cys Met Gln Ser Leu Gln Thr Pro Tyr Thr Phe
1               5                   10

<210> SEQ ID NO 1191
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1191

Cys Met Gln Ser Ser His Trp Pro Lys Thr Phe
1               5                   10

<210> SEQ ID NO 1192
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1192

Cys Met Gln Thr Leu Lys Ala Pro Leu Thr Phe
1               5                   10

<210> SEQ ID NO 1193
```

```
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1193

Cys Asn Ser Arg Asp Asn Ser Gly Lys His Lys Val Phe
1               5                   10

<210> SEQ ID NO 1194
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1194

Cys Gln Ala Trp Asp Ser Ser Thr Asp Val Val Phe
1               5                   10

<210> SEQ ID NO 1195
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1195

Cys Gln Glu Ser Tyr Ser Ser Pro Tyr Thr Phe
1               5                   10

<210> SEQ ID NO 1196
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1196

Cys Gln His Leu Asn Asn Phe Pro Leu Thr Phe
1               5                   10

<210> SEQ ID NO 1197
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1197

Cys Gln His Leu Asn Ser Tyr Pro Pro Gly Asp Thr Phe
1               5                   10

<210> SEQ ID NO 1198
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1198
```

Cys Gln His Arg Ala Asn Trp Pro Gln Thr Phe
1               5                   10

<210> SEQ ID NO 1199
<211> LENGTH: 7
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1199

Cys Gln His Arg Asn Phe Phe
1               5

<210> SEQ ID NO 1200
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1200

Cys Gln His Arg Thr Ser Trp Pro Leu Thr Phe
1               5                   10

<210> SEQ ID NO 1201
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1201

Cys Gln His Tyr Asn Asn Trp Pro Phe Thr Phe
1               5                   10

<210> SEQ ID NO 1202
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1202

Cys Gln His Tyr Tyr Asn Leu Pro Leu Thr Phe
1               5                   10

<210> SEQ ID NO 1203
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1203

Cys Gln Lys Tyr Asn Arg Ala Pro Phe Thr Phe
1               5                   10

<210> SEQ ID NO 1204
<211> LENGTH: 11
<212> TYPE: PRT
<213> ORGANISM: Artificial Sequence
<220> FEATURE:

```
<223> OTHER INFORMATION: Synthesized molecular recognition unit - light
      CDR3

<400> SEQUENCE: 1204

Cys Gln Gln Ala Asp Ser Phe Pro Leu Thr Phe
1               5                   10

<210> SEQ ID NO 1205
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1205

Cys Gln Gln Ala Asp Ser Phe Pro Pro Thr Phe
1               5                   10

<210> SEQ ID NO 1206
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1206

Cys Gln Gln Ala Asp Thr Phe Pro Pro Thr Phe
1               5                   10

<210> SEQ ID NO 1207
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1207

Cys Gln Gln Ala Ile Ser Phe Pro Leu Thr Phe
1               5                   10

<210> SEQ ID NO 1208
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1208

Cys Gln Gln Ala Asn Ser Phe Pro Ile Thr Phe
1               5                   10

<210> SEQ ID NO 1209
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1209

Cys Gln Gln Ala Asn Ser Phe Pro Leu Thr Phe
1               5                   10
```

```
<210> SEQ ID NO 1210
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1210

Cys Gln Gln Ala Asn Ser Phe Pro Val Thr Phe
1               5                   10

<210> SEQ ID NO 1211
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1211

Cys Gln Gln Ala Asn Ser Phe Pro Tyr Thr Phe
1               5                   10

<210> SEQ ID NO 1212
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1212

Cys Gln Gln Ala Asn Ser Tyr Pro Leu Thr Phe
1               5                   10

<210> SEQ ID NO 1213
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1213

Cys Gln Gln Ala Asn Thr Phe Pro Phe Thr Phe
1               5                   10

<210> SEQ ID NO 1214
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1214

Cys Gln Gln Ala Asn Thr Val Pro Phe Thr Phe
1               5                   10

<210> SEQ ID NO 1215
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1215
```

Cys Gln Gln Ala Tyr Ser Phe Pro Gln Thr Phe
1               5                   10

<210> SEQ ID NO 1216
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1216

Cys Gln Gln Ala Tyr Ser Phe Pro Trp Thr Phe
1               5                   10

<210> SEQ ID NO 1217
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1217

Cys Gln Gln Gly Phe Asn Phe Pro Leu Thr Phe
1               5                   10

<210> SEQ ID NO 1218
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1218

Cys Gln Gln Gly Asn Asn Phe Pro Leu Thr Phe
1               5                   10

<210> SEQ ID NO 1219
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1219

Cys Gln Gln Gly Tyr Asn Ile Pro Trp Thr Phe
1               5                   10

<210> SEQ ID NO 1220
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1220

Cys Gln Gln Gly Tyr Ser Ala Pro Trp Thr Phe
1               5                   10

<210> SEQ ID NO 1221
<211> LENGTH: 11
<212> TYPE: PRT
<213> ORGANISM: Artificial Sequence

```
<220> FEATURE:
<223> OTHER INFORMATION: Synthesized molecular recognition unit - light
      CDR3

<400> SEQUENCE: 1221

Cys Gln Gln His Asn Ala Tyr Pro Leu Thr Phe
1               5                   10

<210> SEQ ID NO 1222
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1222

Cys Gln Gln Leu Ser Arg Tyr Pro Ser Leu Phe
1               5                   10

<210> SEQ ID NO 1223
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1223

Cys Gln Gln Asn Asp Tyr Leu Pro Leu Thr Phe
1               5                   10

<210> SEQ ID NO 1224
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1224

Cys Gln Gln Asn Tyr Ala Thr Pro Arg Thr Phe
1               5                   10

<210> SEQ ID NO 1225
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1225

Cys Gln Gln Arg Asn Asn Trp Leu Tyr Thr Phe
1               5                   10

<210> SEQ ID NO 1226
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1226

Cys Gln Gln Arg Ser Asn Trp Pro Ile Thr Phe
1               5                   10
```

<210> SEQ ID NO 1227
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1227

Cys Gln Gln Arg Ser Asn Trp Pro Pro Gln Ile Thr Phe
1               5                   10

<210> SEQ ID NO 1228
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1228

Cys Gln Gln Arg Thr Asn Trp Pro Pro Arg Val Thr Phe
1               5                   10

<210> SEQ ID NO 1229
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1229

Cys Gln Gln Arg Tyr Lys Ser Tyr Thr Phe
1               5                   10

<210> SEQ ID NO 1230
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1230

Cys Gln Gln Arg Tyr Asn Trp Pro Pro Ser Ile Thr Phe
1               5                   10

<210> SEQ ID NO 1231
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1231

Cys Gln Gln Arg Tyr Ser Thr Pro Leu Thr Phe
1               5                   10

<210> SEQ ID NO 1232
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

```
<400> SEQUENCE: 1232

Cys Gln Gln Ser Phe Ile Met Pro Leu Thr Phe
1               5                   10

<210> SEQ ID NO 1233
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1233

Cys Gln Gln Ser Phe Ser Ala Pro Ile Thr Phe
1               5                   10

<210> SEQ ID NO 1234
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1234

Cys Gln Gln Ser Phe Ser Ser Trp Thr Phe
1               5                   10

<210> SEQ ID NO 1235
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1235

Cys Gln Gln Ser His Ile Thr Pro Tyr Thr Phe
1               5                   10

<210> SEQ ID NO 1236
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1236

Cys Gln Gln Ser His Ser Pro Pro Gly Thr Phe
1               5                   10

<210> SEQ ID NO 1237
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1237

Cys Gln Gln Ser His Ser Ser Pro Arg Thr Phe
1               5                   10

<210> SEQ ID NO 1238
<211> LENGTH: 10
<212> TYPE: PRT
```

```
<213> ORGANISM: Artificial Sequence
<220> FEATURE:
<223> OTHER INFORMATION: Synthesized molecular recognition unit - light
      CDR3

<400> SEQUENCE: 1238

Cys Gln Gln Ser Ser Arg Phe Trp Thr Phe
1               5                   10

<210> SEQ ID NO 1239
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1239

Cys Gln Gln Ser Tyr Gly Ala Pro Leu Thr Phe
1               5                   10

<210> SEQ ID NO 1240
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1240

Cys Gln Gln Ser Tyr Asn Ser Pro Ile Thr Phe
1               5                   10

<210> SEQ ID NO 1241
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1241

Cys Gln Gln Ser Tyr Asn Thr Pro Phe Thr Phe
1               5                   10

<210> SEQ ID NO 1242
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1242

Cys Gln Gln Ser Tyr Asn Thr Pro Arg Thr Phe
1               5                   10

<210> SEQ ID NO 1243
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1243

Cys Gln Gln Ser Tyr Asn Thr Pro Trp Thr Phe
1               5                   10
```

<210> SEQ ID NO 1244
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1244

Cys Gln Gln Ser Tyr Asn Val Pro Tyr Thr Phe
1               5                   10

<210> SEQ ID NO 1245
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1245

Cys Gln Gln Ser Tyr Arg Thr Pro Leu Thr Phe
1               5                   10

<210> SEQ ID NO 1246
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1246

Cys Gln Gln Ser Tyr Arg Thr Pro Arg Thr Phe
1               5                   10

<210> SEQ ID NO 1247
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1247

Cys Gln Gln Ser Tyr Arg Thr Pro Tyr Thr Phe
1               5                   10

<210> SEQ ID NO 1248
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1248

Cys Gln Gln Ser Tyr Ser Ala Pro Tyr Thr Phe
1               5                   10

<210> SEQ ID NO 1249
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1249

Cys Gln Gln Ser Tyr Ser His Thr Ala Phe Thr Phe
1               5                   10

<210> SEQ ID NO 1250
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1250

Cys Gln Gln Ser Tyr Ser Ile Pro Phe Thr Phe
1               5                   10

<210> SEQ ID NO 1251
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1251

Cys Gln Gln Ser Tyr Ser Lys Pro Thr Phe
1               5                   10

<210> SEQ ID NO 1252
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1252

Cys Gln Gln Ser Tyr Ser Leu Pro Tyr Thr Phe
1               5                   10

<210> SEQ ID NO 1253
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1253

Cys Gln Gln Ser Tyr Ser Met Pro Gln Thr Phe
1               5                   10

<210> SEQ ID NO 1254
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1254

Cys Gln Gln Ser Tyr Ser Pro Pro Phe Thr Phe
1               5                   10

<210> SEQ ID NO 1255
<211> LENGTH: 11

```
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1255

Cys Gln Gln Ser Tyr Ser Pro Pro Leu Thr Phe
1               5                   10

<210> SEQ ID NO 1256
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1256

Cys Gln Gln Ser Tyr Ser Pro Pro Pro Tyr Thr Phe
1               5                   10

<210> SEQ ID NO 1257
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1257

Cys Gln Gln Ser Tyr Ser Ser Pro Leu Thr Phe
1               5                   10

<210> SEQ ID NO 1258
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1258

Cys Gln Gln Ser Tyr Ser Ser Pro Pro Thr Phe
1               5                   10

<210> SEQ ID NO 1259
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1259

Cys Gln Gln Ser Tyr Ser Thr Pro Ala Phe Thr Phe
1               5                   10

<210> SEQ ID NO 1260
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1260

Cys Gln Gln Ser Tyr Ser Thr Pro Phe Thr Phe
```

-continued

<210> SEQ ID NO 1261
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1261

Cys Gln Gln Ser Tyr Ser Thr Pro His Thr Phe
1               5                   10

<210> SEQ ID NO 1262
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1262

Cys Gln Gln Ser Tyr Ser Thr Pro Leu Ala Phe
1               5                   10

<210> SEQ ID NO 1263
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1263

Cys Gln Gln Ser Tyr Ser Thr Pro Leu Phe Thr Phe
1               5                   10

<210> SEQ ID NO 1264
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1264

Cys Gln Gln Ser Tyr Ser Thr Pro Leu Thr Phe
1               5                   10

<210> SEQ ID NO 1265
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1265

Cys Gln Gln Ser Tyr Ser Thr Pro Arg Thr Phe
1               5                   10

<210> SEQ ID NO 1266
<211> LENGTH: 12
<212> TYPE: PRT
<213> ORGANISM: Artificial Sequence
<220> FEATURE:
<223> OTHER INFORMATION: Synthesized molecular recognition unit - light

```
                                CDR3

<400> SEQUENCE: 1266

Cys Gln Gln Ser Tyr Ser Thr Pro Arg Val Thr Phe
1               5                   10

<210> SEQ ID NO 1267
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1267

Cys Gln Gln Ser Tyr Ser Thr Pro Ser Phe
1               5                   10

<210> SEQ ID NO 1268
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1268

Cys Gln Gln Ser Tyr Ser Thr Pro Thr Phe
1               5                   10

<210> SEQ ID NO 1269
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1269

Cys Gln Gln Ser Tyr Ser Thr Pro Val Thr Phe
1               5                   10

<210> SEQ ID NO 1270
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1270

Cys Gln Gln Ser Tyr Ser Thr Pro Trp Thr Phe
1               5                   10

<210> SEQ ID NO 1271
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1271

Cys Gln Gln Ser Tyr Ser Thr Pro Tyr Thr Phe
1               5                   10

<210> SEQ ID NO 1272
```

```
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1272

Cys Gln Gln Ser Tyr Ser Val Pro Asp Thr Phe
1               5                   10

<210> SEQ ID NO 1273
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1273

Cys Gln Gln Ser Tyr Thr Ser Thr Pro Leu Asn Ser Phe
1               5                   10

<210> SEQ ID NO 1274
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1274

Cys Gln Gln Ser Tyr Thr Thr Pro Phe Thr Phe
1               5                   10

<210> SEQ ID NO 1275
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1275

Cys Gln Gln Thr Phe Ser Pro Pro Leu Thr Phe
1               5                   10

<210> SEQ ID NO 1276
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1276

Cys Gln Gln Thr Phe Ser Val Pro Trp Thr Phe
1               5                   10

<210> SEQ ID NO 1277
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1277
```

Cys Gln Gln Thr Asn Leu Phe Pro Tyr Thr Phe
1               5                   10

<210> SEQ ID NO 1278
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1278

Cys Gln Gln Thr Asn Thr Phe Pro Phe Thr Phe
1               5                   10

<210> SEQ ID NO 1279
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1279

Cys Gln Gln Thr Ser Ser Thr Pro Leu Thr Phe
1               5                   10

<210> SEQ ID NO 1280
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1280

Cys Gln Gln Thr Tyr Asn Ile Pro Ile Thr Phe
1               5                   10

<210> SEQ ID NO 1281
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1281

Cys Gln Gln Thr Tyr Asn Pro Pro Arg Thr Phe
1               5                   10

<210> SEQ ID NO 1282
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1282

Cys Gln Gln Thr Tyr Asn Thr Pro Arg Thr Phe
1               5                   10

<210> SEQ ID NO 1283
<211> LENGTH: 11
<212> TYPE: PRT
<213> ORGANISM: Artificial Sequence
<220> FEATURE:

```
<223> OTHER INFORMATION: Synthesized molecular recognition unit - light
      CDR3

<400> SEQUENCE: 1283

Cys Gln Gln Thr Tyr Ser Ile Pro Phe Thr Phe
1               5                   10

<210> SEQ ID NO 1284
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1284

Cys Gln Gln Thr Tyr Ser Met Pro Ile Thr Phe
1               5                   10

<210> SEQ ID NO 1285
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1285

Cys Gln Gln Thr Tyr Ser Ser Pro Leu Thr Phe
1               5                   10

<210> SEQ ID NO 1286
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1286

Cys Gln Gln Thr Tyr Ser Thr Pro Arg Thr Phe
1               5                   10

<210> SEQ ID NO 1287
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1287

Cys Gln Gln Thr Tyr Ser Thr Pro Thr Thr Phe
1               5                   10

<210> SEQ ID NO 1288
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1288

Cys Gln Gln Thr Tyr Ser Thr Pro Trp Thr Phe
1               5                   10
```

<210> SEQ ID NO 1289
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1289

Cys Gln Gln Thr Tyr Thr Pro Pro Phe Thr Phe
1               5                   10

<210> SEQ ID NO 1290
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1290

Cys Gln Gln Thr Tyr Thr Thr Pro Arg Phe
1               5                   10

<210> SEQ ID NO 1291
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1291

Cys Gln Gln Val Asn Ser Tyr Pro Pro Thr Phe
1               5                   10

<210> SEQ ID NO 1292
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1292

Cys Gln Gln Tyr Ala Ile Ser Tyr Thr Phe
1               5                   10

<210> SEQ ID NO 1293
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1293

Cys Gln Gln Tyr Ala Asn Ser Pro Trp Thr Phe
1               5                   10

<210> SEQ ID NO 1294
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1294

```
<210> SEQ ID NO 1295
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1295

Cys Gln Gln Tyr Asp Thr Pro Leu Arg Thr Phe
1               5                   10

<210> SEQ ID NO 1296
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1296

Cys Gln Gln Tyr Asp Thr Ser Pro Pro Thr Phe
1               5                   10

<210> SEQ ID NO 1297
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1297

Cys Gln Gln Tyr Glu Thr Trp Pro Val Leu Thr Phe
1               5                   10

<210> SEQ ID NO 1298
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1298

Cys Gln Gln Tyr Gly Ala Ser Pro Trp Thr Phe
1               5                   10

<210> SEQ ID NO 1299
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1299

Cys Gln Gln Tyr Gly Ile Ala Pro Thr Phe
1               5                   10

<210> SEQ ID NO 1300
<211> LENGTH: 11
<212> TYPE: PRT
<213> ORGANISM: Artificial Sequence
```

Cys Gln Gln Tyr Asp Ser Trp Pro Pro Thr Phe
1               5                   10

```
<220> FEATURE:
<223> OTHER INFORMATION: Synthesized molecular recognition unit - light
      CDR3

<400> SEQUENCE: 1300

Cys Gln Gln Tyr Gly Ser Ser Pro Ile Thr Phe
1               5                   10

<210> SEQ ID NO 1301
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1301

Cys Gln Gln Tyr Gly Ser Ser Pro Pro Phe Thr Phe
1               5                   10

<210> SEQ ID NO 1302
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1302

Cys Gln Gln Tyr Gly Ser Ser Pro Pro Thr Phe
1               5                   10

<210> SEQ ID NO 1303
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1303

Cys Gln Gln Tyr Gly Ser Ser Pro Thr Phe
1               5                   10

<210> SEQ ID NO 1304
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1304

Cys Gln Gln Tyr Gly Ser Ser Pro Tyr Asn Phe
1               5                   10

<210> SEQ ID NO 1305
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1305

Cys Gln Gln Tyr Gly Ser Ser Pro Tyr Thr Phe
1               5                   10
```

<210> SEQ ID NO 1306
<211> LENGTH: 11
<212> TYPE: PRT
<213> ORGANISM: Artificial Sequence
<220> FEATURE:
<223> OTHER INFORMATION: Synthesized molecular recognition unit - light CDR3

<400> SEQUENCE: 1306

Cys Gln Gln Tyr Gly Thr Ser Leu Leu Thr Phe
1               5                   10

<210> SEQ ID NO 1307
<211> LENGTH: 10
<212> TYPE: PRT
<213> ORGANISM: Artificial Sequence
<220> FEATURE:
<223> OTHER INFORMATION: Synthesized molecular recognition unit - light CDR3

<400> SEQUENCE: 1307

Cys Gln Gln Tyr Lys Asp Trp Pro Thr Phe
1               5                   10

<210> SEQ ID NO 1308
<211> LENGTH: 11
<212> TYPE: PRT
<213> ORGANISM: Artificial Sequence
<220> FEATURE:
<223> OTHER INFORMATION: Synthesized molecular recognition unit - light CDR3

<400> SEQUENCE: 1308

Cys Gln Gln Tyr Asn Asp Trp Pro Pro Thr Phe
1               5                   10

<210> SEQ ID NO 1309
<211> LENGTH: 13
<212> TYPE: PRT
<213> ORGANISM: Artificial Sequence
<220> FEATURE:
<223> OTHER INFORMATION: Synthesized molecular recognition unit - light CDR3

<400> SEQUENCE: 1309

Cys Gln Gln Tyr Asn His Trp Pro Pro Leu Phe Thr Phe
1               5                   10

<210> SEQ ID NO 1310
<211> LENGTH: 11
<212> TYPE: PRT
<213> ORGANISM: Artificial Sequence
<220> FEATURE:
<223> OTHER INFORMATION: Synthesized molecular recognition unit - light CDR3

<400> SEQUENCE: 1310

Cys Gln Gln Tyr Asn Ile Trp Pro Arg Thr Phe
1               5                   10

<210> SEQ ID NO 1311
<211> LENGTH: 10
<212> TYPE: PRT
<213> ORGANISM: Artificial Sequence
<220> FEATURE:
<223> OTHER INFORMATION: Synthesized molecular recognition unit - light CDR3

```
<400> SEQUENCE: 1311

Cys Gln Gln Tyr Asn Lys Ser Pro Ser Phe
1               5                   10

<210> SEQ ID NO 1312
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1312

Cys Gln Gln Tyr Asn Asn Trp Pro Arg Asn Tyr Thr Phe
1               5                   10

<210> SEQ ID NO 1313
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1313

Cys Gln Gln Tyr Asn Ser Trp Pro Leu Thr Phe
1               5                   10

<210> SEQ ID NO 1314
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1314

Cys Gln Gln Tyr Asn Thr Phe Pro Ile Thr Phe
1               5                   10

<210> SEQ ID NO 1315
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1315

Cys Gln Gln Tyr Asn Tyr Trp Pro Pro Ala Phe
1               5                   10

<210> SEQ ID NO 1316
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1316

Cys Gln Gln Tyr Ser Asn Trp Pro Phe Thr Phe
1               5                   10

<210> SEQ ID NO 1317
<211> LENGTH: 11
<212> TYPE: PRT
```

```
<213> ORGANISM: Artificial Sequence
<220> FEATURE:
<223> OTHER INFORMATION: Synthesized molecular recognition unit - light
      CDR3

<400> SEQUENCE: 1317

Cys Gln Gln Tyr Ser Ser Tyr Pro Tyr Thr Ile
1               5                   10

<210> SEQ ID NO 1318
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1318

Cys Gln Gln Tyr Val Ser Tyr Pro Leu Thr Phe
1               5                   10

<210> SEQ ID NO 1319
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1319

Cys Gln Gln Tyr Tyr Ser Tyr Pro Trp Thr Ser
1               5                   10

<210> SEQ ID NO 1320
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1320

Cys Gln Gln Tyr Tyr Thr Tyr Pro Tyr Thr Phe
1               5                   10

<210> SEQ ID NO 1321
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1321

Cys Gln Ser Tyr Asp Ser Ser Leu Arg Ala Ser Val Phe
1               5                   10

<210> SEQ ID NO 1322
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1322

Cys Gln Ser Tyr Asp Tyr Asp His Arg Trp Val Phe
1               5                   10
```

```
<210> SEQ ID NO 1323
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1323

Cys Gln Val Trp Asp Ser Ser Thr Val Val Phe
1               5                   10

<210> SEQ ID NO 1324
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1324

Cys Ser Ala Trp Asp Asp Asn Leu Asn Gly Val Val Phe
1               5                   10

<210> SEQ ID NO 1325
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1325

Cys Thr Gln Thr Val Gln Phe Pro Ile Thr Phe
1               5                   10

<210> SEQ ID NO 1326
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1326

Cys Val Gln Thr Thr Gln Ser Pro Leu Thr Phe
1               5                   10

<210> SEQ ID NO 1327
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1327

Phe Ser Phe Ser Ser His Ala Met Ser
1               5

<210> SEQ ID NO 1328
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

```
<400> SEQUENCE: 1328

Gly Thr Phe Ser Ser Tyr Ala Ile Thr
1               5

<210> SEQ ID NO 1329
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1329

Gly Thr Phe Ser Ser Tyr Gly Ile Ser
1               5

<210> SEQ ID NO 1330
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1330

Gly Tyr Thr Phe Thr Asn Tyr Asp Ile Asn
1               5                   10

<210> SEQ ID NO 1331
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1331

His Thr Phe Thr Ser His Tyr Met His
1               5

<210> SEQ ID NO 1332
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1332

Tyr Met Phe Thr Gly His Asp Met His
1               5

<210> SEQ ID NO 1333
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1333

Tyr Ser Phe Thr Gly Tyr Tyr Leu His
1               5

<210> SEQ ID NO 1334
<211> LENGTH: 9
```

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1334

Tyr Ser Phe Thr Asn Tyr Tyr Met His
1               5

<210> SEQ ID NO 1335
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1335

Tyr Thr Phe Ala Lys Tyr Tyr Ile His
1               5

<210> SEQ ID NO 1336
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1336

Tyr Thr Phe Asn Gly Tyr Tyr Met His
1               5

<210> SEQ ID NO 1337
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1337

Tyr Thr Phe Ser Arg His Tyr Ile His
1               5

<210> SEQ ID NO 1338
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1338

Tyr Thr Phe Thr Asp His Tyr Phe His
1               5

<210> SEQ ID NO 1339
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1339

Tyr Thr Phe Thr Asp Ser Tyr Ile His
```

```
<210> SEQ ID NO 1340
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1340

Tyr Thr Phe Thr Gly His Tyr Met His
1               5

<210> SEQ ID NO 1341
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1341

Tyr Thr Phe Thr Gly Tyr Tyr Ile His
1               5

<210> SEQ ID NO 1342
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1342

Tyr Thr Phe Thr Gly Tyr Tyr Met His
1               5

<210> SEQ ID NO 1343
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1343

Tyr Thr Phe Thr Asn Tyr Tyr Met His
1               5

<210> SEQ ID NO 1344
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1344

Tyr Thr Phe Thr Arg Tyr Tyr Ile His
1               5

<210> SEQ ID NO 1345
<211> LENGTH: 9
<212> TYPE: PRT
<213> ORGANISM: Artificial Sequence
<220> FEATURE:
<223> OTHER INFORMATION: Synthesized molecular recognition unit - heavy
```

CDR1

<400> SEQUENCE: 1345

Tyr Thr Phe Thr Arg Tyr Tyr Leu His
1               5

<210> SEQ ID NO 1346
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1346

Tyr Thr Phe Thr Ser Ser Tyr Ile His
1               5

<210> SEQ ID NO 1347
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 1347

Tyr Trp Phe Thr Ala Ser Tyr Met His
1               5

<210> SEQ ID NO 1348
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1348

Gly Asp Ile Ile Pro Ile Phe Gly Ser Ala Asn Tyr Ala
1               5                   10

<210> SEQ ID NO 1349
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1349

Gly Ile Ile Asn Pro Ser Gly Gly Gly Ala Val Tyr Ala
1               5                   10

<210> SEQ ID NO 1350
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1350

Gly Ile Ile Asn Pro Ser Gly Gly Ser Thr Ser Tyr Ala
1               5                   10

<210> SEQ ID NO 1351

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1351

Gly Ile Val Asn Pro Ser Gly Gly Thr Asn Tyr Ala
1               5                   10

<210> SEQ ID NO 1352
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1352

Gly Arg Ile Asn Pro His Asn Gly Asn Thr Asn Tyr Ala
1               5                   10

<210> SEQ ID NO 1353
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1353

Gly Trp Ala Asn Pro Ser Ser Gly Asn Thr Gly Thr Ala
1               5                   10

<210> SEQ ID NO 1354
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1354

Gly Trp Ile Asn Pro Asn Ser Gly Asn Thr Gly Tyr Ala
1               5                   10

<210> SEQ ID NO 1355
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1355

Gly Trp Met Asp Pro Asn Ser Gly Tyr Thr Gly Tyr Ala
1               5                   10

<210> SEQ ID NO 1356
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1356
```

```
Gly Trp Met Lys Pro Asp Ser Gly Asn Thr Gly Tyr Ala
1               5                   10
```

<210> SEQ ID NO 1357
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1357

```
Gly Trp Met Asn Pro Asn Ser Ala Asn Ala Gly Tyr Ala
1               5                   10
```

<210> SEQ ID NO 1358
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1358

```
Gly Trp Met Asn Pro Asn Ser Gly Ser Thr Gly Tyr Ala
1               5                   10
```

<210> SEQ ID NO 1359
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1359

```
Ser Ala Ile Ser Gly Ser Gly His Ser Thr Tyr Tyr Ala
1               5                   10
```

<210> SEQ ID NO 1360
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 1360

```
Trp Ile Tyr Pro Arg Asp Gly Ser Thr Lys Tyr Asn Glu Lys Phe Lys
1               5                   10                  15
Gly
```

<210> SEQ ID NO 1361
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1361

```
Cys Ala Asn Pro Lys His Tyr Trp
1               5
```

<210> SEQ ID NO 1362
<211> LENGTH: 19
<212> TYPE: PRT

```
<213> ORGANISM: Artificial Sequence
<220> FEATURE:
<223> OTHER INFORMATION: Synthesized molecular recognition unit - heavy
      CDR3

<400> SEQUENCE: 1362

Cys Ala Arg Ala Asn Arg Gly Leu Arg Lys Asn Tyr Tyr Tyr Gly Met
1               5                   10                  15

Asp Val Trp

<210> SEQ ID NO 1363
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1363

Cys Ala Arg Ala Thr Arg Val Ser Ala Ala Gly Thr Val His Phe Gln
1               5                   10                  15

His Trp

<210> SEQ ID NO 1364
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1364

Cys Ala Arg Asp His Gly Thr Met Ile Ala Val Ala Gly Thr Phe Asp
1               5                   10                  15

Tyr Tyr Tyr Tyr Met Asp Val Trp
            20

<210> SEQ ID NO 1365
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1365

Cys Ala Arg Glu Asp Asp Phe Trp Ser Gly Gly Met Asp Val Trp
1               5                   10                  15

<210> SEQ ID NO 1366
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1366

Cys Ala Arg Glu Gly Leu Arg Gly Trp Ser Ile Phe Asp Ile Trp
1               5                   10                  15

<210> SEQ ID NO 1367
<211> LENGTH: 13
<212> TYPE: PRT
<213> ORGANISM: Artificial Sequence
<220> FEATURE:
```

```
<223> OTHER INFORMATION: Synthesized molecular recognition unit - heavy
      CDR3

<400> SEQUENCE: 1367

Cys Ala Arg Glu Leu Gly Leu Gly Trp Phe Asp Pro Trp
1               5                   10

<210> SEQ ID NO 1368
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1368

Cys Ala Arg Gly Asp Ile Asn Tyr Gly Asn Phe Asp Tyr Trp
1               5                   10

<210> SEQ ID NO 1369
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1369

Cys Ala Arg Gly Asp Ile Val Ala Thr Met Gly Met Lys Lys Val Asp
1               5                   10                  15

Tyr Tyr Tyr Tyr Met Asp Val Trp
                20

<210> SEQ ID NO 1370
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1370

Cys Ala Arg Gly Gly His Thr Gly Tyr Ser Ser Gly Trp Tyr Asn His
1               5                   10                  15

Trp

<210> SEQ ID NO 1371
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1371

Cys Ala Arg Gly Gly Asn Tyr Gly Arg Trp Leu Gln Pro Trp Tyr Phe
1               5                   10                  15

Asp Leu Trp

<210> SEQ ID NO 1372
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 1372

Cys Ala Arg Gly Ile Gly Tyr Trp
1               5

<210> SEQ ID NO 1373
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1373

Cys Ala Arg Gly Ile His Gly Asp Tyr Gly Leu Asp Tyr Tyr Tyr Met
1               5                   10                  15

Asp Val Trp

<210> SEQ ID NO 1374
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1374

Cys Ala Arg Gly Leu Gly Tyr Phe Asp Leu Trp
1               5                   10

<210> SEQ ID NO 1375
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1375

Cys Ala Arg Gly Met Glu Tyr Trp
1               5

<210> SEQ ID NO 1376
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1376

Cys Ala Arg Gly Pro Ala Asp Phe Trp Ser Gly Tyr Lys Asn Asp Tyr
1               5                   10                  15

Phe Asp Phe Trp
            20

<210> SEQ ID NO 1377
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1377

Cys Ala Arg Gly Ser Gly Tyr Phe Asp Leu Trp
```

```
1               5                   10
```

<210> SEQ ID NO 1378
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1378

```
Cys Ala Arg His Lys Arg His Thr Pro Tyr Ala Phe Asp Ile Trp
1               5                   10                  15
```

<210> SEQ ID NO 1379
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1379

```
Cys Ala Arg Gln Gly Gly Ser Tyr Ser Met Gly Leu Asp Pro Trp
1               5                   10                  15
```

<210> SEQ ID NO 1380
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1380

```
Cys Ala Arg Arg Ser Ser Ser Trp Gly Trp Tyr Phe Asp Leu Trp
1               5                   10                  15
```

<210> SEQ ID NO 1381
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1381

```
Cys Ala Arg Ser Pro Asp Phe Trp Ser Gly Glu Gly Tyr Phe Asp Leu
1               5                   10                  15

Trp
```

<210> SEQ ID NO 1382
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1382

```
Cys Ala Arg Ser Arg Leu Arg Trp Asp Trp Tyr Phe Asp Leu Trp
1               5                   10                  15
```

<210> SEQ ID NO 1383
<211> LENGTH: 15
<212> TYPE: PRT
<213> ORGANISM: Artificial Sequence

```
<220> FEATURE:
<223> OTHER INFORMATION: Synthesized molecular recognition unit - heavy
      CDR3

<400> SEQUENCE: 1383

Cys Ala Arg Ser Tyr Tyr Gly Val Ile Asp Ala Phe Asp Ile Trp
1               5                   10                  15

<210> SEQ ID NO 1384
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1384

Cys Ala Arg Val Gly Asp Tyr Asp Arg Phe Asn Trp Tyr Phe Asp Leu
1               5                   10                  15

Trp

<210> SEQ ID NO 1385
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1385

Cys Ala Arg Val Arg Phe Leu Glu Glu Met Asp Val Trp
1               5                   10

<210> SEQ ID NO 1386
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1386

Cys Ala Arg Trp Thr Thr Val Val Thr Gly Ala Ala Phe Asp Ile Trp
1               5                   10                  15

<210> SEQ ID NO 1387
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 1387

Val Arg Ser Ala Trp Gly Phe Ala Tyr
1               5

<210> SEQ ID NO 1388
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1388

Lys Ala Ser Gln Asp Val Gly Thr Ala Val Ala
```

<210> SEQ ID NO 1389
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1389

Lys Ser Ser Gln Ser Val Leu His Ser Ser Asn Asn Lys Asn Tyr Leu
1               5                   10                  15

Ala

<210> SEQ ID NO 1390
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1390

Arg Ala Ser Gln Ala Ile Gly Arg Arg Leu Ala
1               5                   10

<210> SEQ ID NO 1391
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1391

Arg Ala Ser Gln Asp Ile Ser Asn Asn Leu Asn
1               5                   10

<210> SEQ ID NO 1392
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1392

Arg Ala Ser Gln Asp Ile Ser Arg Gly Leu Gly
1               5                   10

<210> SEQ ID NO 1393
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1393

Arg Ala Ser Gln Gly Ile Arg Asn Asp Leu Asn
1               5                   10

<210> SEQ ID NO 1394
<211> LENGTH: 11
<212> TYPE: PRT
<213> ORGANISM: Artificial Sequence

```
<220> FEATURE:
<223> OTHER INFORMATION: Synthesized molecular recognition unit - light
      CDR1

<400> SEQUENCE: 1394

Arg Ala Ser Gln Gly Ile Ser Lys Tyr Leu Ala
1               5                   10

<210> SEQ ID NO 1395
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1395

Arg Ala Ser Gln Gly Ile Ser Ser Trp Leu Ala
1               5                   10

<210> SEQ ID NO 1396
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1396

Arg Ala Ser Gln Gly Val Ser Thr Tyr Leu Ala
1               5                   10

<210> SEQ ID NO 1397
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1397

Arg Ala Ser Gln Asn Ile Asn Ser Trp Leu Ala
1               5                   10

<210> SEQ ID NO 1398
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1398

Arg Ala Ser Gln Ser Ile Ala Arg Tyr Leu Asn
1               5                   10

<210> SEQ ID NO 1399
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1399

Arg Ala Ser Gln Ser Ile Gly Asn Tyr Leu Asn
1               5                   10
```

```
<210> SEQ ID NO 1400
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1400

Arg Ala Ser Gln Ser Ile Ile Ser Tyr Leu Asn
1               5                   10

<210> SEQ ID NO 1401
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1401

Arg Ala Ser Gln Ser Ile Ser Lys Trp Leu Ala
1               5                   10

<210> SEQ ID NO 1402
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1402

Arg Ala Ser Gln Ser Ile Thr Thr Tyr Leu Asn
1               5                   10

<210> SEQ ID NO 1403
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1403

Arg Ala Ser Gln Ser Leu Ser Ser Trp Leu Ala
1               5                   10

<210> SEQ ID NO 1404
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1404

Arg Ala Ser Gln Ser Val Ser Ser Trp Leu Ala
1               5                   10

<210> SEQ ID NO 1405
<211> LENGTH: 11
<212> TYPE: PRT
<213> ORGANISM: Artificial Sequence
<220> FEATURE:
<223> OTHER INFORMATION: Synthesized molecular recognition unit - light
      CDR1
```

```
<400> SEQUENCE: 1405

Arg Ala Ser Gln Thr Ile Ser Ser Tyr Leu Asn
1               5                   10

<210> SEQ ID NO 1406
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 1406

Arg Ala Ser Arg Thr Val Tyr Asn Phe Leu Ala
1               5                   10

<210> SEQ ID NO 1407
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1407

Ala Ala Ser Arg Leu Gln Thr
1               5

<210> SEQ ID NO 1408
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1408

Ala Ala Ser Ser Leu Gln Thr
1               5

<210> SEQ ID NO 1409
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1409

Ala Ala Ser Thr Leu Tyr Arg
1               5

<210> SEQ ID NO 1410
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1410

Asp Ala Ser Asn Leu Gly Thr
1               5

<210> SEQ ID NO 1411
<211> LENGTH: 7
<212> TYPE: PRT
```

```
<213> ORGANISM: Artificial Sequence
<220> FEATURE:
<223> OTHER INFORMATION: Synthesized molecular recognition unit - light
      CDR2

<400> SEQUENCE: 1411

Asp Ala Ser Asn Leu Arg Thr
1               5

<210> SEQ ID NO 1412
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1412

Asp Ala Ser Thr Leu Gln Ser
1               5

<210> SEQ ID NO 1413
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1413

Gly Ala Ser Ala Leu Arg Ser
1               5

<210> SEQ ID NO 1414
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1414

Gly Ala Ser His Leu Gln Thr
1               5

<210> SEQ ID NO 1415
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1415

Lys Ala Ser Thr Leu His Asn
1               5

<210> SEQ ID NO 1416
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1416

Lys Thr Ser Ser Leu Gln Ser
1               5
```

```
<210> SEQ ID NO 1417
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1417

Leu Gly Ser Ser Arg Ala Ser
1               5

<210> SEQ ID NO 1418
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1418

Trp Ala Ser Thr Arg Glu Ser
1               5

<210> SEQ ID NO 1419
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 1419

Trp Ala Ser Thr Arg His Thr
1               5

<210> SEQ ID NO 1420
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1420

Cys Leu Gln Tyr Asn Thr Tyr Pro Trp Thr Phe
1               5                   10

<210> SEQ ID NO 1421
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1421

Cys Gln Gln Ala Phe Arg Phe Pro Pro Thr Phe
1               5                   10

<210> SEQ ID NO 1422
<211> LENGTH: 11
<212> TYPE: PRT
<213> ORGANISM: Artificial Sequence
<220> FEATURE:
<223> OTHER INFORMATION: Synthesized molecular recognition unit - light
      CDR3
```

<400> SEQUENCE: 1422

Cys Gln Gln Gly Asp Ser Phe Pro Tyr Thr Phe
1               5                   10

<210> SEQ ID NO 1423
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1423

Cys Gln Gln Ser Phe Arg Leu Pro Leu Thr Phe
1               5                   10

<210> SEQ ID NO 1424
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1424

Cys Gln Gln Ser His Ser Thr Pro Leu Thr Phe
1               5                   10

<210> SEQ ID NO 1425
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1425

Cys Gln Gln Ser Ser Arg Ile Pro Pro Thr Phe
1               5                   10

<210> SEQ ID NO 1426
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1426

Cys Gln Gln Ser Trp Arg Phe Pro Tyr Thr Phe
1               5                   10

<210> SEQ ID NO 1427
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1427

Cys Gln Gln Ser Tyr Ser Thr Pro Pro Thr Phe
1               5                   10

<210> SEQ ID NO 1428
<211> LENGTH: 11

```
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1428

Cys Gln Gln Ser Tyr Ser Thr Pro Tyr Ser Phe
1               5                   10

<210> SEQ ID NO 1429
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1429

Cys Gln Gln Thr Lys Ser Phe Pro Leu Thr Phe
1               5                   10

<210> SEQ ID NO 1430
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1430

Cys Gln Gln Tyr Asp Thr Tyr Trp Thr Phe
1               5                   10

<210> SEQ ID NO 1431
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1431

Cys Gln Gln Tyr Tyr Ser Phe Pro Leu Thr Phe
1               5                   10

<210> SEQ ID NO 1432
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1432

Cys Gln Gln Tyr Tyr Ser Ser Pro Gln Thr Phe
1               5                   10

<210> SEQ ID NO 1433
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1433

Cys Gln Gln Tyr Tyr Ser Thr Pro Phe Thr Phe
```

```
<210> SEQ ID NO 1434
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1434

Cys Gln Gln Tyr Tyr Ser Thr Pro Pro Thr Phe
1               5                   10

<210> SEQ ID NO 1435
<211> LENGTH: 9
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 1435

Gln Gln Tyr Ser Thr Tyr Pro Leu Thr
1               5

<210> SEQ ID NO 1436
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1436

Cys Ala Ser Ser Ala Glu Lys Ala Thr Tyr Tyr Tyr Gly Met Asp Val
1               5                   10                  15
Trp

<210> SEQ ID NO 1437
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1437

Cys Ala Ser Ser Lys Glu Ala Ala Thr Tyr Tyr Tyr Gly Met Asp Val
1               5                   10                  15
Trp

<210> SEQ ID NO 1438
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1438

Cys Ala Ser Ser Lys Glu Lys Ala Ala Tyr Tyr Tyr Gly Met Asp Val
1               5                   10                  15
Trp
```

```
<210> SEQ ID NO 1439
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1439

Cys Ala Ser Ser Lys Glu Lys Ala Thr Ala Tyr Tyr Gly Met Asp Val
1               5                   10                  15

Trp

<210> SEQ ID NO 1440
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1440

Cys Ala Ser Ser Lys Glu Lys Ala Thr Tyr Ala Tyr Gly Met Asp Val
1               5                   10                  15

Trp

<210> SEQ ID NO 1441
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1441

Cys Ala Ser Ser Lys Glu Lys Ala Thr Tyr Tyr Ala Gly Met Asp Val
1               5                   10                  15

Trp

<210> SEQ ID NO 1442
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1442

Cys Ala Ser Ser Lys Glu Lys Ala Thr Tyr Tyr Tyr Ala Met Asp Val
1               5                   10                  15

Trp

<210> SEQ ID NO 1443
<211> LENGTH: 17
<212> TYPE: PRT
<213> ORGANISM: Artificial Sequence
<220> FEATURE:
<223> OTHER INFORMATION: Synthesized molecular recognition unit - Heavy
      CDR3

<400> SEQUENCE: 1443

Cys Ala Ser Ser Lys Glu Lys Ala Thr Tyr Tyr Tyr Gly Met Asp Ala
1               5                   10                  15

Trp
```

<210> SEQ ID NO 1444
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1444

Cys Ala Leu Tyr Leu Gly Arg Gly Ile Trp Val Phe
1               5                   10

<210> SEQ ID NO 1445
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1445

Cys Leu Ala Tyr Leu Gly Arg Gly Ile Trp Val Phe
1               5                   10

<210> SEQ ID NO 1446
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1446

Cys Leu Leu Ala Leu Gly Arg Gly Ile Trp Val Phe
1               5                   10

<210> SEQ ID NO 1447
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1447

Cys Leu Leu Tyr Ala Gly Arg Gly Ile Trp Val Phe
1               5                   10

<210> SEQ ID NO 1448
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1448

Cys Leu Leu Tyr Leu Ala Arg Gly Ile Trp Val Phe
1               5                   10

<210> SEQ ID NO 1449
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

```
<400> SEQUENCE: 1449

Cys Leu Leu Tyr Leu Gly Ala Gly Ile Trp Val Phe
1               5                   10

<210> SEQ ID NO 1450
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1450

Cys Leu Leu Tyr Leu Gly Arg Ala Ile Trp Val Phe
1               5                   10

<210> SEQ ID NO 1451
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1451

Cys Leu Leu Tyr Leu Gly Arg Gly Ala Trp Val Phe
1               5                   10

<210> SEQ ID NO 1452
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1452

Cys Leu Leu Tyr Leu Gly Arg Gly Ile Ala Val Phe
1               5                   10

<210> SEQ ID NO 1453
<211> LENGTH: 12
<212> TYPE: PRT
<213> ORGANISM: Artificial Sequence
<220> FEATURE:
<223> OTHER INFORMATION: Synthesized molecular recognition unit - Light
      CDR3

<400> SEQUENCE: 1453

Cys Leu Leu Tyr Leu Gly Arg Gly Ile Trp Ala Phe
1               5                   10

<210> SEQ ID NO 1454
<211> LENGTH: 140
<212> TYPE: PRT
<213> ORGANISM: Artificial Sequence
<220> FEATURE:
<223> OTHER INFORMATION: Made in Lab - human Fzd1 fragment with His tag

<400> SEQUENCE: 1454

Gln Tyr Asn Gly Glu Arg Gly Ile Ser Val Pro Asp His Gly Tyr Cys
1               5                   10                  15

Gln Pro Ile Ser Ile Pro Leu Cys Thr Asp Ile Ala Tyr Asn Gln Thr
                20                  25                  30

Ile Met Pro Asn Leu Leu Gly His Thr Asn Gln Glu Asp Ala Gly Leu
            35                  40                  45
```

Glu Val His Gln Phe Tyr Pro Leu Val Lys Val Gln Cys Ser Ala Glu
 50                  55                  60

Leu Lys Phe Phe Leu Cys Ser Met Tyr Ala Pro Val Cys Thr Val Leu
 65                  70                  75                  80

Glu Gln Ala Leu Pro Pro Cys Arg Ser Leu Cys Glu Arg Ala Arg Gln
                 85                  90                  95

Gly Cys Glu Ala Leu Met Asn Lys Phe Gly Phe Gln Trp Pro Asp Thr
            100                 105                 110

Leu Lys Cys Glu Lys Phe Pro Val His Gly Ala Gly Glu Leu Cys Val
        115                 120                 125

Gly Gln Gly Ser His His His His His His His
        130                 135                 140

<210> SEQ ID NO 1455
<211> LENGTH: 138
<212> TYPE: PRT
<213> ORGANISM: Artificial Sequence
<220> FEATURE:
<223> OTHER INFORMATION: Made in Lab - human Fzd2 fragment with His tag

<400> SEQUENCE: 1455

Gln Phe His Gly Glu Lys Gly Ile Ser Ile Pro Asp His Gly Phe Cys
 1               5                  10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
 50                  55                  60

Leu Arg Phe Phe Leu Cys Ser Met Tyr Ala Pro Val Cys Thr Val Leu
 65                  70                  75                  80

Glu Gln Ala Ile Pro Pro Cys Arg Ser Ile Cys Glu Arg Ala Arg Gln
                 85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln His His His His His His His His
        130                 135

<210> SEQ ID NO 1456
<211> LENGTH: 134
<212> TYPE: PRT
<213> ORGANISM: Artificial Sequence
<220> FEATURE:
<223> OTHER INFORMATION: Made in Lab - human Fzd3 fragment with His tag

<400> SEQUENCE: 1456

His Ser Leu Phe Ser Cys Glu Pro Ile Thr Leu Arg Met Cys Gln Asp
 1               5                  10                  15

Leu Pro Tyr Asn Thr Thr Phe Met Pro Asn Leu Leu Asn His Tyr Asp
            20                  25                  30

Gln Gln Thr Ala Ala Leu Ala Met Glu Pro Phe His Pro Met Val Asn
        35                  40                  45

Leu Asp Cys Ser Arg Asp Phe Arg Pro Phe Leu Cys Ala Leu Tyr Ala
 50                  55                  60

Pro Ile Cys Met Glu Tyr Gly Arg Val Thr Leu Pro Cys Arg Arg Leu

```
                65                  70                  75                  80

Cys Gln Arg Ala Tyr Ser Glu Cys Ser Lys Leu Met Glu Met Phe Gly
                85                  90                  95

Val Pro Trp Pro Glu Asp Met Glu Cys Ser Arg Phe Pro Asp Cys Asp
            100                 105                 110

Glu Pro Tyr Pro Arg Leu Val Asp Leu Asn Leu Ala Gly Glu His His
        115                 120                 125

His His His His His His
    130

<210> SEQ ID NO 1457
<211> LENGTH: 138
<212> TYPE: PRT
<213> ORGANISM: Artificial Sequence
<220> FEATURE:
<223> OTHER INFORMATION: Made in Lab - human Fzd4 fragment with His tag

<400> SEQUENCE: 1457

Gly Asp Glu Glu Glu Arg Arg Cys Asp Pro Ile Arg Ile Ser Met Cys
1               5                   10                  15

Gln Asn Leu Gly Tyr Asn Val Thr Lys Met Pro Asn Leu Val Gly His
                20                  25                  30

Glu Leu Gln Thr Asp Ala Glu Leu Gln Leu Thr Thr Phe Thr Pro Leu
            35                  40                  45

Ile Gln Tyr Gly Cys Ser Ser Gln Leu Gln Phe Phe Leu Cys Ser Val
        50                  55                  60

Tyr Val Pro Met Cys Thr Glu Lys Ile Asn Ile Pro Ile Gly Pro Cys
65                  70                  75                  80

Gly Gly Met Cys Leu Ser Val Lys Arg Arg Cys Glu Pro Val Leu Lys
                85                  90                  95

Glu Phe Gly Phe Ala Trp Pro Glu Ser Leu Asn Cys Ser Lys Phe Pro
            100                 105                 110

Pro Gln Asn Asp His Asn His Met Cys Met Glu Gly Pro Gly Asp Glu
        115                 120                 125

Glu Val His His His His His His His
    130                 135

<210> SEQ ID NO 1458
<211> LENGTH: 134
<212> TYPE: PRT
<213> ORGANISM: Artificial Sequence
<220> FEATURE:
<223> OTHER INFORMATION: Made in Lab - human Fzd5 fragment with His tag

<400> SEQUENCE: 1458

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
                20                  25                  30

Thr Gln Asp Glu Ala Gly Leu Glu Val His Gln Phe Trp Pro Leu Val
            35                  40                  45

Glu Ile Gln Cys Ser Pro Asp Leu Arg Phe Phe Leu Cys Ser Met Tyr
        50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95
```

```
Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg His His
        115                 120                 125

His His His His His His
        130

<210> SEQ ID NO 1459
<211> LENGTH: 135
<212> TYPE: PRT
<213> ORGANISM: Artificial Sequence
<220> FEATURE:
<223> OTHER INFORMATION: Made in Lab - human Fzd6 fragment with His tag

<400> SEQUENCE: 1459

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly His
        115                 120                 125

His His His His His His His
        130                 135

<210> SEQ ID NO 1460
<211> LENGTH: 138
<212> TYPE: PRT
<213> ORGANISM: Artificial Sequence
<220> FEATURE:
<223> OTHER INFORMATION: Made in Lab - human Fzd7 fragment with His tag

<400> SEQUENCE: 1460

His Gly Glu Lys Gly Ile Ser Val Pro Asp His Gly Phe Cys Gln Pro
1               5                   10                  15

Ile Ser Ile Pro Leu Cys Thr Asp Ile Ala Tyr Asn Gln Thr Ile Leu
            20                  25                  30

Pro Asn Leu Leu Gly His Thr Asn Gln Glu Asp Ala Gly Leu Glu Val
        35                  40                  45

His Gln Phe Tyr Pro Leu Val Lys Val Gln Cys Ser Pro Glu Leu Arg
    50                  55                  60

Phe Phe Leu Cys Ser Met Tyr Ala Pro Val Cys Thr Val Leu Asp Gln
65                  70                  75                  80

Ala Ile Pro Pro Cys Arg Ser Leu Cys Glu Arg Ala Arg Gln Gly Cys
                85                  90                  95

Glu Ala Leu Met Asn Lys Phe Gly Phe Gln Trp Pro Glu Arg Leu Arg
            100                 105                 110

Cys Glu Asn Phe Pro Val His Gly Ala Gly Glu Ile Cys Val Gly Gln
        115                 120                 125
```

Asn Thr His His His His His His His
        130                 135

<210> SEQ ID NO 1461
<211> LENGTH: 134
<212> TYPE: PRT
<213> ORGANISM: Artificial Sequence
<220> FEATURE:
<223> OTHER INFORMATION: Made in Lab - human Fzd8 fragment with His tag

<400> SEQUENCE: 1461

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg His His
        115                 120                 125

His His His His His His
        130

<210> SEQ ID NO 1462
<211> LENGTH: 145
<212> TYPE: PRT
<213> ORGANISM: Artificial Sequence
<220> FEATURE:
<223> OTHER INFORMATION: Made in Lab - human Fzd9 fragment with His tag

<400> SEQUENCE: 1462

Leu Glu Ile Gly Arg Phe Asp Pro Glu Arg Gly Arg Gly Ala Ala Pro
1               5                   10                  15

Cys Gln Ala Val Glu Ile Pro Met Cys Arg Gly Ile Gly Tyr Asn Leu
            20                  25                  30

Thr Arg Met Pro Asn Leu Leu Gly His Thr Ser Gln Gly Glu Ala Ala
        35                  40                  45

Ala Glu Leu Ala Glu Phe Ala Pro Leu Val Gln Tyr Gly Cys His Ser
50                  55                  60

His Leu Arg Phe Phe Leu Cys Ser Leu Tyr Ala Pro Met Cys Thr Asp
65                  70                  75                  80

Gln Val Ser Thr Pro Ile Pro Ala Cys Arg Pro Met Cys Glu Gln Ala
                85                  90                  95

Arg Leu Arg Cys Ala Pro Ile Met Glu Gln Phe Asn Phe Gly Trp Pro
            100                 105                 110

Asp Ser Leu Asp Cys Ala Arg Leu Pro Thr Arg Asn Asp Pro His Ala
        115                 120                 125

Leu Cys Met Glu Ala Pro Glu Asn Ala His His His His His His
        130                 135                 140

His

-continued

145

<210> SEQ ID NO 1463
<211> LENGTH: 141
<212> TYPE: PRT
<213> ORGANISM: Artificial Sequence
<220> FEATURE:
<223> OTHER INFORMATION: Made in Lab - human Fzd10 fragment with His tag

<400> SEQUENCE: 1463

Ser Ser Met Asp Met Glu Arg Pro Gly Asp Gly Lys Cys Gln Pro Ile
1               5                   10                  15

Glu Ile Pro Met Cys Lys Asp Ile Gly Tyr Asn Met Thr Arg Met Pro
            20                  25                  30

Asn Leu Met Gly His Glu Asn Gln Arg Glu Ala Ala Ile Gln Leu His
        35                  40                  45

Glu Phe Ala Pro Leu Val Glu Tyr Gly Cys His Gly His Leu Arg Phe
    50                  55                  60

Phe Leu Cys Ser Leu Tyr Ala Pro Met Cys Thr Glu Gln Val Ser Thr
65                  70                  75                  80

Pro Ile Pro Ala Cys Arg Val Met Cys Glu Gln Ala Arg Leu Lys Cys
                85                  90                  95

Ser Pro Ile Met Glu Gln Phe Asn Phe Lys Trp Pro Asp Ser Leu Asp
            100                 105                 110

Cys Arg Lys Leu Pro Asn Lys Asn Asp Pro Asn Tyr Leu Cys Met Glu
        115                 120                 125

Ala Pro Asn Asn Gly His His His His His His
    130                 135                 140

<210> SEQ ID NO 1464
<211> LENGTH: 213
<212> TYPE: PRT
<213> ORGANISM: Artificial Sequence
<220> FEATURE:
<223> OTHER INFORMATION: Made in Lab - Fzd1:1RC07 complex

<400> SEQUENCE: 1464

Ser Tyr Val Leu Thr Gln Pro Pro Ser Val Ser Val Ser Pro Gly Gln
1               5                   10                  15

Thr Ala Ser Ile Thr Cys Ser Gly Asp Lys Val Gly His Lys Tyr Ala
            20                  25                  30

Ser Trp Tyr Gln Gln Lys Pro Gly Gln Ser Pro Val Leu Val Ile Tyr
        35                  40                  45

Glu Asp Ser Gln Arg Pro Ser Gly Ile Pro Val Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Asp Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210

<210> SEQ ID NO 1465
<211> LENGTH: 238
<212> TYPE: PRT
<213> ORGANISM: Artificial Sequence
<220> FEATURE:
<223> OTHER INFORMATION: Made in Lab - Fzd1:1RC07 complex

<400> SEQUENCE: 1465

Gln Val Gln Leu Gln Gln Trp Gly Ala Gly Leu Leu Lys Pro Ser Glu
1               5                   10                  15

Thr Leu Ser Leu Thr Cys Ala Val Ser Gly Ala Ser Phe Ser Gly His
            20                  25                  30

Tyr Trp Thr Trp Ile Arg Gln Pro Pro Gly Lys Gly Leu Glu Trp Ile
            35                  40                  45

Gly Glu Ile Asp His Thr Gly Ser Thr Asn Tyr Glu Pro Ser Leu Arg
50                  55                  60

Ser Arg Val Thr Ile Ser Val Asp Thr Ser Lys Asn Gln Phe Ser Leu
65                  70                  75                  80

Asn Leu Lys Ser Val Thr Ala Ala Asp Thr Ala Val Tyr Tyr Cys Ala
                85                  90                  95

Arg Gly Gly Gln Gly Gly Tyr Asp Trp Gly His Tyr His Gly Leu Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys Gly Ser Gly Ser Gly His His His His His His
225                 230                 235

<210> SEQ ID NO 1466
<211> LENGTH: 214
<212> TYPE: PRT
<213> ORGANISM: Artificial Sequence
<220> FEATURE:
<223> OTHER INFORMATION: Made in Lab - Fzd1:R2M9 complex

<400> SEQUENCE: 1466

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Thr Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 1467
<211> LENGTH: 243
<212> TYPE: PRT
<213> ORGANISM: Artificial Sequence
<220> FEATURE:
<223> OTHER INFORMATION: Made in lab - Fzd1:R2M9 complex

<400> SEQUENCE: 1467

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Asn
            20                  25                  30

Phe Met His Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Val Gly Glu Val Gly Ala Thr Met Leu Gly Ile Gly Val
            100                 105                 110

Trp Tyr Trp Phe Asp Pro Trp Gly Gln Gly Thr Leu Val Thr Val Ser
        115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160
```

```
Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Gly Ser Gly Ser His His His His
225                 230                 235                 240

His His His

<210> SEQ ID NO 1468
<211> LENGTH: 214
<212> TYPE: PRT
<213> ORGANISM: Artificial Sequence
<220> FEATURE:
<223> OTHER INFORMATION: Made in Lab - Fzd4:003S-D10 complex

<400> SEQUENCE: 1468

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Leu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 1469
<211> LENGTH: 232
<212> TYPE: PRT
<213> ORGANISM: Artificial Sequence
<220> FEATURE:
<223> OTHER INFORMATION: Made in Lab - Fzd4:003S-D10 complex

<400> SEQUENCE: 1469
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Phe Gly Ile Tyr
            20                  25                  30

Ser Met Thr Trp Val Arg Gln Ala Pro Gly Lys Gly Leu Glu Trp Ile
            35                  40                  45

Ser Tyr Ile Ser Gly Asp Ser Gly Tyr Thr Asn Tyr Ala Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Val Gly Pro Gly Gly Trp Phe Asp Pro Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Gly Ser Gly
            210                 215                 220

Ser Gly His His His His His His
225                 230

<210> SEQ ID NO 1470
<211> LENGTH: 216
<212> TYPE: PRT
<213> ORGANISM: Artificial Sequence
<220> FEATURE:
<223> OTHER INFORMATION: Made in Lab - Fzd5:R2M3 complex

<400> SEQUENCE: 1470

Gln Ala Val Val Leu Gln Glu Pro Ser Leu Ser Val Ser Pro Gly Gly
1               5                   10                  15

Thr Val Thr Leu Thr Cys Gly Leu Ser Ser Gly Ser Val Ser Thr Asn
            20                  25                  30

Tyr Tyr Pro Ser Trp Tyr Gln Gln Thr Pro Gly Gln Ala Pro Arg Thr
            35                  40                  45

Leu Ile Tyr Tyr Thr Asn Thr Arg Ser Ser Asp Val Pro Glu Arg Phe
        50                  55                  60

Ser Gly Ser Ile Val Gly Asn Lys Ala Ala Leu Thr Ile Thr Gly Ala
65                  70                  75                  80

Gln Pro Asp Asp Glu Ser Val Tyr Phe Cys Leu Leu Tyr Leu Gly Arg
                85                  90                  95

Gly Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

-continued

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 1471
<211> LENGTH: 236
<212> TYPE: PRT
<213> ORGANISM: Artificial Sequence
<220> FEATURE:
<223> OTHER INFORMATION: Made in Lab - Fzd5:R2M3 complex

<400> SEQUENCE: 1471

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Ser Lys Glu Lys Ala Thr Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Gly Ser Gly Ser Gly His His His His His
225                 230                 235

<210> SEQ ID NO 1472
<211> LENGTH: 214
<212> TYPE: PRT
<213> ORGANISM: Artificial Sequence -continued

```
<220> FEATURE:
<223> OTHER INFORMATION: Made in Lab - Made in Lab - Fzd5:R2M3 complex

<400> SEQUENCE: 1472

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Met Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 1473
<211> LENGTH: 234
<212> TYPE: PRT
<213> ORGANISM: Artificial Sequence
<220> FEATURE:
<223> OTHER INFORMATION: Made in Lab - Fzd5:R2M3 complex

<400> SEQUENCE: 1473

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Pro Asp Phe Trp Ser Gly Tyr Leu Asp Tyr Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Ser Gly Ser Gly His His His His His His
225                 230
```

<210> SEQ ID NO 1474
<211> LENGTH: 214
<212> TYPE: PRT
<213> ORGANISM: Artificial Sequence
<220> FEATURE:
<223> OTHER INFORMATION: Made in Lab - Fzd5:004S-E05 complex

<400> SEQUENCE: 1474

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Arg
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 1475
<211> LENGTH: 238
<212> TYPE: PRT

```
<213> ORGANISM: Artificial Sequence
<220> FEATURE:
<223> OTHER INFORMATION: Made in Lab - Fzd5:004S-E05 complex

<400> SEQUENCE: 1475

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Lys Gly Leu Glu Trp Val
        35                  40                  45

Ser Gly Val Ser Trp Asn Gly Ser Arg Thr His Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Gln Ser Glu Lys Trp Trp Ser Gly Leu Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Gly Ser Gly Ser Gly His His His His His His
225                 230                 235

<210> SEQ ID NO 1476
<211> LENGTH: 214
<212> TYPE: PRT
<213> ORGANISM: Artificial Sequence
<220> FEATURE:
<223> OTHER INFORMATION: Made in Lab - Fzd5:4A12 complex

<400> SEQUENCE: 1476

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Thr Tyr Pro Leu
                85                  90                  95
```

```
Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 1477
<211> LENGTH: 230
<212> TYPE: PRT
<213> ORGANISM: Artificial Sequence
<220> FEATURE:
<223> OTHER INFORMATION: Made in Lab - Fzd5:4A12 complex

<400> SEQUENCE: 1477

```
Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Ser Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Glu Leu His Ser Leu Thr Ser Glu Asp Ser Ala Val Tyr Phe Cys
                85                  90                  95

Val Arg Ser Ala Trp Gly Phe Ala Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Ser Gly Ser Gly
    210                 215                 220

His His His His His His
225                 230
```

<210> SEQ ID NO 1478
<211> LENGTH: 214
<212> TYPE: PRT
<213> ORGANISM: Artificial Sequence
<220> FEATURE:
<223> OTHER INFORMATION: Made in Lab - Fzd9: 014S-B06 complex

<400> SEQUENCE: 1478

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 1479
<211> LENGTH: 238
<212> TYPE: PRT
<213> ORGANISM: Artificial Sequence
<220> FEATURE:
<223> OTHER INFORMATION: Made in Lab - Fzd9: 014S-B06 complex

<400> SEQUENCE: 1479

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Glu Asn Asp Gly Ser Ile Thr Thr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

```
Ala Arg Ala Pro Tyr Tyr Gly Ser Gly Ser Leu Phe Arg Leu Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Gly Ser Gly Ser Gly His His His His His
225                 230                 235
```

<210> SEQ ID NO 1480
<211> LENGTH: 214
<212> TYPE: PRT
<213> ORGANISM: Artificial Sequence
<220> FEATURE:
<223> OTHER INFORMATION: Made in Lab - Fzd10: 005S-A07 complex

<400> SEQUENCE: 1480

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 1481
<211> LENGTH: 232
<212> TYPE: PRT
<213> ORGANISM: Artificial Sequence
<220> FEATURE:
<223> OTHER INFORMATION: Made in Lab - Fzd10: 005S-A07 complex

<400> SEQUENCE: 1481

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Gly Ser
            20                  25                  30

Ala Val Gln Trp Val Arg Gln Ala Pro Gly Gln Gly Leu Glu Trp Val
        35                  40                  45

Gly Gly Ile Leu Pro Ile Tyr Gly Thr Thr Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Leu Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Ser Gly
    210                 215                 220

Ser Gly His His His His His His
225                 230
```

<210> SEQ ID NO 1482
<211> LENGTH: 214
<212> TYPE: PRT
<213> ORGANISM: Artificial Sequence
<220> FEATURE:
<223> OTHER INFORMATION: Made in Lab - Fzd10:005S-E12 complex

<400> SEQUENCE: 1482

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Arg Trp
            20                  25                  30

Met Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
              65                  70                  75                  80
Glu Asp Phe Ala Thr Tyr Tyr Cys Gln Gln Ala Asn Thr Phe Pro Phe
                    85                  90                  95

Thr Phe Gly Pro Gly Thr Lys Val Asp Ile Lys Arg Thr Val Ala Ala
                100                 105                 110

Pro Ser Val Phe Ile Phe Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 1483
<211> LENGTH: 234
<212> TYPE: PRT
<213> ORGANISM: Artificial Sequence
<220> FEATURE:
<223> OTHER INFORMATION: Made in Lab - Fzd10:005S-E12 complex

<400> SEQUENCE: 1483

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
                20                  25                  30

Tyr Met His Trp Val Arg Gln Ala Pro Gly Gln Gly Leu Glu Trp Met
            35                  40                  45

Gly Val Ile Phe Pro Val Tyr Pro Thr Pro Asp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Thr Gly Tyr Tyr Gly Met Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Gly
```

Ser Gly Ser Gly His His His His His His
225                 230

<210> SEQ ID NO 1484
<211> LENGTH: 214
<212> TYPE: PRT
<213> ORGANISM: Artificial Sequence
<220> FEATURE:
<223> OTHER INFORMATION: Made in Lab - FZD3:029S-E03 COMPLEX

<400> SEQUENCE: 1484

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Arg Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 1485
<211> LENGTH: 234
<212> TYPE: PRT
<213> ORGANISM: Artificial Sequence
<220> FEATURE:
<223> OTHER INFORMATION: Made in Lab - FZD3:029S-E03 COMPLEX

<400> SEQUENCE: 1485

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

-continued

```
Gln Gly Arg Val Thr Met Thr Arg Asp Thr Ser Thr Ser Thr Val Tyr
 65              70              75              80

Met Glu Leu Ser Ser Leu Arg Ser Glu Asp Thr Ala Val Tyr Tyr Cys
             85              90                      95

Ala Arg Ser Tyr Tyr Gly Val Ile Asp Ala Phe Asp Ile Trp Gly Gln
            100             105             110

Gly Thr Met Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Gly
    210             215             220

Ser Gly Ser Gly His His His His His His
225             230
```